(12) United States Patent
Goldberg et al.

(10) Patent No.: US 10,975,057 B2
(45) Date of Patent: Apr. 13, 2021

(54) 6-AMINOPYRIDIN-3-YL PYRAZOLES AS MODULATORS OF RORGT

(71) Applicant: Janssen Pharmaceutica NV, Beerse (BE)

(72) Inventors: Steven Goldberg, Carlsbad, CA (US); Connor L. Martin, San Diego, CA (US); Elizabeth G. Fennema, La Mesa, CA (US); David A. Kummer, San Diego, CA (US); Rachel T. Nishimura, San Diego, CA (US); Anne M. Fourie, San Diego, CA (US); Xiaohua Xue, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/442,897

(22) Filed: Jun. 17, 2019

(65) Prior Publication Data

US 2019/0382373 A1     Dec. 19, 2019

Related U.S. Application Data

(60) Provisional application No. 62/686,335, filed on Jun. 18, 2018.

(51) Int. Cl.
| C07D 401/14 | (2006.01) |
| A61P 37/02 | (2006.01) |
| C07D 401/04 | (2006.01) |

(52) U.S. Cl.
CPC .......... *C07D 401/14* (2013.01); *A61P 37/02* (2018.01); *C07D 401/04* (2013.01)

(58) Field of Classification Search
CPC .................................................. C07D 401/14
USPC ....................................................... 546/275.4
See application file for complete search history.

(56) References Cited

U.S. PATENT DOCUMENTS

| 5,342,835 | A | 8/1994 | Pepin et al. |
| 8,809,547 | B2 | 8/2014 | Bretschneider et al. |
| 10,369,146 | B2 * | 8/2019 | Leonard ............. A61K 31/4709 |
| 2005/0014805 | A1 | 1/2005 | Zhang et al. |
| 2012/0245137 | A1 | 9/2012 | Pajouhesh |
| 2014/0163001 | A1 | 6/2014 | Yamamoto |
| 2015/0038350 | A1 | 2/2015 | Nishinaga et al. |
| 2015/0072890 | A1 | 3/2015 | James |
| 2015/0111870 | A1 | 4/2015 | Leonard |
| 2015/0266824 | A1 | 9/2015 | Beck |
| 2016/0120850 | A1 | 5/2016 | Goldberg et al. |
| 2016/0122326 | A1 | 5/2016 | Goldberg et al. |
| 2016/0122335 | A1 | 5/2016 | Goldberg et al. |
| 2016/0122336 | A1 | 5/2016 | Goldberg et al. |
| 2016/0304476 | A1 | 10/2016 | Aicher |
| 2016/0304505 | A1 | 10/2016 | Aicher |
| 2017/0253591 | A1 | 9/2017 | Yammamoto |
| 2017/0313691 | A1 | 11/2017 | Goldberg |
| 2019/0269134 | A1 | 9/2019 | Fublein et al. |
| 2019/0382349 | A1 | 12/2019 | Goldberg et al. |
| 2019/0382350 | A1 | 12/2019 | Goldberg et al. |
| 2019/0382354 | A1 | 12/2019 | Goldberg et al. |
| 2019/0382373 | A1 | 12/2019 | Goldberg et al. |

FOREIGN PATENT DOCUMENTS

| CL | 201102650 | 10/2011 |
| CL | 201200534 | 2/2012 |
| CL | 201803050 | 10/2018 |
| CL | 201901343 | 5/2019 |
| CN | 103833672 | 6/2014 |
| EP | 360701 A1 | 3/1990 |
| EP | 2433938 | 3/2012 |
| EP | 2474543 | 7/2012 |
| EP | 2738170 | 6/2014 |
| JP | 2005507932 | 3/2005 |
| WO | WO 1996003392 A1 | 2/1996 |
| WO | WO 2002083111 A2 | 10/2002 |

(Continued)

OTHER PUBLICATIONS

PCT/US2015/058193, Written Opinion dated Jan. 26, 2016.

(Continued)

*Primary Examiner* — Nizal S Chandrakumar
(74) *Attorney, Agent, or Firm* — Yuriy P. Stercho

(57) ABSTRACT

The present invention comprises compounds of Formula I.

Formula I

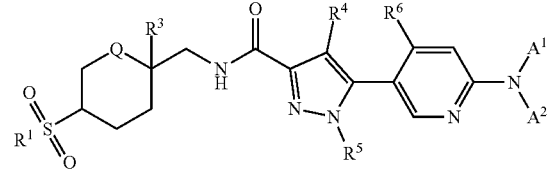

wherein:
$R^1$, Q, $R^3$, $R^4$, $R^5$, $R^6$, $A^1$, and $A^2$ are defined in the specification.

The invention also comprises a method of treating or ameliorating a ROR-γ-t mediated syndrome, disorder or disease, including wherein the syndrome, disorder or disease is selected from the group consisting of rheumatoid arthritis, psoriatic arthritis, and psoriasis. The invention also comprises a method of modulating RORγt activity in a mammal by administration of a therapeutically effective amount of at least one compound of Formula I.

28 Claims, No Drawings

Specification includes a Sequence Listing.

(56) References Cited

FOREIGN PATENT DOCUMENTS

| WO | WO 2003015776 A1 | 2/2003 |
| WO | WO 2006087355 | 8/2006 |
| WO | WO 2006124687 A1 | 11/2006 |
| WO | WO 2007087427 A2 | 8/2007 |
| WO | WO 2008064317 A1 | 5/2008 |
| WO | WO 2008064318 A2 | 5/2008 |
| WO | WO 2009011850 | 1/2009 |
| WO | WO 2010006713 | 1/2010 |
| WO | WO 2011053948 A1 | 5/2011 |
| WO | WO 2011112263 A1 | 9/2011 |
| WO | WO 2011112264 A1 | 9/2011 |
| WO | WO 2011115892 A1 | 9/2011 |
| WO | WO 2012027965 | 3/2012 |
| WO | WO 2012074547 A2 | 6/2012 |
| WO | WO 2012129491 | 9/2012 |
| WO | WO 2012158784 A2 | 11/2012 |
| WO | WO 2012174362 | 12/2012 |
| WO | WO 2013029338 | 3/2013 |
| WO | WO 2013036912 A2 | 3/2013 |
| WO | WO 2013079223 A | 6/2013 |
| WO | WO 2013092939 A1 | 6/2013 |
| WO | WO 2013171729 | 11/2013 |
| WO | WO 2013178362 A1 | 12/2013 |
| WO | WO 2014023367 | 2/2014 |
| WO | WO 2014093191 | 6/2014 |
| WO | WO 2015035278 A1 | 3/2015 |
| WO | WO 2015042212 A1 | 3/2015 |
| WO | WO 2015082533 A1 | 6/2015 |
| WO | WO 2015103507 A1 | 7/2015 |
| WO | WO 2015103508 A1 | 7/2015 |
| WO | WO 2015103509 A1 | 7/2015 |
| WO | WO 2015103510 A1 | 7/2015 |
| WO | WO 2015145371 A1 | 10/2015 |
| WO | WO 2016069974 | 5/2016 |
| WO | WO 2017/189823 | 11/2017 |
| WO | WO 2017/189829 | 11/2017 |
| WO | WO 2018123918 | 7/2018 |
| WO | WO 2018185236 | 10/2018 |

OTHER PUBLICATIONS

PCT/US2015/058198, Written Opinion dated Jan. 21, 2016.
PCT/US2015/058200, Written Opinion dated Jan. 27, 2016.
PCT/US2015/058193, International Search Report, dated Jan. 26, 2016.
PCT/US2015/058198, International Search Report, dated Jan. 21, 2016.
PCT/US2015/058200, International Search Report, dated Jan. 27, 2016.
PCT/US2017/029531, International Search Report, dated Sep. 15, 2017.
PCT/US2017/029531, International Preliminary Report on Patentability, dated Oct. 30, 2018.
PCT/IB2019/055043, International Search Report, dated Sep. 30, 2019.
PCT/IB2019/055045, International Search Report, dated Sep. 30, 2019.
PCT/IB2019/055046, International Search Report, dated Oct. 4, 2019.
PCT/IB2019/055048, International Search Report, dated Sep. 27, 2019.
Angew. Chem. Int. Ed. Engl. 1982, 21, 567-583.
Barczyk, A., W. Pierzchala, et al. (2003). "Interleukin-17 in sputum correlates with airway hyperresponsiveness to methacholine." Respir Med 97(6): 726-33.
Beurel, E., Harrington, L. E., Jope, R. S. (2013) "Inflammatory T helper 17 cells promote depression-like behavior in mice." Biol Psychiatry 73(7): 622-30.
Bimekizumab demonstrates impressive joint and skin responses for psoriatic arthritis patients. Dec. 20, 2017. https://www.ucb.com/stories-media/Press-Releases/article/Bimekizumab-demonstrates-impressive-joint-and-skin-responses-for-psoriatic-arthritis-patients-nbsp.
Bowes, J. and A. Barton "The genetics of psoriatic arthritis: lessons from genome-wide association studies." Discov Med 10(52): 177-83 (2010).
Chang M, "Pharmacologic Repression of Retinoic Acid Receptor-Related Orphan Nuclear Receptor Is Therapeutic in the Collagen-Induced Arthritis Experimental Model", Arthritis & Rheumatology (2014), 66(3), 579-588.
Chang, M. R. et al. (2015) "Antiobesity Effect of a Small Molecule Repressor of RORγ." Mol Pharmacol. 88(1): 48-56.
Chen, Y., et al. (2011). "Emerging tendency towards autoimmune process in major depressive patients: A novel insight from Th17 cells." Psychiatry Research 188(2): 224-230.
Cheng, Chia-Chung et al., The Friedlander synthesis of quinolines, Organic Reactions, 1982, 28, pp. 37-201.
Cua, D. J., J. Sherlock, et al. (2003). "Interleukin-23 rather than interleukin-12 is the critical cytokine for autoimmune inflammation of the brain." Nature 421(6924): 744-8.
De Wit et al., RORγt inhibitors suppress TH17 responses in inflammatory arthritis and inflammatory bowel disease. Journal of Allergy and Clinical Immunology, vol. 137 , Issue 3, (2016), 960-963.
Dolff S et al., Disturbed Th1, Th2, Th17 and T-reg balance in patients with systemic lupus erythematosus, Clinical Immunology 141(2):197-204 Aug. 2011.
Dong, C. (2006). "Diversification of T-helper-cell lineages: finding the family root of IL-17-producing cells." Nat Rev Immunol 6(4): 329-33.
Fauber et al., J. Med. Chem. 2014, 57, 5871-5892.
Feagan BG, et al. Ustekinumab as induction and maintenance therapy for Crohn's disease. N Engl J Med. 2016;375(20):1946-60.
Fitzpatrick, Leo Robert. Ror-gamma T inhibition as a Pharmacological Approach for Inflammatory Bowel Disease. Medical Research Archives, [S.1], v. 2, n. 2, Aug. 2015.
Fujino, S., A. Andoh, et al. (2003). "Increased expression of interleukin 17 in inflammatory bowel disease." Gut 52(1): 65-70.
Garber K. (2011). "Psoriasis: from bed to bench and back" Nat Biotech 29, 563-566.
Gazouli, M., I. Pachoula, et al. "NOD2/CARD15, ATG16L1 and IL23R gene polymorphisms and childhood-onset of Crohn's disease." World J Gastroenterol 16(14): 1753-8 (2010).
Hodgson et al., Ustekinumab for Treating Moderately to Severely Active Crohn's Disease after Prior Therapy: An Evidence Review Group Perspective of a NICE Single Technology Appraisal. PharmacoEconomics (2018) 36:4, 387-398.
Hueber, W., Patel, D.D., Dryja, T., Wright, A.M., Koroleva, I., Bruin, G., Antoni, C., Draelos, Z., Gold, M.H., Durez, P., Tak, P.P., Gomez-Reino, J.J., Foster, C.S., Kim, R.Y., Samson, C.M., Falk, N.S., Chu, D.S., Callanan, D., Nguyen, Q.D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.
Innovimmune: ROR Gamma Inhibitor (INV-17) Tested in Lupus Model. 2015 Eular Congress News. https://static1.squarespace.com/static/577aff0015d5db17f97d2d57/t/584f44f9725e254d6b032644/1481590043630/150611_INV-17+Lupus+Thursday_EULAR_2015+small+size.pdf.
Ivanov, II, B. S. McKenzie, et al. (2006). "The orphan nuclear receptor RORgammat directs the differentiation program of proinflammatory IL-17+ T helper cells." Cell 126(6): 1121-33.
Jethwa H at al., The interleukin (IL)-23/IL-17 axis in ankylosing spondylitis: new advances and potentials for treatment, Clinical and Experimental Immunology, 2015, 183: 30-36.
Kochi, Y., Y. Okada, et al. (2010) "A regulatory variant in CCR6 is associated with rheumatoid arthritis susceptibility." Nat Genet 42(6): 515-9.
Kolls, J. K. and A. Linden (2004). "Interleukin-17 family members and inflammation." Immunity 21(4): 467-76.
Korn, T., E. Bettelli, et al. (2009). "IL-17 and Th17 Cells." Annu Rev Immunol 27: 485-517.

(56) References Cited

OTHER PUBLICATIONS

Krueger, J. G., S. Fretzin, et al. "IL-17A is essential for cell activation and inflammatory gene circuits in subjects with psoriasis." J Allergy Clin Immunol 130(1): 145-154 e9 (2012).
Kumar N, "The Benzenesulfoamide T0901317 [N-(2,2,2-Trifluoroethyl)-N-[4-[2,2,2-trifluoro-1-hydroxy-1-(trifluoromethyl)ethyl]phenyl]-benzenesulfonamide] Is a Novel Retinoic Acid Receptor-Related Orphan Receptor—Inverse Agonist", Molecular Pharmacology (2010), 77(2), 228-236.
Langrish, C. L., Y. Chen, et al. (2005). "IL-23 drives a pathogenic T cell population that induces autoimmune inflammation." J Exp Med 201(2): 233-40.
Leonardi, C., R. Matheson, et al. "Anti-interleukin-17 monoclonal antibody ixekizumab in chronic plaque psoriasis." N Engl J Med 366(13): 1190-9 (2012).
Liegault, et al., "Establishment of Broadly Applicable reaction condisions for the Palladium-Catalyzed Direct Arylation of Heteroatom-Containing Aromatic Compounds", The Journal of Organic Chemistry, (2009), vol. 74, No. 5, 6, pp. 1826-1834.
Lock, C., G. Hermans, et al. (2002). "Gene-microarray analysis of multiple sclerosis lesions yields new targets validated in autoimmune encephalomyelitis." Nat Med 8(5): 500-8.
Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66.
McGinley et al., (2018) Th17 cells, γδ T cells and their interplay in EAE and multiple sclerosis. *Journal of Autoimmunity* 87, 97-108.
McKenzie, B. S., R. A. Kastelein, et al. (2006). "Understanding the IL-23-IL-17 immune pathway." Trends Immunol 27(1): 17-23.
Mease, P. J. et al. Brodalumab, an anti-IL17RA monoclonal antibody, in psoriatic arthritis, The New England Journal of Medicine 370, 2295-2306 (2014).
Meissburger, B. et al. (2011) "Adipogenesis and insulin sensitivity in obesity are regulated by retinoid-related orphan receptor gamma." EMBO Mol Med. 3(11): 637-651.
Nunez, C., B. Dema, et al. (2008). "IL23R: a susceptibility locus for celiac disease and multiple sclerosis?" Genes Immun 9(4): 289-93.
Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40.
Papp, K. A., "Brodalumab, an anti-interleukin-17-receptor antibody for psoriasis." N Engl J Med 2012 366(13): 1181-9.
Poddhubnyy et al., Ann Rheum Dis 2014;0:1-7.
Pure & Appl. Chem. 45, 1976, 11-30.
Qian et al., Clin. Invest. (2012) 2(4), 417-421.
Registry(STN)[online], [Search Date: May 13, 2019]CAS Registration No. 791058-42-9,263386-02-3.
Sandborn WJ et al. Ustekinumab Induction and Maintenance Therapy in Refractory Crohn's Disease N Engl J Med 2012; 367:1519-1528.
Silva MJ et al, Glucocorticoid Resistant Asthma: The Potential Contribution of IL-17. Biomark J. 2016, 1:6.
Stamp, L. K., M. J. James, et al. (2004). "Interleukin-17: the missing link between T-cell accumulation and effector cell actions in rheumatoid arthritis" Immunol Cell Biol 82(1): 1-9.
Tonel, G., C. Conrad, et al. "Cutting edge: A critical functional role for IL-23 in psoriasis." J Immunol 185(10): 5688-91 (2010).
Wang X, Wei Y, Xiao H, et al. A novel IL-23p19/Ebi3 (IL-39) cytokine mediates inflammation in Lupus-like mice. Eur J Immunol. 2016;46(6):1343-1350.
Weitz JE et al., Ustekinumab: Targeting the IL-17 Pathway to Improve Outcomes in Psoriatic Arthritis. Expert Opin Biol Ther 2104 14, 515-526.
Withers DR, et al. Transient inhibition of ROR-γt therapeutically limits intestinal inflammation by reducing TH17 cells and preserving group 3 innate lymphoid cells Nature Medicine 2016, 22, 319.
Yang et al., Trends in Pharmacological Sciences, Oct. 2014, vol. 35, No. 10, 493-500.
Yang X et al. Does IL-17 Respond to the Disordered Lung Microbiome and Contribute to the Neutrophilic Phenotype in Asthma? Mediators of Inflammation. vol. 2016 (2016), Article ID 6470364, pp. 1-7.
Yao, et al, "Preparation Method of N-butyl-5-phenylthiazole-4-Formamide Derivative Via Coupling Reaction Under Catalysis of Copper Catalyst", Database accession No. 2014:924023.
Yen, D., J. Cheung, et al. (2006). "IL-23 is essential for T cell-mediated colitis and promotes inflammation via IL-17 and IL-6." J Clin Invest 116(5): 1310-6.
Zhang, et al., "Decarboxylative Cross-Coupling of Azoyl Carboxylic Acids with Aryl Halides", Organic Letters, (2010) vol. 12, No. 21, pp. 4745-47457.
Eastman; Oncotarget. 2017, 8, 8854-8866. DOI: 10.18632/oncotarget. 12673 (Year: 2017).
Guendisch; PLoS One 2017, 12, e0188391. DOI: 10.1371/journal. pone.0188391 (Year: 2017).
Huh; Eur. J. Immunol. 2012. 42, 2232-2237. DOI: 10.1002/eji. 201242740 (Year: 2012).
Isono; Drug Discovery Today, 2014, 19, 1205-1211. DOI: 10.1016/j.drudis.2014.04.012 (Year: 2014).
Kiaei; Basic Clin Neurosci. 2013, 4, 3-4. URL: http://bcn.iums.ac.ir/article-1-307-en.html (Year: 2013).
Xue; Scientific Reports 2016, 6, Article No. 37977. DOI: 10.1038/srep37977 (Year: 2016).

\* cited by examiner

SEQUENCE LISTING

<160> NUMBER OF SEQ ID NOS: 4

<210> SEQ ID NO 1
<211> LENGTH: 3054
<212> TYPE: DNA

<213> ORGANISM: Homo sapiens

<400> SEQUENCE: 1

```
agagagctag gtgcagagct tcaggctgag gcgctgctga gagggcctcg ccccgcctct      60
gccgccagct gcaccccact cctgaccac ccctgctga aaggacagg gagccaaggc        120
cggcagagcc aaggctcagt catgagaaca caaattgaag tgatcccttg caaaatctgt     180
ggggacaagt cgtctgggat ccactacggg gttatcacct gtgaggggtg caagggcttc     240
ttccgccgga gccagcgctg taacgcggcc tactcctgca cccgtcagca gaactgcccc    300
atcgaccgca ccagccgaaa ccgatgccag cactgccgcc tgcagaaatg cctggcgctg   360
ggcatgtccc gagatgctgt caagttcggc cgcatgtcca agaagcagag ggacagcctg    420
catgcagaag tgcagaaaca gctgcagcag cggcaacagc agcaacagga accagtggtc    480
aagacccctc cagcagggc ccaaggagca gatacccctca cctacacctt ggggctccca   540
gacgggcagc tgcccctggg ctcctcgcct gacctgcctg aggcttctgc ctgtccccct    600
ggcctcctga agcctcagg ctctgggccc tcatattcca acaacttggc caaggcaggg    660
ctcaatgggg cctcatgcca ccttgaatac agccctgagc ggggcaaggc tgagggcaga   720
gagagcttct atagcacagg cagccagctg acccctgacc gatgtggact tcgttttgag    780
gaacacaggc atcctgggct tggggaactg gacagggcc cagacagcta cggcagcccc    840
agtttccgca gcacaccgga ggcacctat gcctccctga cagagataga gcacctggtg     900
cagagcgtct gcaagtccta cagggagaca tgccagctgc ggctggagga cctgctgcgg    960
cagcgctcca acatcttctc ccgggaggaa gtgactggct accagaggaa gtccatgtgg   1020
gagatgtggg aacggtgtgc ccaccacctc accgaggcca ttcagtacgt ggtggagttc    1080
gccaagaggc tctcaggctt tatggagctc tgccagaatg accagattgt gcttctcaaa    1140
gcaggagcaa tggaagtggt gctggttagg atgtgccggg cctacaatgc tgacaaccgc    1200
acggtctttt tgaaggcaa atacggtggc atggagctgt tccgagcctt gggctgcagc    1260
gagctcatca gctccatctt tgacttctcc cactccctaa gtgccttgca cttttccgag    1320
gatgagattg ccctctacac agcccttgtt ctcatcaatg cccatcggcc agggctccaa    1380
gagaaaagga agtagaaca gctgcagtac aatctggagc tggcctttca tcatcatctc   1440
tgcaagactc atcgccaaag catcctggca aagctgccac ccaagggaa gcttcggagc    1500
ctgtgtagcc agcatgtgga aaggctgcag atcttccagc acctccaccc catcgtggtc    1560
caagccgctt tccctccact ctacaaggag ctcttcagca ctgaaaccga gtcacctgtg   1620
gggctgtcca agtgacctgg aagagggact ccttgcctct ccctatggcc tgctggccca    1680
cctccctgga cccgttcca ccctcaccct tttcctttcc catgaaccct ggagggtggt     1740
ccccaccagc tctttggaag tgagcagatg ctgcggctgg ctttctgtca gcaggccggc    1800
ctggcagtgg gacaatcgcc agagggtggg gctggcagaa caccatctcc agcctcagct   1860
ttgacctgtc tcatttccca tattccttca cacccagctt ctggaaggca tggggtggct    1920
gggatttaag gacttctggg ggaccaagac atcctcaaga aaacaggggc atccagggct    1980
ccctggatga atagaatgca attcattcag aagctcagaa gctaagaata agcctttgaa   2040
atacctcatt gcatttccct tgggcttcg gcttgggag atggatcaag ctcagagact      2100
ggcagtgaga gcccagaagg acctgtataa aatgaatctg gagctttaca ttttctgcct    2160
ctgccttcct cccagctcag caaggaagta tttgggcacc ctacccttta cctgggtct     2220
aaccaaaaat ggatgggatg aggatgagag gctggagata attgttttat gggatttggg   2280
```

```
tgtgggacta gggtacaatg aaggccaaga gcatctcaga catagagtta aaactcaaac  2340
ctcttatgtg cactttaaag atagacttta ggggctggca caaatctgat cagagacaca  2400
tatccataca caggtgaaac acatacagac tcaacagcaa tcatgcagtt ccagagacac  2460
atgaacctga cacaatctct cttatccttg aggccacagc ttggaggagc ctagaggcct  2520
caggggaaag tcccaatcct gagggaccct cccaaacatt tccatggtgc tccagtccac  2580
tgatcttggg tctggggtga tccaaatacc accccagctc cagctgtctt ctaccactag  2640
aagacccaag agaagcagaa gtcgctcgca ctggtcagtc ggaaggcaag atcagatcct  2700
ggaggacttt cctggcctgc ccgccagccc tgctcttgtt gtggagaagg aagcagatgt  2760
gatcacatca ccccgtcatt gggcaccgct gactccagca tggaggacac cagggagcag  2820
ggcctgggcc tgtttcccca gctgtgatct tgcccagaac ctctcttggc ttcataaaca  2880
gctgtgaacc ctcccctgag ggattaacag caatgatggg cagtcgtgga gttgggggg   2940 ttgggggtgg gattgtgtcc tctaagggga cgggttcatc tgagtaaaca taaaccccaa  3000
cttgtgccat tctttataaa atgattttaa aggcaaaaaa aaaaaaaaaa aaaa         3054
```

```
<210> SEQ ID NO 2
<211> LENGTH: 786
<212> TYPE: DNA
<213> ORGANISM: Homo sapiens

<400> SEQUENCE: 2
agcacaccgg aggcacccta tgcctccctg acagagatag agcacctggt gcagagcgtc    60
tgcaagtcct acagggagac atgccagctg cggctggagg acctgctgcg gcagcgctcc   120
aacatcttct cccggagga agtgactggc taccagagga gtccatgtg ggagatgtgg     180 gaacggtgtg cccaccacct caccgaggcc attcagtacg tggtggagtt cgccaagagg   240
ctctcaggct ttatggagct ctgccagaat gaccagattg tgcttctcaa agcaggagca   300
atggaagtgg tgctggttag gatgtgccgg gcctacaatg ctgacaaccg cacggtcttt   360
tttgaaggca aatacggtgg catggagctg ttccgagcct tgggctgcag cgagctcatc   420
agctccatct ttgacttctc ccactcccta agtgccttgc acttttccga ggatgagatt   480
gccctctaca cagcccttgt tctcatcaat gcccatcggc cagggctcca agagaaaagg   540
aaagtagaac agctgcagta caatctggag ctggcctttc atcatcatct ctgcaagact   600
catcgccaaa gcatcctggc aaagctgcca cccaagggga agcttcggag cctgtgtagc   660
cagcatgtgg aaaggctgca gatcttccag cacctccacc ccatcgtggt ccaagccgct   720
ttccctccac tctacaagga gctcttcagc actgaaaccg agtcacctgt ggggctgtcc   780
aagtga                                                              786
```

```
<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5
```

```
<210> SEQ ID NO 4
<211> LENGTH: 283
```

```
<212> TYPE: PRT
<213> ORGANISM: Artificial Sequence
<220> FEATURE:
<223> OTHER INFORMATION: Construct used in the Thermofluor assay

<400> SEQUENCE: 4

Met Ala His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
            20                  25                  30

Thr Glu Ile Glu His Leu Val Gln Ser Val Cys Lys Ser Tyr Arg Glu
        35                  40                  45

Thr Cys Gln Leu Arg Leu Glu Asp Leu Leu Arg Gln Arg Ser Asn Ile
50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
            100                 105                 110

Asp Gln Ile Val Leu Leu Lys Ala Gly Ala Met Glu Val Val Leu Val
            115                 120                 125

Arg Met Cys Arg Ala Tyr Asn Ala Asp Asn Arg Thr Val Phe Phe Glu
130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175

Phe Ser Glu Asp Glu Ile Ala Leu Tyr Thr Ala Leu Val Leu Ile Asn
            180                 185                 190

Ala His Arg Pro Gly Leu Gln Glu Lys Arg Lys Val Glu Gln Leu Gln
        195                 200                 205

Tyr Asn Leu Glu Leu Ala Phe His His His Leu Cys Lys Thr His Arg
210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                245                 250                 255

Ile Val Val Gln Ala Ala Phe Pro Pro Leu Tyr Lys Glu Leu Phe Ser
            260                 265                 270

Thr Glu Thr Glu Ser Pro Val Gly Leu Ser Lys
            275                 280
```

6-AMINOPYRIDIN-3-YL PYRAZOLES AS MODULATORS OF RORGT

CROSS REFERENCE TO RELATED APPLICATIONS

This application claims priority from U.S. Provisional Application 62/686,335, filed on Jun. 18, 2018, which is incorporated by reference herein in its entirety.

SEQUENCE LISTING

The instant application contains a Sequence Listing which has been filed electronically in ASCII format and is hereby incorporated by reference in its entirety. Said ASCII copy, created on Jun. 11, 2019, is named PRD3479USNP.txt and is 8,209 bytes in size.

FIELD OF THE INVENTION

The invention is directed to substituted pyrazole compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of CD4+ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517.), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23.). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgammat directs the differentiation program of proinflammatory IL-17+ T helper cells." Cell 126(6): 1121-33.). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8.; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6.). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

RORγT deficient mice exhibited resistance to learned helplessness. Treatment with the RORγT inhibitor SR1001, or anti-interleukin-17A antibodies reduced Th17-dependent learned helplessness (Beurel, E., Harrington, L. E., Jope, R. S. (2013) "Inflammatory T helper 17 cells promote depression-like behavior in mice." Biol Psychiatry 73(7): 622-30). In human patients with major depressive disorder, both peripheral blood lymphocyte RORγT mRNA expression and peripheral Th17 cells were found to be elevated relative to the control group (Chen, Y., et al. (2011). "Emerging tendency towards autoimmune process in major depressive patients: A novel insight from Th17 cells." Psychiatry Research 188(2): 224-230).

Administration of RORγ inverse agonist SR1555 to obese diabetic mice resulted in a modest reduction in food intake accompanied with significant reduction in fat mass, resulting in reduced body weight and improved insulin sensitivity (Chang, M. R. et al. (2015) "Antiobesity Effect of a Small Molecule Repressor of RORγ." Mol Pharmacol. 88(1): 48-56). In addition, Rorγ−/− mice are protected from hyperglycemia and insulin resistance in the state of obesity (Meissburger, B. et al. (2011) "Adipogenesis and insulin sensitivity in obesity are regulated by retinoid-related orphan receptor gamma." EMBO Mol Med. 3(11): 637-651).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33.; Fujino, S., A. Andoh, et al. (2003). "Increased expression of interleukin 17 in inflammatory bowel disease." Gut 52(1): 65-70.; Lock, C., G. Hermans, et al. (2002). "Gene-microarray analysis of multiple sclerosis lesions yields new targets validated in autoimmune encephalomyelitis." Nat Med 8(5): 500-8.; Krueger, J. G., S. Fretzin, et al. "IL-17A is essential for cell activation and inflammatory gene circuits in subjects with psoriasis." J Allergy Clin Immunol 130(1): 145-154 e9.). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93.; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9.).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9.; Leonardi, C., R. Matheson, et al. "Anti-interleukin-17 monoclonal antibody ixekizumab in chronic plaque psoriasis." N Engl J Med 366(13): 1190-9.). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.).

All the above evidence supports inhibition of the Th17 pathway by modulating RORγt activity as an effective strategy for the treatment of immune-mediated inflammatory diseases.

SUMMARY OF THE INVENTION

The present invention comprises a compound of Formula I:

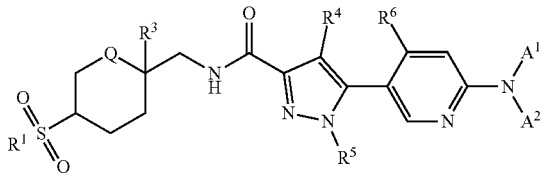

Formula I wherein
$R^1$ is $-C_{(1-4)}$alkyl, $-NH_2$, $-NHC(O)NH_2$, $NHC(O)C_{(1-4)}$alkyl, $-NHC_{(1-4)}$alkyl, $-NHC(O)H$, $-NHC(O)NHC_{(1-4)}$alkyl, or $-N(C_{(1-4)}$alkyl$)_2$;
Q is $CHR^2$, $NC(O)CH_3$, $NCH_2C(O)NH_2$, NH, or O;
$R^2$ is H, $-OH$, or $-NH_2$;
$R^3$ is $-H$, $-OH$, $-CN$, $-NH_2$, $-CONH_2$, $-CO_2H$, $-CO_2C_{(1-4)}$alkyl, $-CH_2OH$, $-CH_2NH_2$, $-CH_2CN$, $-NHC_{(1-4)}$alkyl, or $-CONHC_{(1-4)}$alkyl;
$R^4$ is $-Cl$, $-C_{(1-4)}$alkyl, $-F$, $-CN$, $-C(O)NH_2$,

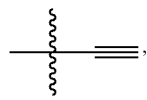 [SMILES: *C#C]

or $-H$; wherein said $-C_{(1-4)}$alkyl is optionally substituted with up to six fluorine atoms;
$R^5$ is $-C_{(1-4)}$alkyl, wherein said $-C_{(1-4)}$alkyl is optionally substituted with $-CN$, $-OH$, $-OCH_3$, $-OCF_3$, or up to six fluorine atoms;
$R^6$ is $-H$, $-F$, $-Cl$, $-OCD_3$, $-CN$, $-C_{(1-3)}$alkyl, or $-OC_{(1-3)}$alkyl, wherein said $-C_{(1-3)}$alkyl and said $OC_{(1-3)}$alkyl are optionally substituted with up to three fluorine atoms;
$A^1$ is

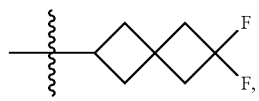 [SMILES: *C1CC2(C1)CC(F)(F)C2]

$-(CH_2)_mC_{(3-6)}$cycloalkyl, wherein said $-(CH_2)_mC_{(3-6)}$cycloalkyl is optionally substituted with two fluorine atoms, $-CF_3$, $-CH_2CF_3$, or $-OH$, and wherein said $-C_{(2-5)}$alkyl is optionally substituted with $-SCF_3$, $-OCH_2CF_3$, cyclopropyl, and up to six fluorine atoms;
m is 0 or 1;
$A^2$ is H; or $A^1$ and $A^2$ are taken together with their attached nitrogen to form

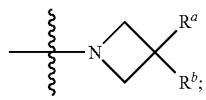

$R^a$ is $-OCHF_2$, $-CH_2CF_3$, $-CF_3$, or F;
$R^b$ is H or F;
and pharmaceutically acceptable salts thereof.

DETAILED DESCRIPTION OF THE INVENTION

The present invention comprises a compound of Formula I:

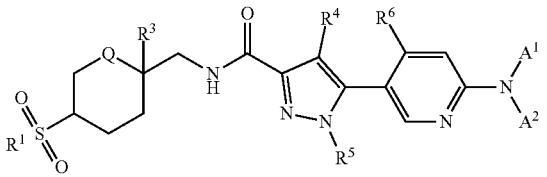

Formula I wherein
$R^1$ is $-C_{(1-4)}$alkyl, $-NH_2$, $-NHC(O)NH_2$, $NHC(O)C_{(1-4)}$alkyl, $-NHC_{(1-4)}$alkyl, $-NHC(O)H$, $-NHC(O)NHC_{(1-4)}$alkyl, or $-N(C_{(1-4)}$alkyl$)_2$;
Q is $CHR^2$, $NC(O)CH_3$, $NCH_2C(O)NH_2$, NH, or O;
$R^2$ is H, $-OH$, or $-NH_2$;
$R^3$ is $-H$, $-OH$, $-CN$, $-CO_2H$, $-CO_2C_{(1-4)}$alkyl, $-CH_2OH$, $-CH_2NH_2$, $-CH_2CN$, $-NHC_{(1-4)}$alkyl, or $-CONHC_{(1-4)}$alkyl;
$R^4$ is $-Cl$, $-C_{(1-4)}$alkyl, $-F$, $-CN$, $-C(O)NH_2$,

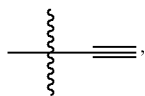

or —H; wherein said —C$_{(1-4)}$alkyl is optionally substituted with up to six fluorine atoms;
R$^5$ is —C$_{(1-4)}$alkyl, wherein said —C$_{(1-4)}$alkyl is optionally substituted with —CN, —OH, —OCH$_3$, —OCF$_3$, or up to six fluorine atoms;
R$^6$ is —H, —F, —Cl, —OCD$_3$, —CN, —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms;
A$^1$ is

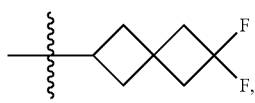 [SMILES: *C1CC2(C1)CC(F)(F)C2]

—(CH$_2$)$_m$C$_{(3-6)}$cycloalkyl, wherein said —(CH$_2$)$_m$C$_{(3-6)}$cycloalkyl is optionally substituted with two fluorine atoms, —CF$_3$, —CH$_2$CF$_3$, or —OH, and wherein said —C$_{(2-5)}$alkyl is optionally substituted with —SCF$_3$, —OCH$_2$CF$_3$, cyclopropyl, and up to six fluorine atoms;
m is 0 or 1;
A$^2$ is H; or A$^1$ and A$^2$ are taken together with their attached nitrogen to form

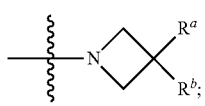

R$^a$ is —OCHF$_2$, —CH$_2$CF$_3$, —CF$_3$, or F;
R$^b$ is H or F;
and pharmaceutically acceptable salts thereof.
In another embodiment of the invention:
R$^1$ is —C$_{(1-2)}$alkyl, —NH$_2$, —NHC(O)NH$_2$, NHC(O)C$_{(1-2)}$alkyl, —NHCH$_3$, —NHC(O)H, —NHC(O)NHCH$_3$, or —N(CH$_3$)$_2$;
Q is CHR$^2$, NC(O)CH$_3$, NCH$_2$C(O)NH$_2$, NH, or O;
R$^2$ is H, —OH, or —NH$_2$;
R$^3$ is —H, —OH, —CN, —NH$_2$, —CONH$_2$, —CO$_2$H, —CO$_2$CH$_2$CH$_3$, or —CH$_2$OH;
R$^4$ is —Cl, —C$_{(1-4)}$alkyl, —F, —CN, —CF$_3$, —C(O)NH$_2$,

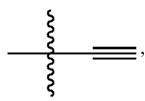

or —H;
R$^5$ is —C$_{(1-4)}$alkyl, wherein said —C$_{(1-4)}$alkyl is optionally substituted with —CN, —OH, or —OCH$_3$;
R$^6$ is —H, —F, —Cl, —OCD$_3$, —CN, —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms;

A$^1$ is

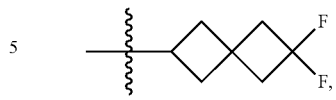

—(CH$_2$)$_m$C$_{(3-6)}$cycloalkyl, wherein said —(CH$_2$)$_m$C$_{(3-6)}$cycloalkyl is optionally substituted with two fluorine atoms, —CF$_3$, —CH$_2$CF$_3$, or —OH, and wherein said —C$_{(2-5)}$alkyl is optionally substituted with —SCF$_3$, —OCH$_2$CF$_3$, cyclopropyl, and up to six fluorine atoms;
m is 0 or 1;
A$^2$ is H; or A$^1$ and A$^2$ are taken together with their attached nitrogen to form

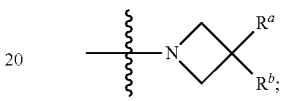

R$^a$ is —OCHF$_2$, —CH$_2$CF$_3$, —CF$_3$, or F;
R$^b$ is H or F;
and pharmaceutically acceptable salts thereof.
In another embodiment of the invention:
R$^1$ is —C$_{(1-2)}$alkyl, —NH$_2$, —NHC(O)NH$_2$, NHC(O)C$_{(1-2)}$alkyl, —NHCH$_3$, —NHC(O)H, or —NHC(O)NHCH$_3$;
Q is CHR$^2$;
R$^2$ is —H or —OH;
R$^3$ is —H, —OH, —CN, or —NH$_2$;
R$^4$ is —Cl, —C$_{(1-4)}$alkyl, —F, or —CN;
R$^5$ is —C$_{(1-4)}$alkyl;
R$^6$ is —H, —F, —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms;
A$^1$ is

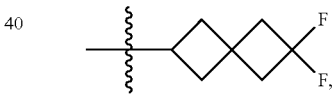

—(CH$_2$)$_m$C$_{(3-6)}$cycloalkyl, wherein said —(CH$_2$)$_m$C$_{(3-6)}$cycloalkyl is optionally substituted with two fluorine atoms, —CF$_3$, —CH$_2$CF$_3$, or —OH, and wherein said —C$_{(2-5)}$alkyl is optionally substituted with —SCF$_3$, —OCH$_2$CF$_3$, cyclopropyl, and up to six fluorine atoms;
m is 0 or 1;
A$^2$ is H; or A$^1$ and A$^2$ are taken together with their attached nitrogen to form

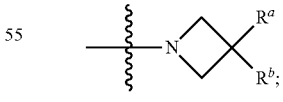

R$^a$ is —OCHF$_2$, —CH$_2$CF$_3$, —CF$_3$, or F;
R$^b$ is H or F;
and pharmaceutically acceptable salts thereof.
In another embodiment of the invention:
R$^1$ is —C$_{(1-2)}$alkyl;
Q is CHR$^2$;
R$^2$ is —H or —OH;
R$^3$ is —H or —OH;
R$^4$ is —Cl or —C$_{(1-4)}$alkyl;

$R^5$ is —$C_{(1-4)}$alkyl;
$R^6$ is —$C_{(1-3)}$alkyl, or —$OC_{(1-3)}$alkyl, wherein said —$C_{(1-3)}$alkyl and said $OC_{(1-3)}$alkyl are optionally substituted with up to three fluorine atoms;
$A^1$ is

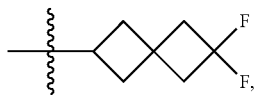 [SMILES: *C1CC2(C1)CC(F)(F)C2]

—$C_{(2-5)}$alkyl, —$(CH_2)_mC_{(3-6)}$cycloalkyl, wherein said —$(CH_2)_mC_{(3-6)}$cycloalkyl is optionally substituted with two fluorine atoms, —$CF_3$, —$CH_2CF_3$, or —OH, and wherein said —$C_{(2-5)}$alkyl is optionally substituted with —$SCF_3$, —$OCH_2CF_3$, cyclopropyl, and up to six fluorine atoms;
m is 0 or 1;
$A^2$ is H; or $A^1$ and $A^2$ are taken together with their attached nitrogen to form

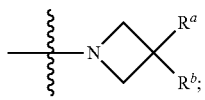

$R^a$ is —$OCHF_2$, —$CH_2CF_3$, —$CF_3$, or F;
$R^b$ is H or F;
and pharmaceutically acceptable salts thereof.

In another embodiment of the invention:
$R^1$ is —$CH_3$;
Q is $CHR^2$;
$R^2$ is —H or —OH;
$R^3$ is —H or —OH;
$R^4$ is —Cl or —$CH_3$;
$R^5$ is —$CH_2CH_3$;
$R^6$ is —$C_{(1-3)}$alkyl, —$OCHF_2$, or —$OCH_3$, wherein said —$C_{(1-3)}$alkyl is optionally substituted with up to three fluorine atoms;
$A^1$ is

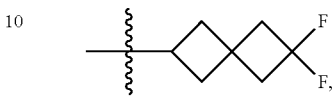

—$C_{(2-5)}$alkyl, —$(CH_2)_mC_{(3-6)}$cycloalkyl, wherein said —$(CH_2)_mC_{(3-6)}$cycloalkyl is optionally substituted with two fluorine atoms, —$CF_3$, or —$CH_2CF_3$, and wherein said —$C_{(2-5)}$alkyl is optionally substituted with —$SCF_3$, —$OCH_2CF_3$, cyclopropyl, and up to six fluorine atoms;
m is 0 or 1;
$A^2$ is H; or $A^1$ and $A^2$ are taken together with their attached nitrogen to form

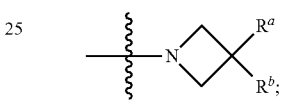

$R^a$ is —$OCHF_2$, —$CH_2CF_3$, —$CF_3$, or F;
$R^b$ is H or F;
and pharmaceutically acceptable salts thereof.

Another embodiment of the invention is a compound selected from the group consisting of:

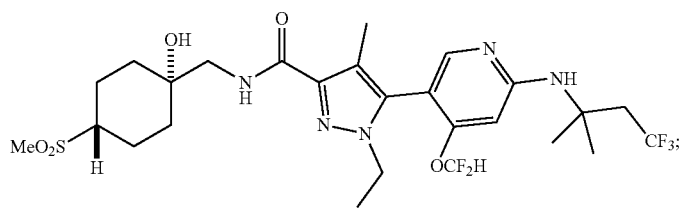

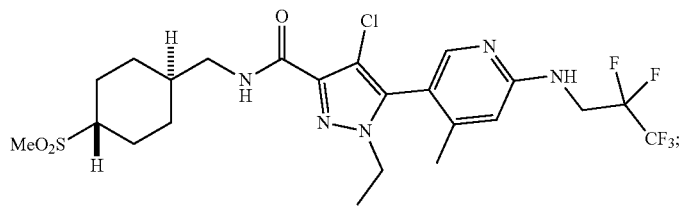

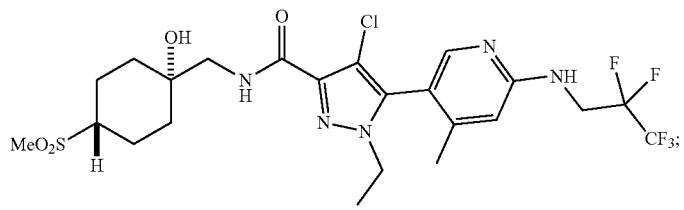

-continued
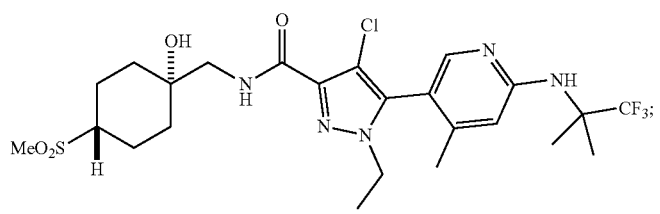
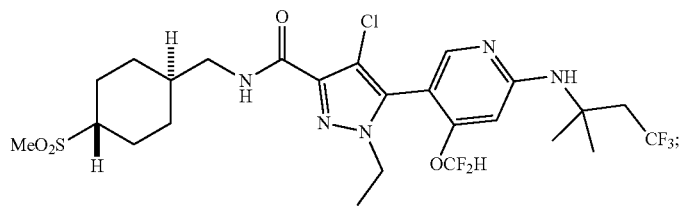
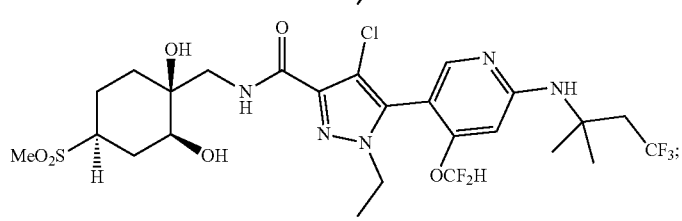
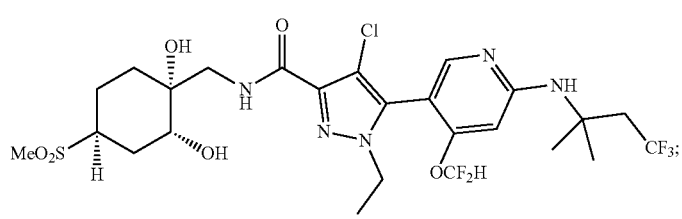
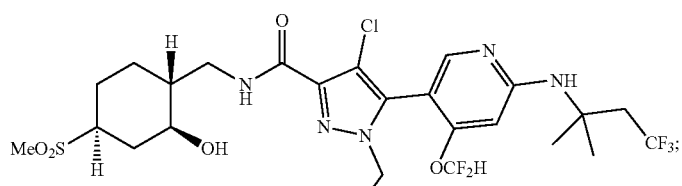
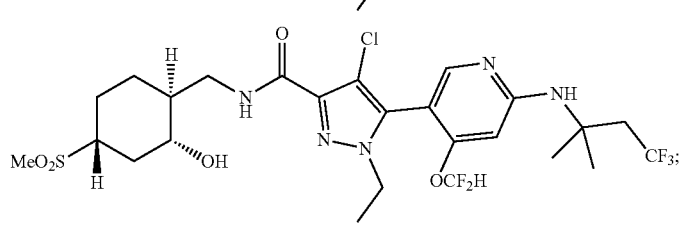
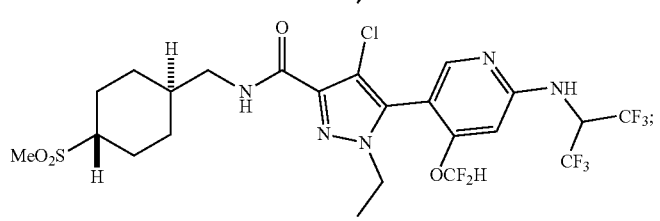
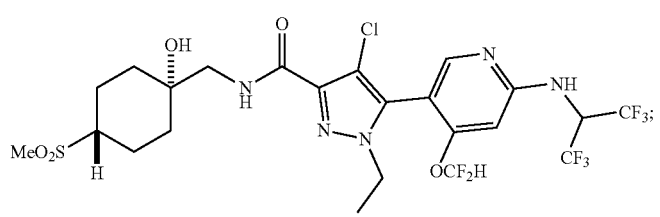

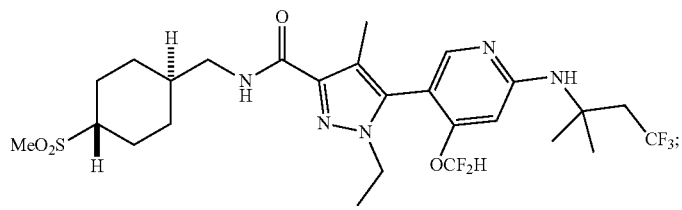
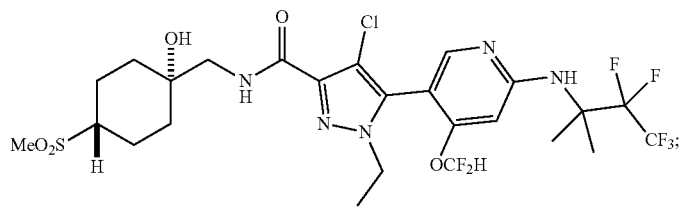
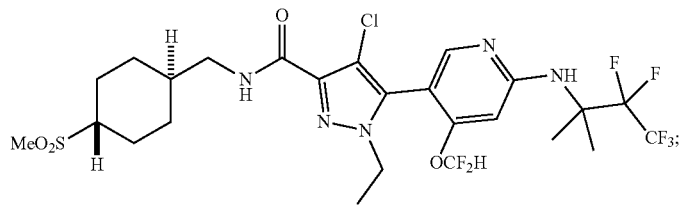
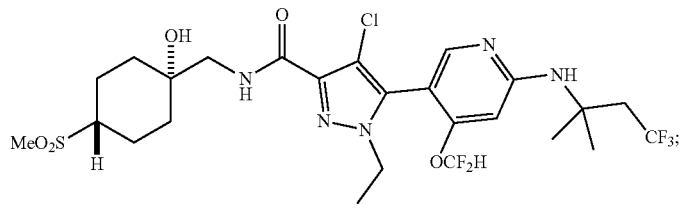
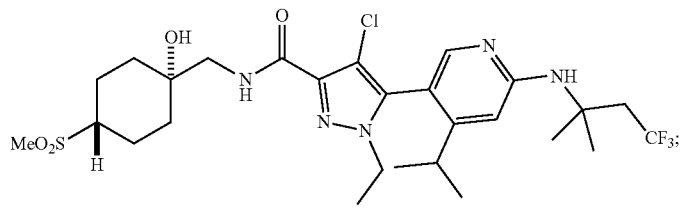
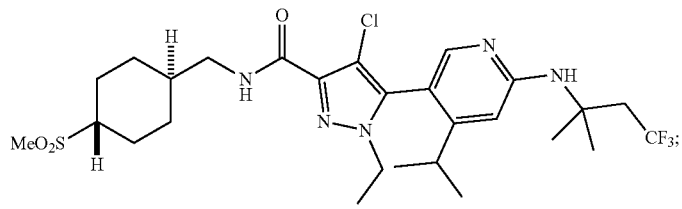
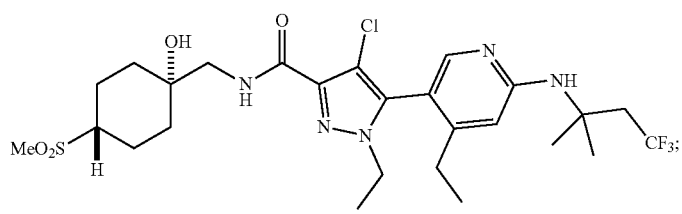
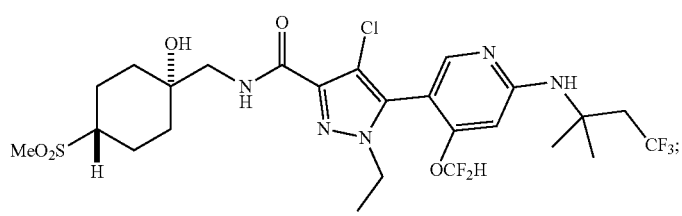

-continued
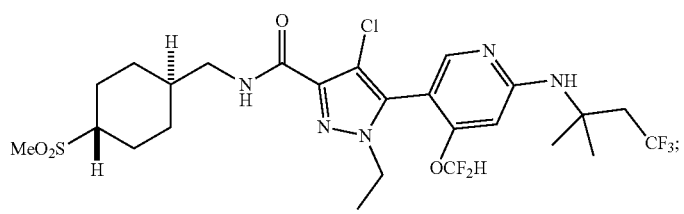
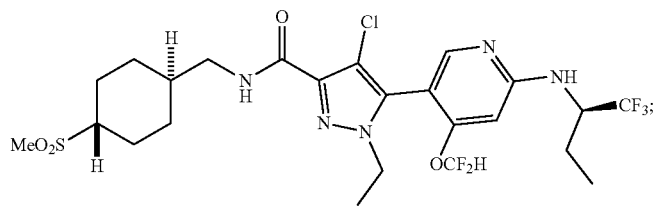
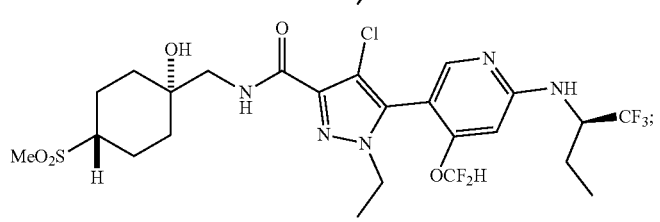
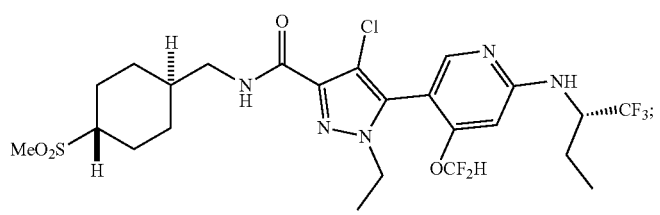
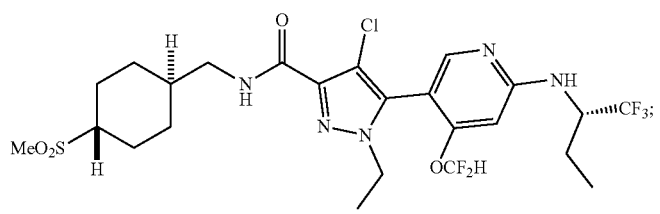
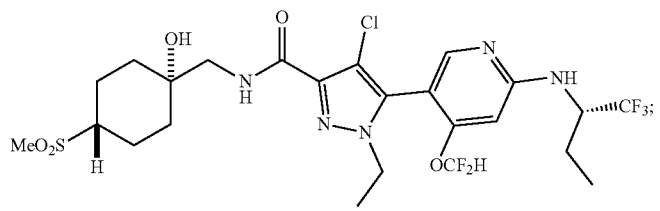
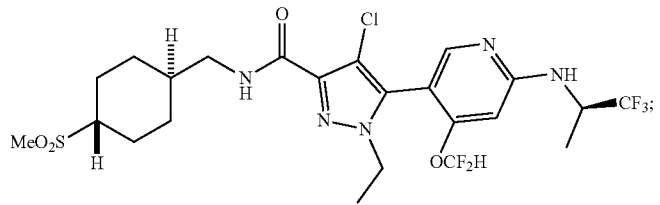
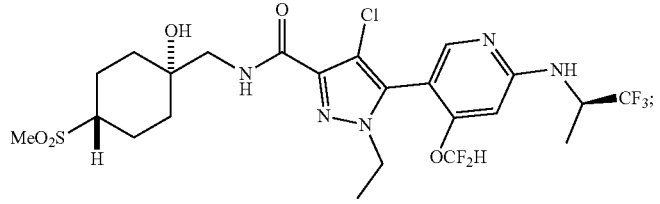

-continued
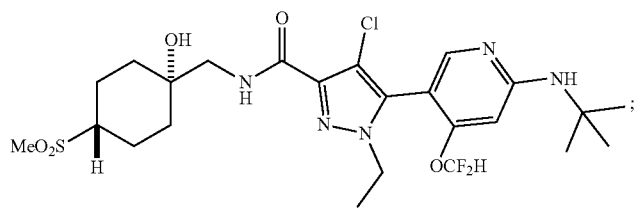
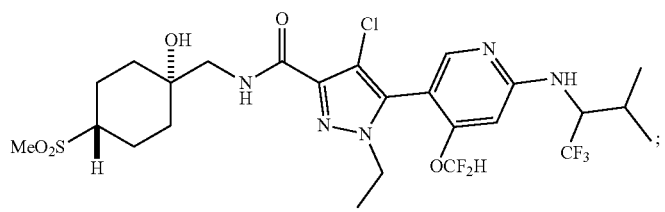
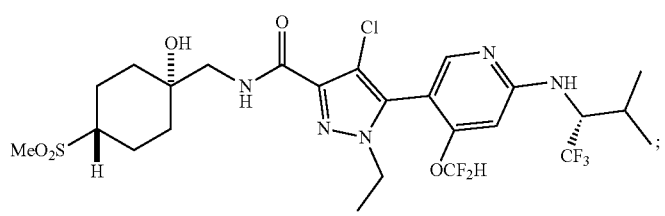
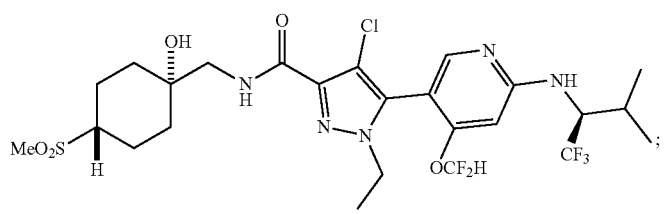
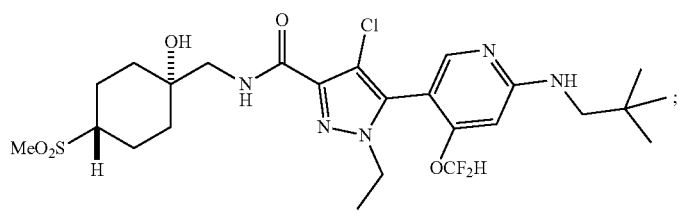
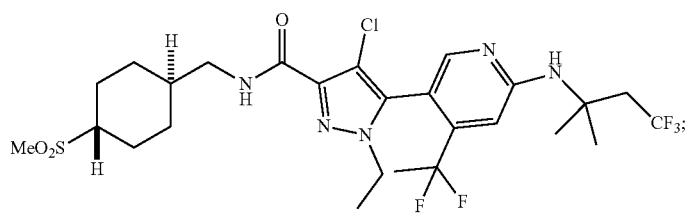
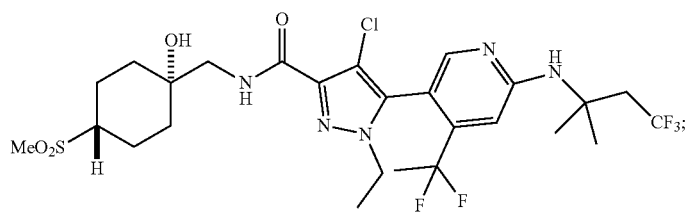
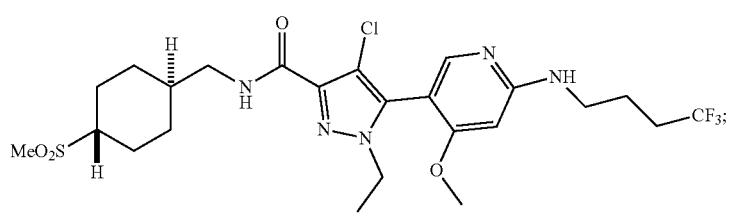

-continued
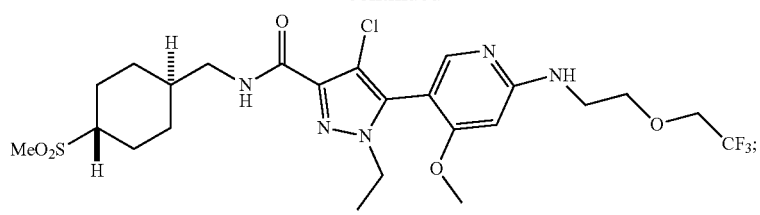
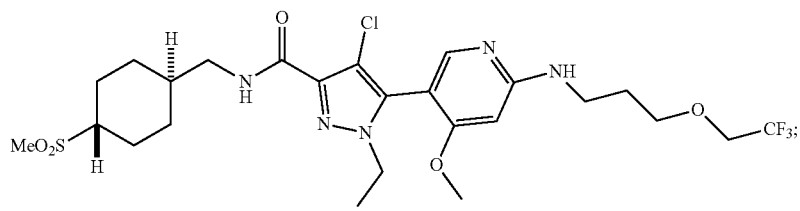
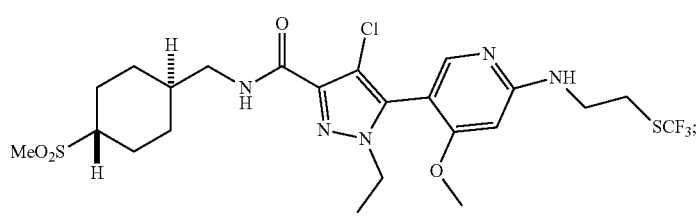
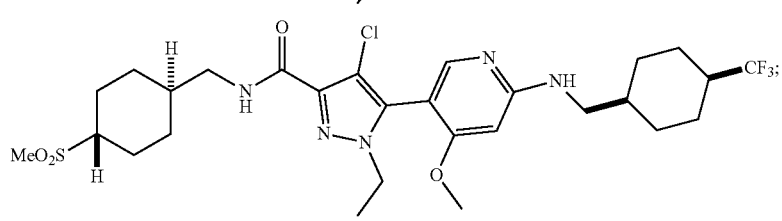
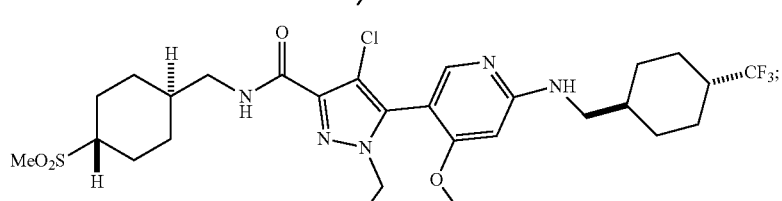
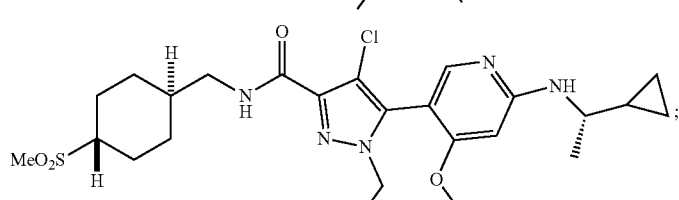
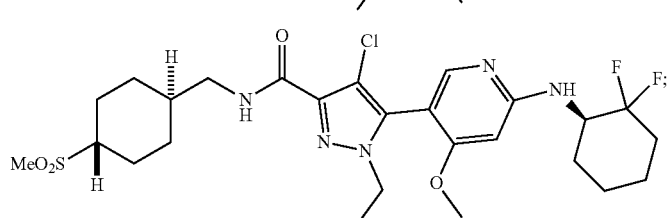
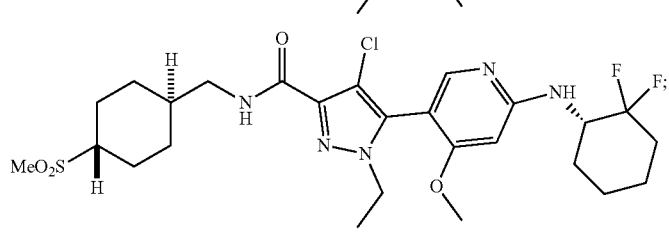

-continued
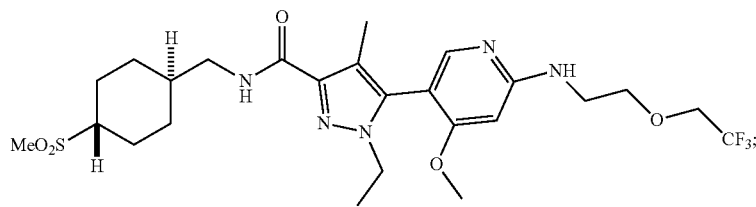
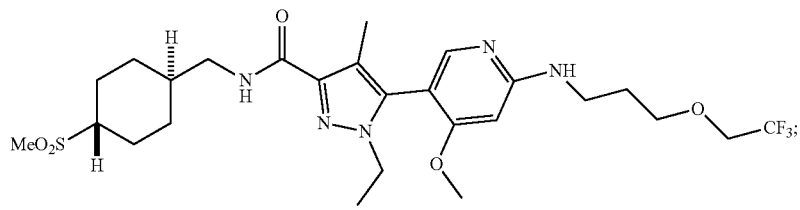
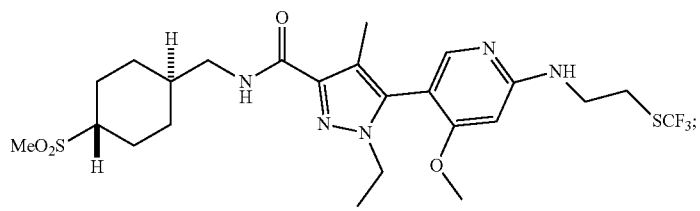
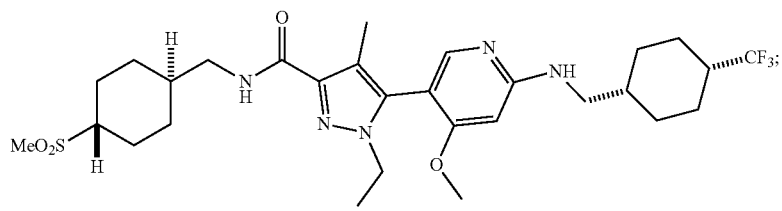
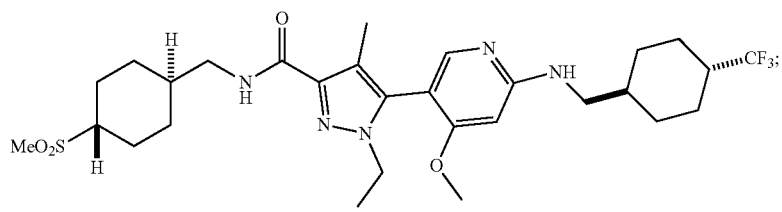
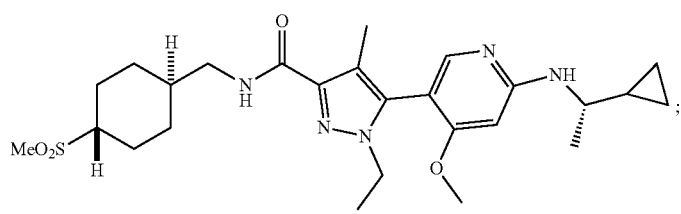
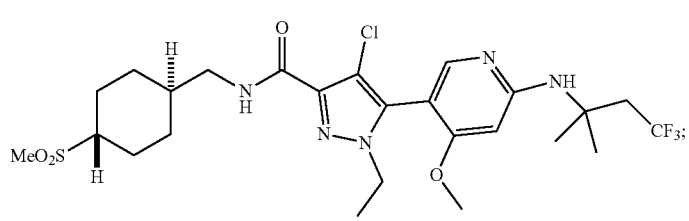
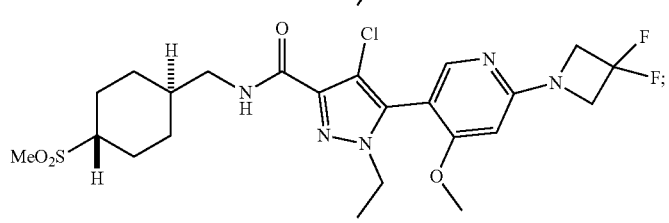

-continued
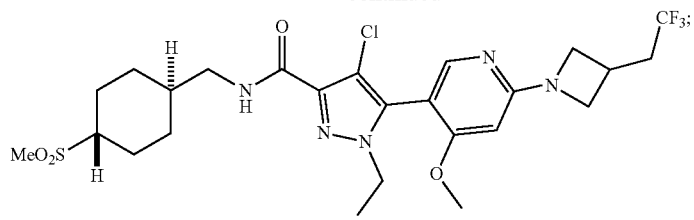
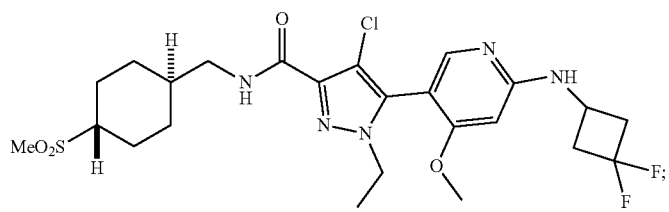
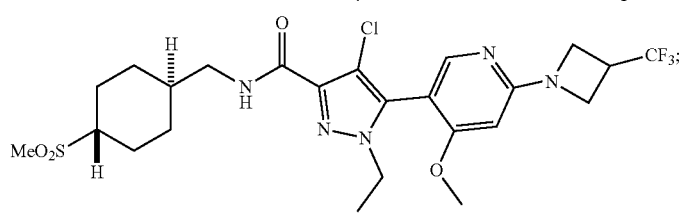
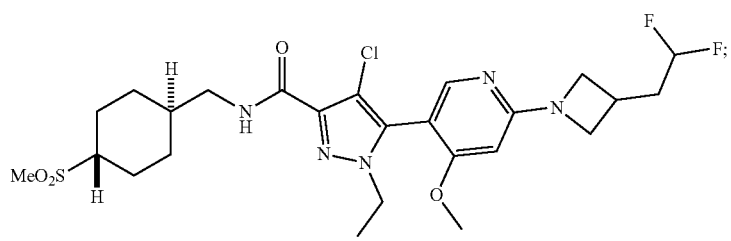
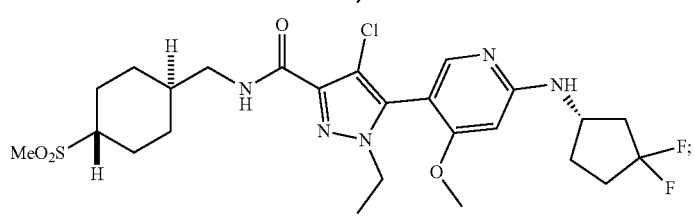
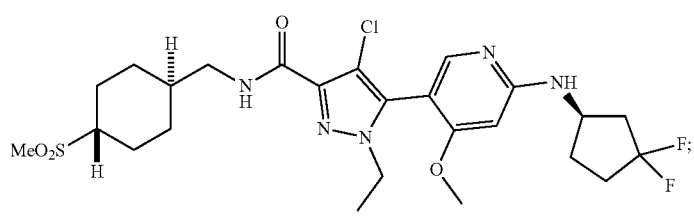
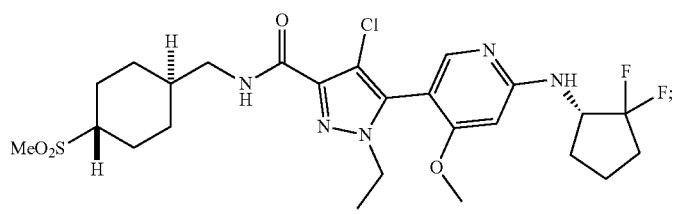
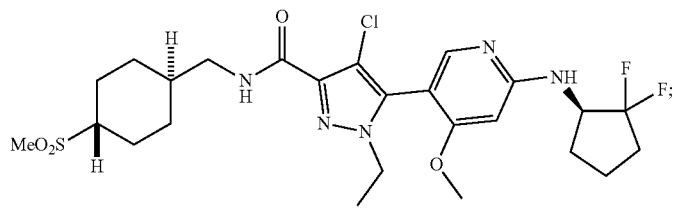

-continued
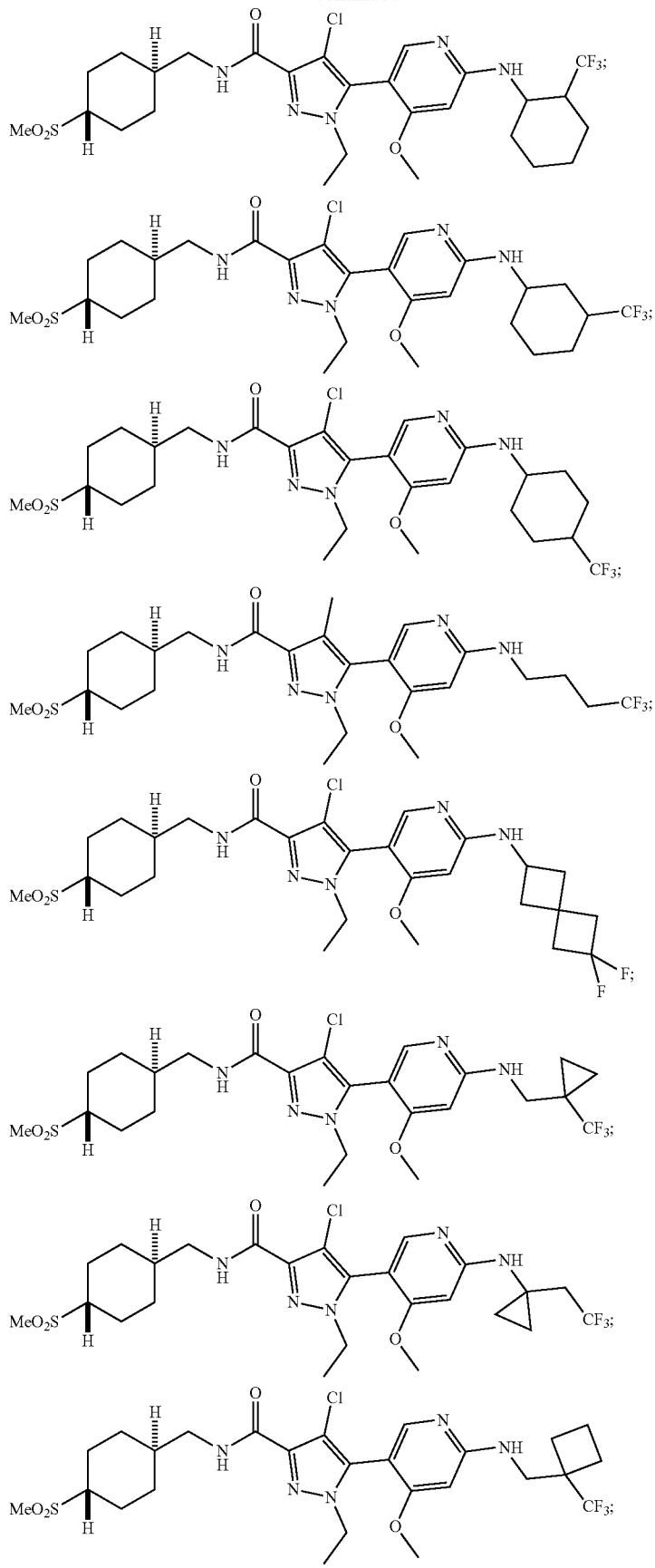

-continued
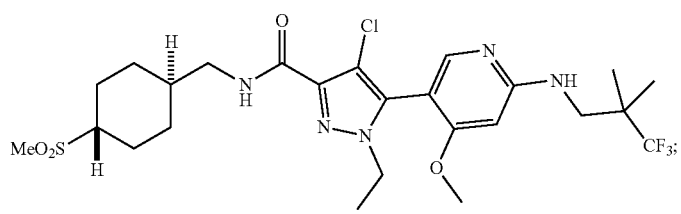
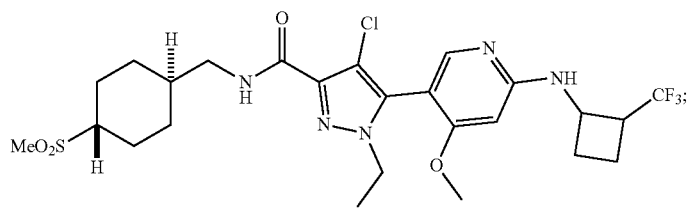
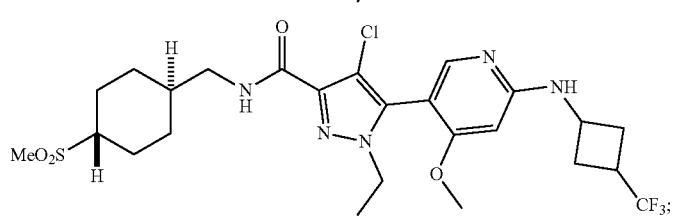
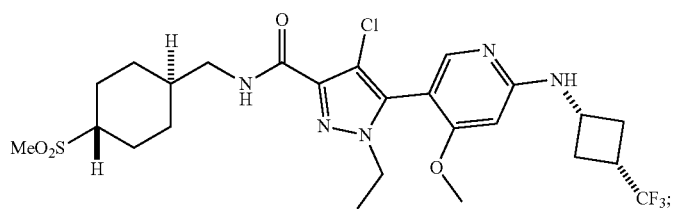
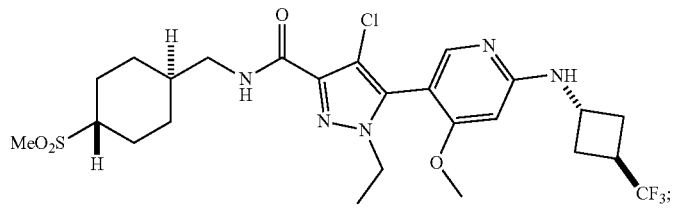
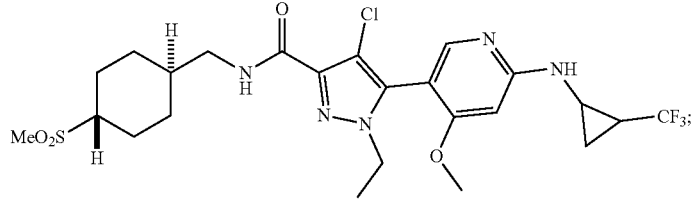
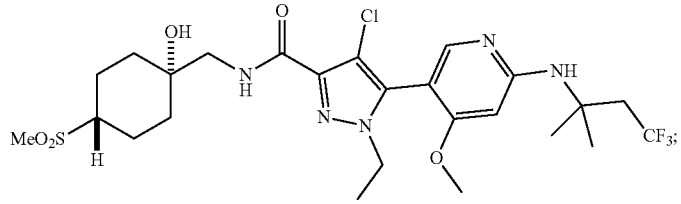
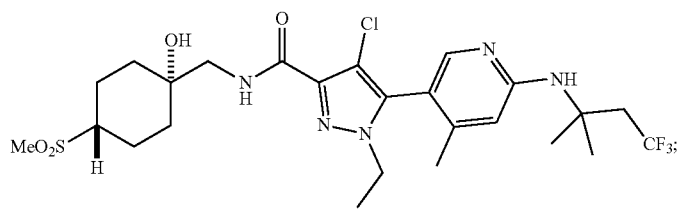

-continued
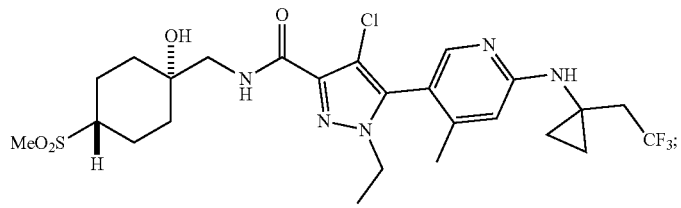
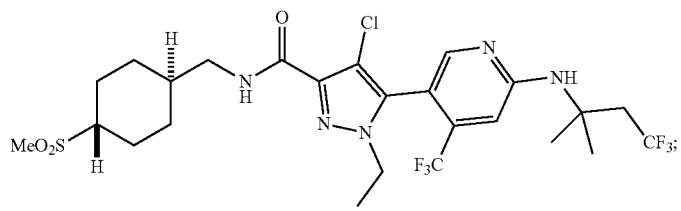
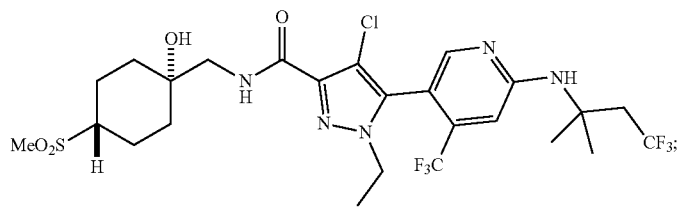
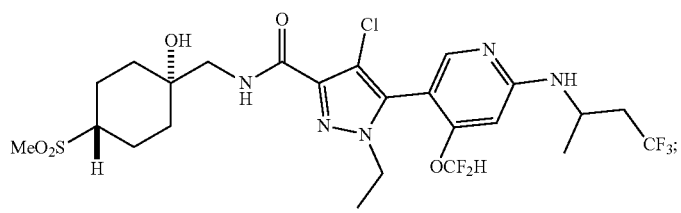
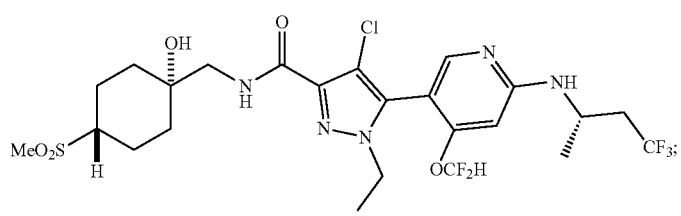
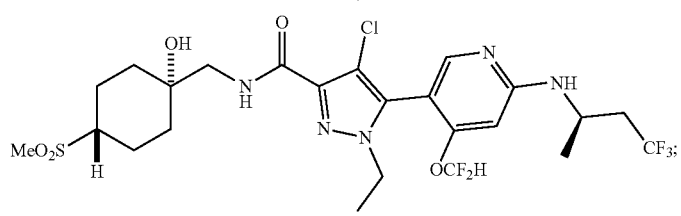
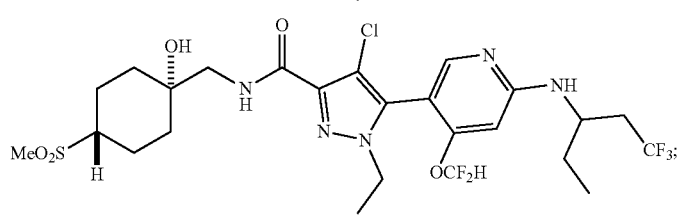
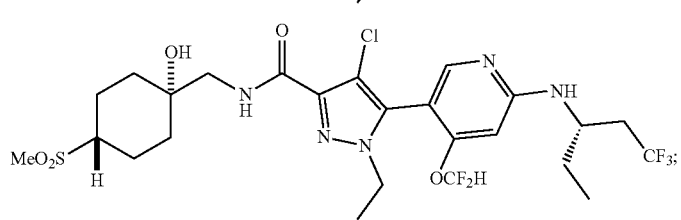

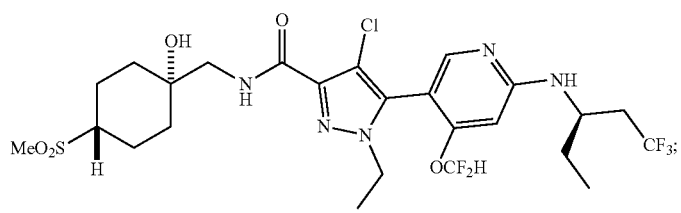
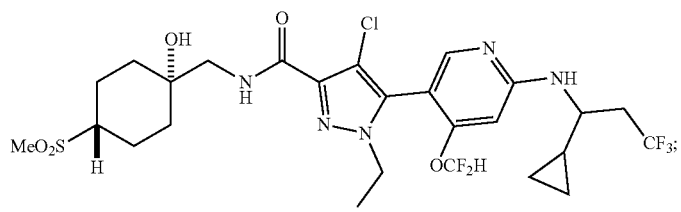
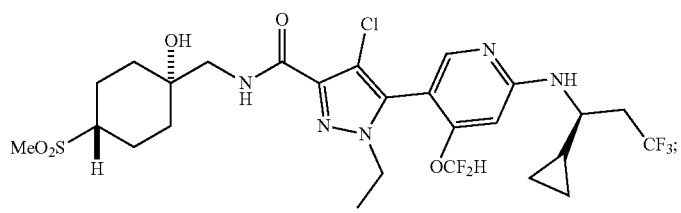
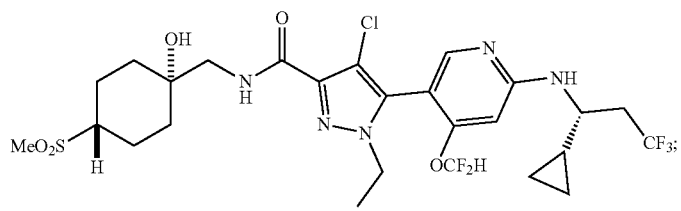
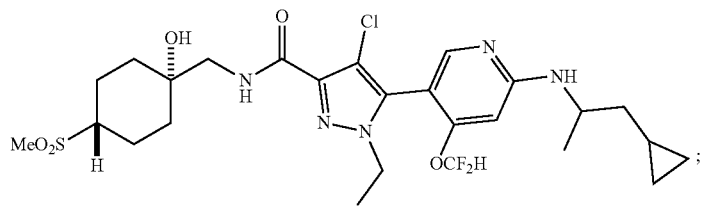
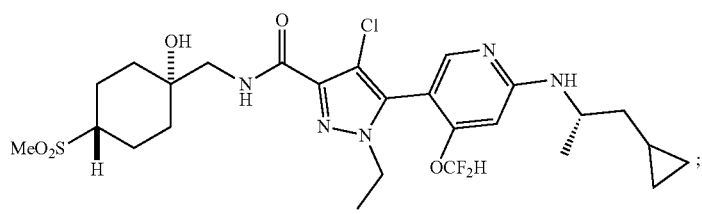
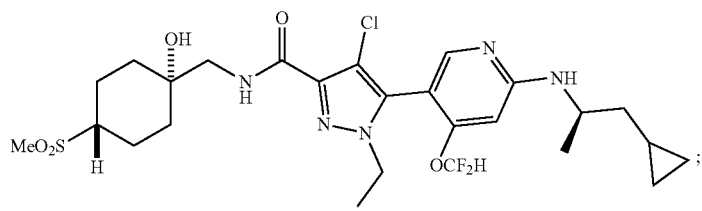
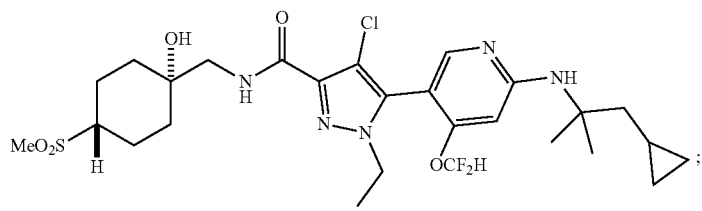

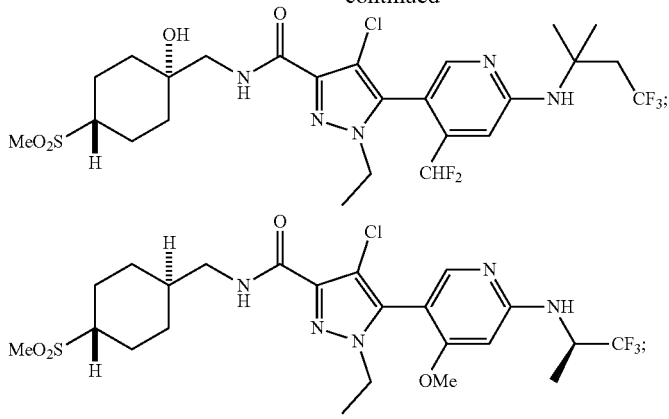

and pharmaceutically acceptable salts thereof.

Another embodiment of the invention comprises a compound of Formula I and a pharmaceutically acceptable carrier.

The present invention also provides a method for preventing, treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, cystic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphylococcia, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, carcinomas of the bladder, breast, cervix, colon, lung, prostate, or stomach, depression and metabolic syndrome comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: depression and metabolic syndrome.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, systemic lupus erythematosus, depression and metabolic syndrome comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: psoriatic arthritis and psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: depression and metabolic syndrome comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: psoriatic arthritis and psoriasis.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: depression and metabolic syndrome.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel disease, wherein said inflammatory bowel disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The present invention provides a method of treating or ameliorating a syndrome, disorder or disease, wherein said syndrome, disorder or disease is depression comprising administering to a subject in need thereof an effective amount of a compound of Formula I or a form, composition or medicament thereof.

The present invention provides a method of treating or ameliorating a syndrome, disorder or disease, wherein said syndrome, disorder or disease is metabolic syndrome comprising administering to a subject in need thereof an effective amount of a compound of Formula I or a form, composition or medicament thereof.

The invention also relates to methods of modulating RORγt activity in a mammal by administration of an effective amount of at least one compound of Formula I.

Another embodiment of the invention is a method of inhibiting production of interleukin-17, comprising administering to a subject in need thereof an effective amount of a compound of Formula I.

Definitions

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with abberant RORγt expression or RORγt overexpression, or a patient with an inflammatory condition that accompanies syndromes, disorders or diseases associated with abberant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. Radiolabelled compounds of Formula I may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereo center, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral column vial HPLC or SFC. In some instances rotamers of compounds may exist which are observable by $^1H$ NMR leading to complex multiplets and peak integration in the $^1H$ NMR spectrum.

Chiral centers, of which the absolute configurations are known, are labelled by prefixes R and S, assigned by the standard sequence-rule procedure, and preceded when necessary by the appropriate locants. Chiral centers, of which the relative but not the absolute configurations are known, are labelled arbitrarily by prefixes R* and S*, preceded when necessary by the appropriate locants. These prefixes are assigned by the standard sequence-rule procedure on the arbitrary assumption that the center of chirality with the lowest locant has chirality R. When a compound contains chiral centers with known absolute configurations and a sterically unrelated set of chiral centers with known relative configurations but unknown absolute configurations, then R* and S* are used to designate the latter. (*Pure & Appl. Chem.* 45, 1976, 11-30). Racemates containing a single chiral center are labelled RS or are not labelled. For racemates with more than one chiral center, the chiral center with the lowest locant is labelled RS and the others are labelled RS or SR according to whether they are R or S when the chiral center with the lowest locant is R. Pseudoasymmetric stereogenic centers are treated in the same way as chiral centers, but are given lower-case symbols, r or s (*Angew. Chem. Int. Ed. Engl.* 1982, 21, 567-583).

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

ABBREVIATIONS

Herein and throughout the application, the following abbreviations may be used.
Ac acetyl
9-BBN 9-borabicyclo[3.3.1]nonane
Boc tert-butyloxycarbonyl
br broad
BrettPhos 2-(dicyclohexylphosphino)3,6-dimethoxy-2',4',6'-triisopropyl-1,1'-biphenyl
BrettPhos G3 [(2-di-cyclohexylphosphino-3,6-dimethoxy-2',4',6'-triisopropyl-1,1'-biphenyl)-2-(2'-amino-1,1'-biphenyl)]palladium(II) methanesulfonate
Bu butyl
Cbz carboxybenzyl
δ NMR chemical shift in parts per million downfield from a standard
d doublet
DCE dichloroethane
DAST (diethylamino)sulfur trifluoride
DCM dichloromethane
Deoxo-Fluor® bis(2-methoxyethyl)aminosulfur trifluoride
DIPEA N,N-diisopropylethylamine (Hünig's base)
DMA N,N-dimethylacetamide
DMAP 4-(dimethylamino)pyridine
DME 1,2-dimethoxyethane
DMEN N,N-dimethylethylenediamine
DMF N,N-dimethylformamide
dppf 1,1'-bis(diphenylphosphino)ferrocene
dtbpf 1,1'-bis(di-tert-butylphosphino)ferrocene
EDCI 1-ethyl-3-(3-dimethylaminopropyl) carbodiimide hydrochloride
ESI electrospray ionization
Et ethyl
g grams(s)
h hour(s)
HATU O-(7-azabenzotriazol-1-yl)-N,N,N',N'-tetramethyluronium hexafluorophosphate
HOBt 1-hydroxybenzotriazole
HPLC high-performance liquid chromatography
Hz Hertz
i iso
IPA isopropanol
J coupling constant (NMR spectroscopy)
L liter(s)
LAH lithium aluminum hydride
LDA lithium diisopropylamide
m milli or multiplet
m/z mass-to-charge ratio
$M^+$ parent molecular ion
M molar (moles/liter) or mega
mCPBA 3-chloroperbenzoic acid
Me methyl
MeCN acetonitrile
min minute(s)
μ micro
MS mass spectrometry
MTBE tert-butyl methyl ether
n normal (chemical nomenclature prefix)
n nano
N normal (equivalent concentration)
NBS N-bromosuccinimide
NCS N-chlorosuccinimide
NMO 4-methylmorpholine N-oxide
NMR nuclear magnetic resonance
Pd/C palladium on carbon
Ph phenyl
Pr propyl
PyBroP® bromotripyrrolidinophosphonium hexafluorophosphate
q quartet
rt room temperature
RuPhos 2-dicyclohexylphosphino-2',6'-diisopropoxybiphenyl
RuPhos G1 chloro-(2-dicyclohexylphosphino-2',6'-diisopropoxy-1,1'-biphenyl)[2-(2-aminoethyl)phenyl]palladium(II)
s singlet
SFC supercritical fluid chromatography
t tert
t triplet
TEA triethylamine
TFA trifluoroacetic acid
THF tetrahydrofuran
TMS trimethylsilyl
TosMIC p-toluenesulfonylmethyl isocyanide
Ts p-toluenesulfonyl
T3P propanephosphonic acid anhydride
v/v volume-to-volume ratio
wt % weight percent
w/w weight-to-weigh ratio General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

Compounds of Formula I can be prepared according to Scheme 1. Aminopyridine pyrazole esters A-I can undergo hydrolysis using aqueous hydroxide solution in a cosolvent such as 1,4-dioxane or THF to give carboxylic acids A-II. Amides of Formula I can be formed by reaction of A-II with an amine or amine salt promoted by a reagent such as HATU or EDCI and a base such as DIPEA in a solvent such as DMF or MeCN. Amides of Formula I can also be formed by Pd-catalyzed amination reaction of chloropyridine pyrazole amides A-III with an amine or amine salt using RuPhos or BrettPhos palladacycle precatalyst, the corresponding RuPhos or BrettPhos ligand, and a base such as $Cs_2CO_3$ or NaOt-Bu in a solvent such as 1,4-dioxane. Alternatively, oxidation of pyridine pyrazole amides A-IV using an oxidant such as mCPBA in a solvent such as DCM, followed by reaction of the ensuing pyridine N-oxides, A-V, with an amine promoted by an activating agent such as tosic anhydride in a solvent such as $CHCl_3$ can give amides of Formula I. Amides of Formula I ($R^4$=Cl) can undergo Suzuki cross-coupling reaction with an organoboron reagent such as trimethylboroxine using a palladacycle precatalyst and ligand combination such as RuPhos G1/RuPhos and a carbonate base such as $K_2CO_3$ in a solvent such as 1,4-dioxane to give amides of Formula I ($R^4$=alkyl).

Scheme 1

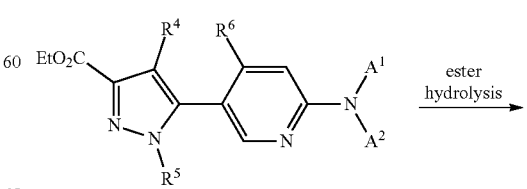

A-I

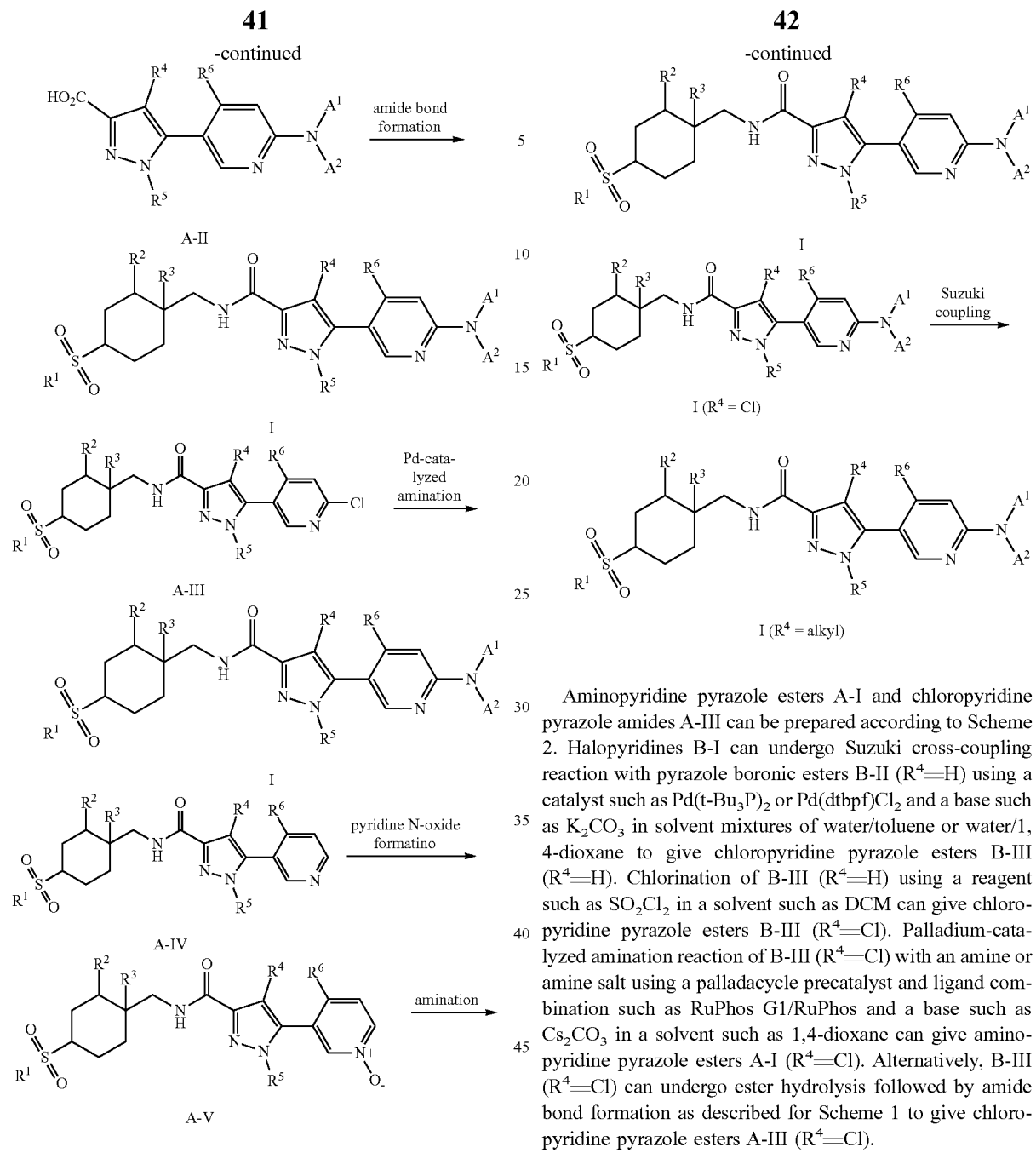

Aminopyridine pyrazole esters A-I and chloropyridine pyrazole amides A-III can be prepared according to Scheme 2. Halopyridines B-I can undergo Suzuki cross-coupling reaction with pyrazole boronic esters B-II ($R^4$=H) using a catalyst such as Pd(t-Bu$_3$P)$_2$ or Pd(dtbpf)Cl$_2$ and a base such as K$_2$CO$_3$ in solvent mixtures of water/toluene or water/1,4-dioxane to give chloropyridine pyrazole esters B-III ($R^4$=H). Chlorination of B-III ($R^4$=H) using a reagent such as SO$_2$Cl$_2$ in a solvent such as DCM can give chloropyridine pyrazole esters B-III ($R^4$=Cl). Palladium-catalyzed amination reaction of B-III ($R^4$=Cl) with an amine or amine salt using a palladacycle precatalyst and ligand combination such as RuPhos G1/RuPhos and a base such as Cs$_2$CO$_3$ in a solvent such as 1,4-dioxane can give aminopyridine pyrazole esters A-I ($R^4$=Cl). Alternatively, B-III ($R^4$=Cl) can undergo ester hydrolysis followed by amide bond formation as described for Scheme 1 to give chloropyridine pyrazole esters A-III ($R^4$=Cl).

Scheme 2

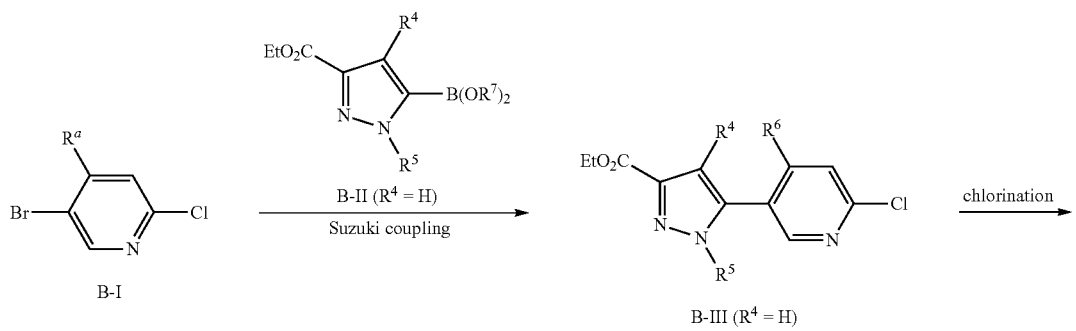

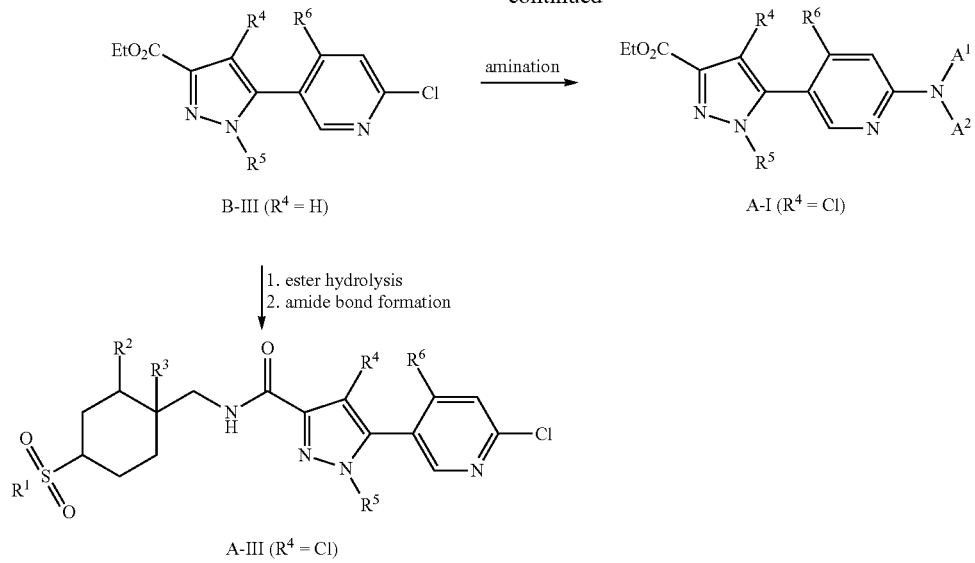

B-III (R$^4$ = H)

A-I (R$^4$ = Cl)

1. ester hydrolysis
2. amide bond formation

A-III (R$^4$ = Cl)

Aminopyridine pyrazole esters A-I and pyridine pyrazole amides A-IV (R$^4$=Cl) can be prepared according to Scheme 3. Bromopyridines C-I can undergo Suzuki cross-coupling reaction with pyrazole boronic acids or esters B-II (R$^4$=H) using a catalyst such as Pd(t-Bu$_3$P)$_2$ and a base such as LiOH or K$_2$CO$_3$ in a solvent such as DMF or 1,4-dioxane/water to give pyridine pyrazole esters C-II (R$^4$=H). Chlorination of C-II (R$^4$=H) using a reagent such as SO$_2$Cl$_2$ in a solvent such as DCM can give pyridine chloropyrazole esters C-II (R$^4$=Cl). Oxidation of C-II (R$^4$=Cl) using an oxidant such as mCPBA in a solvent such as DCM, followed by reaction of the ensuing pyridine N-oxides with an amine promoted by an activating agent such as tosic anhydride in a solvent such as α,α,α-trifluorotoluene can give aminopyridine pyrazole esters A-I (R$^4$=Cl). Suzuki cross-coupling reaction of A-I (R$^4$=Cl) with an organoboron reagent such as trimethylboroxine using a palladacycle precatalyst and ligand combination such as RuPhos G1/RuPhos and a carbonate base such as K$_2$CO$_3$ in a solvent such as 1,4-dioxane can give aminopyridine pyrazole esters A-I (R$^4$=alkyl). Alternatively, C-II (R$^4$=Cl) can undergo ester hydrolysis followed by amide bond formation as described for Scheme 1 to give pyridine pyrazole esters A-IV (R$^4$=Cl).

Scheme 3

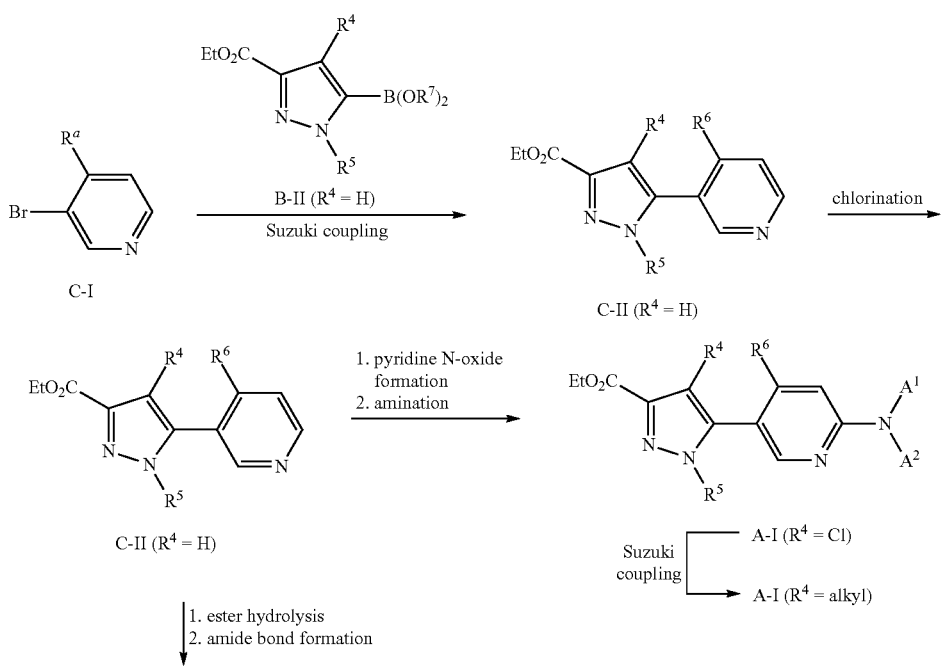

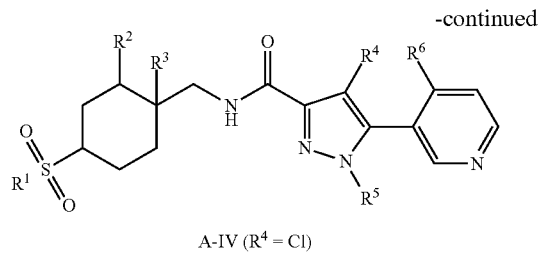

A-IV (R⁴ = Cl)

An alternative preparation of chloropyridine pyrazole esters B-III (R⁴=H) is described in Scheme 4. Crossed-Claisen condensation reaction between acetophenones (D-I) and diethyl oxalate, followed by condensation of the resulting ethyl dioxobutanoates with an alkylhydrazine can give B-III (R⁴=H).

Pyrazole boronic acids and esters B-II (R⁴=H) can be prepared as described in Scheme 5. Alkylation of pyrazole esters E-1 with an iodoalkane using a base such as $K_2CO_3$ in a solvent such as THF can give N-alkylpyrazole esters E-II. Iridium-catalyzed C—H borylation of E-II using pinacolborane, a catalyst such as (1,5-cyclooctadiene)(methoxy)iridium(I) dimer, and a ligand such as 1,10-phenanthroline in a solvent mixture such as pentane/THF can give pyrazole pinacol boronates B-II (R⁴=H, (OR⁷)₂=pinacoloto). These boronic esters can undergo conversion to the corresponding potassium trifluoroborates by treatment with aqueous $KHF_2$ in a solvent such as MeOH. Subsequent hydrolysis of the potassium trifluoroborate using TMSCl and water in a solvent such as MeCN can give boronic acids B-II (R⁴=R⁷=H).

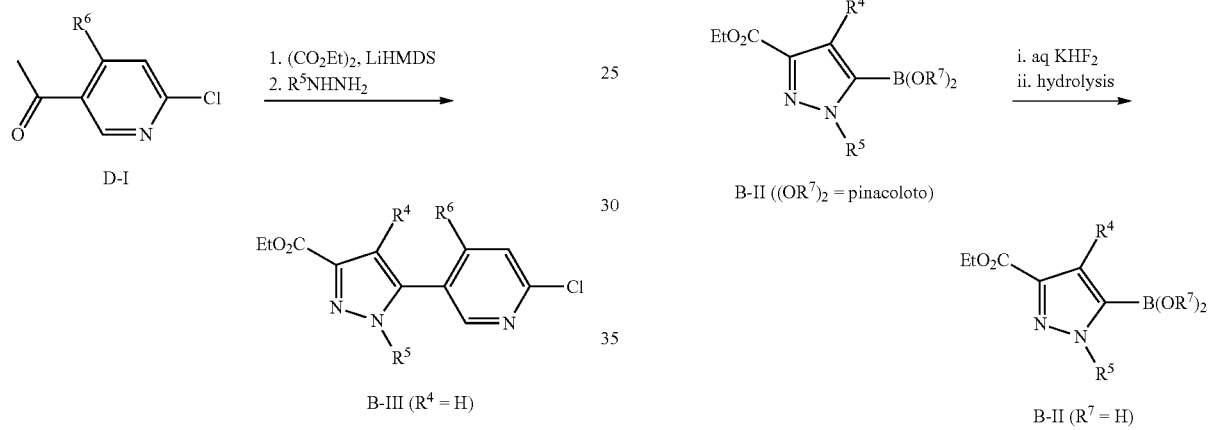

Acetophenones D-I can be prepared as described in Scheme 6. Hydrolysis of chloropyridine esters F-I using aqueous NaOH in a cosolvent such as 1,4-dioxane, followed by conversion of the resulting carboxylic acids to the corresponding Weinreb amides using N,O-dimethylhydroxylamine hydrochloride and a combination of reagents such as EDCl, HOBt, and TEA in a solvent such as MeCN can give Weinreb amides F-II. Grignard addition reaction between MeMgBr and F-II in a solvent such as THF can give acetophenones D-1. Alternatively, Stille cross-coupling reaction between halopyridines B-I and tributyl(1-ethoxyvinyl)stannane using a catalyst such as Pd(PPh₃)₄ in a solvent such as toluene can give vinyl ethers F-III Hydrolysis of these vinyl ethers using an aqueous acid such as HCl can give acetophenones D-1.

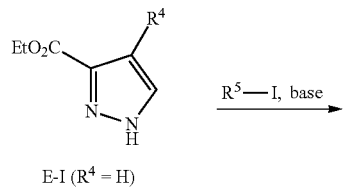

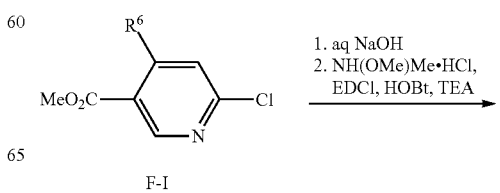

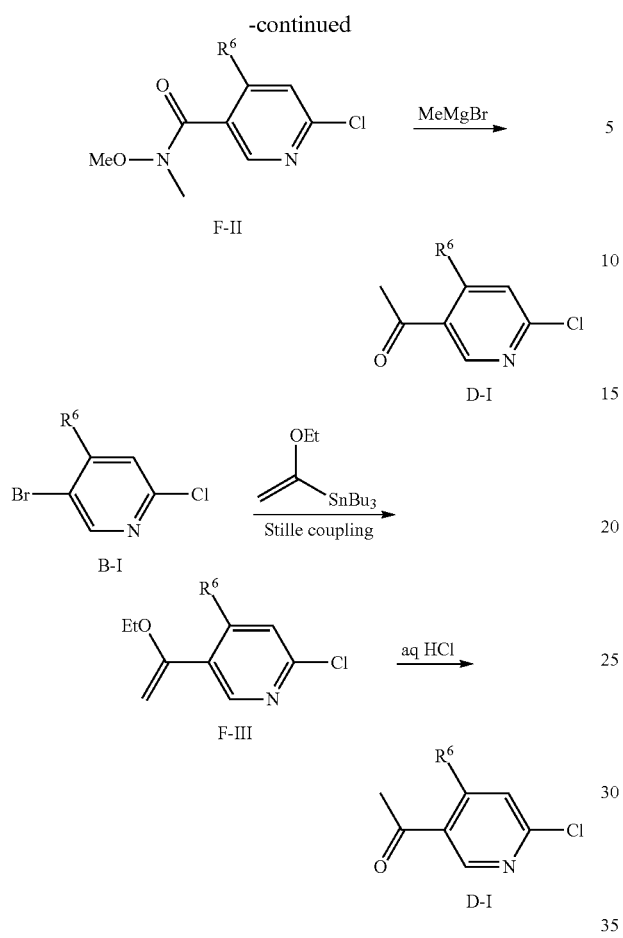

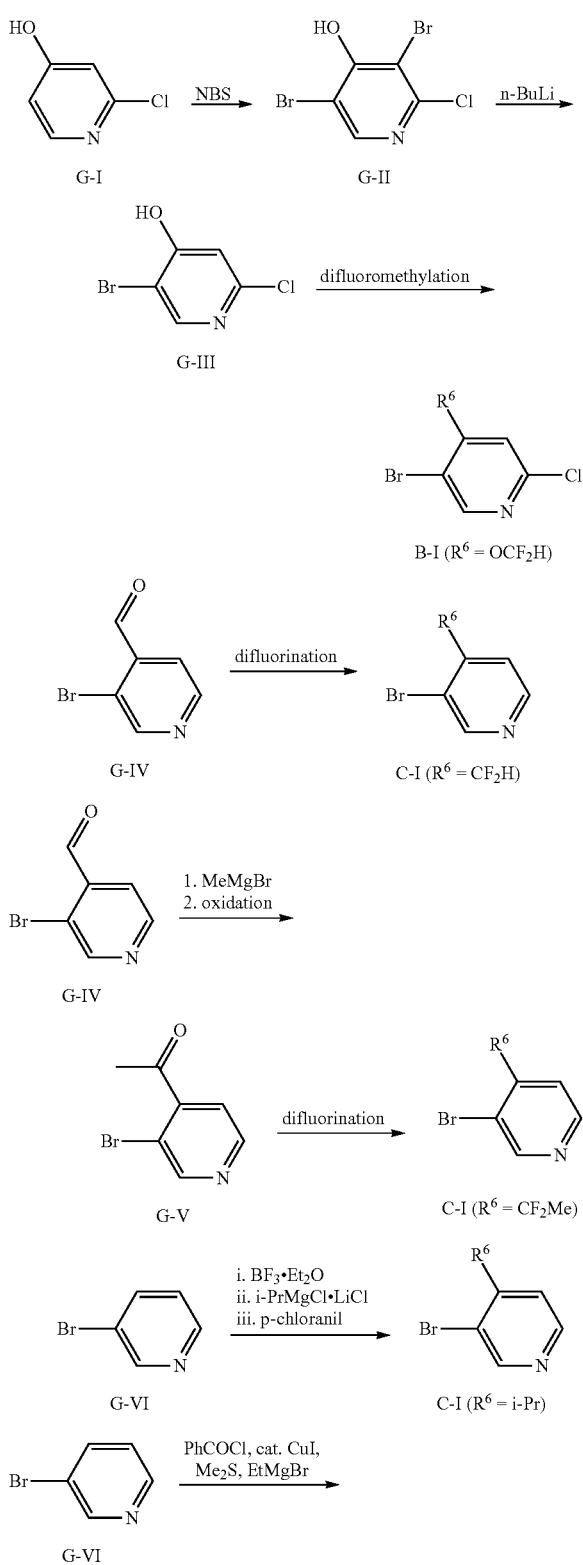

such as sodium chlorodifluoroacetate and a base such as Cs$_2$CO$_3$ in a solvent such as DMF can give 3-bromo-4-(difluoromethoxy)pyridine (C-I, R$^6$=OCF$_2$H).

Halopyridines B-I and C—I can be purchased from commercial suppliers or prepared as described in Scheme 7. Bromination of 2-chloropyridin-4-ol (G-I) using a reagent such as NBS in a solvent such as AcOH can give 3,5-dibromo-2-chloropyridin-4-ol (G-II). Lithium-halogen exchange reaction between GII and n-BuLi in a solvent such as THF, followed by protodemetalation using a proton source such as water can give 5-bromo-2-chloropyridin-4-ol (G-III). Difluoromethylation of G-III using a reagent such as sodium chlorodifluoroacetate and a base such as Cs$_2$CO$_3$ in a solvent such as DMF can give 5-bromo-2-chloro-4-(difluoromethoxy)pyridine (B-I, R$^6$=OCF$_2$H). Difluorination of 3-bromoisonicotinaldehyde (G-IV) using a reagent such as Deoxo-Fluor® in a solvent such as DCM can give 3-bromo-4-(difluoromethyl)pyridine (C-I, R$^6$=CF$_2$H). Grignard addition reaction between MeMgBr and G-IV in a solvent such as THF, followed by oxidation of the resulting alcohol using MnO$_2$ in a solvent such as toluene can give 1-(3-bromopyridin-4-yl)ethan-1-one (G-V). Difluorination of G-V using a reagent such as DAST in a solvent such as DCM can give 3-bromo-4-(difluoromethyl)pyridine (C-I, R$^6$=CF$_2$Me). Sequential treatment of 3-bromopyridine (G-VI) with BF$_3$.Et$_2$O, i-PrMgCl.LiCl, and then p-chloranil in a solvent such as THF can give 3-bromo-4-isopropylpyridine (C-I, R$^6$=i-Pr). If instead G-VI is treated with phenyl chloroformate, dimethylsulfide, ethylmagnesium bromide, and a catalytic quantity of CuI in a solvent such as THF, it can be transformed to dihydropyridine G-VII. This intermediate can be oxidized with a reagent such as o-chloranil to give 3-bromo-4-ethylpyridine (C-I, R$^6$=Et). Difluoromethylation of 3-bromopyridin-4-ol (G-VIII) using a reagent

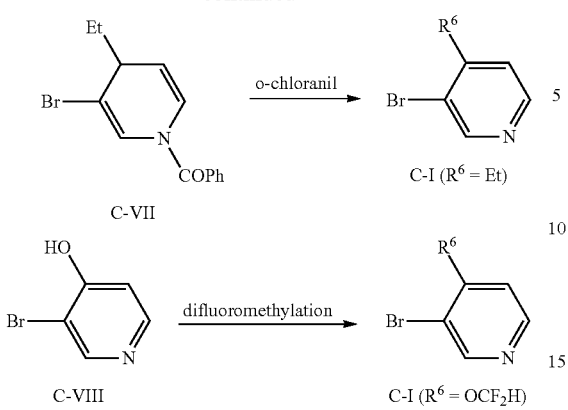

(1s,4s)-1-(Aminomethyl)-4-(methyl sulfonyl)cyclohexan-1-ol hydrochloride ((s,s)-H-VI) can be prepared according to Scheme 8. Reduction of 1,4-dioxaspiro[4.5]decan-8-one (H-I) with a reagent such as NaBH$_4$, followed by mesylation of the resulting secondary alcohol can give cyclohexane mesylate H-II. Reaction of H-II with sodium thiomethoxide in a polar aprotic solvent, followed by hydrolytic cleavage of the 1,3-dioxolane group promoted by an aqueous acid such as HCl can give cyclohexanone sulfide H-III Oxidation of the sulfide with a reagent such as mCPBA can give cyclohexanone sulfone H-IV. Cyanosilylation of H-IV using TMSCN and TEA can give nitrile H-V. Reduction of H-V with borane, followed by quenching with HCl can give a diastereomeric mixture of amino alcohol HCl salts, H-VI. Equilibration of the isomeric mixture can be promoted by heating with an alkoxide base, such as t-BuONa, in THF/t-BuOH to enrich the mixture in the s,s isomer. Once the thermodynamic ratio is reached, the mixture can undergo reaction with Boc$_2$O, and the resulting product can be triturated with EtOAc/n-heptane to provide the stereochemically pure hydroxy carbamate (s,s)-H-VII. Removal of the Boc group under acidic conditions, such as ethanolic HCl, can give amine salt (s,s)-H-VI.

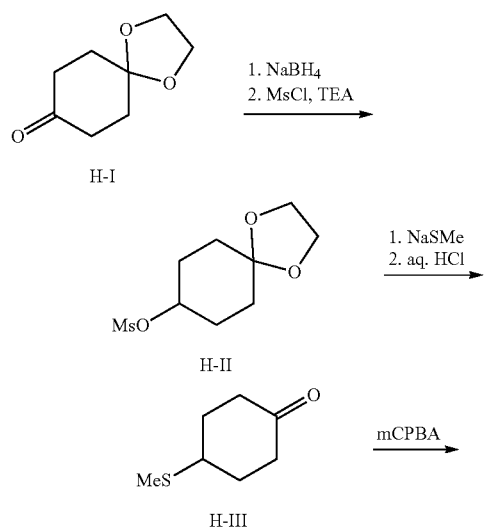

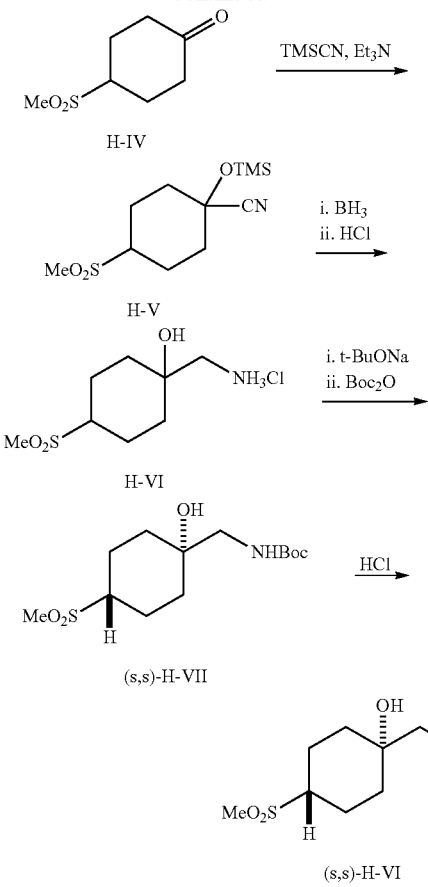

((1r,4r)-4-(Methylsulfonyl)cyclohexyl)methanamine hydrochloride (trans-I-III.HCl) can be prepared according to Scheme 9. Reductive cyanation of cyclohexanone sulfide H-III using TosMIC with an alkoxide base, such as t-BuONa, in an ethereal solvent can give cyanocyclohexane sulfide I-I. Oxidation of I-I with a reagent system such as Oxone® in acetone/water can give cyanocyclohexane sulfone I-II. Reduction of I-II with LAH in an ethereal solvent can give amine I-III as a mixture of cis and trans isomers. The corresponding Boc carbamate intermediate, I-IV, can be prepared if I-III is not isolated, but instead Boc$_2$O is added to the solution generated after quenching and filtering the LAH reduction reaction mixture. Isolation of I-IV followed by sequential triturations using IPA/n-heptanes and then EtOAc/n-heptanes can provide stereochemically pure trans-I-IV. Removal of the Boc group under acidic conditions, such as ethanolic HCl, can give amine salt trans-I-III.HCl.

Scheme 9

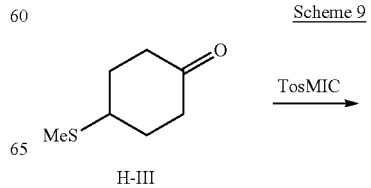

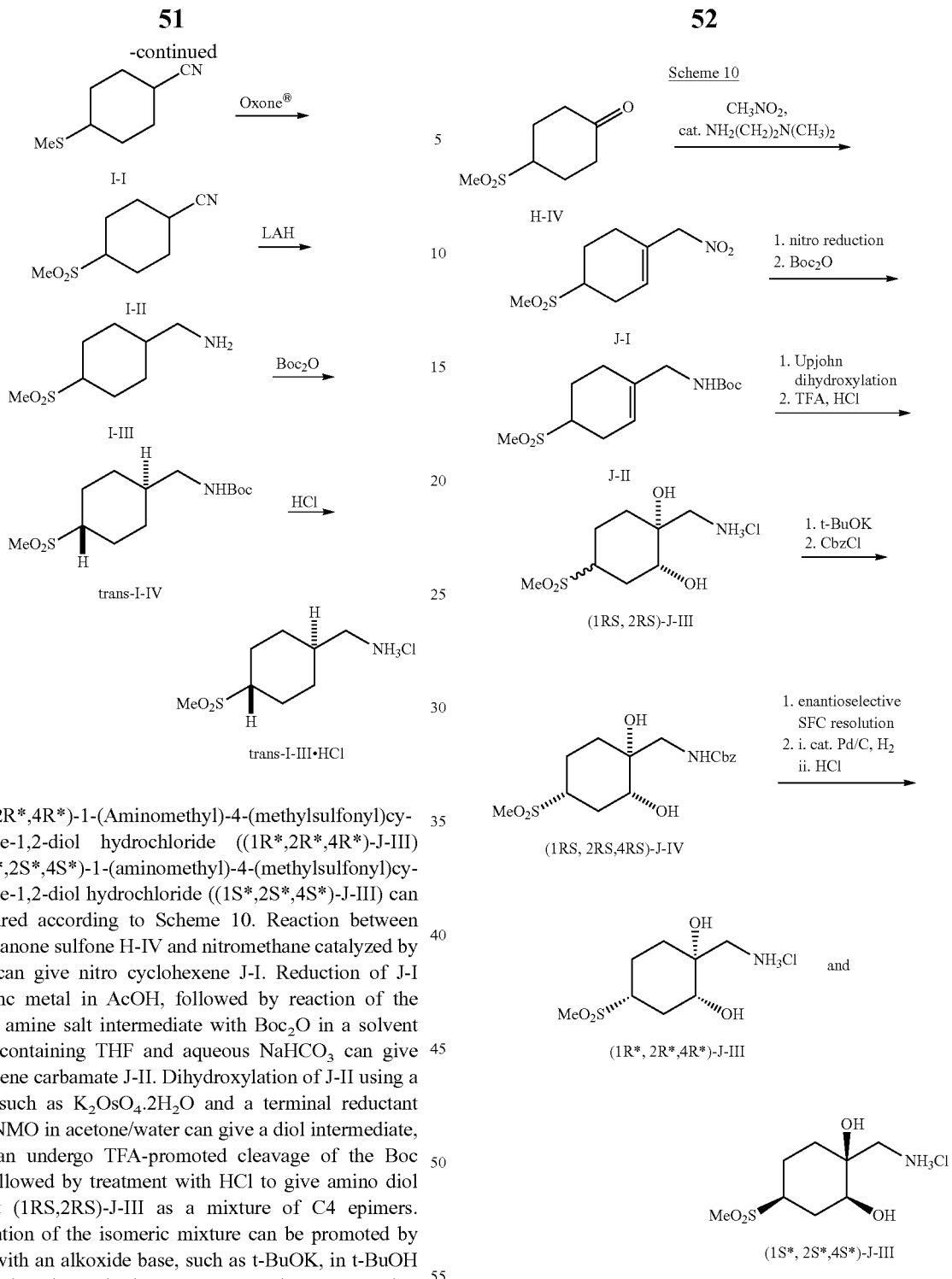

(1R*,2R*,4R*)-1-(Aminomethyl)-4-(methylsulfonyl)cyclohexane-1,2-diol hydrochloride ((1R*,2R*,4R*)-J-III) and (1S*,2S*,4S*)-1-(aminomethyl)-4-(methylsulfonyl)cyclohexane-1,2-diol hydrochloride ((1S*,2S*,4S*)-J-III) can be prepared according to Scheme 10. Reaction between cyclohexanone sulfone H-IV and nitromethane catalyzed by DMEN can give nitro cyclohexene J-I. Reduction of J-I using zinc metal in AcOH, followed by reaction of the resulting amine salt intermediate with $Boc_2O$ in a solvent mixture containing THF and aqueous $NaHCO_3$ can give cyclohexene carbamate J-II. Dihydroxylation of J-II using a catalyst such as $K_2OsO_4 \cdot 2H_2O$ and a terminal reductant such as NMO in acetone/water can give a diol intermediate, which can undergo TFA-promoted cleavage of the Boc group followed by treatment with HCl to give amino diol HCl salt (1RS,2RS)-J-III as a mixture of C4 epimers. Equilibration of the isomeric mixture can be promoted by heating with an alkoxide base, such as t-BuOK, in t-BuOH to enrich the mixture in the 1RS,2RS,4RS isomer. Reaction of this equilibrated mixture with CbzCl in aqueous $NaHCO_3$ solution, followed by trituration of the product with EtOAc/hexanes can give carbamate (1RS,2RS,4RS)-J-IV as a single diastereomer. Resolution of (1RS,2RS,4RS)-J-IV by SFC using a chiral stationary phase can give (1R*,2R*,4R*)-J-IV and (1S*,2S*,4S*)-J-IV in stereochemically pure form. Hydrogenolysis of the Cbz carbamates with hydrogen gas using a catalyst such as Pd/C, followed by treatment of the resulting amines with HCl can give amino diol salts (1R*,2R*,4R*)-J-III and (1S*,2S*,4S*)-J-III.

(1RS,2SR,5RS)-2-(Aminomethyl)-5-(methylsulfonyl)cyclohexan-1-ol hydrochloride ((1RS,2SR,5RS)-K-II) can be prepared according to Scheme 11. Sequential hydroboration and oxidation of cyclohexene carbamate J-II in THF using first $BH_3 \cdot THF$ and then aqueous hydrogen peroxide and sodium hydroxide can give secondary alcohol (1RS,2SR)-K-I as a mixture of C4 epimers. Chromatographic separation of the epimers can give (1RS,2SR,4SR)-K-I. Treatment of (1RS,2SR,4SR)-K-I with TFA and HCl can give amino alcohol salt (1RS,2SR,5RS)-K-II.

Scheme 11

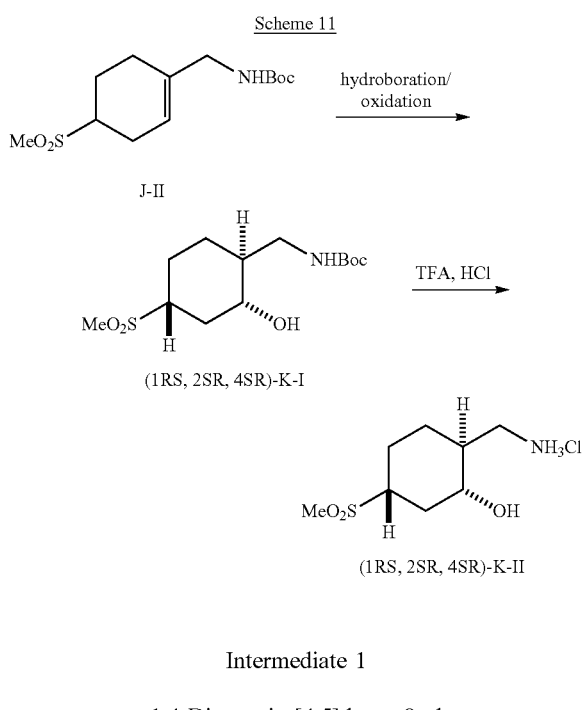

Intermediate 1

1,4-Dioxaspiro[4.5]decan-8-ol

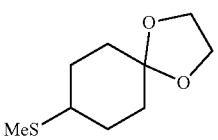 [SMILES: CSC1CCC2(CC1)OCCO2]

Sodium borohydride (83.4 g, 2.21 mol) was added in portions over 2 h to a stirring 0-5° C. solution of 1,4-dioxaspiro[4.5]decan-8-one (1150 g, 7.372 mol) and MeOH (7.0 L) at a rate that maintained the internal temperature below 5° C. After the reaction went to completion, water was added, and the mixture was concentrated. The residue was then diluted with DCM and water, the layers were separated, and the aqueous layer was extracted twice with DCM. The organic layers were combined, washed with brine, dried with anhydrous $Na_2SO_4$, filtered, and then concentrated to afford the title compound as a colorless liquid (65.9% w/w).

Intermediate 2

1,4-Dioxaspiro[4.5]decan-8-yl Methanesulfonate

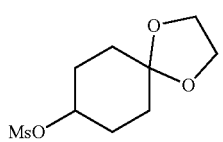

Methanesulfonyl chloride (1000 g, 8.790 mol) was added dropwise to a stirring solution of 1,4-dioxaspiro[4.5]decan-8-ol (1722 g, 65.9% w/w, 7.17 mol, Intermediate 1) and TEA (2178 g, 21.52 mol) in DCM (10 L) at a rate that maintained the internal temperature between 10 and 20° C. After the reaction went to completion, it was combined with another mixture prepared in a similar way. The combined mixture was washed with water and then concentrated. The residue was slurried in n-heptane and EtOH (10:1 v/v) at rt, and the suspension was filtered. The filter cake was dried under vacuum to afford the title compound as a yellow solid.

Intermediate 3

8-(Methylthio)-1,4-dioxaspiro[4.5]decane

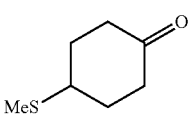

Sodium thiomethoxide (249 g, 3.56 mol) was added in five portions to a stirring 0-5° C. solution of 1,4-dioxaspiro[4.5]decan-8-yl methanesulfonate (800 g, 3.39 mol, Intermediate 2) in DMF (4.8 L), and the reaction mixture was allowed to warm to 15-20° C. over 24 h. An additional portion of NaSMe (23.7 g, 0.339 mol) was then added, and stirring was continued until the reaction went to completion. Water and MTBE were then added, and the layers were separated. The organic layer was washed three times with water, concentrated, and then dried under vacuum to afford the title compound as a yellow oil.

Intermediate 4

4-(Methylthio)cyclohexan-1-one

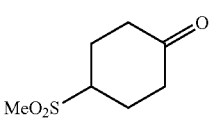

A mixture of 8-(methylthio)-1,4-dioxaspiro[4.5]decane (680 g, 3.61 mol, Intermediate 3), 1-PrOAc (6.8 L), and 3 N aqueous HCl (680 mL) was stirred at 20-25° C. for 30 min. After this time, the layers were separated. The organic layer was treated with a 3 N aqueous HCl (680 mL) as described in the process above eight additional times. During the final washing, the mixture was stirred for 1 h. The organic layer was then concentrated to afford the title compound as a yellow oil.

Intermediate 5

4-(Methylsulfonyl)cyclohexan-1-one m-Chloroperbenzoic acid (1151 g, 85% w/w, 5.668 mol) was added in portions to a stirring −5 to 5° C. solution of 4-(methylthio)cyclohexan-1-one (545 g, 3.78 mol, Intermediate 4) in DCM (11 L) at a rate that maintained the internal temperature below 5° C. After the addition was complete, stirring was continued for 45 min before an additional portion of mCPBA (231 g, 85% w/w, 1.13 mol) was added, and stirring was continued for 30 min. A third portion of mCPBA (76.9 g, 85% w/w, 0.378 mol) was added, and stirring was continued at −5 to 5° C. for 30 min. The reaction mixture was then filtered. The filter cake was rinsed with DCM, and the filtrate and rinse were combined and then concentrated. The residual DCM was then removed by three cycles of sequential dilution with MTBE and concentration. The concentrate was then diluted with MTBE and stirred at 50° C. for 1 h before it was allowed to cool to rt and stir for 16 h. The slurry was then filtered, and the filter cake was rinsed with MTBE and dried under vacuum to afford the title compound as a colorless solid.

Intermediate 6

4-(Methylsulfonyl)-1-((trimethylsilyl)oxy)cyclohexane-1-carbonitrile

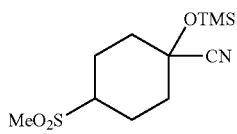

Trimethylsilyl cyanide (410 g, 4.13 mol) was added dropwise to a stirring solution of 4-(methylsulfonyl)cyclohexan-1-one (560 g, 3.18 mol, Intermediate 5) and TEA (113 g, 1.11 mol) in DCM (5.6 L) at a rate that maintained an internal temperature of 25-30° C., and the resulting mixture was stirred for 30 min. After this time, a saturated aqueous NaHCO$_3$ solution was added, and the layers were separated. The organic layer was washed with brine and then concentrated. The residual DCM was then removed by two cycles of sequential dilution with n-heptane and concentration. The concentrate was then stirred as a slurry in n-heptane at rt for 16 h before it was filtered. The filter cake was rinsed with n-heptane and then dried under vacuum to afford the title compound as a colorless solid.

Intermediate 7

1-(Aminomethyl)-4-(methylsulfonyl)cyclohexan-1-ol Hydrochloride

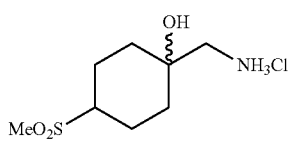

Borane (1.74 L, 1.0 M in THF, 1.74 mol) was added dropwise to a stirring 60° C. solution of 4-(methylsulfonyl)-1-((trimethylsilyl)oxy)cyclohexane-1-carbonitrile (400 g, 1.45 mol, Intermediate 6) in THF (1.6 L), and the solution was stirred until the reaction went to completion. The solution was then cooled in an ice-water bath and quenched by carefully adding MeOH. After the quench was completed, the mixture was acidified with 33% ethanolic HCl solution (200 mL) and stirred for 30 min. The mixture was then filtered, and the filter cake was rinsed with MTBE and then dried under vacuum to afford the title compound as a colorless solid.

Intermediate 8 tert-Butyl (((1s,4s)-1-hydroxy-4-(methylsulfonyl)cyclohexyl)methyl)carbamate

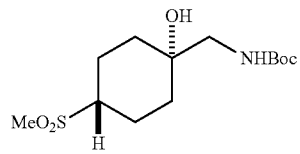

Sodium tert-butoxide (118 g, 1.05 mol) was added in portions to a stirring solution of 1-(aminomethyl)-4-(methylsulfonyl)cyclohexan-1-ol hydrochloride (170 g, 0.70 mol, Intermediate 7) in t-BuOH (850 mL) and THF (850 mL) at rt. The resulting mixture was then heated to 60° C. and stirred until the cis and trans isomers reached equilibrium as judged by HPLC analysis. The reaction mixture was then allowed to cool to rt before 3 N aqueous HCl (70 mL, 0.21 mol) was added. A solution of Boc$_2$O (159 g, 0.728 mol) in THF (510 mL) was then added dropwise at rt, and the mixture was stirred until the reaction went to completion. The resulting mixture was combined with another mixture prepared in a similar way on a similar scale. The combined mixture was filtered, and the filter cake was rinsed with DCM. The filtrate and wash were combined and then concentrated to afford an off-white solid, which was stirred as a slurry in EtOAc/n-heptane (0.8 L, 1:1 v/v) at 60° C. for 1 h. The suspension was allowed to cool and then filtered. The filter cake was rinsed with EtOAc/n-heptane (1:1 v/v) and then dried under vacuum to afford the title compound as a colorless solid.

Intermediate 9

(1s,4s)-1-(Aminomethyl)-4-(methylsulfonyl)cyclohexan-1-ol Hydrochloride

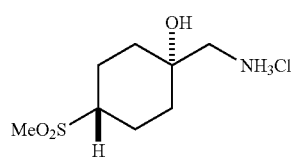

Ethanolic HCl (0.9 L, 33 wt %) was added dropwise to a solution of tert-butyl (((1s,4s)-1-hydroxy-4-(methylsulfonyl)cyclohexyl)methyl)carbamate (290 g, 0.94 mol, Intermediate 8) in EtOH (0.9 L), and the mixture was stirred at rt. After the reaction went to completion, the suspension was filtered, and the filter cake was rinsed with EtOH. The filter cake was then stirred as a slurry in EtOH at reflux temperature for 2 h before it was allowed to cool to rt. The suspension was then filtered, and the filter cake was washed three times with EtOH. The filter cake was then dried at under vacuum at 50° C. the title compound as a colorless solid.

Intermediate 10

4-(Methylthio)cyclohexane-1-carbonitrile

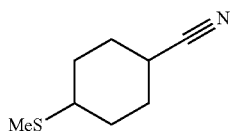

Sodium tert-butoxide (655 g, 5.82 mol) was added in portions to a stirring −38° C. mixture of 4-(methylthio) cyclohexan-1-one (350 g, 2.43 mol, Intermediate 4), Tos-MIC (616 g, 3.15 mol) and EtOH (263 mL, 4.50 mol) in MTBE (7.0 L) at a rate that maintained the internal temperature between −40 and −35° C., and the resulting mixture was stirred for 1 h. After this time, the mixture was allowed to warm to 3° C., and then it was filtered. The filter cake was washed with water, and the layers of the combined filtrate and wash were separated. The filter cake was then suspended in the aqueous layer, and the resulting mixture was filtered. The filter cake was washed with MTBE. Then the layers of the combined filtrate and wash were separated, and the aqueous layer was extracted with MTBE. The organic layers were combined, washed with water, washed with brine, and then concentrated. The concentrate was purified by vacuum distillation to afford the title compound as a light-yellow oil.

Intermediate 11

4-(Methylsulfonyl)cyclohexane-1-carbonitrile

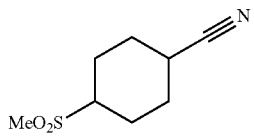 [SMILES: CS(=O)(=O)C1CCC(C#N)CC1]

Oxone (2238 g, 3.640 mol) was added to a stirring −10° C. mixture of 4-(methylthio)cyclohexane-1-carbonitrile (255 g, 1.64 mol, Intermediate 10), acetone (2.5 L), and water (2.5 L) over 45 min at a rate that maintained the internal temperature below 2° C., and the resulting mixture was stirred for 40 min. The reaction mixture was then filtered, and the filter cake was washed with acetone. The filtrate was concentrated to remove most of acetone, and the residue was extracted with five times with EtOAc. The organic layers were combined, dried over anhydrous Na$_2$SO$_4$, filtered, and concentrated to afford a colorless solid. This solid was stirred as a slurry in n-heptane at rt overnight, and then the suspension was filtered. The filter cake was dried under vacuum to afford the title compound as a colorless solid.

Intermediate 12 tert-Butyl (((1r,4r)-4-(methylsulfonyl)cyclohexyl)methyl)carbamate

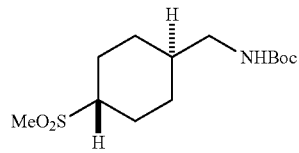

A solution of 4-(methylsulfonyl)cyclohexane-1-carbonitrile (200 g, 1.07 mol, Intermediate 11) in THF (3.0 L) was added dropwise to a stirring −10 to −5° C. suspension of LAH (123 g, 3.24 mol) in THF (1.0 L) over 3 h at a rate that maintained an internal temperature of −10 to 10° C., and the resulting mixture stirred for 2 h. After the reaction went to completion, a solution of THF and water (246 g, 1:1 w/w), 15% aqueous NaOH (123 g), and water (369 g) were sequentially added. The mixture was then filtered, and the filter cake was rinsed with THF. Di-tert-butyl dicarbonate (245 g, 3.40 mol) was then added to the combined filtrate and rinse, and the mixture was stirred at rt overnight. The mixture was then concentrated. The residue was diluted with water, and the mixture was extracted three times with EtOAc. The organic layers were combined, washed with brine, dried with anhydrous Na$_2$SO$_4$, filtered, and then concentrated. This concentrate was combined with an additional concentrate prepared in a similar way on a similar scale, diluted with i-PrOH (0.6 L), and stirred at 85° C. for 30 min. n-Heptane (1.2 L) was added dropwise, and the resulting mixture was stirred for 30 min. The mixture was allowed to cool to 25° C., and stirring was continued for 2 h. The mixture was then filtered, and the filter cake was washed with n-heptane and dried under vacuum at 45° C. to give a colorless solid. This solid was combined with another batch prepared in a similar way but on one-fourth scale, dissolved in EtOAc (0.6 L), and stirred at 60° C. for about 2 h. n-Heptane (2.4 L) was then added dropwise over 2 h, and stirring was continued at 60° C. for 1 h. The resulting mixture was then allowed to cool to 25° C. and was stirred for 2 h. The mixture was then filtered, and the filter cake was washed with n-heptane and dried under vacuum at 40° C. to afford the title compound as a colorless solid.

Intermediate 13

((1r,4r)-4-(Methylsulfonyl)cyclohexyl)methanamine Hydrochloride

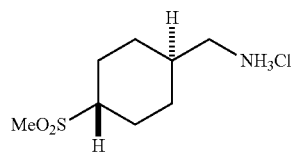

Ethanolic HCl (684 g, 33 wt %, 6.27 mol) was added dropwise to a solution of tert-butyl (((1r,4r)-4-(methyl sulfonyl)cyclohexyl)methyl)carbamate (180 g, 0.62 mol, Intermediate 12) in EtOH (0.6 L), and the resulting mixture was stirred at rt. After the reaction went to completion, MTBE

Intermediate 14

4-(Methylsulfonyl)-1-(nitromethyl)cyclohex-1-ene

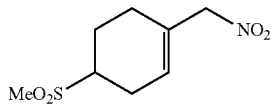 [SMILES: CS(=O)(=O)C1CC=C(C[N+](=O)[O-])CC1]

A solution of 4-(methylsulfonyl)cyclohexanone (15.27 g, 86.65 mmol, Intermediate 5), nitromethane (15 mL, 350 mmol), and DMEN (2.8 mL, 26 mmol) in benzene (220 mL) was stirred at reflux temperature for 16 h in a reactor fitted with a Dean-Stark trap. After this time, the solution was allowed to cool and then diluted with 1 N aqueous HCl (200 mL). The layers of the resulting mixture were mixed then separated, and the aqueous layer was extracted EtOAc. The organic layers were combined, washed with brine, dried with anhydrous MgSO$_4$, filtered, and then concentrated to afford the title compound as a colorless solid.

Intermediate 15

(4-(Methylsulfonyl)cyclohex-1-en-1-yl)methanamine Hydrochloride

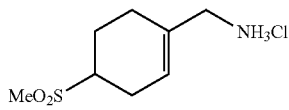

A warm solution of 4-(methylsulfonyl)-1-(nitromethyl)cyclohex-1-ene (15.52 g, 70.78 mmol, Intermediate 14) in AcOH (80 mL) was added dropwise over 1.5 h to a stirring suspension of zinc (50 g, 760 mmol) in AcOH (100 mL), which was submerged in a 70° C. bath. The drip rate was periodically adjusted to maintain the internal reaction temperature below 85° C. After the addition was complete, stirring was continued at 70° C. for 4 h before the reaction mixture was allowed to cool. The mixture was then diluted with an equal volume of EtOAc and filtered through Celite®. The filtrate was concentrated, diluted with IPA (300 mL), and filtered. The filtrate was then concentrated to half its original volume before a dioxane solution of HCl (18 mL, 4.0 M, 72 mmol) was added. The resulting mixture was concentrated, diluted with MeOH (200 mL), and stirred until the solids were well-dispersed. The resulting suspension was concentrated to half the original volume, diluted with an equal volume of EtOAc, and then filtered. The filter cake was dried by aspiration to afford the title compound as a colorless solid.

Intermediate 16 tert-Butyl ((4-(methylsulfonyl)cyclohex-1-en-1-yl)methyl)carbamate

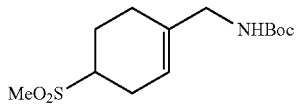

A solution of (4-(methylsulfonyl)cyclohex-1-en-1-yl)methanamine hydrochloride (22.0 g, 97.5 mmol, Intermediate 15) in THF (100 mL) was diluted with a saturated aqueous NaHCO$_3$ solution, Boc$_2$O (20.9 mL, 97.5 mmol) was added, and then the mixture was stirred at rt for 16 h. After this time, the mixture was diluted with EtOAc and filtered. The layers were separated, and the aqueous layer was extracted with EtOAc. The organic layers combined, were washed with brine, dried with anhydrous MgSO$_4$, filtered, and then concentrated to afford the title compound as a tan solid.

Intermediate 17 tert-Butyl (((1RS,2RS)-1,2-dihydroxy-4-(methylsulfonyl)cyclohexyl)methyl)carbamate

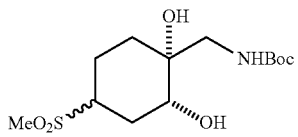

Potassium osmate(VI) dihydrate (470 mg, 1.3 mmol) was added to a solution of tert-butyl ((4-(methylsulfonyl)cyclohex-1-en-1-yl)methyl)carbamate (17.55 g, 57.01 mmol, 94%, Intermediate 16) and NMO (8.7 g, 61 mmol) in acetone/water (250 mL, 4:1 v/v), and the mixture was stirred at rt for 20 h. After this time, a solution of Na$_2$S$_2$O$_4$ (3.1 g, 15 mmol) in water (15 mL) was added, and the mixture was stirred for 30 min. After this time, the mixture was concentrated to one-third its original volume. The concentrate was diluted with EtOAc and enough hexanes to make the mixture biphasic. The pH of the aqueous layer was adjusted to pH<4 with 10 M aqueous H$_2$SO$_4$, and the layers were mixed and then separated. The aqueous layer was extracted four times with EtOAc, and then the organic layers were combined, dried anhydrous MgSO$_4$, filtered, and concentrated to afford the title compound as a pale-purple gum.

Intermediate 18

(1RS,2RS)-1-(Aminomethyl)-4-(methylsulfonyl)cyclohexane-1,2-diol Hydrochloride

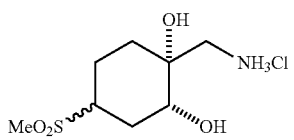

Trifluoroacetic acid (48 mL, 0.63 mol) was added to a solution of tert-butyl (((1RS,2RS)-1,2-dihydroxy-4-(methylsulfonyl)cyclohexyl)methyl)carbamate (17.77 g, 51.65 mmol, 94 wt %, Intermediate 17) in DCM (180 mL), and the resulting solution was maintained at rt for 2 h. After this time, the solution was concentrated, MeOH was added, and the solution was concentrated again. The concentrate was dissolved in MeOH (50 mL), a solution of HCl in 1,4-dioxane (14.2 mL, 4.0 M, 56.8 mmol) was added, and the solution was concentrated to give a brown oil. This oil was dissolved in MeOH (50 mL) and then EtOAc (200 mL) was added over 30 min to induce crystallization. The resulting slurry was filtered, and the solids were washed with EtOAc and then dried by aspiration to afford the title compound as a tan solid (dr=1.6:1.0 according to NMR analysis).

Intermediate 19

(1RS,2RS,4RS)-1-(Aminomethyl)-4-(methylsulfonyl)cyclohexane-1,2-diol Hydrochloride

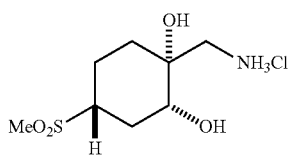

Potassium tert-butoxide (7.7 g, 68 mmol) was added to a suspension of (1RS,2RS)-1-(aminomethyl)-4-(methylsulfonyl)cyclohexane-1,2-diol hydrochloride (11.84 g, 45.58 mmol, Intermediate 18) in t-BuOH (120 mL), and the resulting thick, heterogeneous mixture was stirred at 60° C. for 65 h. After this time, the mixture was allowed to cool, and then a solution of HCl in 1,4-dioxane (18.2 mL, 4.0 M, 72.9 mmol) was added. The mixture was then concentrated to afford the title compound as a tan solid (dr=10:1.0 according to NMR analysis).

Intermediate 20

Benzyl (((1RS,2RS,4RS)-1,2-dihydroxy-4-(methylsulfonyl)cyclohexyl)methyl)carbamate

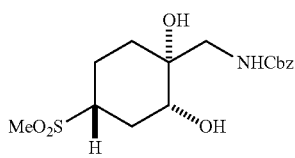 [SMILES: CS(=O)(=O)[C@@H]1CC[C@@](O)(CNC(=O)OCc2ccccc2)[C@H](O)C1]

Benzyl chloroformate (16.6 mL, 112 mmol) was added to a 0-5° C. mixture of (1RS,2RS,4RS)-1-(aminomethyl)-4-(methylsulfonyl)cyclohexane-1,2-diol hydrochloride (19.81 g, 56.05 mmol, Intermediate 19) and NaHCO$_3$ (14.1 g, 168 mmol) in water (160 mL), and the resulting mixture was stirred vigorously and allowed to gradually warm to rt over 24 h. After this time, the resulting suspension was filtered, and the filter cake was washed with water and then dried by aspiration. The solids were diluted with hexanes and EtOAc (100 mL, 3:1 v/v) and stirred for 3 h. The slurry was filtered, and the filter cake was washed with hexanes and then dried by aspiration to afford the title compound as a light-tan solid (dr>100:1 according to NMR analysis).

Intermediate 21

Benzyl (((1S*,2S*,4S*)-1,2-dihydroxy-4-(methylsulfonyl)cyclohexyl)methyl)carbamate

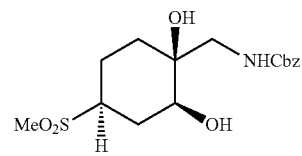 [SMILES: CS(=O)(=O)[C@H]1CC[C@](O)(CNC(=O)OCc2ccccc2)[C@@H](O)C1]

Intermediate 22

Benzyl (((1R*,2R*,4R*)-1,2-dihydroxy-4-(methylsulfonyl)cyclohexyl)methyl)carbamate

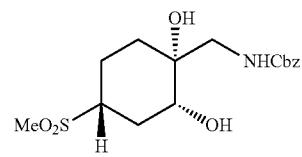

Intermediate 20 was purified by SFC using a chiral stationary phase (Chiralpak IA, 60% CO$_2$, 40% EtOH/i-PrOH (1:1 v/v)) to give a pair of enantiomers. The first-eluting enantiomer was Intermediate 21, and the second-eluting enantiomer was Intermediate 22.

Intermediate 23

(1R*,2R*,4R*)-1-(Aminomethyl)-4-(methylsulfonyl)cyclohexane-1,2-diol Hydrochloride

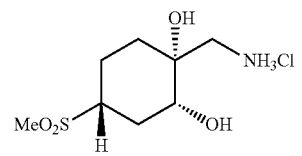

A vessel containing benzyl (((1R*,2R*,4R*)-1,2-dihydroxy-4-(methylsulfonyl)cyclohexyl)methyl)carbamate (4.22 g, 11.8 mmol, Intermediate 22) and Pd/C (2.5 g, 10% Pd, 50% water, Degussa E101 NE/W, 1.2 mmol Pd) was evacuated and backfilled three times with nitrogen before EtOH (130 mL) was added, and the mixture was stirred under an atmosphere of hydrogen at rt for 16 h. After this time, the suspension was diluted with enough water to dissolve the newly-formed precipitate, filtered through Celite®, and then concentrated. This concentrate was dissolved in MeOH and water (30 mL, 1:1 v/v) before a solution of HCl in 1,4-dioxane (3.0 mL, 4.0 M, 12 mmol) was added, and the resulting mixture was concentrated. The oily residue was diluted with EtOH and concentrated again to afford a colorless solid. This solid was suspended in EtOAc and then isolated by filtration. The moist filter cake was dried under vacuum to afford the title compound as a colorless solid. $[\alpha]_{589}^{20}$+1.9, $[\alpha]_{436}^{20}$+5.2, $[\alpha]_{365}^{20}$+10 (c 1.1, MeOH).

Intermediate 24

(1S*,2S*,4S*)-1-(Aminomethyl)-4-(methylsulfonyl)cyclohexane-1,2-diol Hydrochloride

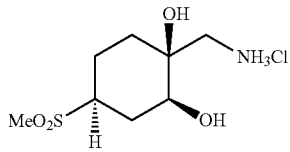

The title compound was prepared as described for the synthesis of Intermediate 23, using benzyl (((1S*,2S*,4S*)-1,2-dihydroxy-4-(methyl sulfonyl)cyclohexyl)methyl)carbamate (Intermediate 21) in place of benzyl (((1R*,2R*,4R*)-1,2-dihydroxy-4-(methylsulfonyl)cyclohexyl)methyl)carbamate. $[\alpha]_{589}^{20}$–1.7, $[\alpha]_{436}^{20}$–5.1, $[\alpha]_{365}^{20}$–10 (c 1.7, MeOH).

Intermediate 25 tert-Butyl (((1RS,2SR,4SR)-2-hydroxy-4-(methylsulfonyl)cyclohexyl)methyl)carbamate

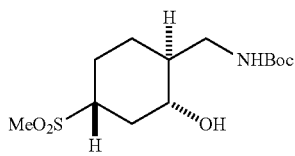

A solution of BH$_3$.THF in THF (30 mL, 1.0 M, 30 mmol) was added to a 0-5° C. solution of tert-butyl ((4-(methylsulfonyl)cyclohex-1-en-1-yl)methyl)carbamate (2.9 g, 10 mmol, Intermediate 16) in THF (30 mL), and the resulting solution was allowed to warm to rt over 16 h with stirring. After this time, the resulting mixture was cooled to 0-5° C. and then quenched with drops of water. When the bubbling ceased, 10% aqueous NaOH (8.0 mL, 22 mmol) and then H$_2$O$_2$ (2.5 mL, 50% w/w, 43 mmol) were added, and the mixture was stirred at rt for 5 h. After this time, the mixture was diluted with brine, and the layers were mixed then separated. The aqueous layer was extracted twice with EtOAc, and the combine organic layers were dried with anhydrous MgSO$_4$, filtered, and then concentrated to afford a colorless gum. This residue was purified by silica gel chromatography (75→100% EtOAc/hexanes) to afford the first-eluting diastereomer as a colorless solid. This solid was purified further by crystallizing it from boiling i-PrOAc (12 mL) to afford the title compound as a colorless solid.

Intermediate 26

(1RS,2SR,5RS)-2-(Aminomethyl)-5-(methylsulfonyl)cyclohexan-1-ol Hydrochloride

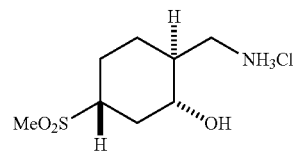

tert-Butyl (((1RS,2SR,4SR)-2-hydroxy-4-(methylsulfonyl)cyclohexyl)methyl)carbamate (470 mg, 1.53 mmol, Intermediate 25) was diluted with DCM (5.3 mL) and then TFA (1.4 mL, 18 mmol), and the resulting solution was maintained at rt for 2 h. After this time, the solution was concentrated and then diluted with the minimum volume of DCM and MeOH (1:1 v/v) to obtain a solution. A solution of HCl in 1,4-dioxane (0.38 mL, 4.0 M, 1.5 mmol) was then added, and the resulting suspension was concentrated. The residue was triturated with EtOAc, filtered, and washed with EtOAc. The solids were crystallized from EtOH to afford the title compound as a colorless solid.

Intermediate 27

3-Bromo-4-(difluoromethoxy)pyridine

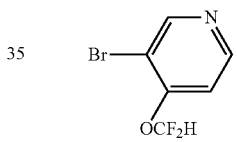

Sodium chlorodifluoroacetate (24.1 g, 158 mmol), 3-bromopyridin-4-ol (25.0 g, 144 mmol), and Cs$_2$CO$_3$ (70.0 g, 216 mmol) were diluted with DMF (375 mL), and the resulting mixture was stirred at 100° C. for 1 h. After this time, the reaction mixture was cooled in an ice bath for 10 min before it was diluted with water and Et$_2$O (2:1 v/v). The layers were mixed and then separated, and the aqueous layer was extracted with Et$_2$O. The organic layers were combined, washed with water, washed with brine, dried with anhydrous MgSO$_4$, filtered, and then concentrated to afford the title compound as a yellow oil.

Intermediate 28

Ethyl 1-ethyl-1H-pyrazole-3-carboxylate

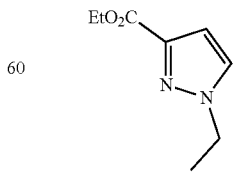

Iodoethane (836 g, 5.36 mol) was added dropwise to a mixture of ethyl 1H-pyrazole-3-carboxylate (500 g, 3.57 mol) and K$_2$CO$_3$ (987 g, 7.14 mol) in THF (15 L), and the resulting mixture was stirred at reflux temperature for 24 h. The mixture was then allowed to cool to rt before it was filtered, and the filter cake was washed with THF. The filtrate and wash were combined and then concentrated. The concentrate was purified by silica gel chromatography (9→33% EtOAc/petroleum ether) to afford the title compound as a light-yellow oil.

Intermediate 29

Ethyl 1-ethyl-5-(4,4,5,5-tetramethyl-1,3,2-dioxaborolan-2-yl)-1H-pyrazole-3-carboxylate

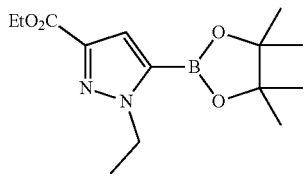 [SMILES: CCOC(=O)c1cc(B2OC(C)(C)C(C)(C)O2)n(CC)n1]

A mixture of (1,5-cyclooctadiene)(methoxy)iridium(I) dimer (1.18 g, 1.78 mmol), 1,10-phenanthroline (840 mg, 3.6 mmol), pinacolborane (37.2 g, 291 mmol) and pentane (180 mL) was stirred for 20 min at 10° C. before ethyl 1-ethyl-1H-pyrazole-3-carboxylate (30 g, 178 mmol, Intermediate 28) in pentane/THF (2:1 v/v) was added, and the resulting mixture was stirred at rt for 16 h. The mixture was then concentrated, and the concentrate was purified by silica gel chromatography (9→11%, EtOAc/petroleum ether) to afford the title compound as a colorless solid.

Intermediate 30

(3-(Ethoxycarbonyl)-1-ethyl-1H-pyrazol-5-yl)boronic Acid

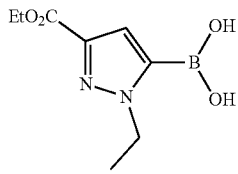

A solution of potassium hydrogen fluoride (27 g, 350 mmol) in water (78 mL) was added to a solution of ethyl 1-ethyl-5-(4,4,5,5-tetramethyl-1,3,2-dioxaborolan-2-yl) pyrazole-3-carboxylate (18.0 g, 61.2 mmol, Intermediate 29) in MeOH (180 mL), and the resulting suspension was stirred at rt for 18 h. After this time, the mixture was concentrated, and the residue was extracted with two portions of hot acetone. The extracts were filtered while hot and then concentrated to afford a colorless oil. This oil was crystallized from acetone and Et$_2$O, and then the crystals were washed with Et$_2$O to afford a colorless solid. Water (3.3 mL, 180 mmol) and then TMSCl (23.3 mL, 183 mmol) were added to a solution of this solid in MeCN (550 mL), and the resulting suspension was stirred at rt for 1 h. The mixture was then diluted with saturated aqueous NaHCO$_3$ solution (50 mL), stirred for 10 min, dried with anhydrous MgSO$_4$, filtered, and then concentrated to afford the title compound as a colorless solid.

Intermediate 31

Ethyl 5-(4-(difluoromethoxy)pyridin-3-yl)-1-ethyl-1H-pyrazole-3-carboxylate

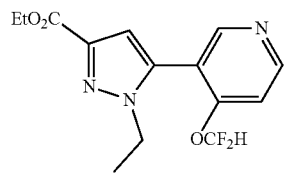

Lithium hydroxide (1.16 g, 48.5 mmol) was ground into a powder and then dried under vacuum at 140° C. for 14 h. The vessel was allowed to cool before Pd(t-Bu$_3$P)$_2$ (1.15 g, 2.25 mmol) was added, and the vessel was evacuated and backfilled three times with nitrogen. A solution of (3-(ethoxycarbonyl)-1-ethyl-1H-pyrazol-5-yl)boronic acid (11.82 g, 55.75 mmol, Intermediate 30) and 3-bromo-4-(difluoromethoxy)pyridine (10.4 g, 46.4 mmol, Intermediate 27) in DMF (100 mL) was then added by cannula transfer, and the remaining residue was in the transfer vessel was rinsed into the reaction mixture with additional portions of DMF (40 mL×2). The reaction mixture was stirred at 80° C. for 18 h. After this time, the mixture was allowed to cool and then concentrated. The concentrate was diluted with water and EtOAc, and the layers were mixed then separated. The aqueous layer was extracted with EtOAc, and then the organic layers were combined, washed with water, washed with brine, dried with anhydrous MgSO$_4$, filtered, and concentrated. The residue was purified by silica gel chromatography (50→100% EtOAc/hexanes) to afford the title compound as a pale-yellow solid.

Intermediate 32

Ethyl 4-chloro-5-(4-(difluoromethoxy)pyridin-3-yl)-1-ethyl-1H-pyrazole-3-carboxylate

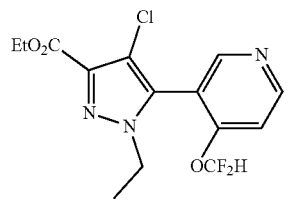

Sulfuryl chloride (2.8 mL, 34 mmol) was added to a solution of ethyl 5-(4-(difluoromethoxy)pyridin-3-yl)-1-ethyl-1H-pyrazole-3-carboxylate (9.71 g, 91 wt %, 28.4 mmol, Intermediate 31) in MeCN (56 mL), and the solution was stirred at rt for 1 h before it was warmed to 50° C. for an additional 30 min. After this time, the resulting heterogeneous mixture was allowed to cool and then diluted with saturated aqueous NaHCO$_3$ solution and DCM. The layers were mixed and then separated, and the aqueous layer was extracted twice with DCM. The combined organic layers

Intermediate 33

3-(4-Chloro-3-(ethoxycarbonyl)-1-ethyl-1H-pyrazol-5-yl)-4-(difluoromethoxy)pyridine 1-oxide

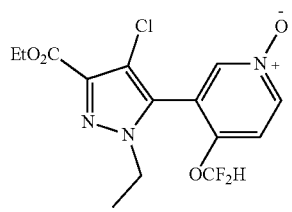

m-Chloroperbenzoic acid (7.7 g, 77 wt %, 34 mmol) was added to a solution of ethyl 4-chloro-5-(4-(difluoromethoxy)pyridin-3-yl)-1-ethyl-1H-pyrazole-3-carboxylate (10.9 g, 91 wt %, 28.7 mmol, Intermediate 32) in DCM (190 mL), and the resulting mixture was stirred at rt for 16 h. After this time, an additional portion of mCPBA (1.3 g, 77 wt %, 5.7 mmol) was added, and stirring was continued for 24 h. After this time, the mixture was washed with an aqueous solution of $Na_2S_2O_3$, washed twice with a saturated aqueous $NaHCO_3$ solution, dried with anhydrous $MgSO_4$, filtered, and then concentrated to afford the title compound as a colorless foam.

Intermediate 34

Ethyl 4-chloro-5-(4-(difluoromethoxy)-6-((4,4,4-trifluoro-2-methylbutan-2-yl)amino)pyridin-3-yl)-1-ethyl-1H-pyrazole-3-carboxylate

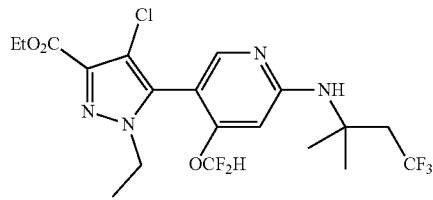

p-Toluenesulfonic anhydride (11.9 g, 36.3 mmol) was added in three portions over 15 min to a 0-5° C. solution of 3-(4-chloro-3-(ethoxycarbonyl)-1-ethyl-1H-pyrazol-5-yl)-4-(difluoromethoxy)pyridine 1-oxide (6.77 g, 18.2 mmol, Intermediate 33) and 4,4,4-trifluoro-2-methylbutan-2-amine (11.5 mL, 90.8 mmol) in α,α,α-trifluorotoluene (95 mL), and the resulting thick, heterogeneous mixture was stirred at 0-5° C. for 30 min. The mixture was then diluted with DCM and a saturated aqueous $NaHCO_3$ solution, and the resulting mixture was allowed to warm to rt with stirring. The layers were then separated, and the aqueous layer was extracted with DCM. The combined organic layers were washed with a saturated aqueous $NaHCO_3$ solution, dried with anhydrous $MgSO_4$, filtered, and then concentrated. The residue was purified by silica gel chromatography (10→40% EtOAc/hexanes) to afford the title compound as a pale yellow foam.

Intermediate 35

Ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate

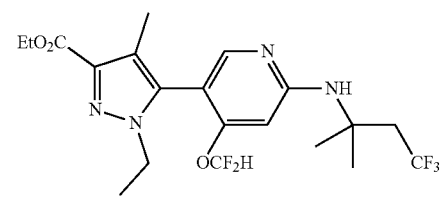

Ethyl 4-chloro-5-(4-(difluoromethoxy)-6-((4,4,4-trifluoro-2-methylbutan-2-yl)amino)pyridin-3-yl)-1-ethyl-1H-pyrazole-3-carboxylate (95 mg, 0.20 mmol, Intermediate 34), RuPhos G1 (8 mg, 0.01 mmol), RuPhos (5 mg, 0.01 mmol), and $K_2CO_3$ (110 mg, 0.78 mmol) were combined in a vessel, and the vessel was evacuated and backfilled three times with nitrogen. 1,4-Dioxane (1.1 mL) and trimethylboroxine (0.080 mL, 0.55 mmol) were successively added, and the resulting mixture was stirred at 90° C. for 30 min. After this time, the mixture was allowed to cool and then diluted with EtOAc and water. The layers were separated, and the aqueous layer was extracted with EtOAc. The combined organic layers were then concentrated to afford a brown residue. This residue was purified by silica gel chromatography (20→60% EtOAc/hexanes) to afford the title compound as a pale yellow residue.

Intermediate 36

Ethyl 5-(6-chloro-4-methylpyridin-3-yl)-1-ethyl-1H-pyrazole-3-carboxylate

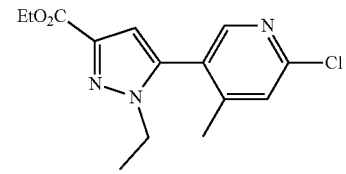

A mixture of 5-bromo-2-chloro-4-methylpyridine (10 g, 48 mmol), ethyl 1-ethyl-5-(4,4,5,5-tetramethyl-1,3,2-dioxaborolan-2-yl)-1H-pyrazole-3-carboxylate (14.2 g, 48.3 mmol, Intermediate 29), and $K_2CO_3$ (20.1 g, 145 mmol) in 1,4-dioxane and water (120 mL, 5:1 v/v) was sparged with argon for 5 min before Pd(dtbpf)Cl$_2$ (1.26 g, 1.93 mmol) was added, and the mixture was sparged with argon for another 5 min. The mixture was then stirred at 100° C. for 1 h before it was allowed to cool to rt and diluted with water. The resulting mixture was extracted twice with EtOAc, and the organic extracts were combined, dried with anhydrous $Na_2SO_4$, filtered, and then concentrated. The residue was purified by silica gel chromatography (2→33% EtOAc/petroleum ether) to afford the title compound as a yellow oil.

Intermediate 37

Ethyl 4-chloro-5-(6-chloro-4-methylpyridin-3-yl)-1-ethyl-1H-pyrazole-3-carboxylate

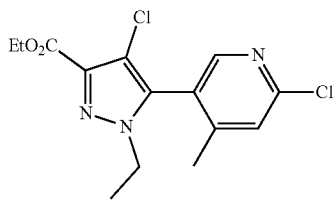 [SMILES: CCOC(=O)c1nn(CC)c(-c2cnc(Cl)cc2C)c1Cl]

Sulfuryl chloride (15.2 g, 113 mmol) was added dropwise to a solution of ethyl 5-(6-chloro-4-methylpyridin-3-yl)-1-ethyl-1H-pyrazole-3-carboxylate (11 g, 37 mmol, Intermediate 36) in DCM (100 mL), and the resulting mixture was stirred at rt for 6 h. After this time, the mixture was poured into a saturated aqueous NaHCO$_3$ solution, and the resulting mixture was extracted three times with DCM. The organic extracts were combined, dried with anhydrous Na$_2$SO$_4$, filtered, and then concentrated. The residue was purified by silica gel chromatography (9→33% EtOAc/petroleum ether) to afford the title compound.

Intermediate 38

3-Bromo-4-isopropylpyridine

Neat BF$_3$.OEt$_2$ (8.9 g, 63 mmol) was added dropwise to a 0-5° C. solution of 3-bromopyridine (9.0 g, 57 mmol) in THF (100 mL), and the resulting mixture was stirred at 0-5° C. for 15 min. After this time, the mixture was cooled to −50° C., a THF solution of i-PrMgCl.LiCl (53 mL, 1.3 M, 69 mol) was added, and the resulting mixture was stirred at −50° C. for 30 min. The mixture was then allowed to warm to 0° C., at which point chloranil (28.0 g, 114 mmol) was added, and the resulting mixture was allowed to warm to rt over 2 h with stirring. After this time, an aqueous ammonia solution (90 mL, 25% w/w) was added, and the resulting mixture was extracted three times with EtOAc. The organic extracts were combined, washed with brine, dried with anhydrous Na$_2$SO$_4$, filtered, and then concentrated. The residue was purified by silica gel chromatography (0→20% EtOAc/petroleum ether) to afford the title compound as a red oil.

Intermediate 39

Ethyl 1-ethyl-5-(4-isopropylpyridine-3-yl)-1H-pyrazole-3-carboxylate

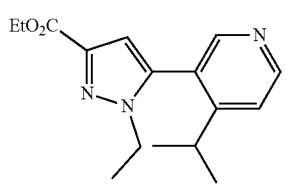 [SMILES: CCOC(=O)c1cc(-c2cnccc2C(C)C)n(CC)n1]

A mixture of 3-bromo-4-isopropylpyridine (3.5 g, 17 mmol, Intermediate 38), ethyl 1-ethyl-5-(4,4,5,5-tetramethyl-1,3,2-dioxaborolan-2-yl)-1H-pyrazole-3-carboxylate (5.66 g, 19.2 mmol, Intermediate 29), and K$_2$CO$_3$ (7.25 g, 52.5 mmol) in 1,4-dioxane and water (30 mL, 5:1 v/v) were sparged with argon for 5 min before Pd(t-Bu$_3$P)$_2$ (894 mg, 1.75 mmol) was added, and the mixture was sparged with argon for another 5 min. The mixture was then stirred at 100° C. for 16 h before it was allowed to cool to rt and diluted with water. The resulting mixture was extracted twice with EtOAc, and the organic extracts were combined, dried with anhydrous Na$_2$SO$_4$, filtered, and then concentrated. The residue was purified by silica gel chromatography (5→50% EtOAc/petroleum ether) to afford the title compound as a yellow oil.

Intermediate 40

Ethyl 4-chloro-1-ethyl-5-(4-isopropylpyridine-3-yl)-1H-pyrazole-3-carboxylate

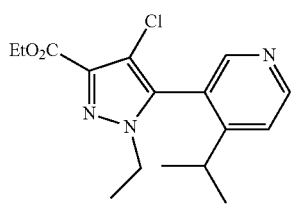 [SMILES: CCOC(=O)c1nn(CC)c(-c2cnccc2C(C)C)c1Cl]

Sulfuryl chloride (7.28 g, 53.9 mmol) was added dropwise to a solution of ethyl 1-ethyl-5-(4-isopropylpyridine-3-yl)-1H-pyrazole-3-carboxylate (3.1 g, 11 mmol, Intermediate 39) in DMF (30 mL), and the resulting mixture was stirred at rt for 16 h. After time, the mixture was poured into a saturated aqueous NaHCO$_3$ solution (150 ml), and the resulting suspension was filtered. The filter cake was washed with water and then dried by aspiration to afford the title compound as a yellow solid.

Intermediate 41

3-(4-Chloro-3-(ethoxycarbonyl)-1-ethyl-1H-pyrazol-5-yl)-4-isopropylpyridine 1-oxide

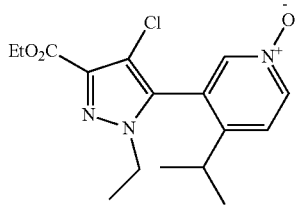 [SMILES: CCOC(=O)c1nn(CC)c(-c2c[n+](O)ccc2C(C)C)c1Cl]

The title compound was prepared as described for the synthesis of Intermediate 33, using ethyl 4-chloro-1-ethyl-5-(4-isopropylpyridine-3-yl)-1H-pyrazole-3-carboxylate (Intermediate 40) in place of ethyl 4-chloro-5-(4-(difluoromethoxy)pyridin-3-yl)-1-ethyl-1H-pyrazole-3-carboxylate.

Intermediate 42

Ethyl 4-chloro-1-ethyl-5-(4-isopropyl-6-((4,4,4-trifluoro-2-methylbutan-2-yl)amino)pyridin-3-yl)-1H-pyrazole-3-carboxylate

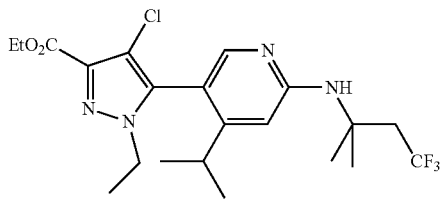 [SMILES: CCOC(=O)c1nn(CC)c(-c2cnc(NC(C)(C)CC(F)(F)F)cc2C(C)C)c1Cl]

The title compound was prepared as described for the synthesis of Intermediate 34, using 3-(4-chloro-3-(ethoxycarbonyl)-1-ethyl-1H-pyrazol-5-yl)-4-isopropylpyridine 1-oxide (Intermediate 41) in place of 3-(4-chloro-3-(ethoxycarbonyl)-1-ethyl-1H-pyrazol-5-yl)-4-(difluoromethoxy)pyridine 1-oxide.

Intermediate 43

1-(3-Bromopyridin-4-yl)ethan-1-ol

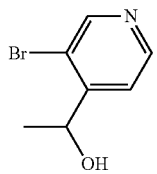

A solution of MeMgBr in Et$_2$O (54 mL, 3.0 M, 160 mmol) was added dropwise to a −65° C. solution of 3-bromoisonicotinaldehyde (10 g, 54 mmol) in THF (100 mL), and the resulting mixture was stirred and allowed to warm to 0° C. over 3 h. After this time, a saturated aqueous NH$_4$Cl solution was added, and the resulting mixture was extracted three times with EtOAc. The organic extracts were combined, washed with brine, dried with anhydrous Na$_2$SO$_4$, filtered, and then concentrated to afford the title compound as a colorless solid.

Intermediate 44

1-(3-Bromopyridin-4-yl)ethan-1-one

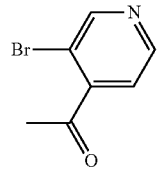

A mixture of the crude 1-(3-bromopyridin-4-yl)ethanol from the previous step (9.5 g, 47 mmol, Intermediate 43) and MnO$_2$ (33.0 g, 380 mmol) in toluene (100 mL) was stirred at 120° C. for 3 h. After this time, the mixture was allowed to cool to rt and then filtered through a pad of Celite®. The pad was washed with EtOAc, and the filtrate and wash were combined and then concentrated to afford the title compound as a yellow oil.

Intermediate 45

3-Bromo-4-(1,1-difluoroethyl)pyridine

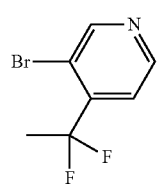

(Diethylamino)sulfur trifluoride (14.5 g, 90.0 mmol) was added to a 0-5° C. solution of 1-(3-bromopyridin-4-yl)ethan-1-one (6.0 g, 30 mmol, Intermediate 44) in DCM (80 mL), and the resulting mixture was stirred at 0-5° C. for 2 h before it was allowed to warm to rt over 16 h. After this time, a saturated aqueous NaHCO$_3$ solution was added, and the resulting mixture was extracted three times with DCM. The organic extracts were combined, dried with anhydrous Na$_2$SO$_4$, filtered, and then concentrated. The residue was purified by silica gel chromatography (2→10% EtOAc/petroleum ether) afford the title compound as a yellow oil.

Intermediate 46

Ethyl 4-chloro-5-(4-(1,1-difluoroethyl)-6-((4,4,4-trifluoro-2-methylbutan-2-yl)amino)pyridin-3-yl)-1-ethyl-1H-pyrazole-3-carboxylate

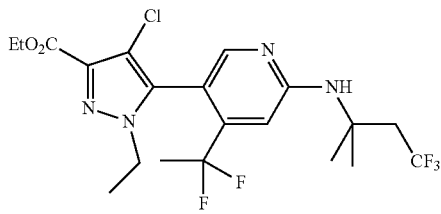 [SMILES: CCOC(=O)c1nn(CC)c(-c2cnc(NC(C)(C)CC(F)(F)F)cc2C(C)(F)F)c1Cl]

The title compound was prepared as described for the synthesis of Intermediate 42, using 3-bromo-4-(1,1-difluoroethyl)pyridine (Intermediate 45) in place of 3-bromo-4-isopropylpyridine.

Intermediate 47

2-Chloro-5-(1-ethoxyvinyl)-4-(trifluoromethyl)pyridine

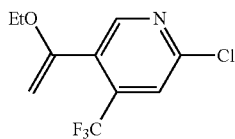 [SMILES: C=C(OCC)c1cnc(Cl)cc1C(F)(F)F]

A mixture of 5-bromo-2-chloro-4-(trifluoromethyl)pyridine (6.0 g, 23 mmol), tributyl(1-ethoxyvinyl)stannane (8.3 g, 23 mmol), and Pd(PPh$_3$)$_4$ (1.3 g, 1.2 mmol) in toluene (50 mL) was sparged with nitrogen for 5 min and then stirred at 120° C. for 1 h. After this time, the mixture was allowed to cool to rt and then poured into saturated aqueous KF solution (100 mL). The resulting mixture was stirred vigorously for 30 min and then extracted twice with EtOAc. The organic extracts were combined, dried with anhydrous Na$_2$SO$_4$, filtered, and then concentrated. The residue was purified by silica gel chromatography (0→5% EtOAc/petroleum ether) to afford the title compound as a yellow oil.

Intermediate 48

1-(6-Chloro-4-(trifluoromethyl)pyridin-3-yl)ethan-1-one

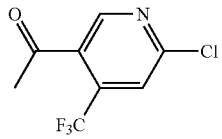

A mixture of the crude 2-chloro-5-(1-ethoxyvinyl)-4-(trifluoromethyl)pyridine from the previous step (3.2 g, 14 mmol, Intermediate 47) and aqueous HCl (20 mL, 36% w/w) was stirred at rt for 1 h before the pH of the mixture was adjusted to pH=8 with a saturated aqueous NaHCO$_3$ solution. The resulting mixture was extracted twice with EtOAc, and the organic extracts were combined, dried with anhydrous Na$_2$SO$_4$, filtered, and then concentrated. The residue was purified by silica gel chromatography (2→20% EtOAc/petroleum ether) to afford the title compound as a yellow oil.

Intermediate 49

Ethyl 4-(6-chloro-4-(trifluoromethyl)pyridin-3-yl)-2,4-dioxobutanoate

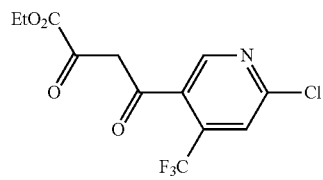 [SMILES: CCOC(=O)C(=O)CC(=O)c1cnc(Cl)cc1C(F)(F)F]

A THF solution of LiHMDS (23.5 mL, 1.0 M, 23.5 mmol) was added dropwise to a −65° C. solution of 1-(6-chloro-4-(trifluoromethyl)pyridin-3-yl)ethanone (3.5 g, 16 mmol, Intermediate 48) in THF (40 mL), and the resulting mixture was stirred at −65° C. for 30 min. After this time, a solution of diethyl oxalate (3.4 g, 23 mmol) in THF (10 mL) was added, and the resulting mixture was stirred and allowed to warm to rt over 18 h. A saturated aqueous NH$_4$Cl solution was then added, and the resulting mixture was extracted with three times with EtOAc. The organic extracts were combined, dried with anhydrous Na$_2$SO$_4$, filtered, and then concentrated to afford the title compound as a yellow oil.

Intermediate 50

Ethyl 5-(6-chloro-4-(trifluoromethyl)pyridin-3-yl)-1-ethyl-1H-pyrazole-3-carboxylate

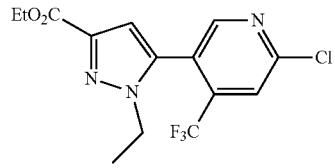 [SMILES: CCOC(=O)c1cc(-c2cnc(Cl)cc2C(F)(F)F)n(CC)n1]

A mixture of ethyl 4-(6-chloro-4-(trifluoromethyl)pyridin-3-yl)-2,4-dioxobutanoate (4.5 g, 14 mmol, Intermediate 49) and ethylhydrazine oxalate (3.2 g, 21 mmol) in EtOH (50 mL) was stirred at 80° C. for 18 h. After this time, the mixture was allowed to cool to rt, and then it was concentrated. The concentrate was diluted with saturated aqueous NaHCO$_3$ solution, and the resulting mixture was extracted three times with EtOAc. The organic extracts were combined, dried with anhydrous Na$_2$SO$_4$, filtered, and concentrated. The residue was purified by silica gel chromatography (2→33% EtOAc/petroleum ether) to afford the title compound as a colorless solid.

Intermediate 51

Ethyl 4-chloro-5-(6-chloro-4-(trifluoromethyl)pyridin-3-yl)-1-ethyl-1H-pyrazole-3-carboxylate

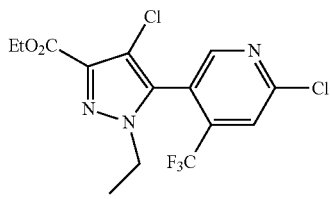 [SMILES: CCOC(=O)c1nn(CC)c(-c2cnc(Cl)cc2C(F)(F)F)c1Cl]

The title compound was prepared as described for the synthesis of Intermediate 37, using ethyl 5-(6-chloro-4-(trifluoromethyl)pyridin-3-yl)-1-ethyl-1H-pyrazole-3-carboxylate (Intermediate 50) in place of ethyl 5-(6-chloro-4-methylpyridin-3-yl)-1-ethyl-1H-pyrazole-3-carboxylate.

Intermediate 52

3,5-Dibromo-2-chloropyridin-4-ol

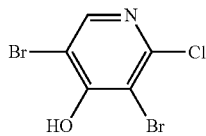

Bromine (3.70 kg, 23.3 mol) was added dropwise to a solution of 2-chloropyridin-4-ol (1.43 kg, 11.1 mol) in AcOH (7.0 L), and the resulting solution was stirred at 25° C. for 2 h. The solution was then poured into water, and the resulting suspension was filtered. The filter cake was slurried with water, filtered, and then dried to afford the title compound as light-yellow solid.

Intermediate 53

5-Bromo-2-chloropyridin-4-ol

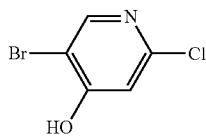

n-Butyllithium (2.71 L, 2.5 M, 6.8 mol) was added dropwise to a stirring −78° C. solution of 3,5-dibromo-2-chloropyridin-4-ol (1.13 kg, 3.93 mol, Intermediate 52) in THF (13.6 L), and the resulting mixture was stirred at −78° C. for 10 min. After this time, water (2 L) was added dropwise to the reaction mixture, and then it was allowed to warm to 0-5° C. The mixture was then washed three times with 2 N aqueous HCl, and the combined aqueous washes were back-extracted twice with EtOAc. All the organic layers were then combined and concentrated. The concentrate was slurried with heptane at 25-30° C., stirred for 3 h, filtered, and then dried under vacuum to afford the title compound as a light-yellow solid.

Intermediate 54

5-Bromo-2-chloro-4-(difluoromethoxy)pyridine

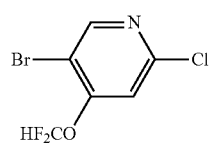

A solution of 5-bromo-2-chloropyridin-4-ol (200 g 0.960 mol, Intermediate 53) and sodium chlorodifluoroacetate (264 g, 1.73 mol) in DMF (1.0 L) was added dropwise to a 110-115° C. suspension of $Cs_2CO_3$ (469 g, 1.44 mol) in DMF (1.0 L), and the resulting mixture was stirred at 110-115° C. After the reaction went to completion, mixture was allowed to cool to 50-60° C., and then it was poured into ice water. The resulting mixture was extracted twice with MTBE, and the combined organic layers were washed with water and then concentrated. The concentrate was purified by distillation to afford the title compound as a colorless liquid (bp 75-78° C. at 1-2 mmHg).

Intermediate 55

Ethyl 5-(6-chloro-4-(difluoromethoxy)pyridin-3-yl)-1-ethyl-1H-pyrazole-3-carboxylate

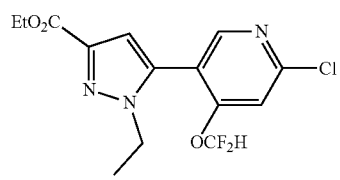

5-Bromo-2-chloro-4-(difluoromethoxy)pyridine (243 g, 0.938 mol, Intermediate 54), ethyl 1-ethyl-5-(4,4,5,5-tetramethyl-1,3,2-dioxaborolan-2-yl)-1H-pyrazole-3-carboxylate (230 g, 0.780 mol, Intermediate 29), $K_2CO_3$ (216 g, 1.56 mol), $Pd_2(dba)_3$ (35.8 g, 39.1 mmol), and $P(t-Bu)_3 \cdot HBF_4$ (22.7 g, 78.2 mmol) were diluted with toluene (3.5 L) and $H_2O$ (69 mL), and the resulting mixture was stirred at 25-30° C. for 7 h. The reaction mixture was then allowed to cool to 15-20° C. before it was filtered. The layers of the filtrate were separated, and the organic layer was washed twice with water. The organic layer was then concentrated, and the concentrate underwent two cycles of successive dilution with heptane and concentration. The concentrate was slurried with heptane, stirred, and then filtered. The filter cake was slurried with DME and heptane (1:2 v/v), stirred, and then filtered. The filter cake was dried to afford the title compound as an off-white solid.

Intermediate 56

Ethyl 4-chloro-5-(6-chloro-4-(difluoromethoxy)pyridin-3-yl)-1-ethyl-1H-pyrazole-3-carboxylate

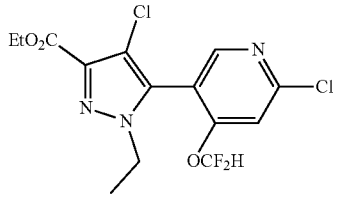

Sulfuryl chloride (35.1 g, 260 mmol) was added dropwise to solution of ethyl 5-(6-chloro-4-(difluoromethoxy)pyridin-3-yl)-1-ethyl-1H-pyrazole-3-carboxylate (45.0 g, 118 mmol, Intermediate 55) in DCM (450 mL), and the resulting mixture was stirred at rt until the reaction went to completion. The mixture was then cooled in an ice bath, and a saturated aqueous NaHCO₃ solution was added at a rate that maintained the internal temperature at 5-15° C. The pH of the aqueous layer was then adjusted to pH 7, and the layers were separated. The organic layer was washed with a saturated aqueous NaHCO₃ solution, the layers were separated, and the aqueous layer was back-extracted with DCM. The organic layers were combined, washed with water, and then concentrated. The concentrate was then slurried with heptane, filtered, and the filter cake was dried by aspiration to afford the title compound as an off-white solid.

Intermediate 57

Ethyl 4-chloro-1-ethyl-5-(4-methyl-6-((2,2,3,3,3-pentafluoropropyl)amino)pyridin-3-yl)-1H-pyrazole-3-carboxylate

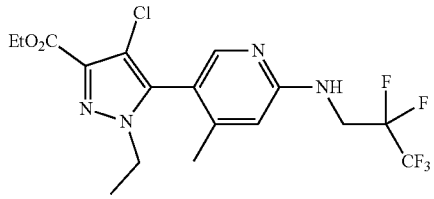 [SMILES: CCOC(=O)c1nn(CC)c(-c2cnc(NCC(F)(F)C(F)(F)F)cc2C)c1Cl]

Ethyl 4-chloro-5-(6-chloro-4-methylpyridin-3-yl)-1-ethyl-1H-pyrazole-3-carboxylate (150 mg, 0.456 mmol, Intermediate 37), RuPhos G1 precatalyst (19 mg, 0.023 mmol), RuPhos (11 mg, 0.023 mmol), and Cs₂CO₃ (0.45 g, 1.4 mmol) were combined in a vessel, and the vessel was evacuated and backfilled with nitrogen three times. 1,4-Dioxane (0.92 mL) and then 2,2,3,3,3-pentafluoropropylamine (0.15 mL, 1.4 mmol) were added, and the mixture was stirred at 110° C. for 24 h. After this time, the mixture was allowed to cool and diluted with EtOAc and water. The layers were separated, and the aqueous layer was extracted twice with EtOAc. The organic layers were combined, dried with anhydrous MgSO₄, filtered, and then concentrated. The residue was purified by silica gel chromatography (20→50% EtOAc/hexanes) to afford the title compound as a pale yellow oil.

Intermediate 58

4-Chloro-5-(4-(difluoromethoxy)-6-((4,4,4-trifluoro-2-methylbutan-2-yl)amino)pyridin-3-yl)-1-ethyl-N-(((1RS,2SR,4SR)-2-hydroxy-4-(methylsulfonyl)cyclohexyl)methyl)-1H-pyrazole-3-carboxamide

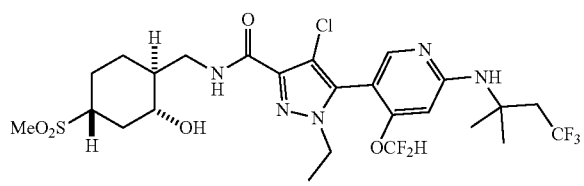

The title compound was prepared as described for the synthesis of Example 1, using ethyl 4-chloro-5-(4-(difluoromethoxy)-6-((4,4,4-trifluoro-2-methylbutan-2-yl)amino)pyridin-3-yl)-1-ethyl-1H-pyrazole-3-carboxylate (Intermediate 34) and (1RS,2SR,5RS)-2-(aminomethyl)-5-(methylsulfonyl)cyclohexan-1-ol hydrochloride (Intermediate 26) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate and (1s,4s)-1-(aminomethyl)-4-(methylsulfonyl)cyclohexanol hydrochloride.

Intermediate 59, Step a

4-Chloro-5-(4-(difluoromethoxy)pyridin-3-yl)-1-ethyl-1H-pyrazole-3-carboxylic Acid

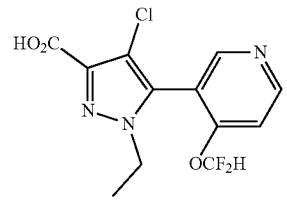

An aqueous NaOH solution (3.4 mL, 1.0 M, 3.4 mmol) was added to a solution of ethyl 4-chloro-5-(4-(difluoromethoxy)pyridin-3-yl)-1-ethyl-1H-pyrazole-3-carboxylate (300 mg, 0.84 mmol, Intermediate 32) in 1,4-dioxane (3.3 mL), and the mixture was stirred at 65° C. for 20 min. The resulting solution was allowed to cool, and its pH was adjusted to pH=4 with a 1 N aqueous HCl solution. The resulting mixture was extracted three times with EtOAc, and after each extraction the pH of the aqueous layer was readjusted to pH=4. The organic layers were combined, dried with anhydrous MgSO₄, filtered, and then concentrated to afford the title compound.

Intermediate 59, Step b

4-Chloro-5-(4-(difluoromethoxy)pyridin-3-yl)-1-ethyl-N-(((1r,4r)-4-(methylsulfonyl)cyclohexyl)methyl)-1H-pyrazole-3-carboxamide

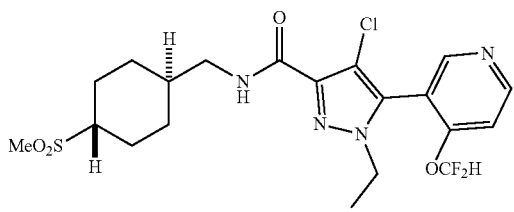

4-Chloro-5-(4-(difluoromethoxy)pyridin-3-yl)-1-ethyl-1H-pyrazole-3-carboxylic acid (146 mg, 91% w/w, 0.418 mmol, Intermediate 59, Step a), ((1r,4r)-4-(methyl sulfonyl)cyclohexyl)methanamine hydrochloride (95 mg, 0.42 mmol, Intermediate 13), and HOBt (57 mg, 0.42 mmol) were diluted with MeCN (0.84 mL) before DIPEA (0.16 mL, 0.92 mmol) and then EDCI (80 mg, 0.42 mmol) were added, and the mixture was stirred at rt for 20 h. The resulting suspension was diluted with EtOAc and water, the layers were separated, and the aqueous layer was extracted with EtOAc. The organic layers were combined, washed with brine, dried with anhydrous MgSO₄, filtered, and then concentrated. The residue was purified by silica gel chromatography (30→100% acetone/hexanes) to afford the title compound as a colorless film.

Intermediate 60

3-(4-Chloro-1-ethyl-3-(((((1r,4r)-4-(methylsulfonyl)cyclohexyl)methyl)carbamoyl)-1H-pyrazol-5-yl)-4-(difluoromethoxy)pyridine 1-oxide

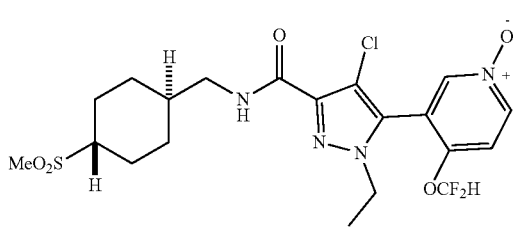

The title compound was prepared as described for the synthesis of Intermediate 33, using 4-chloro-5-(4-(difluoromethoxy)pyridin-3-yl)-1-ethyl-N-(((1r,4r)-4-(methylsulfonyl)cyclohexyl)methyl)-1H-pyrazole-3-carboxamide (Intermediate 59, Step b) in place of ethyl 4-chloro-5-(4-(difluoromethoxy)pyridin-3-yl)-1-ethyl-1H-pyrazole-3-carboxylate.

Intermediate 61

3,3,4,4,4-Pentafluoro-2-methylbutan-2-amine (Solution in α,α,α-Trifluorotoluene)

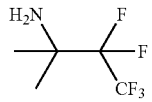

A mixture of anhydrous CeCl₃ (15 g, 61 mmol) in THF (120 mL) was stirred at rt for 1 h. After this time, the slurry was cooled to −78° C., a solution of MeLi in Et₂O (38 mL, 1.6 M, 61 mmol) was added, and the resulting yellow mixture was stirred at −78° C. for 30 min. A solution of 2,2,3,3,3-pentafluoropropanamide (2.0 g, 12 mmol) in THF (10 mL) was then added, and the residue in the transfer vessel was washed into the reactor with additional THF (5 mL). The resulting mixture was stirred at −78° C. for 1 h before it was allowed to warm to 20° C. over 1 h. After this time, water (1.2 mL) was added, and the mixture was maintained to rt overnight. Celite® was then added and the mixture was filtered. The filter cake was washed with Et₂O, the filtrate and wash were combined, and the resulting solution was distilled under atmospheric pressure into a −78° C. receiving flask. The distillate was allowed to warm to rt, a solution of HCl in 1,4-dioxane (3.1 mL, 4.0 M, 12 mmol) was added, and the resulting mixture was concentrated. The residue was suspended in hexanes, filtered, and the solids were dried under vacuum to afford the HCl salt of the title compound as a free-flowing colorless solid. The salt (500 mg, 2.34 mmol) was dissolved in a minimum volume of water (0.2 mL) and then NaOH (120 mg, 3.0 mmol) was added. After the NaOH dissolved, the mixture was extracted with α,α,α-trifluorotoluene (2×1 mL), and the combined extracts were dried with anhydrous MgSO₄ and filtered to afford a α,α,α-trifluorotoluene solution of the title compound (1.85 mL, 17% w/w, d: 1.19 g/mL).

Intermediate 62

Phenyl 3-bromo-4-ethylpyridine-1(4H)-carboxylate

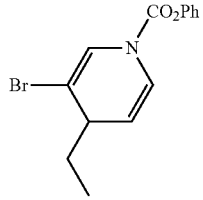

Phenyl chloroformate (9.7 mL, 77.5 mmol) was added to a −20° C. mixture of 3-bromopyridine (12.0 g, 76.0 mmol), CuI (720 mg, 3.8 mmol), and dimethyl sulfide (18 mL, 250 mmol) in THF (190 mL), and the resulting dark brown mixture was stirred for 5 min. After this time, a solution of EtMgBr in THF (38 mL, 2.0 M, 76 mmol) was added dropwise over 15 min at a rate that maintained the internal temperature at −15 to −20° C. After the addition was complete, the resulting pale yellow solution was allowed to warm to rt over 2 h. The solution was then diluted with a saturated aqueous NH₄Cl solution and Et₂O. The layers were mixed and then separated, and the organic layer was washed twice with a solution of 20% aqueous NH₄Cl and 20% aqueous NH₄OH (1:1 v/v), washed with water, washed with 10% aqueous HCl, washed with brine, and then dried with anhydrous MgSO₄. The solution was filtered and then concentrated to afford the title compound as a yellow oil, which was used directly in the next step.

Intermediate 63

3-Bromo-4-ethylpyridine

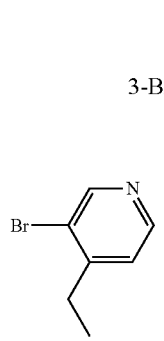

A solution of phenyl 3-bromo-4-ethylpyridine-1(4H)-carboxylate (18 g, crude from the previous step, Intermediate 62) in toluene (75 mL) was added dropwise over 20 min to a solution of o-chloranil (18.7 g, 76.0 mmol) in AcOH (50 mL), and the resulting dark red solution was maintained at rt overnight. The reaction mixture was then diluted with toluene/Et₂O (150 mL, 1:1 v/v) and 10% aqueous NaOH. Celite® was added, and the mixture was stirred for 5 min. The mixture was then filtered through Celite®. The layers of the filtrate were separated, and the organic layer was washed with 10% aqueous NaOH and then filtered again through Celite®. The layers of the filtrate were separated, and the organic layer was concentrated to a volume of ~50 mL. The concentrate was extracted 10% aqueous HCl (4×30 mL), and the combined extracts were concentrated to a volume of ~70 mL. The concentrate was made basic with 15% aqueous NaOH and then extracted three times with DCM. The organic layers were combined, dried with anhydrous MgSO₄, filtered, and then concentrated. The residue was purified by silica gel chromatography (10→30% EtOAc/hexanes) to afford the title compound as a colorless oil.

Intermediate 64

Ethyl 4-chloro-1-ethyl-5-(4-ethyl-6-((4,4,4-trifluoro-2-methylbutan-2-yl)amino)pyridin-3-yl)-1H-pyrazole-3-carboxylate

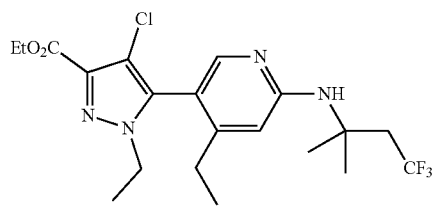 [SMILES: CCc1cc(NC(C)(C)CC(F)(F)F)ncc1-c1c(Cl)c(C(=O)O)nn1CC]

The title compound was prepared as described for the synthesis of Intermediate 34, using 3-bromo-4-ethylpyridine (Intermediate 63) in place of 3-bromo-4-(difluoromethoxy)pyridine.

Intermediate 65

4-Chloro-1-ethyl-5-(4-ethyl-6-((4,4,4-trifluoro-2-methylbutan-2-yl)amino)pyridin-3-yl)-1H-pyrazole-3-carboxylic Acid

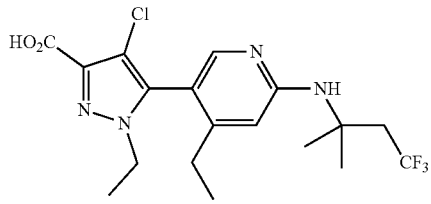

The title compound was prepared as described for the synthesis of Example 1, Step a, using ethyl 4-chloro-1-ethyl-5-(4-ethyl-6-((4,4,4-trifluoro-2-methylbutan-2-yl)amino)pyridin-3-yl)-1H-pyrazole-3-carboxylate (Intermediate 64) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate.

Intermediate 66

6-Chloro-4-methoxynicotinic Acid

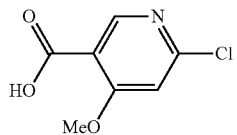 [SMILES: COc1cc(Cl)ncc1C(=O)O]

Aqueous NaOH (200 mL, 1.0 N, 200 mmol) was added to a solution of methyl 6-chloro-4-methoxynicotinate (20 g, 99 mmol) in 1,4-dioxane (250 mL). The mixture was stirred at rt for 2 h. After this time, the mixture concentrated and then diluted with water. The pH of the mixture was adjusted to pH 2 with 1 N aqueous HCl solution, and then the mixture was the then extracted twice with EtOAc. The organic layers were combined, dried with anhydrous MgSO₄, filtered, and concentrated to provide the title compound.

Intermediate 67

6-Chloro-N,4-dimethoxy-N-methylnicotinamide

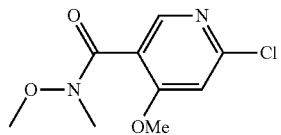

Triethylamine (7.0 mL, 51 mmol) was added to a suspension of 6-chloro-4-methoxynicotinic acid (2.615 g, 13.94 mmol, Intermediate 66) in MeCN (93 mL). N-(3-Dimethylaminopropyl)-N'-ethylcarbodiimide hydrochloride (3.74 g, 19.5 mmol), HOBt (2.64 g, 19.5 mmol), and N,O-dimethylhydroxylamine hydrochloride (2.05 g, 21.0 mmol) were added, and the resulting mixture was stirred at rt for 3 days. After this time, the mixture was concentrated, and the residue was dissolved in EtOAc and water. The layers were mixed and separated, and the aqueous layer was extracted five times with EtOAc. The organic layers were combined, dried with anhydrous MgSO$_4$, filtered, and concentrated. The residue was purified by silica gel chromatography (0→20% EtOAc/hexanes) to provide the title compound.

Intermediate 68

1-(6-Chloro-4-methoxypyridin-3-yl)ethan-1-one

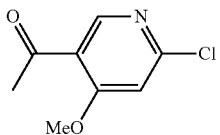

Methylmagnesium chloride (17 mL, 3.0 M in THF, 51 mmol) was added to a 0° C. solution of 6-chloro-N,4-dimethoxy-N-methylnicotinamide (8.88 g, 38.5 mmol, Intermediate 67) in THF (150 mL), and the resulting mixture was stirred at 0° C. for 3 h before it was allowed to gradually warm to rt. Upon reaching rt, the reaction was submerged in an ice bath and quenched with saturated aqueous NH$_4$Cl solution. The mixture was then diluted with water and EtOAc. The layers were separated, and the aqueous layer was extracted five times with EtOAc. The organic layers were combined, dried with anhydrous MgSO$_4$, filtered, and concentrated to provide the title compound.

Intermediate 69

Ethyl 4-(6-chloro-4-methoxypyridin-3-yl)-2,4-dioxobutanoate

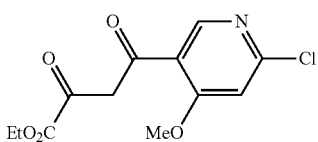

A solution of 1-(6-chloro-4-methoxypyridin-3-yl)ethan-1-one (6.84 g, 36.8 mmol, Intermediate 68) in THF (37 mL) was added to a −78° C. solution of LiHMDS (46 mL, 1.0 M in THF, 46 mmol) in THF (145 mL), and the resulting solution was stirred for 30 min. Diethyl oxalate (6.2 mL, 46 mmol) was then slowly added, and after 10 min of stirring at −78° C., the reaction mixture was allowed to warm to rt over 3 h. The mixture was then quenched with saturated aqueous NH$_4$Cl. The layers were separated, and the aqueous layer was extracted with EtOAc. The organic layers were combined, washed with brine, dried with anhydrous MgSO$_4$, filtered, and concentrated. The residue was triturated with ether, filtered, and dried by aspiration to provide the title compound.

Intermediate 70

Ethyl 5-(6-chloro-4-methoxypyridin-3-yl)-1-ethyl-1H-pyrazole-3-carboxylate

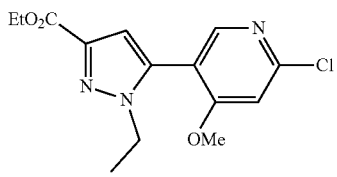 [SMILES: CCOC(=O)c1cc(-c2cnc(Cl)cc2OC)n(CC)n1]

Ethyl 4-(6-chloro-4-methoxypyridin-3-yl)-2,4-dioxobutanoate (8.81 g, 30.8 mmol, Intermediate 69), ethylhydrazine oxalate (5.26 g, 35.0 mmol), and acetic acid (100 mL) were combined and stirred at 100° C. for 2 h. After this time, the mixture was allowed to cool to rt and then concentrated. The residue was diluted with water and the mixture was cooled in an ice bath. A 6 M aqueous NaOH solution was added to neutralize the pH of the mixture, and then EtOAc was added. The layers were mixed and separated, and the aqueous layer was extracted with EtOAc. The organic layers were combined, washed with brine, dried with anhydrous MgSO$_4$, filtered, and concentrated. The residue was purified by silica gel chromatography (0→50% EtOAc/hexanes) to provide the title compound.

Intermediate 71

Ethyl 4-chloro-5-(6-chloro-4-methoxypyridin-3-yl)-1-ethyl-1H-pyrazole-3-carboxylate

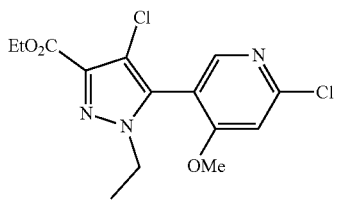 [SMILES: CCOC(=O)c1nn(CC)c(-c2cnc(Cl)cc2OC)c1Cl]

Sulfuryl dichloride (0.8 mL, 10 mmol) was added to a solution of ethyl 5-(6-chloro-4-methoxypyridin-3-yl)-1-ethyl-1H-pyrazole-3-carboxylate (2.0 g, 6.5 mmol, Intermediate 70) in DCM (30 mL), and the resulting mixture was stirred at rt overnight. After this time, the reaction was quenched with a saturated aqueous NaHCO$_3$ solution. The layers were separated and the aqueous layer was extracted with EtOAc. The organic layers were combined, dried with anhydrous MgSO$_4$, filtered, and concentrated. The residue was purified by silica gel chromatography (0→40% EtOAc/hexanes) to provide the title compound.

Intermediate 72

Ethyl 4-chloro-5-(4-(difluoromethoxy)-6-((1,1,1-trifluoro-2-methylpropan-2-yl)amino)pyridin-3-yl)-1-ethyl-1H-pyrazole-3-carboxylate

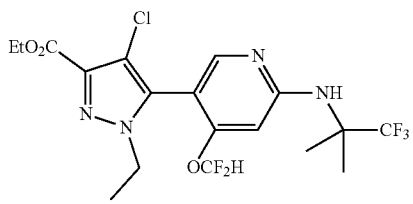

The title compound was prepared as described for the synthesis of Intermediate 34, using 1,1,1-trifluoro-2-methylpropan-2-amine in place of 4,4,4-trifluoro-2-methylbutan-2-amine.

Intermediate 73

Ethyl (R)-4-chloro-5-(4-(difluoromethoxy)-6-((1,1,1-trifluorobutan-2-yl)amino)pyridin-3-yl)-1-ethyl-1H-pyrazole-3-carboxylate

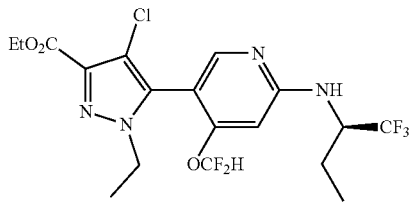

The title compound was prepared as described for the synthesis of Intermediate 34, using (R)-1,1,1-trifluorobutan-2-amine in place of 4,4,4-trifluoro-2-methylbutan-2-amine.

Intermediate 74

Ethyl (S)-4-chloro-5-(4-(difluoromethoxy)-6-((1,1,1-trifluorobutan-2-yl)amino)pyridin-3-yl)-1-ethyl-1H-pyrazole-3-carboxylate

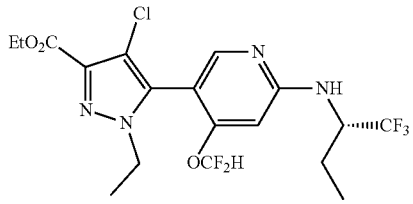

The title compound was prepared as described for the synthesis of Intermediate 34, using (S)-1,1,1-trifluorobutan-2-amine in place of 4,4,4-trifluoro-2-methylbutan-2-amine.

Intermediate 75

Ethyl (R)-4-chloro-5-(4-(difluoromethoxy)-6-((1,1,1-trifluoropropan-2-yl)amino)pyridin-3-yl)-1-ethyl-1H-pyrazole-3-carboxylate

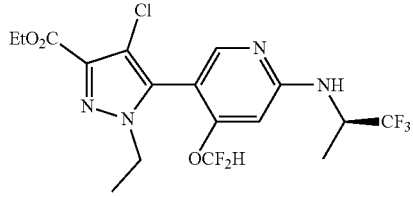

The title compound was prepared as described for the synthesis of Intermediate 34, using (R)-1,1,1-trifluoropropan-2-amine in place of 4,4,4-trifluoro-2-methylbutan-2-amine.

Intermediate 76

Ethyl 5-(6-(tert-butylamino)-4-(difluoromethoxy)pyridin-3-yl)-4-chloro-1-ethyl-1H-pyrazole-3-carboxylate

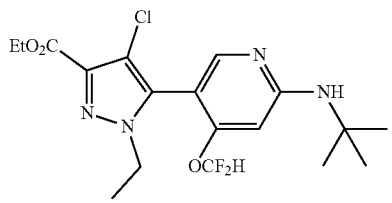

The title compound was prepared as described for the synthesis of Intermediate 34, using 2-methylpropan-2-amine in place of 4,4,4-trifluoro-2-methylbutan-2-amine.

Intermediate 77

Ethyl 4-chloro-5-(4-(difluoromethoxy)-6-((1,1,1-trifluoro-3-methylbutan-2-yl)amino)pyridin-3-yl)-1-ethyl-1H-pyrazole-3-carboxylate

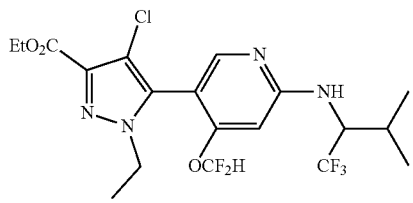

The title compound was prepared as described for the synthesis of Intermediate 34, using 1,1,1-trifluoro-3-methylbutan-2-amine in place of 4,4,4-trifluoro-2-methylbutan-2-amine.

Intermediate 78

Ethyl 4-chloro-5-(4-(difluoromethoxy)-6-(neopentylamino)pyridin-3-yl)-1-ethyl-1H-pyrazole-3-carboxylate

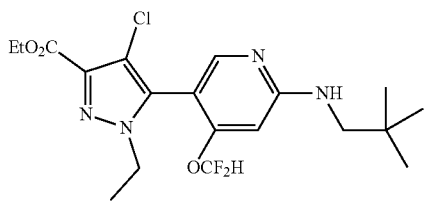

Diisopropylethylamine (0.048 mL, 0.28 mmol), PyBroP® (46 mg, 0.099 mmol), and then 2,2-dimethylpropan-1-amine (0.025 mL, 0.21 mmol) were added to a solution of 3-(4-chloro-3-(ethoxycarbonyl)-1-ethyl-1H-pyrazol-5-yl)-4-(difluoromethoxy)pyridine 1-oxide (27 mg, 0.074 mmol, Intermediate 33) in DCM (0.5 mL), and the resulting mixture was stirred at rt for 18 h. After this time, the mixture was diluted with DCM and washed with a saturated aqueous NaHCO₃ solution. The organic layer was dried with anhydrous MgSO₄, filtered, and then concentrated. The residue was purified by silica gel chromatography (10→50% EtOAc/hexanes) to afford the title compound as a colorless film.

Intermediate 79

4-Chloro-5-(6-chloro-4-methoxypyridin-3-yl)-1-ethyl-N-(((1s,4s)-1-hydroxy-4-(methylsulfonyl)cyclohexyl)methyl)-1H-pyrazole-3-carboxamide

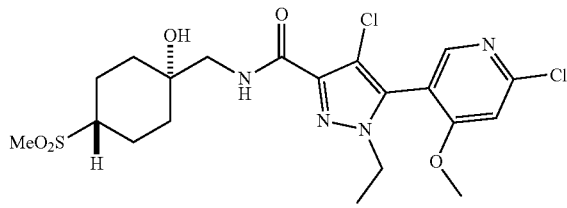 [SMILES: CCn1nc(C(=O)NC[C@]2(O)CC[C@@H](S(C)(=O)=O)CC2)c(Cl)c1-c1cnc(Cl)cc1OC]

The title compound was prepared as described for the synthesis of Intermediate 87, using (1s,4s)-1-(aminomethyl)-4-(methyl sulfonyl)cyclohexan-1-ol hydrochloride (Intermediate 9) in place of ((1r,4r)-4-(methyl sulfonyl)cyclohexyl)methanamine hydrochloride.

Intermediate 80

4-Chloro-5-(6-chloro-4-(trifluoromethyl)pyridin-3-yl)-1-ethyl-N-(((1s,4s)-1-hydroxy-4-(methylsulfonyl)cyclohexyl)methyl)-1H-pyrazole-3-carboxamide

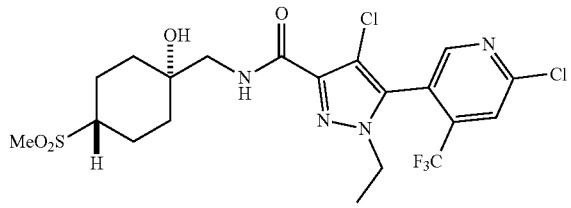 [SMILES: CCn1nc(C(=O)NC[C@]2(O)CC[C@@H](S(C)(=O)=O)CC2)c(Cl)c1-c1cnc(Cl)cc1C(F)(F)F]

The title compound was prepared as described for the synthesis of Example 1, using ethyl 4-chloro-5-(6-chloro-4-(trifluoromethyl)pyridin-3-yl)-1-ethyl-1H-pyrazole-3-carboxylate (Intermediate 51) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate.

Intermediate 81

4-Chloro-5-(6-chloro-4-(trifluoromethyl)pyridin-3-yl)-1-ethyl-N-(((1r,4r)-4-(methylsulfonyl)cyclohexyl)methyl)-1H-pyrazole-3-carboxamide

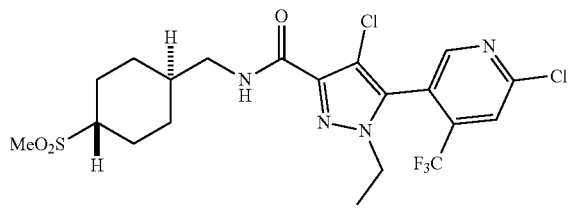 [SMILES: CCn1nc(C(=O)NC[C@H]2CC[C@H](S(C)(=O)=O)CC2)c(Cl)c1-c1cnc(Cl)cc1C(F)(F)F]

The title compound was prepared as described for the synthesis of Example 1, using ethyl 4-chloro-5-(6-chloro-4-(trifluoromethyl)pyridin-3-yl)-1-ethyl-1H-pyrazole-3-carboxylate (Intermediate 51) and ((1r,4r)-4-(methylsulfonyl)cyclohexyl)methanamine hydrochloride (Intermediate 13) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate and (1s,4s)-1-(aminomethyl)-4-(methylsulfonyl)cyclohexanol hydrochloride.

Intermediate 82

Ethyl 4-chloro-5-(4-(difluoromethoxy)-6-((4,4,4-trifluorobutan-2-yl)amino)pyridin-3-yl)-1-ethyl-1H-pyrazole-3-carboxylate

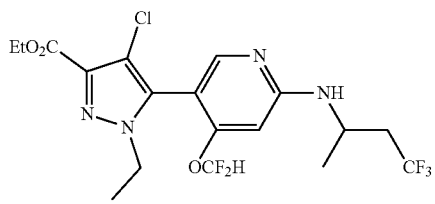

The title compound was prepared as described for the synthesis of Example 34, using 4,4,4-trifluorobutan-2-amine in place of 4,4,4-trifluorobutan-1-amine and ethyl 4-chloro-5-(6-chloro-4-(difluoromethoxy)pyridin-3-yl)-1-ethyl-1H-pyrazole-3-carboxylate (Intermediate 56) in place of 4-chloro-5-(6-chloro-4-methoxypyridin-3-yl)-1-ethyl-N-(((1r,4r)-4-(methyl sulfonyl)cyclohexyl)methyl)-1H-pyrazole-3-carboxamide.

Intermediate 83

Ethyl 4-chloro-5-(4-(difluoromethoxy)-6-((1,1,1-trifluoropentan-3-yl)amino)pyridin-3-yl)-1-ethyl-1H-pyrazole-3-carboxylate

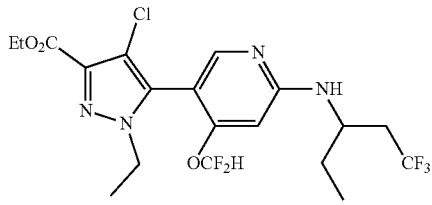

The title compound was prepared as described for the synthesis of Example 34, using 1,1,1-trifluoropentan-3-amine hydrochloride in place of 4,4,4-trifluorobutan-1-amine and ethyl 4-chloro-5-(6-chloro-4-(difluoromethoxy)pyridin-3-yl)-1-ethyl-1H-pyrazole-3-carboxylate (Intermediate 56) in place of 4-chloro-5-(6-chloro-4-methoxypyridin-3-yl)-1-ethyl-N-(((1r,4r)-4-(methylsulfonyl)cyclohexyl)methyl)-1H-pyrazole-3-carboxamide.

Intermediate 84

Ethyl 4-chloro-5-(6-((1-cyclopropyl-3,3,3-trifluoropropyl)amino)-4-(difluoromethoxy)pyridin-3-yl)-1-ethyl-1H-pyrazole-3-carboxylate

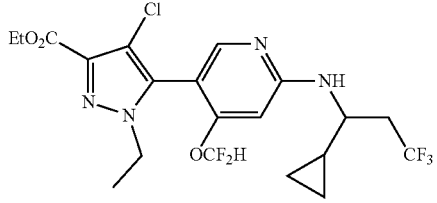

The title compound was prepared as described for the synthesis of Example 34, using 1-cyclopropyl-3,3,3-trifluoropropan-1-amine hydrochloride in place of 4,4,4-trifluorobutan-1-amine and ethyl 4-chloro-5-(6-chloro-4-(difluoromethoxy)pyridin-3-yl)-1-ethyl-1H-pyrazole-3-carboxylate (Intermediate 56) in place of 4-chloro-5-(6-chloro-4-methoxypyridin-3-yl)-1-ethyl-N-(((1r,4r)-4-(methyl sulfonyl)cyclohexyl)methyl)-1H-pyrazole-3-carboxamide.

Intermediate 85

Ethyl 4-chloro-5-(6-((1-cyclopropylpropan-2-yl)amino)-4-(difluoromethoxy)pyridin-3-yl)-1-ethyl-1H-pyrazole-3-carboxylate

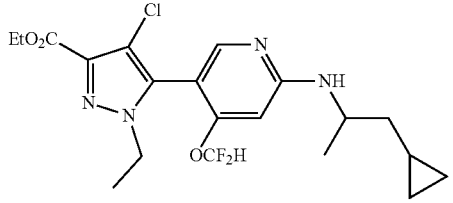

The title compound was prepared as described for the synthesis of Example 34, using 1-cyclopropylpropan-2-amine in place of 4,4,4-trifluorobutan-1-amine and ethyl 4-chloro-5-(6-chloro-4-(difluoromethoxy)pyridin-3-yl)-1-ethyl-1H-pyrazole-3-carboxylate (Intermediate 56) in place of 4-chloro-5-(6-chloro-4-methoxypyridin-3-yl)-1-ethyl-N-(((1r,4r)-4-(methylsulfonyl)cyclohexyl)methyl)-1H-pyrazole-3-carboxamide.

Intermediate 86

Ethyl 4-chloro-5-(6-((1-cyclopropyl-2-methylpropan-2-yl)amino)-4-(difluoromethoxy)pyridin-3-yl)-1-ethyl-1H-pyrazole-3-carboxylate

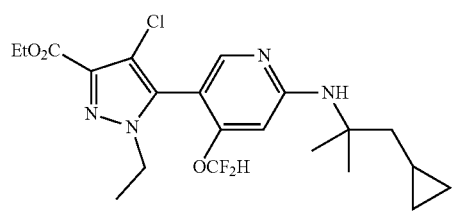

The title compound was prepared as described for the synthesis of Example 34, using 1-cyclopropyl-2-methylpropan-2-amine hydrochloride in place of 4,4,4-trifluorobutan-1-amine and ethyl 4-chloro-5-(6-chloro-4-(difluoromethoxy)pyridin-3-yl)-1-ethyl-1H-pyrazole-3-carboxylate (Intermediate 56) in place of 4-chloro-5-(6-chloro-4-methoxypyridin-3-yl)-1-ethyl-N-(((1r,4r)-4-(methyl sulfonyl)cyclohexyl)methyl)-1H-pyrazole-3-carboxamide.

Intermediate 87

4-Chloro-5-(6-chloro-4-methoxypyridin-3-yl)-1-ethyl-N-(((1r,4r)-4-(methylsulfonyl)cyclohexyl)methyl)-1H-pyrazole-3-carboxamide

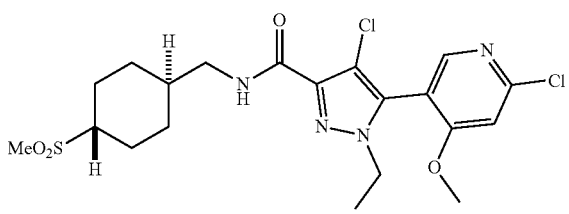 [SMILES: CCn1nc(C(=O)NC[C@H]2CC[C@H](S(C)(=O)=O)CC2)c(Cl)c1-c1cnc(Cl)cc1OC]

The title compound was prepared as described for the synthesis of Example 1, using ethyl 4-chloro-5-(6-chloro-4-methoxypyridin-3-yl)-1-ethyl-1H-pyrazole-3-carboxylate (Intermediate 71) and ((1r,4r)-4-(methylsulfonyl)cyclohexyl)methanamine hydrochloride (Intermediate 13) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate and (1s,4s)-1-(aminomethyl)-4-(methylsulfonyl)cyclohexanol hydrochloride.

Intermediate 88

4-Chloro-5-(6-chloro-4-methylpyridin-3-yl)-1-ethyl-N-(((1s,4s)-1-hydroxy-4-(methylsulfonyl)cyclohexyl)methyl)-1H-pyrazole-3-carboxamide

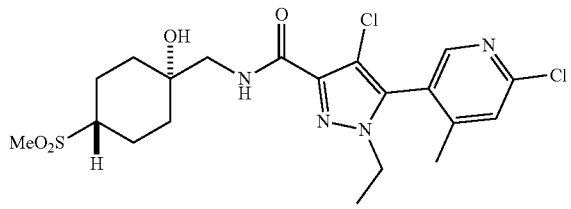 [SMILES: CCn1nc(C(=O)NC[C@]2(O)CC[C@@H](S(C)(=O)=O)CC2)c(Cl)c1-c1cnc(Cl)cc1C]

The title compound was prepared as described for the synthesis of Example 1, using ethyl 4-chloro-5-(6-chloro-4-methylpyridin-3-yl)-1-ethyl-1H-pyrazole-3-carboxylate (Intermediate 37) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate.

Intermediate 89

4-Chloro-1-ethyl-5-(4-methoxy-6-(((4-(trifluoromethyl)cyclohexyl)methyl)amino)pyridin-3-yl)-N-(((1r,4r)-4-(methylsulfonyl)cyclohexyl)methyl)-1H-pyrazole-3-carboxamide

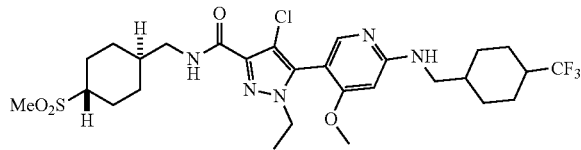 [SMILES: CCn1nc(C(=O)NC[C@H]2CC[C@H](S(C)(=O)=O)CC2)c(Cl)c1-c1cnc(NCC2CCC(C(F)(F)F)CC2)cc1OC]

The title compound was prepared as described for the synthesis of Example 34, using (4-(trifluoromethyl)cyclohexyl)methanamine in place of 4,4,4-trifluorobutan-1-amine.

Intermediate 90

4-Chloro-5-(6-((2,2-difluorocyclohexyl)amino)-4-methoxypyridin-3-yl)-1-ethyl-N-(((1r,4r)-4-(methylsulfonyl)cyclohexyl)methyl)-1H-pyrazole-3-carboxamide

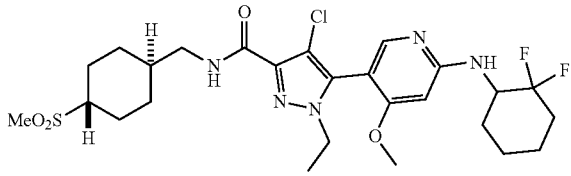

The title compound was prepared as described for the synthesis of Example 34, using 2,2-difluorocyclohexan-1-amine hydrochloride in place of 4,4,4-trifluorobutan-1-amine.

Intermediate 91

1-Ethyl-5-(4-methoxy-6-(((4-(trifluoromethyl)cyclohexyl)methyl)amino)pyridin-3-yl)-4-methyl-N-(((1r,4r)-4-(methylsulfonyl)cyclohexyl)methyl)-1H-pyrazole-3-carboxamide

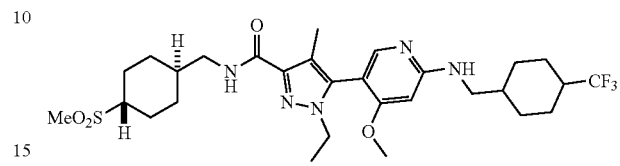

The title compound was prepared as described for the synthesis of Example 43, using 4-chloro-1-ethyl-5-(4-methoxy-6-(((4-(trifluoromethyl)cyclohexyl)methyl)amino)pyridin-3-yl)-N-(((1r,4r)-4-(methyl sulfonyl)cyclohexyl)methyl)-1H-pyrazole-3-carboxamide (Intermediate 89) in place of 4-chloro-1-ethyl-5-(4-methoxy-6-((2-(2,2,2-trifluoroethoxy)ethyl)amino)pyridin-3-yl)-N-(((1r,4r)-4-(methylsulfonyl)cyclohexyl)methyl)-1H-pyrazole-3-carboxamide.

Intermediate 92

4-Chloro-5-(6-((3,3-difluorocyclopentyl)amino)-4-methoxypyridin-3-yl)-1-ethyl-N-(((1r,4r)-4-(methylsulfonyl)cyclohexyl)methyl)-1H-pyrazole-3-carboxamide

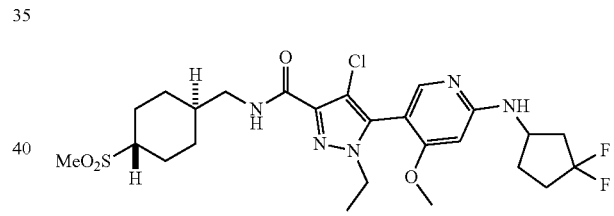

The title compound was prepared as described for the synthesis of Example 34, using 3,3-difluorocyclopentan-1-amine hydrochloride in place of 4,4,4-trifluorobutan-1-amine.

Intermediate 93

4-Chloro-5-(6-((2,2-difluorocyclopentyl)amino)-4-methoxypyridin-3-yl)-1-ethyl-N-(((1r,4r)-4-(methylsulfonyl)cyclohexyl)methyl)-1H-pyrazole-3-carboxamide

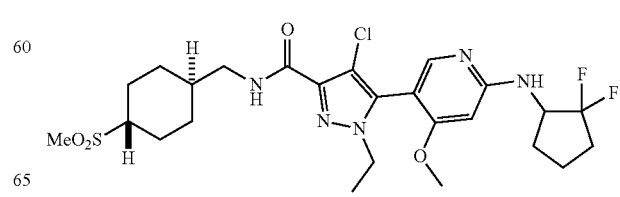

The title compound was prepared as described for the synthesis of Example 34, using 2,2-difluorocyclopentan-1-amine hydrochloride in place of 4,4,4-trifluorobutan-1-amine.

Intermediate 94

4-Chloro-1-ethyl-5-(4-methoxy-6-((2-(trifluoromethyl)cyclohexyl)amino)pyridin-3-yl)-N-(((1r,4r)-4-(methylsulfonyl)cyclohexyl)methyl)-1H-pyrazole-3-carboxamide

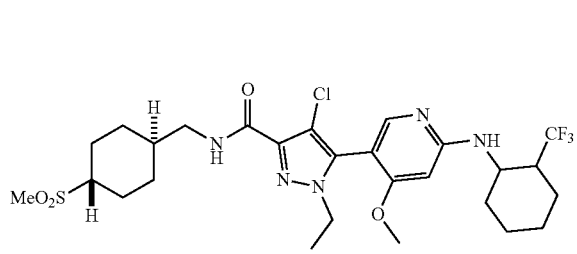 [SMILES: CCn1nc(C(=O)NC[C@H]2CC[C@H](S(C)(=O)=O)CC2)c(Cl)c1-c1cnc(NC2CCCCC2C(F)(F)F)cc1OC]

The title compound was prepared as described for the synthesis of Example 34, using 2-(trifluoromethyl)cyclohexan-1-amine in place of 4,4,4-trifluorobutan-1-amine.

Intermediate 95

4-Chloro-1-ethyl-5-(4-methoxy-6-((3-(trifluoromethyl)cyclohexyl)amino)pyridin-3-yl)-N-(((1r,4r)-4-(methylsulfonyl)cyclohexyl)methyl)-1H-pyrazole-3-carboxamide

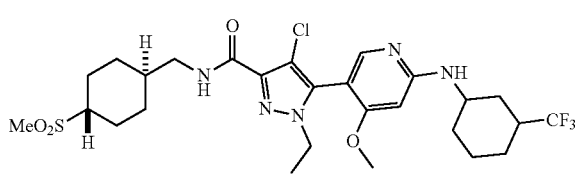 [SMILES: CCn1nc(C(=O)NC[C@H]2CC[C@H](S(C)(=O)=O)CC2)c(Cl)c1-c1cnc(NC2CCCC(C(F)(F)F)C2)cc1OC]

The title compound was prepared as described for the synthesis of Example 34, using 3-(trifluoromethyl)cyclohexan-1-amine in place of 4,4,4-trifluorobutan-1-amine.

Intermediate 96

3-Bromo-4-(difluoromethyl)pyridine

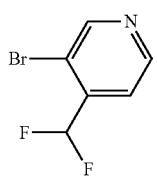

Deoxo-Fluor® (5.9 mL, 32 mmol) was added to a 0° C. solution of 3-bromopyridine-4-carboxaldehyde (3.0 g, 16 mmol) in DCM (70 mL). After stirring for 3 h at 0° C., a saturated aqueous NaHCO$_3$ solution was added, and the mixture was allowed to warm to rt. The layers were separated, and the aqueous layers was extracted with DCM. The organics were combined, dried over Na$_2$SO$_4$, filtered, and concentrated. The residue was purified by silica gel chromatography (EtOAc/hexanes) to provide the title compound.

Intermediate 97

Ethyl 4-chloro-5-(4-(difluoromethyl)-6-((4,4,4-trifluoro-2-methylbutan-2-yl)amino)pyridin-3-yl)-1-ethyl-1H-pyrazole-3-carboxylate

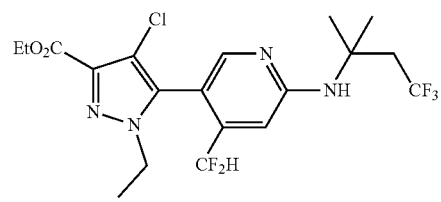 [SMILES: CCOC(=O)c1nn(CC)c(-c2cnc(NC(C)(C)CC(F)(F)F)cc2C(F)F)c1Cl]

The title compound was prepared as described for Intermediate 34, using 3-bromo-4-(difluoromethyl)pyridine (Intermediate 96) in place of 3-bromo-4-(difluoromethoxy)pyridine.

Intermediate 98

Ethyl (R)-4-chloro-1-ethyl-5-(4-methoxy-6-((1,1,1-trifluoropropan-2-yl)amino)pyridin-3-yl)-1H-pyrazole-3-carboxylate

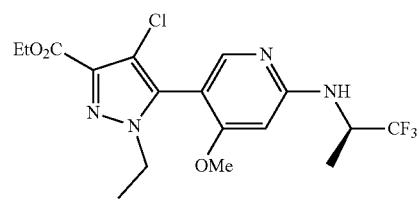 [SMILES: CCOC(=O)c1nn(CC)c(-c2cnc(N[C@H](C)C(F)(F)F)cc2OC)c1Cl]

The title compound was prepared as described for the synthesis of Intermediate 57, using ethyl 4-chloro-5-(6-chloro-4-methoxypyridin-3-yl)-1-ethyl-1H-pyrazole-3-carboxylate (Intermediate 71) and (R)-1,1,1-trifluoropropan-2-amine in place of ethyl 4-chloro-5-(6-chloro-4-methylpyridin-3-yl)-1-ethyl-1H-pyrazole-3-carboxylate and 2,2,3,3,3-pentafluoropropylamine.

Example 1, Step a 5-(4-(Difluoromethoxy)-6-((4,4,4-trifluoro-2-methylbutan-2-yl)amino)pyridin-3-yl)-1-ethyl-4-methyl-1H-pyrazole-3-carboxylic Acid

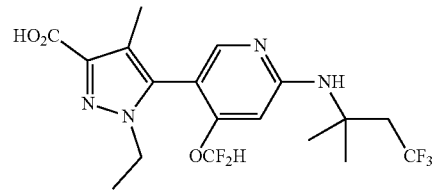

An aqueous NaOH solution (0.61 mL, 1.0 M, 0.61 mmol) was added to a solution of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate (71 mg, 0.15 mmol, Intermediate 35) in 1,4-dioxane (0.61 mL), and the mixture was stirred at rt for 16 h. The pH of the resulting solution was adjusted to pH=4 with a 1 N aqueous HCl solution. The mixture was extracted three times with EtOAc, and after each extraction the pH of the aqueous layer was readjusted to pH=4. The organic layers were combined, dried with anhydrous MgSO$_4$, filtered, and then concentrated to afford the title compound as a pale yellow film.

Example 1, Step b 5-(4-(Difluoromethoxy)-6-((4,4,4-trifluoro-2-methylbutan-2-yl)amino)pyridin-3-yl)-1-ethyl-N-(((1s,4s)-1-hydroxy-4-(methylsulfonyl)cyclohexyl)methyl)-4-methyl-1H-pyrazole-3-carboxamide

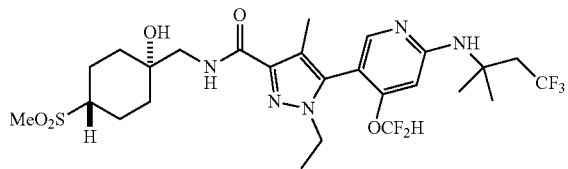

5-(4-(Difluoromethoxy)-6-((4,4,4-trifluoro-2-methylbutan-2-yl)amino)pyridin-3-yl)-1-ethyl-4-methyl-1H-pyrazole-3-carboxylic acid (37 mg, 0.077 mmol, 91 wt %, Example 1, Step a) and (1s,4s)-1-(aminomethyl)-4-(methylsulfonyl)cyclohexanol hydrochloride (21 mg, 0.085 mmol, Intermediate 9) were diluted with DMF (0.4 mL), and then DIPEA (0.031 mL, 0.18 mmol) and HATU (29 mg, 0.077 mmol) were added, and the mixture was stirred at rt for 1 h. After this time, the resulting solution was diluted with MeOH, filtered, and then purified by preparative HPLC (Inersil ODS-3, 5→95% MeCN/water, 0.05% TFA) to afford the title compound as a colorless solid. $^1$H NMR (500 MHz, CDCl$_3$) δ 7.83 (s, 1H), 7.35 (t, J=6.3 Hz, 1H), 6.79-6.48 (m, 1H), 6.69 (s, 1H), 5.60 (br s, 2H), 4.02-3.86 (m, 2H), 3.53-3.37 (m, 2H), 2.87-2.77 (m, 1H), 2.83 (s, 3H), 2.66 (q, J=10.8 Hz, 2H), 2.18-2.09 (m, 2H), 2.15 (s, 3H), 2.03-1.92 (m, 4H), 1.67 (s, 6H), 1.47-1.35 (m, 5H). MS (ESI) m/z: [M+H]$^+$. Found 626.2.

Example 2

4-Chloro-1-ethyl-5-(4-methyl-6-((2,2,3,3,3-pentafluoropropyl)amino)pyridin-3-yl)-N-(((1r,4r)-4-(methylsulfonyl)cyclohexyl)methyl)-1H-pyrazole-3-carboxamide

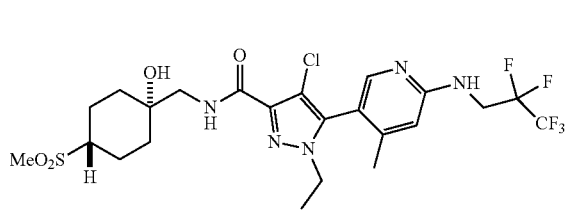 [SMILES: CCn1nc(C(=O)NC[C@]2(O)CC[C@@H](S(C)(=O)=O)CC2)c(Cl)c1-c1cnc(NCC(F)(F)C(F)(F)F)cc1C]

The title compound was prepared as described for the synthesis of Example 1, using ethyl 4-chloro-1-ethyl-5-(4-methyl-6-((2,2,3,3,3-pentafluoropropyl)amino)pyridin-3-yl)-1H-pyrazole-3-carboxylate (Intermediate 57) and ((1r,4r)-4-(methylsulfonyl)cyclohexyl)methanamine hydrochloride (Intermediate 13) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate and (1s,4s)-1-(aminomethyl)-4-(methylsulfonyl)cyclohexanol hydrochloride. $^1$H NMR (500 MHz, CDCl$_3$) δ 10.27 (s, 1H), 7.78 (s, 1H), 6.94 (t, J=6.4 Hz, 1H), 6.79 (s, 1H), 4.10-3.89 (m, 4H), 3.40-3.29 (m, 2H), 2.88-2.80 (m, 1H), 2.83 (s, 3H), 2.32-2.24 (m, 2H), 2.26 (s, 3H), 2.11-2.04 (m, 2H), 1.74-1.64 (m, 1H), 1.60 (qd, J=13.1, 3.7 Hz, 2H), 1.38 (t, J=7.2 Hz, 3H), 1.14 (qd, J=13.3, 3.5 Hz, 2H). MS (ESI) m/z: [M+H]$^+$. Found 586.2.

Example 3

4-Chloro-1-ethyl-N-(((1s,4s)-1-hydroxy-4-(methylsulfonyl)cyclohexyl)methyl)-5-(4-methyl-6-((2,2,3,3,3-pentafluoropropyl)amino)pyridin-3-yl)-1H-pyrazole-3-carboxamide

The title compound was prepared as described for the synthesis of Example 1, using ethyl 4-chloro-1-ethyl-5-(4-methyl-6-((2,2,3,3,3-pentafluoropropyl)amino)pyridin-3-yl)-1H-pyrazole-3-carboxylate (Intermediate 57) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate. $^1$H NMR (500 MHz, CDCl$_3$) δ 10.46 (s, 1H), 7.79 (s, 1H), 7.24 (t, J=6.4 Hz, 1H), 6.81 (s, 1H), 4.10-3.90 (m, 4H), 3.53-3.42 (m, 2H), 3.34 (br s, 1H), 2.86-2.78 (m, 1H), 2.84 (s, 3H), 2.27 (s, 3H), 2.16-2.09 (m, 2H), 2.03-1.92 (m, 4H), 1.46 (td, J=13.8, 3.6 Hz, 2H), 1.39 (t, J=7.2 Hz, 3H). MS (ESI) m/z: [M+H]$^+$. Found 602.2.

Example 4

4-Chloro-1-ethyl-N-(((1s,4s)-1-hydroxy-4-(methylsulfonyl)cyclohexyl)methyl)-5-(4-methyl-6-((1,1,1-trifluoro-2-methylpropan-2-yl)amino)pyridin-3-yl)-1H-pyrazole-3-carboxamide

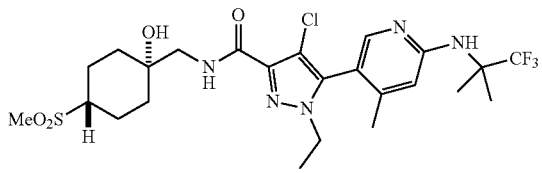 [SMILES: CCn1nc(C(=O)NC[C@]2(O)CC[C@@H](S(C)(=O)=O)CC2)c(Cl)c1-c1cnc(NC(C)(C)C(F)(F)F)cc1C]

The title compound was prepared as described for the synthesis of Intermediate 57, using 4-chloro-5-(6-chloro-4-methylpyridin-3-yl)-1-ethyl-N-(((1s,4s)-1-hydroxy-4-

(methyl sulfonyl)cyclohexyl)methyl)-1H-pyrazole-3-carboxamide (Intermediate 88) and 1,1,1-trifluoro-2-methylpropan-2-amine in place of ethyl 4-chloro-5-(6-chloro-4-methylpyridin-3-yl)-1-ethyl-1H-pyrazole-3-carboxylate and 2,2,3,3,3-pentafluoropropylamine. ¹H NMR (500 MHz, CDCl₃) δ 7.87 (s, 1H), 7.24 (t, J=6.5 Hz, 1H), 6.52 (s, 1H), 4.70 (s, 1H), 4.05-3.89 (m, 2H), 3.51-3.43 (m, 2H), 3.06 (s, 1H), 2.84-2.77 (m, 1H), 2.83 (s, 3H), 2.16-2.10 (m, 2H), 2.06 (s, 3H), 2.03-1.93 (m, 4H), 1.70 (s, 3H), 1.69 (s, 3H), 1.47-1.40 (m, 2H), 1.34 (t, J=7.2 Hz, 3H). MS (ESI) m/z: [M+H]⁺. Found 580.2.

Example 5

4-Chloro-5-(4-(difluoromethoxy)-6-((4,4,4-trifluoro-2-methylbutan-2-yl)amino)pyridin-3-yl)-1-ethyl-N-(((1r,4r)-4-(methylsulfonyl)cyclohexyl)methyl)-1H-pyrazole-3-carboxamide

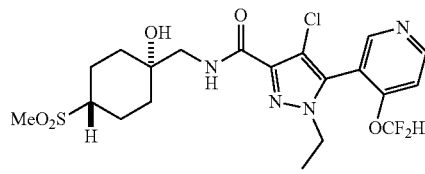

The title compound was prepared as described for the synthesis of Example 1, using ethyl 4-chloro-5-(4-(difluoromethoxy)-6-((4,4,4-trifluoro-2-methylbutan-2-yl)amino)pyridin-3-yl)-1-ethyl-1H-pyrazole-3-carboxylate (Intermediate 34) and ((1r,4r)-4-(methylsulfonyl)cyclohexyl)methanamine hydrochloride (Intermediate 13) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate and (1s,4s)-1-(aminomethyl)-4-(methylsulfonyl)cyclohexanol hydrochloride. ¹H NMR (500 MHz, CDCl₃) δ 8.21 (br s, 1H), 7.90 (s, 1H), 6.96 (t, J=6.4 Hz, 1H), 6.79-6.46 (m, 1H), 6.55 (s, 1H), 4.07-3.92 (m, 2H), 3.40-3.29 (m, 2H), 2.87-2.80 (m, 1H), 2.83 (s, 3H), 2.80-2.65 (m, 2H), 2.31-2.25 (m, 2H), 2.10-2.03 (m, 2H), 1.74-1.54 (m, 9H), 1.41 (t, J=7.2 Hz, 3H), 1.14 (qd, J=13.2, 3.5 Hz, 2H). MS (ESI) m/z: [M+H]⁺. Found 630.1.

Example 6

4-Chloro-5-(4-(difluoromethoxy)-6-((4,4,4-trifluoro-2-methylbutan-2-yl)amino)pyridin-3-yl)-N-(((1S*,2S*,4S*)-1,2-dihydroxy-4-(methylsulfonyl)cyclohexyl)methyl)-1-ethyl-1H-pyrazole-3-carboxamide

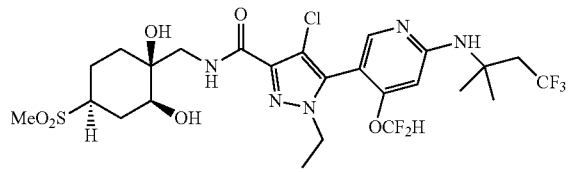

The title compound was prepared as described for the synthesis of Example 1, using ethyl 4-chloro-5-(4-(difluoromethoxy)-6-((4,4,4-trifluoro-2-methylbutan-2-yl)amino)pyridin-3-yl)-1-ethyl-1H-pyrazole-3-carboxylate (Intermediate 34) and (1S*,2S*,4S*)-1-(aminomethyl)-4-(methylsulfonyl)cyclohexane-1,2-diol hydrochloride (Intermediate 24) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate and (1s,4s)-1-(aminomethyl)-4-(methylsulfonyl)cyclohexanol hydrochloride. ¹H NMR (500 MHz, CDCl₃) δ 8.12 (br s, 1H), 7.92 (s, 1H), 7.25 (t, J=5.9 Hz, 1H), 6.79-6.46 (m, 1H), 6.54 (m, 1H), 4.09-3.93 (m, 2H), 3.87 (ddd, J=14.2, 12.6, 8.0 Hz, 1H), 3.77 (br s, 2H), 3.60 (ddd, J=11.5, 4.7, 1.5 Hz, 1H), 3.11 (td, J=13.7, 5.7 Hz, 1H), 2.88-2.66 (m, 6H), 2.30-2.22 (m, 1H), 2.09-2.02 (m, 1H), 2.01-1.87 (m, 3H), 1.66 (s, 3H), 1.65 (s, 3H), 1.57-1.48 (m, 1H), 1.42 (t, J=7.2 Hz, 3H). MS (ESI) m/z: [M+H]⁺. Found 662.2.

Example 7

4-Chloro-5-(4-(difluoromethoxy)-6-((4,4,4-trifluoro-2-methylbutan-2-yl)amino)pyridin-3-yl)-N-(((1R*,2R*,4R*)-1,2-dihydroxy-4-(methylsulfonyl)cyclohexyl)methyl)-1-ethyl-1H-pyrazole-3-carboxamide

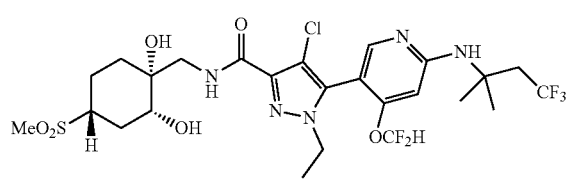

The title compound was prepared as described for the synthesis of Example 1, using ethyl 4-chloro-5-(4-(difluoromethoxy)-6-((4,4,4-trifluoro-2-methylbutan-2-yl)amino)pyridin-3-yl)-1-ethyl-1H-pyrazole-3-carboxylate (Intermediate 34) and (1R*,2R*,4R*)-1-(aminomethyl)-4-(methylsulfonyl)cyclohexane-1,2-diol hydrochloride (Intermediate 23) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate and (1s,4s)-1-(aminomethyl)-4-(methylsulfonyl)cyclohexanol hydrochloride. ¹H NMR (500 MHz, CDCl₃) δ 8.31 (br s, 1H), 7.93 (s, 1H), 7.27 (t, J=6.8 Hz, 1H), 6.80-6.48 (m, 1H), 6.56 (appar d, J=3.3 Hz, 1H), 4.81 (br s, 2H), 4.08-3.94 (m, 2H), 3.86 (ddd, J=14.2, 12.1, 8.0 Hz, 1H), 3.60 (ddd, J=11.5, 4.7, 1.8 Hz, 1H), 3.12 (ddd, J=14.1, 12.7, 5.7 Hz, 1H), 2.89-2.80 (m, 4H), 2.80-2.65 (m, 2H), 2.29-2.23 (m, 1H), 2.08-2.02 (m, 1H), 2.01-1.86 (m, 3H), 1.66 (s, 3H), 1.65 (s, 3H), 1.57-1.48 (m, 1H), 1.42 (t, J=7.2 Hz, 3H). MS (ESI) m/z: [M+H]⁺. Found 662.2.

Example 8

4-Chloro-5-(4-(difluoromethoxy)-6-((4,4,4-trifluoro-2-methylbutan-2-yl)amino)pyridin-3-yl)-1-ethyl-N-(((1R*,2S*,4S*)-2-hydroxy-4-(methylsulfonyl)cyclohexyl)methyl)-1H-pyrazole-3-carboxamide

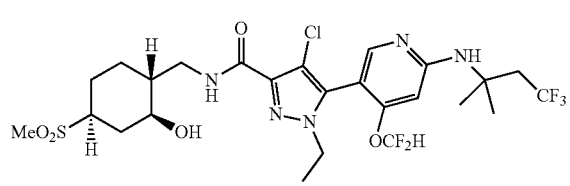

Example 9

4-Chloro-5-(4-(difluoromethoxy)-6-((4,4,4-trifluoro-2-methylbutan-2-yl)amino)pyridin-3-yl)-1-ethyl-N-(((1S*,2R*,4R*)-2-hydroxy-4-(methylsulfonyl)cyclohexyl)methyl)-1H-pyrazole-3-carboxamide

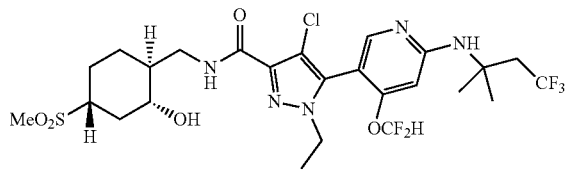

Intermediate 58 was purified by SFC using a chiral stationary phase ((S,S)-Whelk-O 1, 50% $CO_2$, 50% i-PrOH) to give a pair of enantiomers. The first-eluting isomer was Example 8, and the second-eluting isomer was Example 9. Example 8: $^1$H NMR (500 MHz, $CDCl_3$) δ 8.18-8.14 (m, 1H), 7.97 (s, 1H), 7.33 (t, J=72.2 Hz, 1H), 7.19 (s, 1H), 6.46 (s, 1H), 5.17 (d, J=5.1 Hz, 1H), 4.01-3.89 (m, 2H), 3.45-3.37 (m, 1H), 3.37-3.24 (m, 2H), 3.17-3.00 (m, 3H), 2.90 (s, 3H), 2.25-2.18 (m, 1H), 2.05-1.97 (m, 1H), 1.86 (dq, J=13.5, 3.5 Hz, 1H), 1.48 (s, 6H), 1.46-1.39 (m, 1H), 1.38-1.26 (m, 5H), 1.09 (qd, J=13.3, 3.6 Hz, 1H). MS (ESI) m/z: [M+H]$^+$. Found 646.2. Example 9: $^1$H NMR (500 MHz, $CDCl_3$) δ 8.18-8.14 (m, 1H), 7.97 (s, 1H), 7.33 (t, J=72.2 Hz, 1H), 7.19 (s, 1H), 6.46 (s, 1H), 5.17 (d, J=5.1 Hz, 1H), 4.01-3.89 (m, 2H), 3.45-3.37 (m, 1H), 3.37-3.24 (m, 2H), 3.17-3.00 (m, 3H), 2.90 (s, 3H), 2.25-2.18 (m, 1H), 2.05-1.97 (m, 1H), 1.86 (dq, J=13.5, 3.5 Hz, 1H), 1.48 (s, 6H), 1.46-1.39 (m, 1H), 1.38-1.26 (m, 5H), 1.09 (qd, J=13.3, 3.6 Hz, 1H). MS (ESI) m/z: [M+H]$^+$. Found 646.2.

Example 10

4-Chloro-5-(4-(difluoromethoxy)-6-((1,1,1,3,3,3-hexafluoropropan-2-yl)amino)pyridin-3-yl)-1-ethyl-N-(((1r,4r)-4-(methylsulfonyl)cyclohexyl)methyl)-1H-pyrazole-3-carboxamide

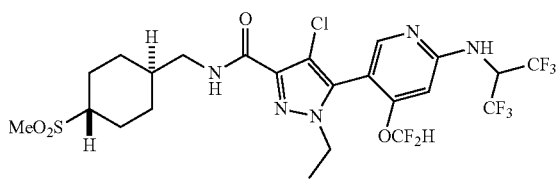

p-Toluenesulfonic anhydride (83 mg, 0.26 mmol) was added to a 0-5° C. solution of 3-(4-chloro-1-ethyl-3-((((1r,4r)-4-(methylsulfonyl)cyclohexyl)methyl)carbamoyl)-1H-pyrazol-5-yl)-4-(difluoromethoxy)pyridine 1-oxide (68 mg, 0.13 mmol, Intermediate 60) and 1,1,1,3,3,3-hexafluoropropan-2-amine (0.070 mL, 0.65 mmol) in $CHCl_3$ (0.64 mL). The resulting heterogeneous mixture was stirred at 0-5° C. for 30 min before additional $CHCl_3$ (0.7 mL) was added, and the thick mixture was allowed to warm to rt over 3 h. The mixture was then warmed to 60° C. for 1.5 h before additional 1,1,1,3,3,3-hexafluoropropan-2-amine (0.030 mL, 0.28 mmol) and then p-toluenesulfonic anhydride (22 mg, 0.067 mmol) were added, and stirring was continued at 60° C. for 15 h. After this time, the mixture was allowed to cool and was then diluted with DCM and a saturated aqueous $NaHCO_3$ solution. The layers were separated, and the aqueous layer was extracted twice with DCM. The organic layers were combined, concentrated, diluted with MeOH, filtered, and then purified by purified by preparative HPLC (XBridge C18, 30→100% MeCN/water, 0.05% TFA) to afford a colorless powder after lyophilization. This powder was purified by silica gel chromatography (40→100% EtOAc/hexanes) to afford the title compound as a colorless solid. $^1$H NMR (500 MHz, $CDCl_3$) δ 8.06 (s, 1H), 6.93 (t, J=6.2 Hz, 1H), 6.72-6.39 (m, 1H), 6.50 (s, 1H), 6.05-5.95 (m, 1H), 5.16 (d, J=10.3 Hz, 1H), 4.06-3.91 (m, 2H), 3.40-3.30 (m, 2H), 2.88-2.78 (m, 1H), 2.83 (s, 3H), 2.32-2.25 (m, 2H), 2.11-2.04 (m, 2H), 1.74-1.64 (m, 1H), 1.65-1.53 (m, 2H), 1.40 (t, J=7.2 Hz, 3H), 1.14 (qd, J=13.2, 3.6 Hz, 2H). MS (ESI) m/z: [M+H]$^+$. Found 656.2.

Example 11

4-Chloro-5-(4-(difluoromethoxy)-6-((1,1,1,3,3,3-hexafluoropropan-2-yl)amino)pyridin-3-yl)-1-ethyl-N-(((1s,4s)-1-hydroxy-4-(methylsulfonyl)cyclohexyl)methyl)-1H-pyrazole-3-carboxamide

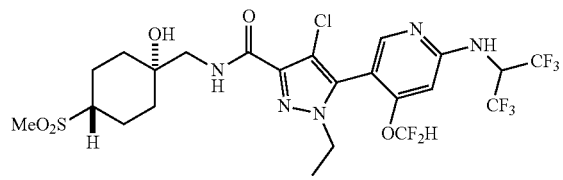

The title compound was prepared as described for the synthesis of Example 10, using (1s,4s)-1-(aminomethyl)-4-(methylsulfonyl)cyclohexan-1-ol hydrochloride (Intermediate 9) in place of ((1r,4r)-4-(methylsulfonyl)cyclohexyl)methanamine hydrochloride. $^1$H NMR (500 MHz, $CDCl_3$) δ 8.06 (s, 1H), 7.23 (t, J=6.3 Hz, 1H), 6.72-6.41 (m, 1H), 6.51 (s, 1H), 6.04-5.96 (m, 1H), 5.19 (d, J=10.3 Hz, 1H), 4.07-3.92 (m, 2H), 3.52-3.42 (m, 2H), 2.98 (s, 1H), 2.85-2.77 (m, 1H), 2.83 (s, 3H), 2.16-2.09 (m, 2H), 2.03-1.93 (m, 4H), 1.49-1.37 (m, 5H). MS (ESI) m/z: [M+H]$^+$. Found 672.1.

Example 12

5-(4-(Difluoromethoxy)-6-((4,4,4-trifluoro-2-methylbutan-2-yl)amino)pyridin-3-yl)-1-ethyl-4-methyl-N-(((1r,4r)-4-(methylsulfonyl)cyclohexyl)methyl)-1H-pyrazole-3-carboxamide

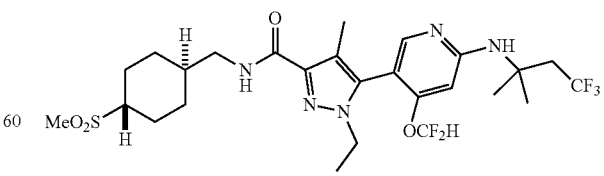

The title compound was prepared as described for the synthesis of Example 1, Step b, using ((1r,4r)-4-(methylsulfonyl)cyclohexyl)methanamine hydrochloride (Intermediate 13) in place of (1s,4s)-1-(aminomethyl)-4-(methylsulfonyl)cyclohexan-1-ol hydrochloride. $^1$H NMR (500 MHz, CDCl$_3$) δ 7.81 (s, 1H), 7.08 (t, J=6.4 Hz, 1H), 6.77-6.47 (m, 1H), 6.67 (s, 1H), 6.19 (br s, 1H), 4.01-3.86 (m, 2H), 3.37-3.27 (m, 2H), 2.87-2.80 (m, 1H), 2.83 (s, 3H), 2.67 (q, J=10.8 Hz, 2H), 2.32-2.25 (m, 2H), 2.16 (s, 3H), 2.07 (dd, J=13.6, 3.7 Hz, 2H), 1.72-1.64 (m, 1H), 1.67 (s, 6H), 1.60 (qd, J=13.0, 3.7 Hz, 2H), 1.38 (t, J=7.2 Hz, 3H), 1.13 (qd, J=13.2, 3.5 Hz, 2H). MS (ESI) m/z: [M+H]$^+$. Found 610.3.

Example 13

4-Chloro-5-(4-(difluoromethoxy)-6-((3,3,4,4,4-pentafluoro-2-methylbutan-2-yl)amino)pyridin-3-yl)-1-ethyl-N-(((1s,4s)-1-hydroxy-4-(methylsulfonyl)cyclohexyl)methyl)-1H-pyrazole-3-carboxamide

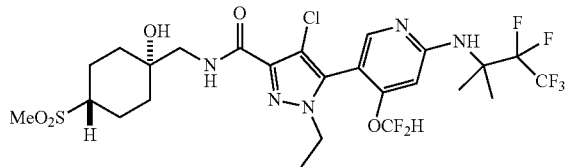

The title compound was prepared as described for the synthesis of Example 5, using 3,3,4,4,4-pentafluoro-2-methylbutan-2-amine solution (Intermediate 61) and (1s,4s)-1-(aminomethyl)-4-(methylsulfonyl)cyclohexan-1-ol hydrochloride (Intermediate 9) in place of 4,4,4-trifluoro-2-methylbutan-2-amine and ((1r,4r)-4-(methylsulfonyl)cyclohexyl)methanamine hydrochloride. $^1$H NMR (500 MHz, CDCl$_3$) δ 9.38 (s, 1H), 7.94 (s, 1H), 7.26 (t, J=6.0 Hz, 1H), 6.95 (s, 1H), 6.65 (dd, J=71.0, 69.0 Hz, 1H), 4.09-3.93 (m, 2H), 3.80 (br s, 1H), 3.54-3.41 (m, 2H), 2.86-2.78 (m, 1H), 2.84 (s, 3H), 2.17-2.08 (m, 2H), 2.02-1.91 (m, 4H), 1.77 (s, 6H), 1.50-1.39 (m, 5H). MS (ESI) m/z: [M+H]$^+$. Found 682.2.

Example 14

4-Chloro-5-(4-(difluoromethoxy)-6-((3,3,4,4,4-pentafluoro-2-methylbutan-2-yl)amino)pyridin-3-yl)-1-ethyl-N-(((1r,4r)-4-(methylsulfonyl)cyclohexyl)methyl)-1H-pyrazole-3-carboxamide

The title compound was prepared as described for the synthesis of Example 5, using 3,3,4,4,4-pentafluoro-2-methylbutan-2-amine solution (Intermediate 61) in place of 4,4,4-trifluoro-2-methylbutan-2-amine. $^1$H NMR (500 MHz, CDCl$_3$) δ 9.23 (s, 1H), 7.92 (s, 1H), 6.96 (t, J=6.4 Hz, 1H), 6.92 (s, 1H), 6.64 (dd, J=71.2, 69.1 Hz, 1H), 4.07-3.92 (m, 2H), 3.40-3.29 (m, 2H), 2.88-2.79 (m, 1H), 2.83 (s, 3H), 2.32-2.24 (m, 2H), 2.10-2.02 (m, 2H), 1.77 (s, 6H), 1.74- 1.65 (m, 1H), 1.60 (qd, J=13.0, 3.7 Hz, 2H), 1.42 (t, J=7.2 Hz, 3H), 1.14 (qd, J=13.2, 3.5 Hz, 2H). MS (ESI) m/z: [M+H]$^+$. Found 666.1.

Example 15

4-Chloro-5-(4-(difluoromethoxy)-6-((4,4,4-trifluoro-2-methylbutan-2-yl)amino)pyridin-3-yl)-1-ethyl-N-(((1s,4s)-1-hydroxy-4-(methylsulfonyl)cyclohexyl)methyl)-1H-pyrazole-3-carboxamide

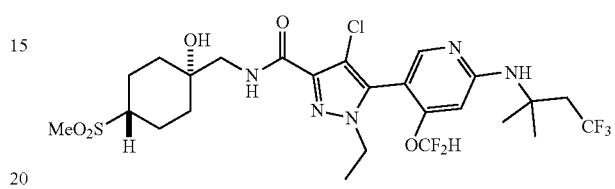

The title compound was prepared as described for the synthesis of Example 1, using ethyl 4-chloro-5-(4-(difluoromethoxy)-6-((4,4,4-trifluoro-2-methylbutan-2-yl)amino)pyridin-3-yl)-1-ethyl-1H-pyrazole-3-carboxylate (Intermediate 34) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate. $^1$H NMR (500 MHz, CDCl$_3$) δ 7.96 (s, 1H), 7.24 (t, J=6.3 Hz, 1H), 6.64-6.34 (m, 1H), 6.16 (s, 1H), 4.66 (s, 1H), 4.07-3.92 (m, 2H), 3.52-3.42 (m, 2H), 3.10 (s, 1H), 3.08-2.85 (m, 2H), 2.85-2.76 (m, 4H), 2.17-2.10 (m, 2H), 2.04-1.93 (m, 4H), 1.61-1.56 (m, 6H), 1.48-1.37 (m, 5H). MS (ESI) m/z: [M+H]$^+$. Found 646.2.

Example 16

4-Chloro-1-ethyl-N-(((1s,4s)-1-hydroxy-4-(methylsulfonyl)cyclohexyl)methyl)-5-(4-isopropyl-6-((4,4,4-trifluoro-2-methylbutan-2-yl)amino)pyridin-3-yl)-1H-pyrazole-3-carboxamide

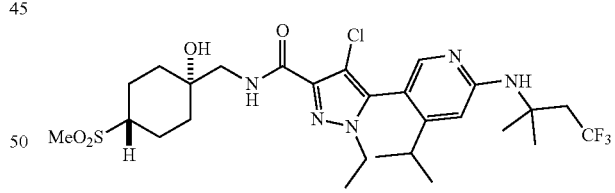

The title compound was prepared as described for the synthesis of Example 1, using ethyl 4-chloro-1-ethyl-5-(4-isopropyl-6-((4,4,4-trifluoro-2-methylbutan-2-yl)amino)pyridin-3-yl)-1H-pyrazole-3-carboxylate (Intermediate 42) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate. $^1$H NMR (500 MHz, CDCl$_3$) δ 9.56 (br s, 1H), 7.75 (s, 1H), 7.27 (t, J=6.4 Hz, 1H), 6.87 (s, 1H), 4.05-3.96 (m, 1H), 3.97 (br s, 1H), 3.96-3.88 (m, 1H), 3.54 (dd, J=14.1, 6.5 Hz, 1H), 3.44 (dd, J=14.1, 6.2 Hz, 1H), 2.87-2.79 (m, 1H), 2.85 (s, 3H), 2.73-2.61 (m, 3H), 2.17-2.10 (m, 2H), 2.04-1.92 (m, 4H), 1.70 (s, 6H), 1.51-1.41 (m, 5H), 1.25 (d, J=6.7 Hz, 3H), 1.15 (d, J=6.8 Hz, 3H). MS (ESI) m/z: [M+H]$^+$. Found 622.3.

Example 17

4-Chloro-1-ethyl-5-(4-isopropyl-6-((4,4,4-trifluoro-2-methylbutan-2-yl)amino)pyridin-3-yl)-N-(((1r,4r)-4-(methylsulfonyl)cyclohexyl)methyl)-1H-pyrazole-3-carboxamide

The title compound was prepared as described for the synthesis of Example 1, using ethyl 4-chloro-1-ethyl-5-(4-isopropyl-6-((4,4,4-trifluoro-2-methylbutan-2-yl)amino)pyridin-3-yl)-1H-pyrazole-3-carboxylate (Intermediate 42) and ((1r,4r)-4-(methylsulfonyl)cyclohexyl)methanamine hydrochloride (Intermediate 13) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate and (1s,4s)-1-(aminomethyl)-4-(methylsulfonyl)cyclohexanol hydrochloride. $^1$H NMR (500 MHz, CDCl$_3$) δ 9.68 (br s, 1H), 7.72 (s, 1H), 6.96 (t, J=6.5 Hz, 1H), 6.86 (s, 1H), 4.03-3.95 (m, 1H), 3.95-3.86 (m, 1H), 3.41-3.30 (m, 2H), 2.88-2.80 (m, 1H), 2.83 (s, 3H), 2.73-2.61 (m, 3H), 2.32-2.26 (m, 2H), 2.11-2.04 (m, 2H), 1.74-1.65 (m, 1H), 1.69 (s, 6H), 1.60 (qd, J=12.9, 3.6 Hz, 2H), 1.43 (t, J=7.2 Hz, 3H), 1.24 (d, J=6.7 Hz, 3H), 1.20-1.10 (m, 5H). MS (ESI) m/z: [M+H]$^+$. Found 606.3.

Example 18

4-Chloro-1-ethyl-5-(4-ethyl-6-((4,4,4-trifluoro-2-methylbutan-2-yl)amino)pyridin-3-yl)-N-(((1s,4s)-1-hydroxy-4-(methylsulfonyl)cyclohexyl)methyl)-1H-pyrazole-3-carboxamide

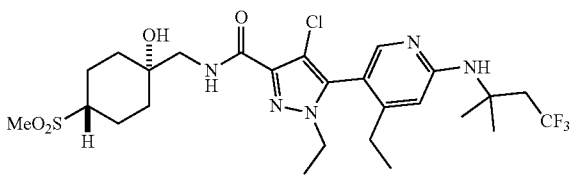 [SMILES: CCc1cc(NC(C)(C)CC(F)(F)F)ncc1-c1c(Cl)c(C(=O)NC[C@]2(O)CC[C@@H](S(C)(=O)=O)CC2)nn1CC]

N,N-Diisopropylethylamine (2.5 mL, 14 mmol) and then (1s,4s)-1-(aminomethyl)-4-(methylsulfonyl)cyclohexanol hydrochloride (1.74 g, 7.14 mmol, Intermediate 9) were added to a mixture of 4-chloro-1-ethyl-5-(4-ethyl-6-((4,4,4-trifluoro-2-methylbutan-2-yl)amino)pyridin-3-yl)-1H-pyrazole-3-carboxylic acid (2.72 g, 6.49 mmol, Intermediate 65), HOBt (920 mg, 6.8 mmol), and EDCI (1.31 g, 6.82 mmol) in MeCN (13 mL), and the mixture was stirred at rt for 19 h. After this time, the mixture was diluted with enough water to make it homogeneous, and then additional water was added until the mixture became heterogeneous again. The resulting mixture was stirred at rt for 2 h, after which time it became a thick slurry. This slurry was filtered, and the filter cake was washed with water. The filter cake was then suspended in water, stirred for 15 min, and then filtered. The filter cake was washed with water and then dried by aspiration to afford the title compound as a colorless solid. $^1$H NMR (400 MHz, CDCl$_3$) δ 7.80 (s, 1H), 7.26 (t, J=6.3 Hz, 1H), 6.31 (s, 1H), 4.51 (s, 1H), 4.03-3.85 (m, 2H), 3.53-3.42 (m, 2H), 3.16 (s, 1H), 3.12-2.98 (m, 1H), 2.94-2.76 (m, 2H), 2.83 (s, 3H), 2.37-2.22 (m, 2H), 2.17-2.09 (m, 2H), 2.05-1.92 (m, 4H), 1.58 (d, J=5.6 Hz, 6H), 1.44 (td, J=13.8, 3.7 Hz, 2H), 1.36 (t, J=7.2 Hz, 3H), 1.06 (t, J=7.5 Hz, 3H). MS (ESI) m/z: [M+H]$^+$. Found 608.2.

Example 19

4-Chloro-5-(4-(difluoromethoxy)-6-((1,1,1-trifluoro-2-methylpropan-2-yl)amino)pyridin-3-yl)-1-ethyl-N-(((1s,4s)-1-hydroxy-4-(methylsulfonyl)cyclohexyl)methyl)-1H-pyrazole-3-carboxamide

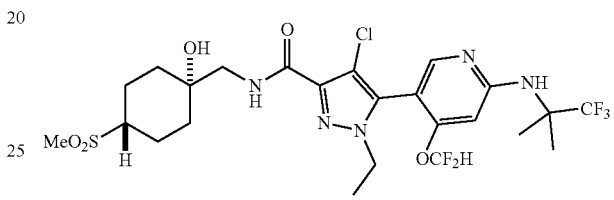

The title compound was prepared as described for the synthesis of Intermediate 59, using ethyl 4-chloro-5-(4-(difluoromethoxy)-6-((1,1,1-trifluoro-2-methylpropan-2-yl)amino)pyridin-3-yl)-1-ethyl-1H-pyrazole-3-carboxylate (Intermediate 72) and (1s,4s)-1-(aminomethyl)-4-(methylsulfonyl)cyclohexan-1-ol hydrochloride (Intermediate 9) in place of ethyl 4-chloro-5-(4-(difluoromethoxy)pyridin-3-yl)-1-ethyl-1H-pyrazole-3-carboxylate and ((1r,4r)-4-(methyl sulfonyl)cyclohexyl)methanamine hydrochloride. $^1$H NMR (400 MHz, CDCl$_3$) δ 8.00 (s, 1H), 7.22 (t, J=6.3 Hz, 1H), 6.71-6.31 (m, 1H), 6.40 (s, 1H), 4.90 (s, 1H), 4.08-3.90 (m, 2H), 3.47 (dd, J=6.3, 2.2 Hz, 2H), 3.02 (s, 1H), 2.86-2.73 (m, 4H), 2.18-2.07 (m, 2H), 2.04-1.90 (m, 4H), 1.71 (d, J=6.3 Hz, 6H), 1.49-1.36 (m, 5H). MS (ESI) m/z: [M+H]$^+$. Found 632.2.

Example 20

4-Chloro-5-(4-(difluoromethoxy)-6-((1,1,1-trifluoro-2-methylpropan-2-yl)amino)pyridin-3-yl)-1-ethyl-N-(((1r,4r)-4-(methylsulfonyl)cyclohexyl)methyl)-1H-pyrazole-3-carboxamide

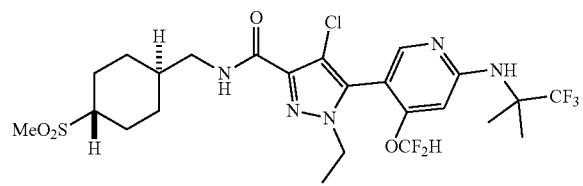

The title compound was prepared as described for the synthesis of Intermediate 59, using ethyl 4-chloro-5-(4-(difluoromethoxy)-6-((1,1,1-trifluoro-2-methylpropan-2-yl)amino)pyridin-3-yl)-1-ethyl-1H-pyrazole-3-carboxylate (Intermediate 72) in place of ethyl 4-chloro-5-(4-(difluoromethoxy)pyridin-3-yl)-1-ethyl-1H-pyrazole-3-carboxylate. ¹H NMR (400 MHz, CDCl₃) δ 8.00 (s, 1H), 6.93 (t, J=6.4 Hz, 1H), 6.50 (dd, J=73.9, 70.1 Hz, 1H), 6.40 (s, 1H), 4.90 (s, 1H), 4.07-3.88 (m, 2H), 3.34 (t, J=6.5 Hz, 2H), 2.90-2.76 (m, 4H), 2.35-2.22 (m, 2H), 2.12-2.02 (m, 2H), 1.76-1.50 (m, 10H), 1.39 (t, J=7.2 Hz, 3H), 1.20-1.05 (m, 2H). MS (ESI) m/z: [M+H]⁺. Found 616.2.

Example 21

4-Chloro-5-(4-(difluoromethoxy)-6-(((R)-1,1,1-trifluorobutan-2-yl)amino)pyridin-3-yl)-1-ethyl-N-(((1r,4R)-4-(methylsulfonyl)cyclohexyl)methyl)-1H-pyrazole-3-carboxamide

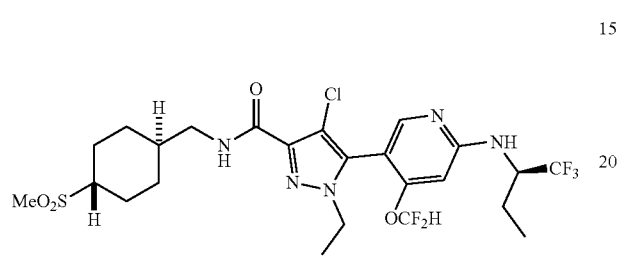

The title compound was prepared as described for the synthesis of Intermediate 59, using ethyl (R)-4-chloro-5-(4-(difluoromethoxy)-6-((1,1,1-trifluorobutan-2-yl)amino)pyridin-3-yl)-1-ethyl-1H-pyrazole-3-carboxylate (Intermediate 73) in place of ethyl 4-chloro-5-(4-(difluoromethoxy)pyridin-3-yl)-1-ethyl-1H-pyrazole-3-carboxylate. ¹H NMR (400 MHz, CDCl₃) δ 8.03-7.97 (m, 1H), 6.97-6.89 (m, 1H), 6.53 (ddd, J=73.7, 69.9, 2.2 Hz, 1H), 6.32 (s, 1H), 4.77-4.66 (m, 1H), 4.08-3.89 (m, 2H), 3.34 (t, J=6.6 Hz, 2H), 2.91-2.76 (m, 4H), 2.34-2.21 (m, 2H), 2.13-1.92 (m, 3H), 1.77-1.50 (m, 3H), 1.44-1.34 (m, 3H), 1.21-1.03 (m, 5H). MS (ESI) m/z: [M+H]⁺. Found 616.2.

Example 22

4-Chloro-5-(4-(difluoromethoxy)-6-(((R)-1,1,1-trifluorobutan-2-yl)amino)pyridin-3-yl)-1-ethyl-N-(((1s,4S)-1-hydroxy-4-(methylsulfonyl)cyclohexyl)methyl)-1H-pyrazole-3-carboxamide

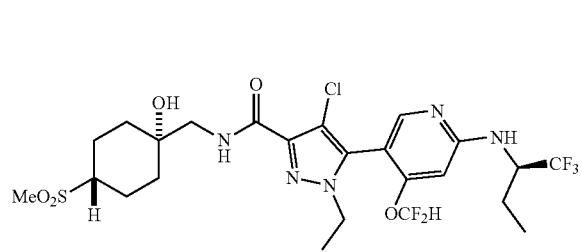

The title compound was prepared as described for the synthesis of Intermediate 59, using ethyl (R)-4-chloro-5-(4-(difluoromethoxy)-6-((1,1,1-trifluorobutan-2-yl)amino)pyridin-3-yl)-1-ethyl-1H-pyrazole-3-carboxylate (Intermediate 73) and (1s,4s)-1-(aminomethyl)-4-(methylsulfonyl)cyclohexan-1-ol hydrochloride (Intermediate 9) in place of ethyl 4-chloro-5-(4-(difluoromethoxy)pyridin-3-yl)-1-ethyl-1H-pyrazole-3-carboxylate and ((1r,4r)-4-(methylsulfonyl)cyclohexyl)methanamine hydrochloride. ¹H NMR (400 MHz, CDCl₃) δ 8.02-7.98 (m, 1H), 7.25-7.19 (m, 1H), 6.73-6.34 (m, 1H), 6.32 (s, 1H), 4.89-4.67 (m, 2H), 4.08-3.91 (m, 2H), 3.52-3.40 (m, 2H), 3.07-3.01 (m, 1H), 2.83 (s, 3H), 2.81-2.74 (m, 1H), 2.18-2.08 (m, 2H), 2.06-1.91 (m, 5H), 1.71-1.59 (m, 1H), 1.49-1.36 (m, 5H), 1.09 (t, J=7.4 Hz, 3H). MS (ESI) m/z: [M+H]⁺. Found 632.2.

Example 23

4-Chloro-5-(4-(difluoromethoxy)-6-(((S)-1,1,1-trifluorobutan-2-yl)amino)pyridin-3-yl)-1-ethyl-N-(((1r,4S)-4-(methylsulfonyl)cyclohexyl)methyl)-1H-pyrazole-3-carboxamide

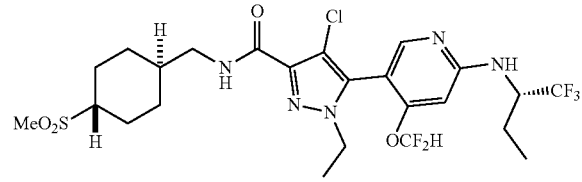

The title compound was prepared as described for the synthesis of Intermediate 59, using ethyl (S)-4-chloro-5-(4-(difluoromethoxy)-6-((1,1,1-trifluorobutan-2-yl)amino)pyridin-3-yl)-1-ethyl-1H-pyrazole-3-carboxylate (Intermediate 74) in place of ethyl 4-chloro-5-(4-(difluoromethoxy)pyridin-3-yl)-1-ethyl-1H-pyrazole-3-carboxylate. ¹H NMR (400 MHz, CDCl₃) δ 8.04-7.97 (m, 1H), 6.97-6.88 (m, 1H), 6.74-6.33 (m, 1H), 6.31 (s, 1H), 4.71 (s, 2H), 4.07-3.89 (m, 2H), 3.34 (t, J=6.6 Hz, 2H), 2.88-2.76 (m, 4H), 2.33-2.23 (m, 2H), 2.12-2.05 (m, 2H), 2.03-1.94 (m, 1H), 1.76-1.56 (m, 4H), 1.39 (td, J=7.2, 1.7 Hz, 3H), 1.20-1.04 (m, 5H). MS (ESI) m/z: [M+H]⁺. Found 616.2.

Example 24

4-Chloro-5-(4-(difluoromethoxy)-6-(((S)-1,1,1-trifluorobutan-2-yl)amino)pyridin-3-yl)-1-ethyl-N-(((1s,4R)-1-hydroxy-4-(methylsulfonyl)cyclohexyl)methyl)-1H-pyrazole-3-carboxamide

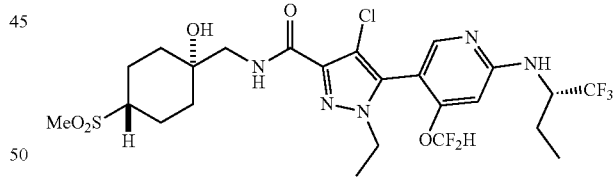

The title compound was prepared as described for the synthesis of Intermediate 59, using ethyl (S)-4-chloro-5-(4-(difluoromethoxy)-6-((1,1,1-trifluorobutan-2-yl)amino)pyridin-3-yl)-1-ethyl-1H-pyrazole-3-carboxylate (Intermediate 74) and (1s,4s)-1-(aminomethyl)-4-(methylsulfonyl)cyclohexan-1-ol hydrochloride (Intermediate 9) in place of ethyl 4-chloro-5-(4-(difluoromethoxy)pyridin-3-yl)-1-ethyl-1H-pyrazole-3-carboxylate and ((1r,4r)-4-(methylsulfonyl)cyclohexyl)methanamine hydrochloride. ¹H NMR (400 MHz, CDCl₃) δ 8.03-7.97 (m, 1H), 7.25-7.20 (m, 1H), 6.73-6.35 (m, 1H), 6.33-6.30 (s, 1H), 4.72 (s, 2H), 4.08-3.91 (m, 2H), 3.51-3.41 (m, 2H), 3.06-2.99 (m, 1H), 2.83 (s, 3H), 2.82-2.74 (m, 1H), 2.20-2.08 (m, 2H), 2.07-1.90 (m, 5H), 1.72-1.58 (m, 1H), 1.49-1.35 (m, 5H), 1.09 (t, J=7.4 Hz, 3H). MS (ESI) m/z: [M+H]⁺. Found 632.2.

Example 25

4-Chloro-5-(4-(difluoromethoxy)-6-(((R)-1,1,1-trifluoropropan-2-yl)amino)pyridin-3-yl)-1-ethyl-N-(((1r,4R)-4-(methylsulfonyl)cyclohexyl)methyl)-1H-pyrazole-3-carboxamide

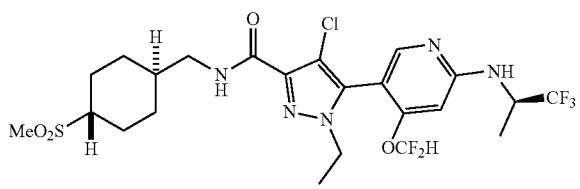

The title compound was prepared as described for the synthesis of Intermediate 59, using ethyl (R)-4-chloro-5-(4-(difluoromethoxy)-6-((1,1,1-trifluoropropan-2-yl)amino)pyridin-3-yl)-1-ethyl-1H-pyrazole-3-carboxylate (Intermediate 75) in place of ethyl 4-chloro-5-(4-(difluoromethoxy)pyridin-3-yl)-1-ethyl-1H-pyrazole-3-carboxylate. $^1$H NMR (400 MHz, CDCl$_3$) δ 8.01 (s, 1H), 6.97-6.89 (m, 1H), 6.72-6.32 (m, 1H), 6.31 (s, 1H), 5.08-4.69 (m, 2H), 4.09-3.89 (m, 2H), 3.34 (t, J=6.6 Hz, 2H), 2.90-2.77 (m, 4H), 2.28 (d, J=12.6 Hz, 2H), 2.07 (d, J=13.2 Hz, 2H), 1.77-1.65 (m, 1H), 1.65-1.57 (m, 2H), 1.48-1.42 (m, 3H), 1.42-1.35 (m, 3H), 1.21-1.06 (m, 2H). MS (ESI) m/z: [M+H]$^+$. Found 602.2.

Example 26

4-Chloro-5-(4-(difluoromethoxy)-6-(((R)-1,1,1-trifluoropropan-2-yl)amino)pyridin-3-yl)-1-ethyl-N-(((1s,4S)-1-hydroxy-4-(methylsulfonyl)cyclohexyl)methyl)-1H-pyrazole-3-carboxamide

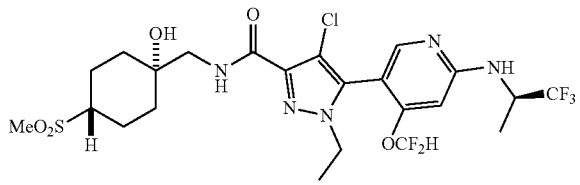

The title compound was prepared as described for the synthesis of Intermediate 59, using ethyl (R)-4-chloro-5-(4-(difluoromethoxy)-6-((1,1,1-trifluoropropan-2-yl)amino)pyridin-3-yl)-1-ethyl-1H-pyrazole-3-carboxylate (Intermediate 75) and (1s,4s)-1-(aminomethyl)-4-(methylsulfonyl)cyclohexan-1-ol hydrochloride (Intermediate 9) in place of ethyl 4-chloro-5-(4-(difluoromethoxy)pyridin-3-yl)-1-ethyl-1H-pyrazole-3-carboxylate and ((1r,4r)-4-(methyl sulfonyl)cyclohexyl)methanamine hydrochloride. $^1$H NMR (400 MHz, CDCl$_3$) δ 8.01 (s, 1H), 7.25-7.17 (m, 1H), 6.73-6.33 (m, 1H), 6.31 (s, 1H), 5.07-4.71 (m, 2H), 4.08-3.90 (m, 2H), 3.54-3.40 (m, 2H), 3.07-2.99 (m, 1H), 2.83 (s, 3H), 2.82-2.74 (m, 1H), 2.18-2.07 (m, 2H), 2.04-1.89 (m, 4H), 1.50-1.34 (m, 8H). MS (ESI) m/z: [M+H]$^+$. Found 618.2.

Example 27

5-(6-(tert-Butylamino)-4-(difluoromethoxy)pyridin-3-yl)-4-chloro-1-ethyl-N-(((1s,4s)-1-hydroxy-4-(methylsulfonyl)cyclohexyl)methyl)-1H-pyrazole-3-carboxamide

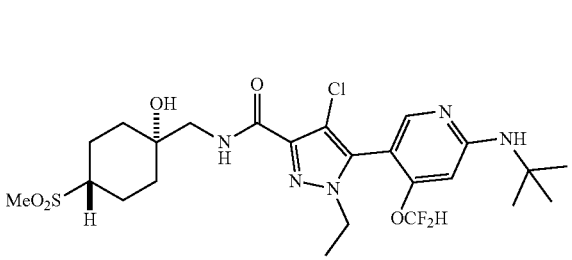

The title compound was prepared as described for the synthesis of Intermediate 59, using ethyl 5-(6-(tert-butylamino)-4-(difluoromethoxy)pyridin-3-yl)-4-chloro-1-ethyl-1H-pyrazole-3-carboxylate (Intermediate 76) and (1s,4s)-1-(aminomethyl)-4-(methylsulfonyl)cyclohexan-1-ol hydrochloride (Intermediate 9) in place of ethyl 4-chloro-5-(4-(difluoromethoxy)pyridin-3-yl)-1-ethyl-1H-pyrazole-3-carboxylate and ((1r,4r)-4-(methylsulfonyl)cyclohexyl)methanamine hydrochloride. $^1$H NMR (400 MHz, CDCl$_3$) δ 7.95 (s, 1H), 7.25-7.19 (m, 1H), 6.49 (dd, J=74.3, 70.2 Hz, 1H), 6.21 (s, 1H), 4.09-3.90 (m, 2H), 3.51-3.42 (m, 2H), 3.07 (s, 1H), 2.83 (s, 3H), 2.81-2.73 (m, 1H), 2.19-2.08 (m, 2H), 2.06-1.89 (m, 4H), 1.50-1.45 (m, 10H), 1.46-1.36 (m, 5H). MS (ESI) m/z: [M+H]$^+$. Found 578.3.

Example 28

4-Chloro-5-(4-(difluoromethoxy)-6-((1,1,1-trifluoro-3-methylbutan-2-yl)amino)pyridin-3-yl)-1-ethyl-N-(((1s,4s)-1-hydroxy-4-(methylsulfonyl)cyclohexyl)methyl)-1H-pyrazole-3-carboxamide

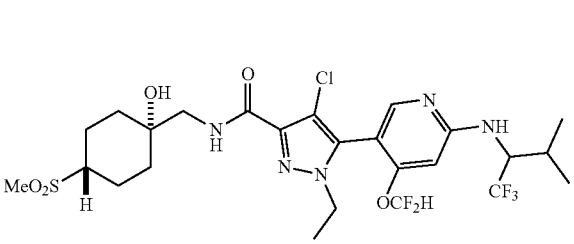

The title compound was prepared as described for the synthesis of Intermediate 59, using ethyl 4-chloro-5-(4-(difluoromethoxy)-6-((1,1,1-trifluoro-3-methylbutan-2-yl)amino)pyridin-3-yl)-1-ethyl-1H-pyrazole-3-carboxylate (Intermediate 77) and (1s,4s)-1-(aminomethyl)-4-(methylsulfonyl)cyclohexan-1-ol hydrochloride (Intermediate 9) in place of ethyl 4-chloro-5-(4-(difluoromethoxy)pyridin-3-yl)-1-ethyl-1H-pyrazole-3-carboxylate and ((1r,4r)-4-(methylsulfonyl)cyclohexyl)methanamine hydrochloride. $^1$H NMR (400 MHz, CDCl$_3$) δ 8.02-7.97 (m, 1H), 7.25-7.19 (m, 1H), 6.54 (dd, J=73.8, 70.0 Hz, 1H), 6.33 (s, 1H), 4.96-4.71 (m, 2H), 4.09-3.90 (m, 2H), 3.53-3.40 (m, 2H), 3.07-2.97

(m, 1H), 2.83 (s, 3H), 2.81-2.73 (m, 1H), 2.34-2.20 (m, 1H), 2.20-2.06 (m, 2H), 2.04-1.90 (m, 4H), 1.49-1.35 (m, 5H), 1.08 (t, J=5.7 Hz, 6H). MS (ESI) m/z: [M+H]$^+$. Found 646.2.

Example 29

4-Chloro-5-(4-(difluoromethoxy)-6-(((R*)-1,1,1-trifluoro-3-methylbutan-2-yl)amino)pyridin-3-yl)-1-ethyl-N-(((1s,4S)-1-hydroxy-4-(methylsulfonyl)cyclohexyl)methyl)-1H-pyrazole-3-carboxamide

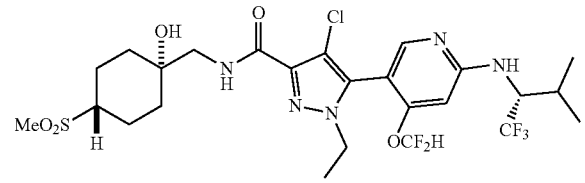

Example 30

4-Chloro-5-(4-(difluoromethoxy)-6-(((S*)-1,1,1-trifluoro-3-methylbutan-2-yl)amino)pyridin-3-yl)-1-ethyl-N-(((1s,4R)-1-hydroxy-4-(methylsulfonyl)cyclohexyl)methyl)-1H-pyrazole-3-carboxamide

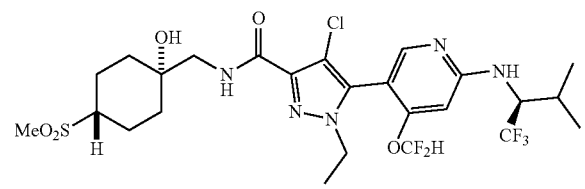

Example 28 was purified by SFC using a chiral stationary phase (Chiralcel OJ-H, 10% MeOH, 90% CO$_2$, 0.2% i-PrNH$_2$) to give a pair of enantiomers. The first-eluting enantiomer was Example 29, and the second-eluting enantiomer was Example 30. Example 29: $^1$H NMR (400 MHz, CDCl$_3$) δ 8.02-7.97 (m, 1H), 7.25-7.19 (m, 1H), 6.54 (dd, J=73.9, 70.0 Hz, 1H), 6.32 (s, 1H), 4.94-4.75 (m, 2H), 4.08-3.90 (m, 2H), 3.53-3.41 (m, 2H), 3.08-2.98 (m, 1H), 2.89-2.74 (m, 4H), 2.33-2.21 (m, 1H), 2.19-2.08 (m, 2H), 2.06-1.90 (m, 4H), 1.49-1.36 (m, 5H), 1.08 (t, J=5.9 Hz, 6H). MS (ESI) m/z: [M+H]$^+$. Found 646.2. Example 30: $^1$H NMR (400 MHz, CDCl$_3$) δ 8.02-7.97 (m, 1H), 7.25-7.19 (m, 1H), 6.74-6.35 (m, 1H), 6.33 (s, 1H), 4.97-4.70 (m, 2H), 4.10-3.90 (m, 2H), 3.53-3.40 (m, 2H), 3.07-2.99 (m, 1H), 2.89-2.74 (m, 4H), 2.36-2.20 (m, 1H), 2.20-2.07 (m, 2H), 2.07-1.89 (m, 4H), 1.50-1.34 (m, 5H), 1.14-1.02 (m, 6H). MS (ESI) m/z: [M+H]$^+$. Found 646.2.

Example 31

4-Chloro-5-(4-(difluoromethoxy)-6-(neopentylamino)pyridin-3-yl)-1-ethyl-N-(((1s,4s)-1-hydroxy-4-(methylsulfonyl)cyclohexyl)methyl)-1H-pyrazole-3-carboxamide

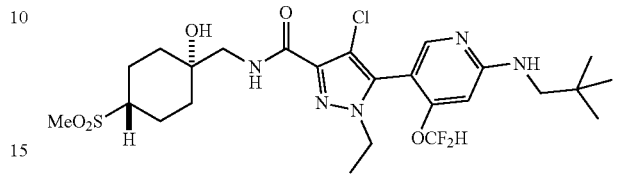

The title compound was prepared as described for the synthesis of Intermediate 59, using ethyl 4-chloro-5-(4-(difluoromethoxy)-6-(neopentylamino)pyridin-3-yl)-1-ethyl-1H-pyrazole-3-carboxylate (Intermediate 78) and (1s,4s)-1-(aminomethyl)-4-(methylsulfonyl)cyclohexan-1-ol hydrochloride (Intermediate 9) in place of ethyl 4-chloro-5-(4-(difluoromethoxy)pyridin-3-yl)-1-ethyl-1H-pyrazole-3-carboxylate and ((1r,4r)-4-(methylsulfonyl)cyclohexyl)methanamine hydrochloride. $^1$H NMR (400 MHz, CDCl$_3$) δ 7.95 (s, 1H), 7.23 (t, J=6.3 Hz, 1H), 6.54 (dd, J=74.3, 70.2 Hz, 1H), 6.19 (s, 1H), 5.07-4.93 (m, 1H), 4.09-3.90 (m, 2H), 3.52-3.40 (m, 2H), 3.19-3.07 (m, 3H), 2.83 (s, 3H), 2.82-2.73 (m, 1H), 2.18-2.07 (m, 2H), 2.03-1.89 (m, 4H), 1.51-1.33 (m, 5H), 1.03 (s, 9H). MS (ESI) m/z: [M+H]$^+$. Found 592.3.

Example 32

4-Chloro-5-(4-(1,1-difluoroethyl)-6-((4,4,4-trifluoro-2-methylbutan-2-yl)amino)pyridin-3-yl)-1-ethyl-N-(((1r,4r)-4-(methylsulfonyl)cyclohexyl)methyl)-1H-pyrazole-3-carboxamide

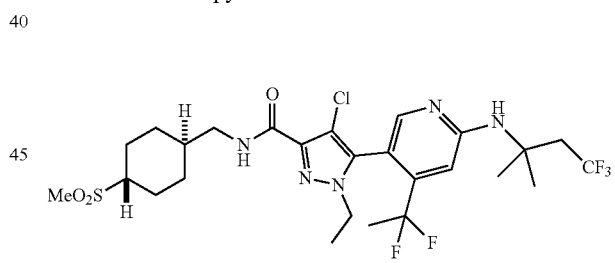

The title compound was prepared as described for the synthesis of Example 1, using ethyl 4-chloro-5-(4-(1,1-difluoroethyl)-6-((4,4,4-trifluoro-2-methylbutan-2-yl)amino)pyridin-3-yl)-1-ethyl-1H-pyrazole-3-carboxylate (Intermediate 46) and ((1r,4r)-4-(methylsulfonyl)cyclohexyl)methanamine hydrochloride (Intermediate 13) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate and (1s,4s)-1-(aminomethyl)-4-(methylsulfonyl)cyclohexanol hydrochloride. $^1$H NMR (400 MHz, CDCl$_3$) δ 7.84 (s, 1H), 6.98 (t, J=6.4 Hz, 1H), 6.68-6.62 (m, 1H), 4.00-3.78 (m, 2H), 3.34 (t, J=6.5 Hz, 2H), 3.07-2.92 (m, 1H), 2.91-2.77 (m, 5H), 2.53 (br s, NH plus excess water), 2.29 (d, J=11.8 Hz, 2H), 2.08 (d, J=13.1 Hz, 2H), 1.77-1.53 (m, 12H), 1.37 (t, J=7.3 Hz, 3H), 1.14 (qd, J=13.1, 3.5 Hz, 2H). MS (ESI) m/z: [M+H]$^+$. Found 628.3.

Example 33

4-Chloro-5-(4-(1,1-difluoroethyl)-6-((4,4,4-trifluoro-2-methylbutan-2-yl)amino)pyridin-3-yl)-1-ethyl-N-(((1s,4s)-1-hydroxy-4-(methylsulfonyl)cyclohexyl)methyl)-1H-pyrazole-3-carboxamide

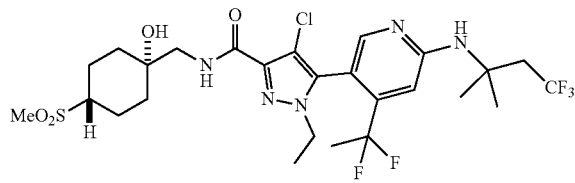 [SMILES: CCn1nc(C(=O)NC[C@]2(O)CC[C@@H](S(C)(=O)=O)CC2)c(Cl)c1-c1cnc(NC(C)(C)CC(F)(F)F)cc1C(C)(F)F]

The title compound was prepared as described for the synthesis of Example 1, using ethyl 4-chloro-5-(4-(1,1-difluoroethyl)-6-((4,4,4-trifluoro-2-methylbutan-2-yl)amino)pyridin-3-yl)-1-ethyl-1H-pyrazole-3-carboxylate (Intermediate 46) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate. $^1$H NMR (500 MHz, CDCl$_3$) δ 7.84 (s, 1H), 7.29-7.26 (m, 1H), 6.67-6.64 (m, 1H), 3.90 (ddt, J=33.8, 13.8, 7.0 Hz, 2H), 3.47 (d, J=6.3 Hz, 2H), 3.06-2.93 (m, 1H), 2.91-2.76 (m, 5H), 2.43 (br s, OH, NH plus excess water), 2.18-2.10 (m, 2H), 2.04-1.93 (m, 4H), 1.71 (t, J=18.9 Hz, 3H), 1.61 (d, J=7.8 Hz, 6H), 1.49-1.40 (m, 2H), 1.37 (t, J=7.3 Hz, 3H). MS (ESI) m/z: [M+H]$^+$. Found 644.2.

Example 34

4-Chloro-1-ethyl-5-(4-methoxy-6-((4,4,4-trifluorobutyl)amino)pyridin-3-yl)-N-(((1r,4r)-4-(methylsulfonyl)cyclohexyl)methyl)-1H-pyrazole-3-carboxamide

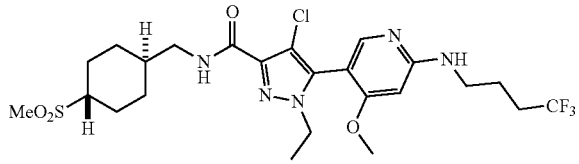 [SMILES: CCn1nc(C(=O)NC[C@H]2CC[C@H](S(C)(=O)=O)CC2)c(Cl)c1-c1cnc(NCCCC(F)(F)F)cc1OC]

4-Chloro-5-(6-chloro-4-methoxypyridin-3-yl)-1-ethyl-N-(((1r,4r)-4-(methylsulfonyl)cyclohexyl)methyl)-1H-pyrazole-3-carboxamide (200 mg, 0.409 mmol, Intermediate 87), RuPhos G1 precatalyst (16.65 mg, 0.02 mmol), RuPhos (10.6 mg, 0.023 mmol), and Cs$_2$CO$_3$ (0.317 g, 0.972 mmol) were combined in a vessel, and the vessel was evacuated and backfilled with argon three times. 1,4-Dioxane (1.8 mL) and then 4,4,4-trifluorobutan-1-amine (0.06 mL, 0.57 mmol) were added, and the mixture was stirred at 110° C. for 3 h. After this time, the mixture was allowed to cool to rt and diluted with EtOAc and water. The layers were separated, and the aqueous layer was extracted with EtOAc. The organic layers were combined, dried with anhydrous MgSO$_4$, filtered, and then concentrated. The residue was purified by HPLC (XBridge C18, 5→99% MeCN/water, 20 mM NH$_4$OH) to afford the title compound. $^1$H NMR (500 MHz, CDCl$_3$) δ 7.84 (s, 1H), 6.93 (t, J=6.4 Hz, 1H), 5.92 (s, 1H), 4.75 (t, J=5.9 Hz, 1H), 4.03-3.90 (m, 2H), 3.80 (s, 3H), 3.52-3.44 (m, 2H), 3.37-3.30 (m, 2H), 2.86-2.79 (m, 4H), 2.32-2.19 (m, 4H), 2.07 (d, J=13.1 Hz, 2H), 1.98-1.90 (m, 2H), 1.73-1.65 (m, 1H), 1.63-1.52 (m, 2H), 1.36 (t, J=7.2 Hz, 3H), 1.19-1.08 (m, 2H). MS (ESI) m/z: [M+H]$^+$. Found 580.2.

Example 35

4-Chloro-1-ethyl-5-(4-methoxy-6-((2-(2,2,2-trifluoroethoxy)ethyl)amino)pyridin-3-yl)-N-(((1r,4r)-4-(methylsulfonyl)cyclohexyl)methyl)-1H-pyrazole-3-carboxamide

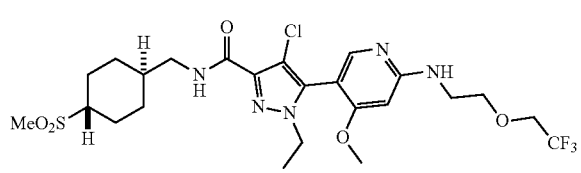 [SMILES: CCn1nc(C(=O)NC[C@H]2CC[C@H](S(C)(=O)=O)CC2)c(Cl)c1-c1cnc(NCCOCC(F)(F)F)cc1OC]

The title compound was prepared as described for the synthesis of Example 34, using 2-(2,2,2-trifluoroethoxy)ethan-1-amine hydrochloride in place of 4,4,4-trifluorobutan-1-amine. $^1$H NMR (500 MHz, CDCl$_3$) δ 7.84 (s, 1H), 6.94 (t, J=6.4 Hz, 1H), 5.99 (s, 1H), 5.03 (t, J=5.8 Hz, 1H), 4.02-3.86 (m, 4H), 3.85 (t, J=5.1 Hz, 2H), 3.79 (s, 3H), 3.70-3.62 (m, 2H), 3.38-3.28 (m, 2H), 2.86-2.79 (m, 4H), 2.31-2.24 (m, 2H), 2.10-2.03 (m, 2H), 1.73-1.66 (m, 1H), 1.63-1.53 (m, 2H), 1.35 (t, J=7.2 Hz, 3H), 1.18-1.08 (m, 2H). MS (ESI) m/z: [M+H]$^+$. Found 596.2.

Example 36

4-Chloro-1-ethyl-5-(4-methoxy-6-((3-(2,2,2-trifluoroethoxy)propyl)amino)pyridin-3-yl)-N-(((1r,4r)-4-(methylsulfonyl)cyclohexyl)methyl)-1H-pyrazole-3-carboxamide

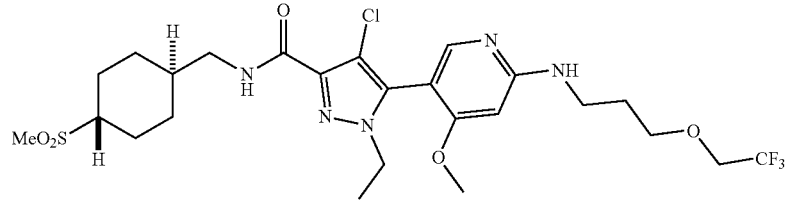

The title compound was prepared as described for the synthesis of Example 34, using 3-(2,2,2-trifluoroethoxy)propan-1-amine hydrochloride in place of 4,4,4-trifluorobutan-1-amine. $^1$H NMR (400 MHz, CDCl$_3$) δ 7.83 (s, 1H), 6.94 (t, J=6.4 Hz, 1H), 5.93 (s, 1H), 5.03 (t, J=5.6 Hz, 1H), 4.05-3.90 (m, 2H), 3.86 (q, J=8.7 Hz, 2H), 3.79 (s, 3H), 3.79-3.76 (m, 2H), 3.53-3.46 (m, 2H), 3.37-3.30 (m, 2H), 2.87-2.78 (m, 4H), 2.33-2.22 (m, 2H), 2.11-2.03 (m, 2H), 2.01-1.94 (m, 2H), 1.73-1.67 (m, 1H), 1.64-1.52 (m, 2H), 1.35 (t, J=7.2 Hz, 3H), 1.19-1.07 (m, 2H). MS (ESI) m/z: [M+H]$^+$. Found 610.2.

Example 37

4-Chloro-1-ethyl-5-(4-methoxy-6-((2-((trifluoromethyl)thio)ethyl)amino)pyridin-3-yl)-N-(((1r,4r)-4-(methylsulfonyl)cyclohexyl)methyl)-1H-pyrazole-3-carboxamide The title compound was prepared as described for the synthesis of Example 34, using 2-((trifluoromethyl)thio)ethan-1-amine in place of 4,4,4-trifluorobutan-1-amine. $^1$H NMR (400 MHz, CDCl$_3$) δ 7.85 (s, 1H), 6.94 (t, J=6.4 Hz, 1H), 5.98 (s, 1H), 5.05 (t, J=6.2 Hz, 1H), 4.06-3.88 (m, 2H), 3.79 (s, 3H), 3.75 (q, J=6.5 Hz, 2H), 3.40-3.30 (m, 2H), 3.25-3.17 (m, 2H), 2.89-2.78 (m, 4H), 2.34-2.23 (m, 2H), 2.13-2.02 (m, 2H), 1.75-1.66 (m, 1H), 1.61-1.51 (m, 2H), 1.36 (t, J=7.2 Hz, 3H), 1.20-1.07 (m, 2H). MS (ESI) m/z: [M+H]$^+$. Found 598.2.

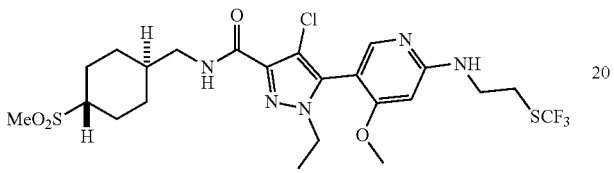

Example 38

4-Chloro-1-ethyl-5-(4-methoxy-6-((((1s*,4s*)-4-(trifluoromethyl)cyclohexyl)methyl)amino)pyridin-3-yl)-N-(((1r,4r)-4-(methylsulfonyl)cyclohexyl)methyl)-1H-pyrazole-3-carboxamide

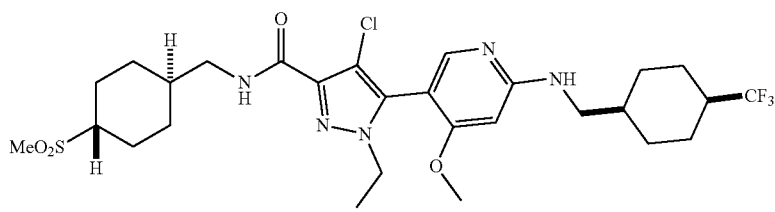

Example 39

4-Chloro-1-ethyl-5-(4-methoxy-6-((((1r*,4r*)-4-(trifluoromethyl)cyclohexyl)methyl)amino)pyridin-3-yl)-N-(((1r,4r)-4-(methylsulfonyl)cyclohexyl)methyl)-1H-pyrazole-3-carboxamide

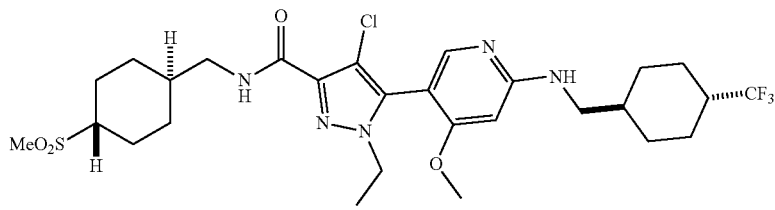

Intermediate 89 was purified by SFC using a chiral stationary phase (Chiralpak IB, 85% CO₂, 15% MeOH, 0.2% TEA) to give a pair of diastereomers. The first-eluting isomer was Example 38, and the second-eluting isomer was Example 39. Example 38: ¹H NMR (400 MHz, CDCl₃) δ 7.82 (s, 1H), 6.97-6.89 (m, 1H), 5.92 (s, 1H), 5.33-5.04 (m, 1H), 4.04-3.89 (m, 2H), 3.82 (s, 3H), 3.42-3.25 (m, 4H), 2.94-2.75 (m, 4H), 2.34-2.22 (m, 2H), 2.19-1.94 (m, 7H), 1.80-0.97 (m, 13H). MS (ESI) m/z: [M+H]⁺. Found 633.7. Example 39: ¹H NMR (400 MHz, CDCl₃) δ 7.82 (s, 1H), 6.95-6.90 (m, 1H), 5.90 (s, 1H), 4.90-4.80 (m, 1H), 4.00-3.91 (m, 2H), 3.80 (s, 3H), 3.36-3.31 (m, 2H), 3.25-3.20 (m, 2H), 2.86-2.78 (m, 4H), 2.31-2.24 (m, 2H), 2.10-1.97 (m, 7H), 1.45-1.32 (m, 8H), 1.19-1.03 (m, 5H). MS (ESI) m/z: [M+H]⁺. Found 633.7.

Example 40

4-Chloro-5-(6-(((S)-1-cyclopropylethyl)amino)-4-methoxypyridin-3-yl)-1-ethyl-N-(((1r,4S)-4-(methylsulfonyl)cyclohexyl)methyl)-1H-pyrazole-3-carboxamide

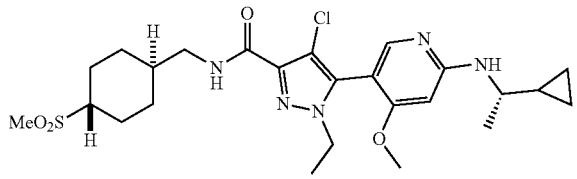 [SMILES: CCn1nc(C(=O)NC[C@H]2CC[C@H](S(C)(=O)=O)CC2)c(Cl)c1-c1cnc(N[C@@H](C)C2CC2)cc1OC]

The title compound was prepared as described for the synthesis of Example 34, using (S)-1-cyclopropylethan-1-amine in place of 4,4,4-trifluorobutan-1-amine. ¹H NMR (400 MHz, CDCl3) δ 7.81 (s, 1H), 6.93 (t, J=6.3 Hz, 1H), 5.88 (s, 1H), 4.77 (d, J=7.5 Hz, 1H), 4.04-3.89 (m, 2H), 3.79 (s, 3H), 3.41-3.30 (m, 3H), 2.86-2.78 (m, 4H), 2.32-2.24 (m, 2H), 2.11-2.03 (m, 2H), 1.72-1.65 (m, 1H), 1.65-1.52 (m, 2H), 1.35 (td, J=7.3, 1.1 Hz, 3H), 1.31 (d, J=6.4 Hz, 3H), 1.20-1.07 (m, 2H), 1.00-0.92 (m, 1H), 0.61-0.48 (m, 2H), 0.40-0.27 (m, 2H). MS (ESI) m/z: [M+H]⁺. Found 538.2.

Example 41

4-Chloro-5-(6-(((R*)-2,2-difluorocyclohexyl)amino)-4-methoxypyridin-3-yl)-1-ethyl-N-(((1r,4R)-4-(methylsulfonyl)cyclohexyl)methyl)-1H-pyrazole-3-carboxamide

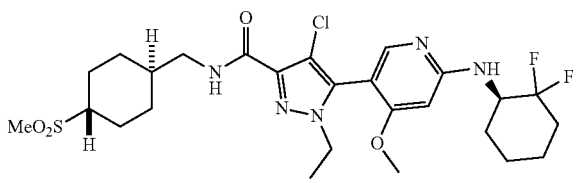 [SMILES: CCn1nc(C(=O)NC[C@H]2CC[C@H](S(C)(=O)=O)CC2)c(Cl)c1-c1cnc(N[C@@H]2CCCCC2(F)F)cc1OC]

Example 42

4-Chloro-5-(6-(((S*)-2,2-difluorocyclohexyl)amino)-4-methoxypyridin-3-yl)-1-ethyl-N-(((1r,4S)-4-(methylsulfonyl)cyclohexyl)methyl)-1H-pyrazole-3-carboxamide

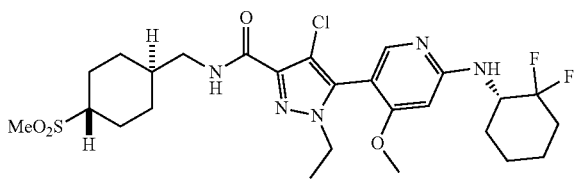 [SMILES: CCn1nc(C(=O)NC[C@H]2CC[C@H](S(C)(=O)=O)CC2)c(Cl)c1-c1cnc(N[C@H]2CCCCC2(F)F)cc1OC]

Intermediate 90 was purified by SFC using a chiral stationary phase (Chiralpak AD-H, 65% CO₂, 35% i-PrOH, 0.3% i-PrNH₂) to give a pair of enantiomers. The first-eluting isomer was Example 41, and the second-eluting isomer was Example 42. Example 41: ¹H NMR (400 MHz, CDCl₃) δ 7.84 (s, 1H), 6.93 (s, 1H), 6.96-6.89 (m, 1H), 4.82 (dd, J=23.0, 9.2 Hz, 1H), 4.01-3.90 (m, 2H), 3.79 (d, J=3.0 Hz, 3H), 3.37-3.31 (m, 2H), 2.87-2.77 (m, 4H), 2.32-2.02 (m, 7H), 1.84-1.76 (m, 2H), 1.72-1.64 (m, 1H), 1.64-1.45 (m, 6H), 1.35 (td, J=7.2, 2.1 Hz, 3H), 1.20-1.06 (m, 2H). MS (ESI) m/z: [M+H]⁺. Found 588.3. Example 42: ¹H NMR (400 MHz, CDCl₃) δ 7.84 (s, 1H), 6.93 (s, 1H), 6.96-6.89 (m, 1H), 4.82 (dd, J=23.0, 9.2 Hz, 1H), 4.01-3.90 (m, 2H), 3.79 (d, J=3.0 Hz, 3H), 3.37-3.31 (m, 2H), 2.87-2.77 (m, 4H), 2.32-2.02 (m, 7H), 1.84-1.76 (m, 2H), 1.72-1.64 (m, 1H), 1.64-1.45 (m, 6H), 1.35 (td, J=7.2, 2.1 Hz, 3H), 1.20-1.06 (m, 2H). MS (ESI) m/z: [M+H]⁺. Found 588.3.

Example 43

1-Ethyl-5-(4-methoxy-6-((2-(2,2,2-trifluoroethoxy)ethyl)amino)pyridin-3-yl)-4-methyl-N-(((1r,4r)-4-(methylsulfonyl)cyclohexyl)methyl)-1H-pyrazole-3-carboxamide

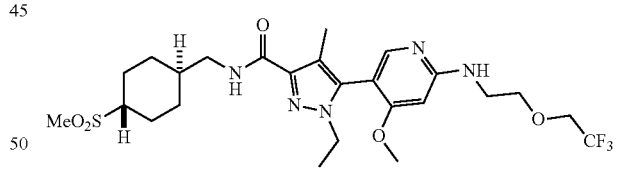

RuPhos G1 precatalyst (5.5 mg, 0.0067 mmol), RuPhos (3.8 mg, 0.008 mmol), and K₂CO₃ (51.7 mg, 0.374 mmol) were combined in a vessel and the vessel was evacuated and backfilled with argon three times. A solution of 4-chloro-1-ethyl-5-(4-methoxy-6-((2-(2,2,2-trifluoroethoxy)ethyl)amino)pyridin-3-yl)-N-(((1r,4r)-4-(methylsulfonyl)cyclohexyl)methyl)-1H-pyrazole-3-carboxamide (54 mg, 0.091 mmol, Example 35) in 1,4-dioxane (0.9 mL) was then added, followed by 2,4,6-trimethyl-1,3,5,2,4,6-trioxatriborinane (0.04 mL, 0.3 mmol). The mixture was stirred at 110° C. for 1.25 h. After this time, the mixture was allowed to cool to rt and then diluted with EtOAc and water. The layers were separated, and the aqueous layer was extracted with EtOAc. The combined organic layers were dried with anhydrous MgSO₄, filtered, and then concentrated. The residue was purified by HPLC (XBridge C18, 5→99% MeCN/water, 20 mM NH$_4$OH) to afford the title compound. $^1$H NMR (400 MHz, CDCl$_3$) δ 7.76 (s, 1H), 7.04 (t, J=6.3 Hz, 1H), 5.99 (s, 1H), 4.94 (t, J=5.9 Hz, 1H), 3.99-3.82 (m, 6H), 3.78 (s, 3H), 3.68-3.62 (m, 2H), 3.34-3.27 (m, 2H), 2.87-2.77 (m, 4H), 2.27 (d, J=12.5 Hz, 2H), 2.16 (s, 3H), 2.08 (d, J=13.2 Hz, 2H), 1.72-1.64 (m, 1H), 1.64-1.52 (m, 2H), 1.32 (t, J=7.2 Hz, 3H), 1.20-1.05 (m, 2H). MS (ESI) m/z: [M+H]$^+$. Found 576.3.

Example 44

1-Ethyl-5-(4-methoxy-6-((3-(2,2,2-trifluoroethoxy)propyl)amino)pyridin-3-yl)-4-methyl-N-(((1r,4r)-4-(methylsulfonyl)cyclohexyl)methyl)-1H-pyrazole-3-carboxamide

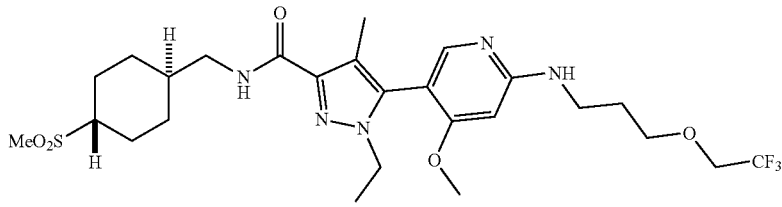 [SMILES: CCn1nc(C(=O)NC[C@H]2CC[C@H](S(C)(=O)=O)CC2)c(C)c1-c1cnc(NCCCOCC(F)(F)F)cc1OC]

The title compound was prepared as described for the synthesis of Example 43, using 4-chloro-1-ethyl-5-(4-methoxy-6-((3-(2,2,2-trifluoroethoxy)propyl)amino)pyridin-3-yl)-N-(((1r,4r)-4-(methylsulfonyl)cyclohexyl)methyl)-1H-pyrazole-3-carboxamide (Example 36) in place of 4-chloro-1-ethyl-5-(4-methoxy-6-((2-(2,2,2-trifluoroethoxy)ethyl)amino)pyridin-3-yl)-N-(((1r,4r)-4-(methylsulfonyl)cyclohexyl)methyl)-1H-pyrazole-3-carboxamide. $^1$H NMR (400 MHz, CDCl$_3$) δ 7.75 (s, 1H), 7.04 (t, J=6.4 Hz, 1H), 5.93 (s, 1H), 4.96-4.90 (m, 1H), 3.98-3.82 (m, 4H), 3.81-3.76 (m, 5H), 3.53-3.46 (m, 2H), 3.33-3.27 (m, 2H), 2.87-2.77 (m, 4H), 2.31-2.23 (m, 2H), 2.16 (s, 3H), 2.12-2.04 (m, 2H), 2.02-1.94 (m, 2H), 1.72-1.65 (m, 1H), 1.64-1.52 (m, 2H), 1.32 (t, J=7.2 Hz, 3H), 1.19-1.06 (m, 2H). MS (ESI) m/z: [M+H]$^+$. Found 590.3.

Example 45

1-Ethyl-5-(4-methoxy-6-((2-((trifluoromethyl)thio)ethyl)amino)pyridin-3-yl)-4-methyl-N-(((1r,4r)-4-(methylsulfonyl)cyclohexyl)methyl)-1H-pyrazole-3-carboxamide

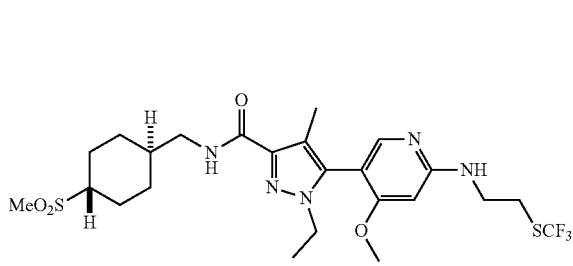

The title compound was prepared as described for the synthesis of Example 43, using 4-chloro-1-ethyl-5-(4-methoxy-6-((2-((trifluoromethyl)thio)ethyl)amino)pyridin-3-yl)-N-(((1r,4r)-4-(methylsulfonyl)cyclohexyl)methyl)-1H-pyrazole-3-carboxamide (Example 37) in place of 4-chloro-1-ethyl-5-(4-methoxy-6-((2-(2,2,2-trifluoroethoxy)ethyl)amino)pyridin-3-yl)-N-(((1r,4r)-4-(methylsulfonyl)cyclohexyl)methyl)-1H-pyrazole-3-carboxamide. $^1$H NMR (400 MHz, CDCl$_3$) δ 7.77 (s, 1H), 7.04 (t, J=6.4 Hz, 1H), 5.97 (s, 1H), 4.97 (t, J=6.2 Hz, 1H), 4.01-3.83 (m, 2H), 3.78 (s, 3H), 3.74 (q, J=6.4 Hz, 2H), 3.35-3.26 (m, 2H), 3.23-3.18 (m, 2H), 2.88-2.77 (m, 4H), 2.27 (d, J=12.5 Hz, 2H), 2.16 (s, 3H), 2.08 (d, J=12.8 Hz, 2H), 1.72-1.64 (m, 1H), 1.64-1.52 (m, 2H), 1.33 (t, J=7.2 Hz, 3H), 1.19-1.06 (m, 2H). MS (ESI) m/z: [M+H]$^+$. Found 578.2.

Example 46

1-Ethyl-5-(4-methoxy-6-(((((1s*,4s*)-4-(trifluoromethyl)cyclohexyl)methyl)amino)pyridin-3-yl)-4-methyl-N-(((1r,4r)-4-(methylsulfonyl)cyclohexyl)methyl)-1H-pyrazole-3-carboxamide

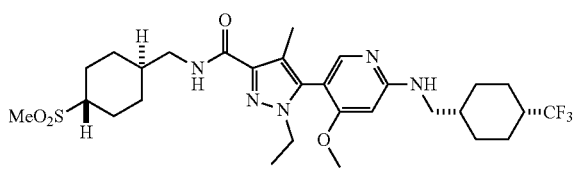

Example 47

1-Ethyl-5-(4-methoxy-6-(((((1r*,4r*)-4-(trifluoromethyl)cyclohexyl)methyl)amino)pyridin-3-yl)-4-methyl-N-(((1r,4r)-4-(methylsulfonyl)cyclohexyl)methyl)-1H-pyrazole-3-carboxamide

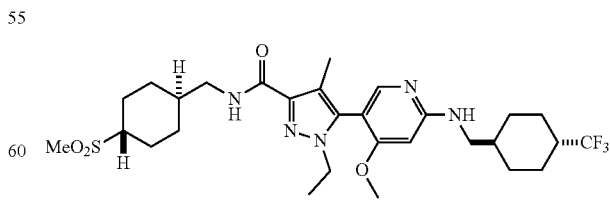

Intermediate 91 was purified by SFC using a chiral stationary phase (Chiralpak IB, 88% CO$_2$, 12% MeOH, 0.2% TEA) to give a pair of diastereomers. The first-eluting isomer was Example 46, and the second-eluting isomer was Example 47. Example 46: ¹H NMR (400 MHz, CDCl₃) δ 7.75 (s, 1H), 7.07-7.02 (m, 1H), 5.90 (s, 1H), 4.75-4.69 (m, 1H), 4.00-3.85 (m, 2H), 3.79 (s, 3H), 3.34-3.27 (m, 2H), 3.25-3.20 (m, 2H), 2.86-2.78 (m, 4H), 2.27 (d, J=12.9 Hz, 2H), 2.16 (s, 3H), 2.11-1.97 (m, 7H), 1.70-1.63 (m, 1H), 1.42-1.23 (m, 7H), 1.18-1.01 (m, 5H). MS (ESI) m/z: [M+H]⁺. Found 613.8. Example 47: 1H NMR (400 MHz, CDCl₃) δ 7.75 (s, 1H), 7.04 (t, J=6.4 Hz, 1H), 5.91 (s, 1H), 4.69 (s, 1H), 4.00-3.84 (m, 2H), 3.80 (s, 3H), 3.37-3.27 (m, 4H), 2.87-2.78 (m, 4H), 2.27 (d, J=12.5 Hz, 2H), 2.16 (s, 3H), 2.08 (d, J=13.4 Hz, 2H), 2.01-1.93 (m, 1H), 1.80-1.52 (m, 12H), 1.33 (t, J=7.2 Hz, 3H), 1.20-1.06 (m, 2H). MS (ESI) m/z: [M+H]⁺. Found 613.8.

Example 48

5-(6-(((S)-1-Cyclopropylethyl)amino)-4-methoxypyridin-3-yl)-1-ethyl-4-methyl-N-(((1r,4S)-4-(methylsulfonyl)cyclohexyl)methyl)-1H-pyrazole-3-carboxamide

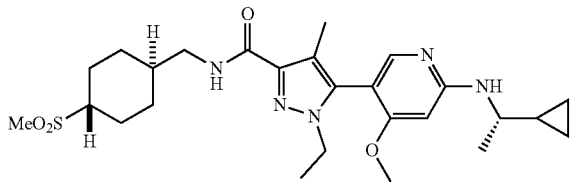 [SMILES: CCn1nc(C(=O)NC[C@H]2CC[C@H](S(C)(=O)=O)CC2)c(C)c1-c1cnc(N[C@@H](C)C2CC2)cc1OC]

The title compound was prepared as described for the synthesis of Example 43, using 4-chloro-5-(6-(((S)-1-cyclopropylethyl)amino)-4-methoxypyridin-3-yl)-1-ethyl-N-(((1r,4r)-4-(methylsulfonyl)cyclohexyl)methyl)-1H-pyrazole-3-carboxamide (Example 40) in place of 4-chloro-1-ethyl-5-(4-methoxy-6-((2-(2,2,2-trifluoroethoxy)ethyl)amino)pyridin-3-yl)-N-(((1r,4r)-4-(methylsulfonyl)cyclohexyl)methyl)-1H-pyrazole-3-carboxamide. ¹H NMR (400 MHz, CDCl₃) δ 7.73 (s, 1H), 7.04 (t, J=6.4 Hz, 1H), 5.89 (s, 1H), 4.72 (d, J=7.4 Hz, 1H), 3.98-3.85 (m, 2H), 3.78 (s, 3H), 3.41-3.34 (m, 1H), 3.33-3.27 (m, 2H), 2.87-2.77 (m, 4H), 2.27 (d, J=12.7 Hz, 2H), 2.16 (d, J=1.2 Hz, 3H), 2.08 (d, J=13.2 Hz, 2H), 1.71-1.65 (m, 1H), 1.65-1.52 (m, 2H), 1.35-1.29 (m, 6H), 1.18-1.06 (m, 2H), 1.00-0.92 (m, 1H), 0.59-0.48 (m, 2H), 0.43-0.27 (m, 2H). MS (ESI) m/z: [M+H]⁺. Found 518.3.

Example 49

4-Chloro-1-ethyl-5-(4-methoxy-6-((4,4,4-trifluoro-2-methylbutan-2-yl)amino)pyridin-3-yl)-N-(((1r,4r)-4-(methylsulfonyl)cyclohexyl)methyl)-1H-pyrazole-3-carboxamide

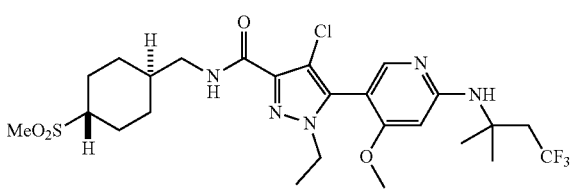 [SMILES: CCn1nc(C(=O)NC[C@H]2CC[C@H](S(C)(=O)=O)CC2)c(Cl)c1-c1cnc(NC(C)(C)CC(F)(F)F)cc1OC]

The title compound was prepared as described for the synthesis of Example 34, using 4,4,4-trifluoro-2-methylbutan-2-amine in place of 4,4,4-trifluorobutan-1-amine. ¹H NMR (400 MHz, CDCl₃) δ 7.82 (s, 1H), 6.94 (t, J=6.2 Hz, 1H), 5.88 (s, 1H), 4.50 (s, 1H), 4.02-3.88 (m, 2H), 3.75 (s, 3H), 3.39-3.29 (m, 2H), 3.15-2.87 (m, 2H), 2.86-2.78 (m, 4H), 2.33-2.23 (m, 2H), 2.11-2.03 (m, 2H), 1.75-1.64 (m, 1H), 1.60-1.51 (m, 8H), 1.36 (t, J=7.2 Hz, 3H), 1.19-1.07 (m, 2H). MS (ESI) m/z: [M+H]⁺. Found 593.7.

Example 50

4-Chloro-5-(6-(3,3-difluoroazetidin-1-yl)-4-methoxypyridin-3-yl)-1-ethyl-N-(((1r,4r)-4-(methylsulfonyl)cyclohexyl)methyl)-1H-pyrazole-3-carboxamide

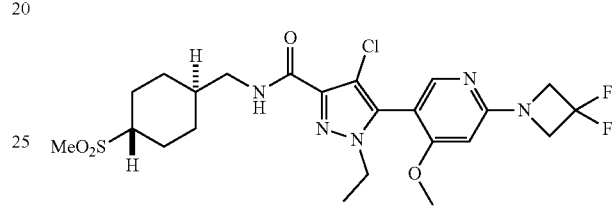

The title compound was prepared as described for the synthesis of Example 34, using 3,3-difluoroazetidine hydrochloride in place of 4,4,4-trifluorobutan-1-amine. ¹H NMR (500 MHz, CDCl₃) δ 7.93 (s, 1H), 6.93 (t, J=6.3 Hz, 1H), 5.87 (s, 1H), 4.50-4.39 (m, 4H), 4.03-3.87 (m, 2H), 3.84 (s, 3H), 3.37-3.30 (m, 2H), 2.86-2.79 (m, 4H), 2.31-2.24 (m, 2H), 2.11-2.03 (m, 2H), 1.73-1.65 (m, 1H), 1.62-1.51 (m, 2H), 1.35 (t, J=7.3 Hz, 3H), 1.18-1.08 (m, 2H). MS (ESI) m/z: [M+H]⁺. Found 545.7.

Example 51

4-Chloro-1-ethyl-5-(4-methoxy-6-(3-(2,2,2-trifluoroethyl)azetidin-1-yl)pyridin-3-yl)-N-(((1r,4r)-4-(methylsulfonyl)cyclohexyl)methyl)-1H-pyrazole-3-carboxamide

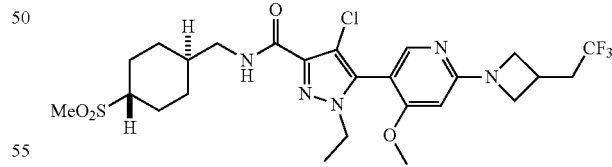

The title compound was prepared as described for the synthesis of Example 34, using 3-(2,2,2-trifluoroethyl)azetidine hydrochloride in place of 4,4,4-trifluorobutan-1-amine. ¹H NMR (400 MHz, CDCl₃) δ 7.89 (s, 1H), 6.93 (t, J=6.3 Hz, 1H), 5.75 (s, 1H), 4.34-4.27 (m, 2H), 4.01-3.83 (m, 4H), 3.81 (s, 3H), 3.36-3.30 (m, 2H), 3.17-3.08 (m, 1H), 2.87-2.77 (m, 4H), 2.58-2.46 (m, 2H), 2.32-2.23 (m, 2H), 2.11-2.02 (m, 2H), 1.73-1.64 (m, 1H), 1.64-1.52 (m, 2H), 1.34 (t, J=7.2 Hz, 3H), 1.19-1.07 (m, 2H). MS (ESI) m/z: [M+H]⁺. Found 591.7.

Example 52

4-Chloro-5-(6-((3,3-difluorocyclobutyl)amino)-4-methoxypyridin-3-yl)-1-ethyl-N-(((1r,4r)-4-(methylsulfonyl)cyclohexyl)methyl)-1H-pyrazole-3-carboxamide

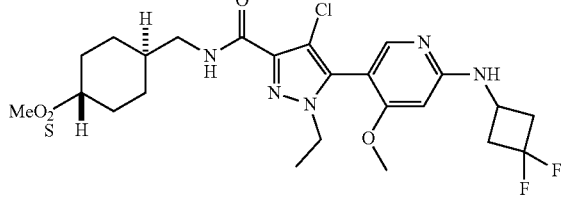

The title compound was prepared as described for the synthesis of Example 34, using 3,3-difluorocyclobutan-1-amine hydrochloride in place of 4,4,4-trifluorobutan-1-amine. $^1$H NMR (400 MHz, CDCl$_3$) δ 7.86 (s, 1H), 6.93 (t, J=6.4 Hz, 1H), 5.91 (s, 1H), 4.96 (d, J=6.2 Hz, 1H), 4.30-4.19 (m, 1H), 4.04-3.88 (m, 2H), 3.80 (s, 3H), 3.38-3.29 (m, 2H), 3.20-3.04 (m, 2H), 2.87-2.78 (m, 4H), 2.61-2.45 (m, 2H), 2.27 (d, J=12.5 Hz, 2H), 2.07 (d, J=13.0 Hz, 2H), 1.74-1.66 (m, 1H), 1.65-1.52 (m, 2H), 1.35 (t, J=7.2 Hz, 3H), 1.20-1.07 (m, 2H). MS (ESI) m/z: [M+H]$^+$. Found 559.8.

Example 53

4-Chloro-1-ethyl-5-(4-methoxy-6-(3-(trifluoromethyl)azetidin-1-yl)pyridin-3-yl)-N-(((1r,4r)-4-(methylsulfonyl)cyclohexyl)methyl)-1H-pyrazole-3-carboxamide

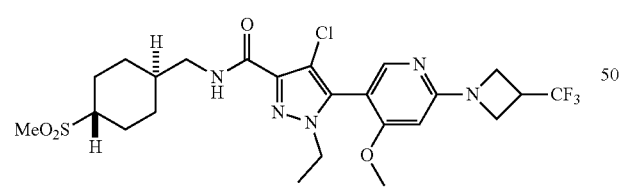

The title compound was prepared as described for the synthesis of Example 34, using 3-(trifluoromethyl)azetidine hydrochloride in place of 4,4,4-trifluorobutan-1-amine. $^1$H NMR (400 MHz, CDCl$_3$) δ 7.91 (s, 1H), 6.93 (t, J=6.3 Hz, 1H), 5.79 (s, 1H), 4.33-4.23 (m, 2H), 4.22-4.14 (m, 2H), 4.03-3.88 (m, 2H), 3.82 (s, 3H), 3.49-3.40 (m, 1H), 3.36-3.31 (m, 2H), 2.87-2.78 (m, 4H), 2.27 (d, J=12.5 Hz, 2H), 2.07 (d, J=13.2 Hz, 2H), 1.73-1.65 (m, 1H), 1.64-1.51 (m, 2H), 1.35 (t, J=7.2 Hz, 3H), 1.19-1.07 (m, 2H). MS (ESI) m/z: [M+H]$^+$. Found 577.6.

Example 54

4-Chloro-5-(6-(3-(difluoromethoxy)azetidin-1-yl)-4-methoxypyridin-3-yl)-1-ethyl-N-(((1r,4r)-4-(methylsulfonyl)cyclohexyl)methyl)-1H-pyrazole-3-carboxamide

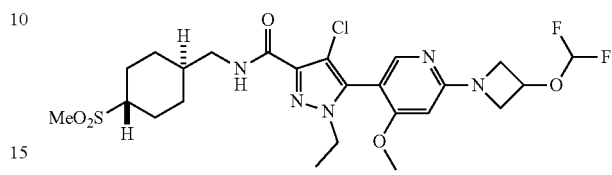

The title compound was prepared as described for the synthesis of Example 34, using 3-(difluoromethoxy)azetidine hydrochloride in place of 4,4,4-trifluorobutan-1-amine. $^1$H NMR (400 MHz, CDCl$_3$) δ 7.90 (s, 1H), 6.93 (t, J=6.4 Hz, 1H), 6.30 (t, J=72.9 Hz, 1H), 5.79 (s, 1H), 5.15 (tt, J=6.7, 4.5 Hz, 1H), 4.45-4.37 (m, 2H), 4.18-4.11 (m, 2H), 4.01-3.89 (m, 2H), 3.82 (s, 3H), 3.36-3.31 (m, 2H), 2.87-2.78 (m, 4H), 2.27 (d, J=12.7 Hz, 2H), 2.07 (d, J=13.9 Hz, 2H), 1.74-1.64 (m, 1H), 1.64-1.50 (m, 2H), 1.34 (t, J=7.2 Hz, 3H), 1.19-1.07 (m, 2H). MS (ESI) m/z: [M+H]$^+$. Found 575.7.

Example 55

4-Chloro-5-(6-(((S*)-3,3-difluorocyclopentyl)amino)-4-methoxypyridin-3-yl)-1-ethyl-N-(((1r,4S)-4-(methylsulfonyl)cyclohexyl)methyl)-1H-pyrazole-3-carboxamide

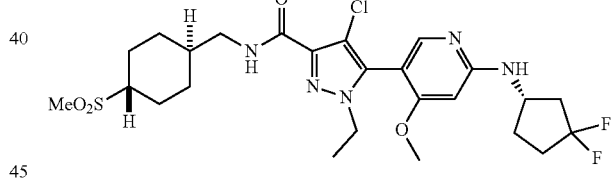

Example 56

4-Chloro-5-(6-(((R*)-3,3-difluorocyclopentyl)amino)-4-methoxypyridin-3-yl)-1-ethyl-N-(((1r,4R)-4-(methylsulfonyl)cyclohexyl)methyl)-1H-pyrazole-3-carboxamide Intermediate 92 was purified by SFC using a chiral stationary phase (Chiralpak AD-H, 65% CO$_2$, 35% MeOH, 0.3% i-PrNH$_2$) to give a pair of enantiomers. The first-eluting isomer was Example 55, and the second-eluting isomer was Example 56. Example 55: ¹H NMR (500 MHz, CDCl₃) δ 7.85 (s, 1H), 6.93 (t, J=6.4 Hz, 1H), 5.93-5.90 (m, 1H), 4.83-4.77 (m, 1H), 4.49-4.41 (m, 1H), 4.01-3.89 (m, 2H), 3.80 (d, J=1.4 Hz, 3H), 3.38-3.29 (m, 2H), 2.86-2.78 (m, 4H), 2.72-2.59 (m, 1H), 2.40-2.23 (m, 4H), 2.23-2.00 (m, 4H), 1.85-1.77 (m, 1H), 1.73-1.64 (m, 1H), 1.64-1.52 (m, 2H), 1.35 (t, J=7.3 Hz, 3H), 1.18-1.08 (m, 2H). MS (ESI) m/z: [M+H]⁺. Found 574.4. Example 56: ¹H NMR (500 MHz, CDCl₃) δ 7.85 (s, 1H), 6.93 (t, J=6.3 Hz, 1H), 5.93-5.90 (m, 1H), 4.83-4.77 (m, 1H), 4.49-4.41 (m, 1H), 4.01-3.90 (m, 2H), 3.80 (d, J=1.4 Hz, 3H), 3.38-3.29 (m, 2H), 2.87-2.78 (m, 4H), 2.71-2.59 (m, 1H), 2.41-2.23 (m, 4H), 2.22-1.99 (m, 4H), 1.85-1.76 (m, 1H), 1.72-1.64 (m, 1H), 1.64-1.52 (m, 2H), 1.35 (t, J=7.3 Hz, 3H), 1.18-1.08 (m, 2H). MS (ESI) m/z: [M+H]⁺. Found 574.4.

Example 57

4-Chloro-5-(6-(((S*)-2,2-difluorocyclopentyl)amino)-4-methoxypyridin-3-yl)-1-ethyl-N-(((1r,4S)-4-(methylsulfonyl)cyclohexyl)methyl)-1H-pyrazole-3-carboxamide

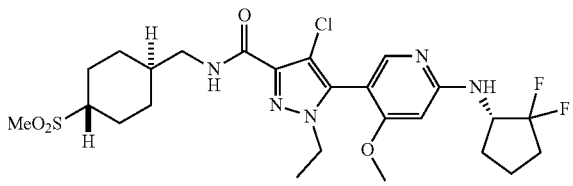 [SMILES: CCn1nc(C(=O)NC[C@H]2CC[C@H](S(C)(=O)=O)CC2)c(Cl)c1-c1cnc(N[C@H]2CCCC2(F)F)cc1OC]

Example 58

4-Chloro-5-(6-(((R*)-2,2-difluorocyclopentyl)amino)-4-methoxypyridin-3-yl)-1-ethyl-N-(((1r,4R)-4-(methylsulfonyl)cyclohexyl)methyl)-1H-pyrazole-3-carboxamide

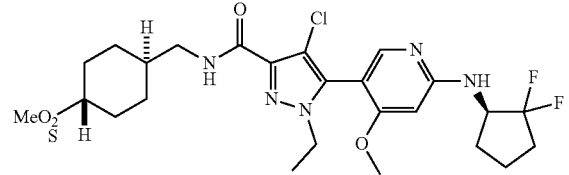 [SMILES: CCn1nc(C(=O)NC[C@H]2CC[C@H](S(C)(=O)=O)CC2)c(Cl)c1-c1cnc(N[C@@H]2CCCC2(F)F)cc1OC]

Intermediate 93 was purified by SFC using a chiral stationary phase (Chiralpak AD-H, 65% CO₂, 35% i-PrOH, 0.3% i-PrNH₂) to give a pair of enantiomers. The first-eluting isomer was Example 57, and the second-eluting isomer was Example 58. Example 57: ¹H NMR (500 MHz, CDCl₃) δ 7.85 (d, J=1.5 Hz, 1H), 6.93 (t, J=6.4 Hz, 1H), 6.04 (d, J=8.2 Hz, 1H), 4.87 (dd, J=28.8, 8.3 Hz, 1H), 4.65-4.40 (m, 1H), 4.01-3.90 (m, 2H), 3.80 (d, J=3.9 Hz, 3H), 3.37-3.29 (m, 2H), 2.86-2.78 (m, 4H), 2.40-2.32 (m, 1H), 2.31-2.13 (m, 4H), 2.10-2.04 (m, 2H), 1.93-1.78 (m, 2H), 1.73-1.49 (m, 4H), 1.35 (td, J=7.2, 3.5 Hz, 3H), 1.20-1.05 (m, 2H). MS (ESI) m/z: [M+H]⁺. Found 574.4. Example 58: ¹H NMR (500 MHz, CDCl₃) δ 7.85 (d, J=1.5 Hz, 1H), 6.95-6.90 (m, 1H), 6.04 (d, J=8.2 Hz, 1H), 4.88 (dd, J=29.8, 8.3 Hz, 1H), 4.62-4.41 (m, 1H), 4.01-3.90 (m, 2H), 3.80 (d, J=3.9 Hz, 3H), 3.37-3.30 (m, 2H), 2.86-2.79 (m, 4H), 2.41-2.32 (m, 1H), 2.31-2.12 (m, 4H), 2.12-2.03 (m, 2H), 1.92-1.75 (m, 2H), 1.73-1.52 (m, 4H), 1.35 (td, J=7.3, 3.5 Hz, 3H), 1.18-1.08 (m, 2H). MS (ESI) m/z: [M+H]⁺. Found 574.4.

Example 59

4-Chloro-1-ethyl-5-(4-methoxy-6-((2-(trifluoromethyl)cyclohexyl)amino)pyridin-3-yl)-N-(((1r,4r)-4-(methylsulfonyl)cyclohexyl)methyl)-1H-pyrazole-3-carboxamide, Fraction A

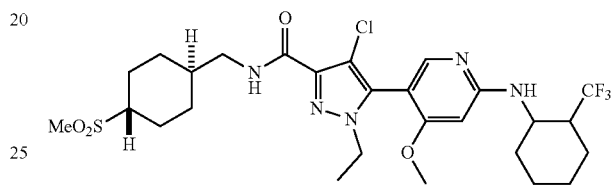

Example 60

4-Chloro-1-ethyl-5-(4-methoxy-6-((2-(trifluoromethyl)cyclohexyl)amino)pyridin-3-yl)-N-(((1r,4r)-4-(methylsulfonyl)cyclohexyl)methyl)-1H-pyrazole-3-carboxamide, Fraction B

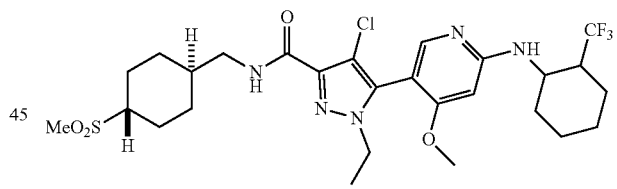

Intermediate 94 was purified by SFC using a chiral stationary phase (Chiralpak AD-H, 70% CO₂, 30% EtOH, 0.3% i-PrNH₂) to give two fractions. The first-eluting fraction was Example 59, and the second-eluting fraction was Example 60. Example 59: ¹H NMR (400 MHz, CDCl₃) δ 7.83 (d, J=2.3 Hz, 1H), 6.93 (t, 1H), 5.95 (s, 1H), 4.99-4.86 (m, 1H), 4.58-4.38 (m, 1H), 4.05-3.90 (m, 2H), 3.83-3.77 (m, 3H), 3.36-3.30 (m, 2H), 2.85-2.76 (m, 4H), 2.51-2.38 (m, 1H), 2.34-2.21 (m, 2H), 2.11-2.02 (m, 3H), 1.97-1.77 (m, 2H), 1.75-1.55 (m, 8H), 1.36 (t, J=7.2 Hz, 3H), 1.20-1.07 (m, 2H). MS (ESI) m/z: [M+H]⁺. Found 620.3. Example 60: ¹H NMR (400 MHz, CDCl₃) δ 7.83 (d, J=2.4 Hz, 1H), 6.93 (t, 1H), 5.96 (s, 1H), 5.00-4.83 (m, 1H), 4.57-4.39 (m, 1H), 4.07-3.89 (m, 2H), 3.83-3.74 (m, 3H), 3.39-3.25 (m, 2H), 2.89-2.75 (m, 4H), 2.55-2.41 (m, 1H), 2.32-2.21 (m, 2H), 2.11-2.01 (m, 3H), 1.97-1.81 (m, 2H), 1.76-1.55 (m, 8H), 1.36 (t, J=7.2 Hz, 3H), 1.21-1.07 (m, 2H). MS (ESI) m/z: [M+H]⁺. Found 620.3.

Example 61

4-Chloro-1-ethyl-5-(4-methoxy-6-((3-(trifluoromethyl)cyclohexyl)amino)pyridin-3-yl)-N-(((1r,4r)-4-(methylsulfonyl)cyclohexyl)methyl)-1H-pyrazole-3-carboxamide, Fraction A

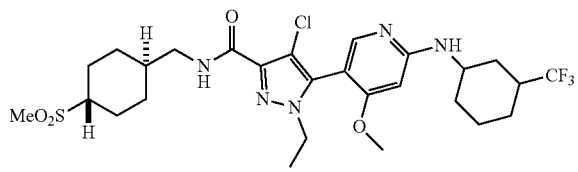 [SMILES: CCn1nc(C(=O)NC[C@H]2CC[C@H](S(C)(=O)=O)CC2)c(Cl)c1-c1cnc(NC2CCCC(C(F)(F)F)C2)cc1OC]

Example 62

4-Chloro-1-ethyl-5-(4-methoxy-6-((3-(trifluoromethyl)cyclohexyl)amino)pyridin-3-yl)-N-(((1r,4r)-4-(methylsulfonyl)cyclohexyl)methyl)-1H-pyrazole-3-carboxamide, Fraction B

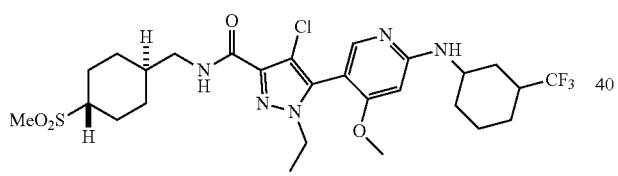

Intermediate 95 was purified by SFC using a chiral stationary phase (Chiralpak AD-H, 70% $CO_2$, 30% i-PrOH, 0.3% i-PrNH$_2$) to give two fractions. The first-eluting fraction was Example 61, and the second-eluting fraction was Example 62. Example 61: $^1$H NMR (500 MHz, CDCl$_3$) δ 7.85-7.82 (m, 1H), 6.94 (t, J=6.3 Hz, 1H), 5.89 (s, 1H), 4.62-4.55 (m, 1H), 4.03-3.90 (m, 2H), 3.90-3.81 (m, 1H), 3.80-3.76 (m, 3H), 3.38-3.29 (m, 2H), 2.87-2.78 (m, 4H), 2.43-2.37 (m, 1H), 2.31-2.13 (m, 4H), 2.11-2.04 (m, 2H), 2.01-1.93 (m, 2H), 1.62-1.53 (m, 2H), 1.52-1.41 (m, 1H), 1.35 (td, J=7.2, 2.5 Hz, 3H), 1.32-1.07 (m, 6H). MS (ESI) m/z: [M+H]$^+$. Found 620.3. Example 62: $^1$H NMR (500 MHz, CDCl$_3$) δ 7.84-7.83 (m, 1H), 6.96-6.91 (m, 1H), 5.88 (s, 1H), 4.57-4.5 (m, 1H), 4.02-3.91 (m, 2H), 3.89-3.76 (m, 4H), 3.36-3.30 (m, 2H), 2.87-2.77 (m, 4H), 2.44-2.37 (m, 1H), 2.32-2.13 (m, 4H), 2.10-1.93 (m, 4H), 1.72-1.64 (m, 1H), 1.54-1.42 (m, 2H), 1.38-1.33 (m, 3H), 1.33-1.07 (m, 6H). MS (ESI) m/z: [M+H]$^+$. Found 620.3.

Example 63

4-Chloro-1-ethyl-5-(4-methoxy-6-((4-(trifluoromethyl)cyclohexyl)amino)pyridin-3-yl)-N-(((1r,4r)-4-(methylsulfonyl)cyclohexyl)methyl)-1H-pyrazole-3-carboxamide

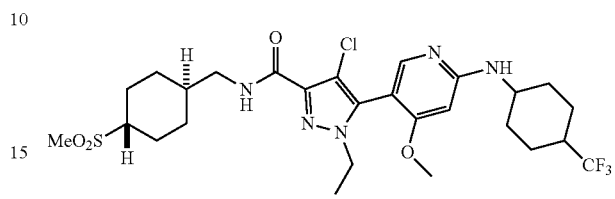

The title compound was prepared as described for the synthesis of Example 34, using 4-(trifluoromethyl)cyclohexan-1-amine in place of 4,4,4-trifluorobutan-1-amine to give a mixture of diastereomers. $^1$H NMR (400 MHz, CDCl$_3$) δ 7.83 (s, 1H), 6.93 (t, J=6.3 Hz, 1H), 5.89 (s, 1H), 4.58 (d, J=8.1 Hz, 1H), 4.06-3.88 (m, 2H), 3.79 (s, 3H), 3.75-3.66 (m, 1H), 3.36-3.30 (m, 2H), 2.87-2.78 (m, 4H), 2.33-2.23 (m, 4H), 2.11-1.94 (m, 5H), 1.74-1.65 (m, 1H), 1.65-1.46 (m, 4H), 1.35 (t, J=7.2 Hz, 3H), 1.32-1.05 (m, 4H). MS (ESI) m/z: [M+H]$^+$. Found 619.6.

Example 64

1-Ethyl-5-(4-methoxy-6-((4,4,4-trifluorobutyl)amino)pyridin-3-yl)-4-methyl-N-(((1r,4r)-4-(methylsulfonyl)cyclohexyl)methyl)-1H-pyrazole-3-carboxamide

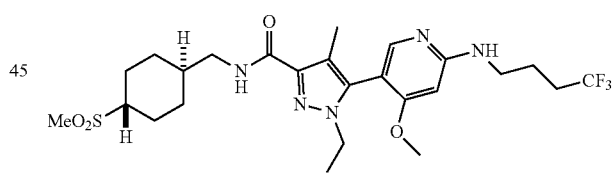

The title compound was prepared as described for the synthesis of Example 43, using 4-chloro-1-ethyl-5-(4-methoxy-6-((4,4,4-trifluorobutyl)amino)pyridin-3-yl)-N-(((1r,4r)-4-(methylsulfonyl)cyclohexyl)methyl)-1H-pyrazole-3-carboxamide (Example 34) in place of 4-chloro-1-ethyl-5-(4-methoxy-6-((2-(2,2,2-trifluoroethoxy)ethyl)amino)pyridin-3-yl)-N-(((1r,4r)-4-(methylsulfonyl)cyclohexyl)methyl)-1H-pyrazole-3-carboxamide. $^1$H NMR (400 MHz, CDCl$_3$) δ 7.76 (s, 1H), 7.04 (t, J=6.4 Hz, 1H), 5.92 (s, 1H), 4.66 (t, J=5.9 Hz, 1H), 4.00-3.84 (m, 2H), 3.79 (s, 3H), 3.51-3.43 (m, 2H), 3.35-3.26 (m, 2H), 2.87-2.78 (m, 4H), 2.31-2.19 (m, 4H), 2.16 (s, 3H), 2.12-2.04 (m, 2H), 1.99-1.89 (m, 2H) 1.71-1.64 (m, 1H), 1.64-1.52 (m, 2H), 1.33 (t, J=7.2 Hz, 3H), 1.18-1.06 (m, 2H). MS (ESI) m/z: [M+H]$^+$. Found 559.8.

Example 65

4-Chloro-5-(6-(((6,6-difluorospiro[3.3]heptan-2-yl)amino)-4-methoxypyridin-3-yl)-1-ethyl-N-(((1r,4r)-4-(methylsulfonyl)cyclohexyl)methyl)-1H-pyrazole-3-carboxamide

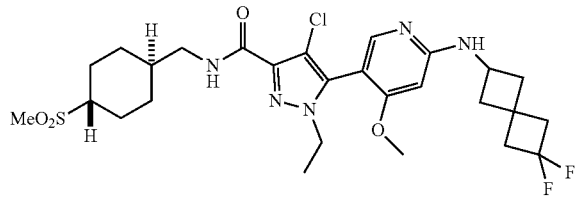 [SMILES: CCn1nc(C(=O)NC[C@H]2CC[C@H](S(C)(=O)=O)CC2)c(Cl)c1-c1cnc(NC2CC3(C2)CC(F)(F)C3)cc1OC]

The title compound was prepared as described for the synthesis of Example 34, using 6,6-difluorospiro[3.3]heptan-2-amine hydrochloride in place of 4,4,4-trifluorobutan-1-amine. $^1$H NMR (400 MHz, CDCl$_3$) δ 7.83 (s, 1H), 6.93 (t, J=6.3 Hz, 1H), 5.82 (s, 1H), 4.91 (d, J=6.6 Hz, 1H), 4.26-4.15 (m, 1H), 4.02-3.89 (m, 2H), 3.80 (s, 3H), 3.37-3.30 (m, 2H), 2.87-2.78 (m, 4H), 2.74-2.54 (m, 6H), 2.27 (d, J=12.6 Hz, 2H), 2.15-2.03 (m, 4H), 1.73-1.65 (m, 1H), 1.65-1.52 (m, 2H), 1.35 (t, J=7.2 Hz, 3H), 1.19-1.07 (m, 2H). MS (ESI) m/z: [M+H]$^+$. Found 599.7.

Example 66

4-Chloro-1-ethyl-5-(4-methoxy-6-(((1-(trifluoromethyl)cyclopropyl)methyl)amino)pyridin-3-yl)-N-(((1r,4r)-4-(methylsulfonyl)cyclohexyl)methyl)-1H-pyrazole-3-carboxamide

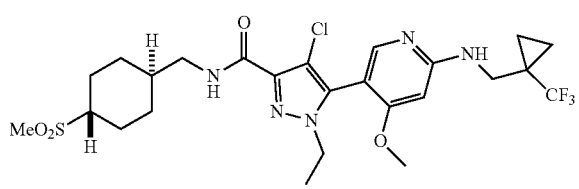 [SMILES: CCn1nc(C(=O)NC[C@H]2CC[C@H](S(C)(=O)=O)CC2)c(Cl)c1-c1cnc(NCC2(C(F)(F)F)CC2)cc1OC]

The title compound was prepared as described for the synthesis of Example 34, using (1-(trifluoromethyl)cyclopropyl)methanamine hydrochloride in place of 4,4,4-trifluorobutan-1-amine. $^1$H NMR (400 MHz, CDCl$_3$) δ 7.82 (s, 1H), 6.93 (t, J=6.4 Hz, 1H), 5.95 (s, 1H), 4.88 (t, J=5.9 Hz, 1H), 4.02-3.89 (m, 2H), 3.80 (s, 3H), 3.70-3.66 (m, 2H), 3.36-3.31 (m, 2H), 2.87-2.76 (m, 4H), 2.32-2.24 (m, 2H), 2.11-2.03 (m, 2H), 1.74-1.65 (m, 1H), 1.65-1.50 (m, 2H), 1.35 (t, J=7.3 Hz, 3H), 1.20-1.04 (m, 4H), 0.92-0.86 (m, 2H). MS (ESI) m/z: [M+H]$^+$. Found 591.7.

Example 67

4-Chloro-1-ethyl-5-(4-methoxy-6-((1-(2,2,2-trifluoroethyl)cyclopropyl)amino)pyridin-3-yl)-N-(((1r,4r)-4-(methylsulfonyl)cyclohexyl)methyl)-1H-pyrazole-3-carboxamide

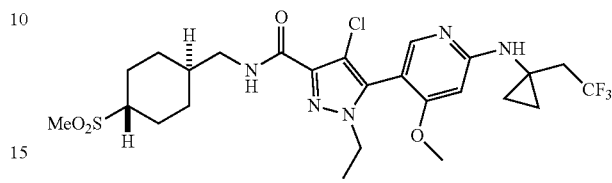

4-Chloro-5-(6-chloro-4-methoxypyridin-3-yl)-1-ethyl-N-(((1r,4r)-4-(methylsulfonyl)cyclohexyl)methyl)-1H-pyrazole-3-carboxamide (51.3 mg, 0.105 mmol, Intermediate 87), BrettPhos G3 precatalyst (5.1 mg, 0.0056 mmol), 1-(2,2,2-trifluoroethyl)cyclopropan-1-amine hydrochloride (29.5 mg, 0.168 mmol), and sodium tert-butoxide (30.5 mg, 0.317 mmol) were combined in a vessel, and the vessel was evacuated and backfilled with argon. 1,4-Dioxane (0.5 mL) was added and argon was bubbled through the reaction mixture for 30 seconds. The reaction was then stirred at 120° C. overnight. After this time, the mixture was allowed to cool to rt and diluted with EtOAc and water. The layers were separated, and the aqueous layer was extracted with EtOAc. The organic layers were combined, dried with anhydrous MgSO$_4$, filtered, and then concentrated to dryness. The residue was purified by HPLC (XBridge C18, 5→99% MeCN/water, 20 mM NH$_4$OH) to afford the title compound. $^1$H NMR (500 MHz, CDCl$_3$) δ 7.88 (s, 1H), 6.94 (t, J=6.3 Hz, 1H), 6.11 (s, 1H), 5.35 (s, 1H), 4.04-3.88 (m, 2H), 3.83 (s, 3H), 3.39-3.27 (m, 2H), 2.87-2.78 (m, 4H), 2.54-2.43 (m, 2H), 2.31-2.24 (m, 2H), 2.10-2.04 (m, 2H), 1.74-1.66 (m, 1H), 1.64-1.54 (m, 2H), 1.37 (t, J=7.2 Hz, 3H), 1.19-1.08 (m, 2H), 1.06-0.98 (m, 4H). MS (ESI) m/z: [M+H]$^+$. Found 592.2.

Example 68

4-Chloro-1-ethyl-5-(4-methoxy-6-(((1-(trifluoromethyl)cyclobutyl)methyl)amino)pyridin-3-yl)-N-(((1r,4r)-4-(methylsulfonyl)cyclohexyl)methyl)-1H-pyrazole-3-carboxamide

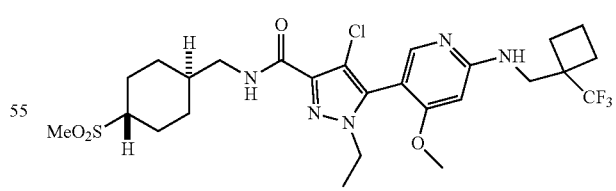

The title compound was prepared as described for the synthesis of Example 67, using (1-(trifluoromethyl)cyclobutyl)methanamine hydrochloride in place of 1-(2,2,2-trifluoroethyl)cyclopropan-1-amine hydrochloride. $^1$H NMR (500 MHz, CDCl$_3$) δ 7.86 (s, 1H), 6.93 (t, J=6.4 Hz, 1H), 5.96 (s, 1H), 4.78 (t, J=6.0 Hz, 1H), 4.03-3.89 (m, 2H), 3.82 (d, J=5.9 Hz, 2H), 3.80 (s, 3H), 3.39-3.29 (m, 2H), 2.86-2.78 (m, 4H), 2.39-2.31 (m, 2H), 2.31-2.24 (m, 2H), 2.12-1.99 (m, 6H), 1.72-1.65 (m, 1H), 1.65-1.53 (m, 2H), 1.38-1.33 (m, 3H), 1.19-1.08 (m, 2H). MS (ESI) m/z: [M+H]⁺. Found 606.1.

Example 69

4-Chloro-1-ethyl-5-(4-methoxy-6-((3,3,3-trifluoro-2,2-dimethylpropyl)amino)pyridin-3-yl)-N-(((1r,4r)-4-(methylsulfonyl)cyclohexyl)methyl)-1H-pyrazole-3-carboxamide

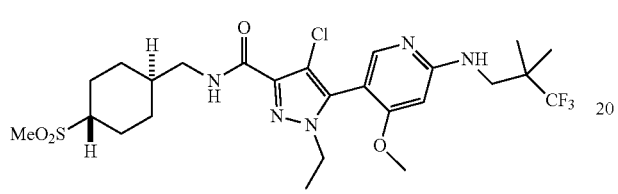

The title compound was prepared as described for the synthesis of Example 67, using 3,3,3-trifluoro-2,2-dimethylpropan-1-amine hydrochloride in place of 1-(2,2,2-trifluoroethyl)cyclopropan-1-amine hydrochloride. ¹H NMR (500 MHz, CDCl₃) δ 7.83 (s, 1H), 6.93 (t, J=6.4 Hz, 1H), 5.96 (s, 1H), 4.79 (t, J=6.3 Hz, 1H), 4.02-3.89 (m, 2H), 3.80 (s, 3H), 3.60 (d, J=6.4 Hz, 2H), 3.39-3.28 (m, 2H), 2.87-2.78 (m, 4H), 2.31-2.24 (m, 2H), 2.10-2.03 (m, 2H), 1.71-1.66 (m, 1H), 1.62-1.52 (m, 2H), 1.35 (t, J=7.3 Hz, 3H), 1.22 (s, 6H), 1.19-1.07 (m, 2H). MS (ESI) m/z: [M+H]⁺. Found 594.3.

Example 70

4-Chloro-1-ethyl-5-(4-methoxy-6-((2-(trifluoromethyl)cyclobutyl)amino)pyridin-3-yl)-N-(((1r,4r)-4-(methylsulfonyl)cyclohexyl)methyl)-1H-pyrazole-3-carboxamide

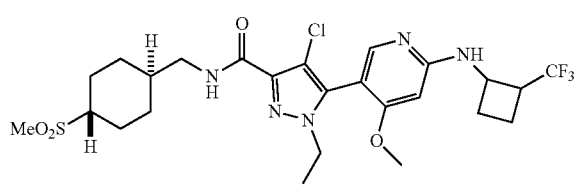 [SMILES: CCn1nc(C(=O)NC[C@H]2CC[C@H](S(C)(=O)=O)CC2)c(Cl)c1-c1cnc(NC2CCC2C(F)(F)F)cc1OC]

The title compound was prepared as described for the synthesis of Example 67, using 2-(trifluoromethyl)cyclobutan-1-amine hydrochloride in place of 1-(2,2,2-trifluoroethyl)cyclopropan-1-amine hydrochloride. ¹H NMR (400 MHz, CDCl₃) δ 7.84 (d, J=3.1 Hz, 1H), 6.93 (t, J=6.3 Hz, 1H), 5.95 (d, J=1.9 Hz, 1H), 5.16-5.07 (m, 1H), 4.39 (dt, J=26.1, 7.8 Hz, 1H), 4.02-3.87 (m, 2H), 3.80 (d, J=2.0 Hz, 3H), 3.39-3.27 (m, 2H), 2.98-2.88 (m, 1H), 2.88-2.77 (m, 4H), 2.55-2.43 (m, 1H), 2.32-2.23 (m, 2H), 2.16-1.86 (m, 6H), 1.64-1.50 (m, 2H), 1.35 (td, J=7.2, 1.9 Hz, 3H), 1.20-1.06 (m, 2H). MS (ESI) m/z: [M+H]⁺. Found 592.2.

Example 71

4-Chloro-1-ethyl-5-(4-methoxy-6-((2-(trifluoromethyl)cyclobutyl)amino)pyridin-3-yl)-N-(((1r,4r)-4-(methylsulfonyl)cyclohexyl)methyl)-1H-pyrazole-3-carboxamide, Fraction A

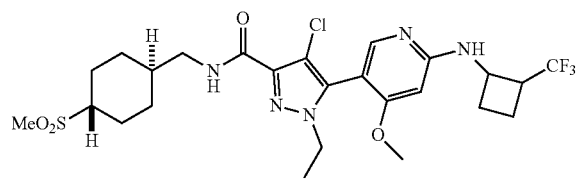 [SMILES: CCn1nc(C(=O)NC[C@H]2CC[C@H](S(C)(=O)=O)CC2)c(Cl)c1-c1cnc(NC2CCC2C(F)(F)F)cc1OC]

Example 72

4-Chloro-1-ethyl-5-(4-methoxy-6-((2-(trifluoromethyl)cyclobutyl)amino)pyridin-3-yl)-N-(((1r,4r)-4-(methylsulfonyl)cyclohexyl)methyl)-1H-pyrazole-3-carboxamide, Fraction B

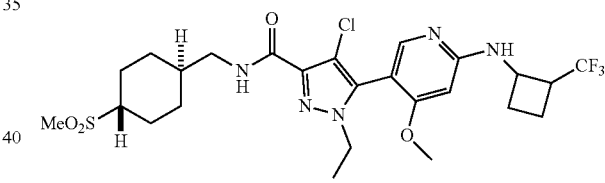

Example 70 was purified by SFC using a chiral stationary phase (Chiralpak AS-H, 75% CO₂, 25% MeOH, 0.3% i-PrNH₂) to give two fractions. The first-eluting fraction was repurified by SFC using an achiral stationary phase (diethylaminopropyl, 80% CO₂, 20% MeOH, 0.3% 1-PrNH₂) to give Example 71. The second-eluting fraction was Example 72. Example 71: ¹H NMR (400 MHz, CDCl₃) δ 7.88-7.79 (m, 1H), 6.93 (t, J=6.2 Hz, 1H), 5.99-5.93 (m, 1H), 5.08 (dd, J=18.1, 7.6 Hz, 1H), 4.49-4.29 (m, 1H), 4.04-3.87 (m, 2H), 3.80 (s, 3H), 3.40-3.26 (m, 2H), 2.99-2.88 (m, 1H), 2.88-2.76 (m, 4H), 2.54-2.43 (m, 1H), 2.33-2.22 (m, 2H), 2.13-2.03 (m, 3H), 2.03-1.87 (m, 3H), 1.73-1.50 (m, 2H), 1.41-1.30 (m, 3H), 1.21-1.06 (m, 2H). MS (ESI) m/z: [M+H]⁺. Found 592.2. Example 72: ¹H NMR (400 MHz, CDCl₃) δ 7.88-7.81 (m, 1H), 6.93 (t, J=6.3 Hz, 1H), 5.99-5.90 (m, 1H), 5.08-4.99 (m, 1H), 4.47-4.29 (m, 1H), 4.03-3.86 (m, 2H), 3.80 (s, 3H), 3.42-3.30 (m, 2H), 3.02-2.88 (m, 1H), 2.88-2.78 (m, 4H), 2.55-2.43 (m, 1H), 2.32-2.22 (m, 2H), 2.14-2.02 (m, 3H), 2.02-1.89 (m, 3H), 1.63-1.51 (m, 2H), 1.41-1.22 (m, 3H), 1.22-1.03 (m, 2H). MS (ESI) m/z: [M+H]⁺. Found 592.2.

Example 73

4-Chloro-1-ethyl-5-(4-methoxy-6-((3-(trifluoromethyl)cyclobutyl)amino)pyridin-3-yl)-N-(((1r,4r)-4-(methylsulfonyl)cyclohexyl)methyl)-1H-pyrazole-3-carboxamide

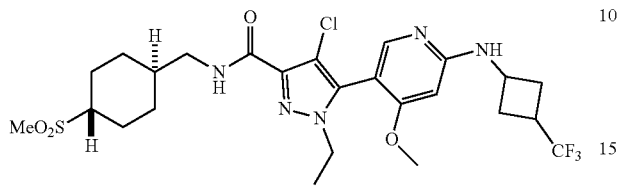

The title compound was prepared as described for the synthesis of Example 67, using 3-(trifluoromethyl)cyclobutan-1-amine hydrochloride in place of 1-(2,2,2-trifluoroethyl)cyclopropan-1-amine hydrochloride. $^1$H NMR (400 MHz, CDCl$_3$) δ 7.84 (s, 1H), 6.93 (t, J=6.3 Hz, 1H), 5.83 (s, 1H), 5.12-5.02 (m, 1H), 4.47-4.32 (m, 1H), 4.02-3.88 (m, 2H), 3.80 (s, 3H), 3.39-3.27 (m, 2H), 3.05-2.92 (m, 1H), 2.89-2.77 (m, 4H), 2.75-2.66 (m, 2H), 2.36-2.17 (m, 3H), 2.14-1.94 (m, 3H), 1.72-1.47 (m, 3H), 1.35 (t, J=7.2 Hz, 3H), 1.20-1.05 (m, 2H). MS (ESI) m/z: [M+H]$^+$. Found 592.2.

Example 74

4-Chloro-1-ethyl-5-(4-methoxy-6-(((1s*,3s*)-3-(trifluoromethyl)cyclobutyl)amino)pyridin-3-yl)-N-(((1r,4r)-4-(methylsulfonyl)cyclohexyl)methyl)-1H-pyrazole-3-carboxamide

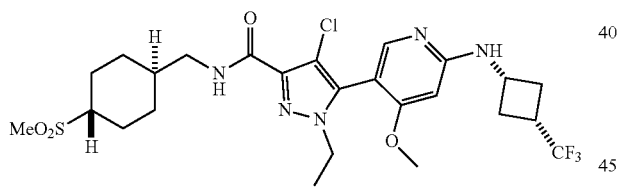

Example 75

4-Chloro-1-ethyl-5-(4-methoxy-6-(((1r*,3r*)-3-(trifluoromethyl)cyclobutyl)amino)pyridin-3-yl)-N-(((1r,4r)-4-(methylsulfonyl)cyclohexyl)methyl)-1H-pyrazole-3-carboxamide

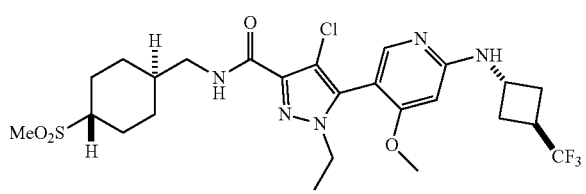

Example 73 was purified by SFC using a chiral stationary phase (Whelk 01 (S,S), 60% CO$_2$, 40% MeOH, 0.3% i-PrNH$_2$) to give a pair of diastereomers. The first-eluting isomer was Example 74, and the second-eluting isomer was Example 75. Example 74: MS (ESI) m/z: [M+H]$^+$. Found 592.3. Example 75: MS (ESI) m/z: [M+H]$^+$. Found 592.3.

Example 76

4-Chloro-1-ethyl-5-(4-methoxy-6-((2-(trifluoromethyl)cyclopropyl)amino)pyridin-3-yl)-N-(((1r,4r)-4-(methylsulfonyl)cyclohexyl)methyl)-1H-pyrazole-3-carboxamide

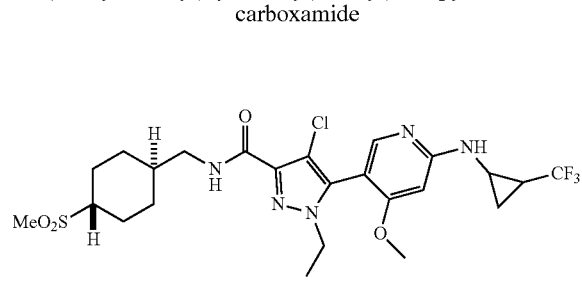

The title compound was prepared as described for the synthesis of Example 67, using 2-(trifluoromethyl)cyclopropan-1-amine hydrochloride in place of 1-(2,2,2-trifluoroethyl)cyclopropan-1-amine hydrochloride. $^1$H NMR (400 MHz, CDCl$_3$) δ 7.86 (s, 1H), 6.94 (t, J=6.4 Hz, 1H), 6.36 (s, 1H), 5.47 (d, J=6.4 Hz, 1H), 4.06-3.88 (m, 2H), 3.86 (s, 3H), 3.40-3.28 (m, 2H), 2.98-2.91 (m, 1H), 2.88-2.77 (m, 4H), 2.32-2.23 (m, 2H), 2.11-2.02 (m, 2H), 1.83-1.72 (m, 1H), 1.65-1.52 (m, 2H), 1.45-1.38 (m, 1H), 1.36 (td, J=7.2, 1.3 Hz, 3H), 1.30-1.21 (m, 2H), 1.20-1.07 (m, 2H). MS (ESI) m/z: [M+H]$^+$. Found 578.2.

Example 77

4-Chloro-1-ethyl-5-(4-methoxy-6-((2-(trifluoromethyl)cyclopropyl)amino)pyridin-3-yl)-N-(((1r,4r)-4-(methylsulfonyl)cyclohexyl)methyl)-1H-pyrazole-3-carboxamide, Fraction A

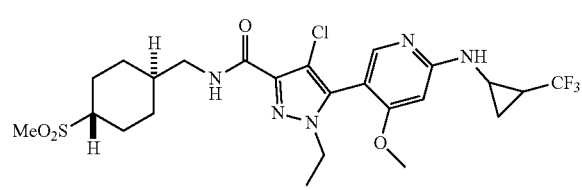 [SMILES: CCn1nc(C(=O)NC[C@H]2CC[C@H](S(C)(=O)=O)CC2)c(Cl)c1-c1cnc(NC2CC2C(F)(F)F)cc1OC]

Example 78

4-Chloro-1-ethyl-5-(4-methoxy-6-((2-(trifluoromethyl)cyclopropyl)amino)pyridin-3-yl)-N-(((1r,4r)-4-(methylsulfonyl)cyclohexyl)methyl)-1H-pyrazole-3-carboxamide, Fraction B

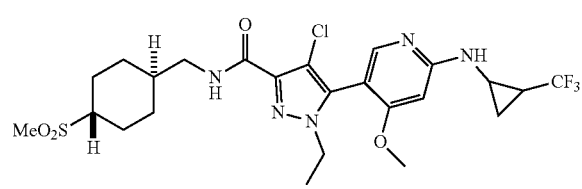 [SMILES: CCn1nc(C(=O)NC[C@H]2CC[C@H](S(C)(=O)=O)CC2)c(Cl)c1-c1cnc(NC2CC2C(F)(F)F)cc1OC]

Example 76 was purified by SFC using a chiral stationary phase (Chiralcel OX, 80% CO₂, 20% EtOH, 0.2% TEA) to give two fractions. The first-eluting fraction was Example 77, and the second-eluting fraction was Example 78. Example 77: ¹H NMR (400 MHz, CDCl₃) δ 7.86 (s, 1H), 6.93 (t, J=6.4 Hz, 1H), 6.36 (s, 1H), 5.28 (s, 1H), 4.04-3.89 (m, 2H), 3.86 (s, 3H), 3.40-3.27 (m, 2H), 2.98-2.89 (m, 1H), 2.89-2.78 (m, 4H), 2.31-2.22 (m, 2H), 2.12-2.02 (m, 2H), 1.82-1.72 (m, 1H), 1.72-1.50 (m, 3H), 1.47-1.31 (m, 4H), 1.31-1.22 (m, 1H), 1.22-1.06 (m, 2H). Example 78: ¹H NMR (400 MHz, CDCl₃) δ 7.86 (s, 1H), 6.93 (t, J=6.3 Hz, 1H), 6.36 (s, 1H), 5.33 (s, 1H), 4.06-3.90 (m, 2H), 3.86 (s, 3H), 3.38-3.28 (m, 2H), 3.00-2.90 (m, 1H), 2.90-2.77 (m, 4H), 2.33-2.23 (m, 2H), 2.12-2.00 (m, 2H), 1.82-1.65 (m, 2H), 1.65-1.53 (m, 2H), 1.45-1.32 (m, 4H), 1.29-1.23 (m, 1H), 1.19-1.07 (m, 2H).

Example 79

4-Chloro-1-ethyl-N-(((1s,4s)-1-hydroxy-4-(methylsulfonyl)cyclohexyl)methyl)-5-(4-methoxy-6-((4,4,4-trifluoro-2-methylbutan-2-yl)amino)pyridin-3-yl)-1H-pyrazole-3-carboxamide

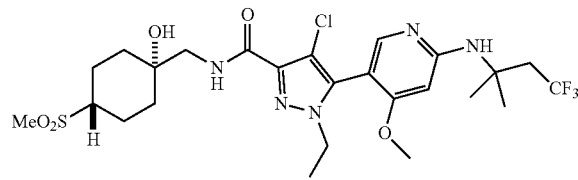 [SMILES: CCn1nc(C(=O)NC[C@]2(O)CC[C@@H](S(C)(=O)=O)CC2)c(Cl)c1-c1cnc(NC(C)(C)CC(F)(F)F)cc1OC]

The title compound was prepared as described for the synthesis of Example 67, using 4,4,4-trifluoro-2-methylbutan-2-amine in place of 1-(2,2,2-trifluoroethyl)cyclopropan-1-amine hydrochloride and 4-chloro-5-(6-chloro-4-methoxypyridin-3-yl)-1-ethyl-N-(((1s,4s)-1-hydroxy-4-(methylsulfonyl)cyclohexyl)methyl)-1H-pyrazole-3-carboxamide (Intermediate 79) in place of 4-chloro-5-(6-chloro-4-methoxypyridin-3-yl)-1-ethyl-N-(((1r,4r)-4-(methylsulfonyl)cyclohexyl)methyl)-1H-pyrazole-3-carboxamide. ¹H NMR (500 MHz, CDCl₃) δ 7.81 (s, 1H), 7.23 (t, J=6.3 Hz, 1H), 5.88 (s, 1H), 4.50 (s, 1H), 4.04-3.89 (m, 2H), 3.76 (s, 3H), 3.52-3.40 (m, 2H), 3.19 (s, 1H), 3.13-3.00 (m, 1H), 2.91-2.76 (m, 5H), 2.16-2.09 (m, 2H), 2.04-1.92 (m, 4H), 1.60-1.56 (m, 6H), 1.46-1.35 (m, 5H). MS (ESI) m/z: [M+H]⁺. Found 610.2.

Example 80

4-Chloro-1-ethyl-N-(((1s,4s)-1-hydroxy-4-(methylsulfonyl)cyclohexyl)methyl)-5-(4-methyl-6-((4,4,4-trifluoro-2-methylbutan-2-yl)amino)pyridin-3-yl)-1H-pyrazole-3-carboxamide

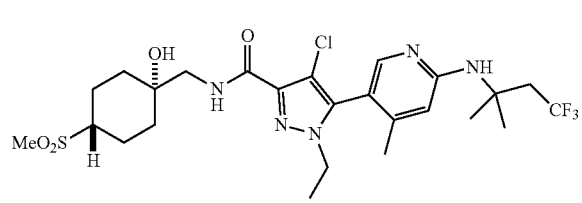 [SMILES: CCn1nc(C(=O)NC[C@]2(O)CC[C@@H](S(C)(=O)=O)CC2)c(Cl)c1-c1cnc(NC(C)(C)CC(F)(F)F)cc1C]

The title compound was prepared as described for the synthesis of Example 67, using 4,4,4-trifluoro-2-methylbutan-2-amine in place of 1-(2,2,2-trifluoroethyl)cyclopropan-1-amine hydrochloride and 4-chloro-5-(6-chloro-4-methylpyridin-3-yl)-1-ethyl-N-(((1s,4s)-1-hydroxy-4-(methylsulfonyl)cyclohexyl)methyl)-1H-pyrazole-3-carboxamide (Intermediate 88) in place of 4-chloro-5-(6-chloro-4-methoxypyridin-3-yl)-1-ethyl-N-(((1r,4r)-4-(methylsulfonyl)cyclohexyl)methyl)-1H-pyrazole-3-carboxamide. ¹H NMR (500 MHz, CDCl₃) δ 7.83 (s, 1H), 7.24 (t, J=6.0 Hz, 1H), 6.30-6.28 (m, 1H), 4.46 (s, 1H), 4.05-3.90 (m, 2H), 3.52-3.42 (m, 2H), 3.08-2.99 (m, 2H), 2.88 (s, 1H), 2.83 (s, 3H), 2.82-2.75 (m, 1H), 2.16-2.10 (m, 2H), 2.06-1.93 (m, 7H), 1.58-1.55 (m, 6H), 1.48-1.40 (m, 2H), 1.37-1.32 (m, 3H). MS (ESI) m/z: [M+H]⁺. Found 594.3.

Example 81

4-Chloro-1-ethyl-N-(((1s,4s)-1-hydroxy-4-(methylsulfonyl)cyclohexyl)methyl)-5-(4-methyl-6-((1-(2,2,2-trifluoroethyl)cyclopropyl)amino)pyridin-3-yl)-1H-pyrazole-3-carboxamide

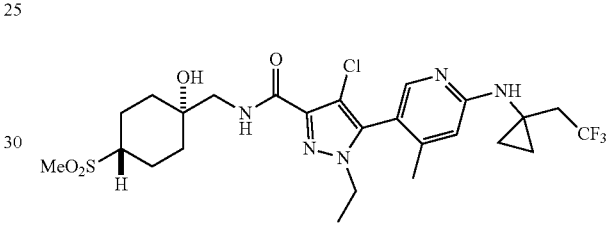

The title compound was prepared as described for the synthesis of Example 67, using 4-chloro-5-(6-chloro-4-methylpyridin-3-yl)-1-ethyl-N-(((1s,4s)-1-hydroxy-4-(methylsulfonyl)cyclohexyl)methyl)-1H-pyrazole-3-carboxamide (Intermediate 88) in place of 4-chloro-5-(6-chloro-4-methoxypyridin-3-yl)-1-ethyl-N-(((1r,4r)-4-(methylsulfonyl)cyclohexyl)methyl)-1H-pyrazole-3-carboxamide. ¹H NMR (400 MHz, CDCl₃) δ 7.90 (s, 1H), 7.26-7.22 (m, 1H), 6.51 (s, 1H), 5.28 (s, 1H), 4.06-3.88 (m, 2H), 3.54-3.41 (m, 2H), 3.09 (s, 1H), 2.86-2.75 (m, 4H), 2.52-2.41 (m, 2H), 2.17-2.06 (m, 5H), 2.05-1.91 (m, 4H), 1.49-1.39 (m, 2H), 1.35 (t, J=7.2 Hz, 3H), 1.04-0.96 (m, 4H). MS (ESI) m/z: [M+H]⁺. Found 592.2.

Example 82

4-Chloro-1-ethyl-N-(((1r,4r)-4-(methylsulfonyl)cyclohexyl)methyl)-5-(6-((4,4,4-trifluoro-2-methylbutan-2-yl)amino)-4-(trifluoromethyl)pyridin-3-yl)-1H-pyrazole-3-carboxamide

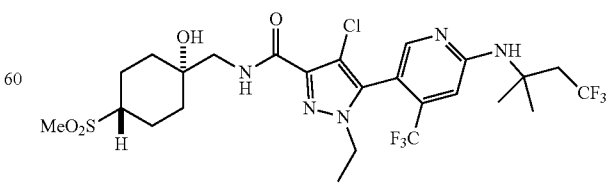

The title compound was prepared as described for the synthesis of Example 67, using 4-chloro-5-(6-chloro-4-(trifluoromethyl)pyridin-3-yl)-1-ethyl-N-(((1r,4r)-4-(methylsulfonyl)cyclohexyl)methyl)-1H-pyrazole-3-carboxamide (Intermediate 81) and 4,4,4-trifluoro-2-methylbutan-2-amine in place of 4-chloro-5-(6-chloro-4-methoxypyridin-3-yl)-1-ethyl-N-(((1r,4r)-4-(methylsulfonyl)cyclohexyl)methyl)-1H-pyrazole-3-carboxamide and 1-(2,2,2-trifluoroethyl)cyclopropan-1-amine hydrochloride. $^1$H NMR (400 MHz, CDCl$_3$) δ 7.98 (s, 1H), 6.94 (t, J=6.3 Hz, 1H), 6.72 (s, 1H), 4.85 (s, 1H), 4.00-3.79 (m, 2H), 3.38-3.30 (m, 2H), 3.15-2.99 (m, 1H), 2.91-2.77 (m, 5H), 2.33-2.24 (m, 2H), 2.12-2.04 (m, 2H), 1.75-1.66 (m, 1H), 1.63-1.53 (m, 8H), 1.38 (t, J=7.3 Hz, 3H), 1.21-1.08 (m, 2H). MS (ESI) m/z: [M+H]$^+$. Found 632.2.

Example 83

4-Chloro-1-ethyl-N-(((1s,4s)-1-hydroxy-4-(methylsulfonyl)cyclohexyl)methyl)-5-(6-((4,4,4-trifluoro-2-methylbutan-2-yl)amino)-4-(trifluoromethyl)pyridin-3-yl)-1H-pyrazole-3-carboxamide

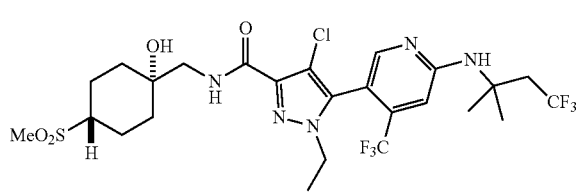 [SMILES: CCn1nc(C(=O)NC[C@]2(O)CC[C@@H](S(C)(=O)=O)CC2)c(Cl)c1-c1cnc(NC(C)(C)CC(F)(F)F)cc1C(F)(F)F]

The title compound was prepared as described for the synthesis of Example 67, using 4,4,4-trifluoro-2-methylbutan-2-amine in place of 1-(2,2,2-trifluoroethyl)cyclopropan-1-amine hydrochloride and 4-chloro-5-(6-chloro-4-(trifluoromethyl)pyridin-3-yl)-1-ethyl-N-(((1s,4s)-1-hydroxy-4-(methylsulfonyl)cyclohexyl)methyl)-1H-pyrazole-3-carboxamide (Intermediate 80) in place of 4-chloro-5-(6-chloro-4-methoxypyridin-3-yl)-1-ethyl-N-(((1r,4r)-4-(methylsulfonyl)cyclohexyl)methyl)-1H-pyrazole-3-carboxamide. $^1$H NMR (400 MHz, CDCl$_3$) δ 7.98 (s, 1H), 7.26-7.20 (m, 1H), 6.72 (s, 1H), 4.87 (s, 1H), 4.02-3.81 (m, 2H), 3.61-3.43 (m, 2H), 3.14-2.98 (m, 2H), 2.88 (s, 1H), 2.87-2.76 (m, 4H), 2.19-1.80 (m, 6H), 1.62-1.60 (m, 6H), 1.50-1.34 (m, 5H). MS (ESI) m/z: [M+H]$^+$. Found 648.3.

Example 84

4-Chloro-5-(4-(difluoromethoxy)-6-((4,4,4-trifluorobutan-2-yl)amino)pyridin-3-yl)-1-ethyl-N-(((1s,4s)-1-hydroxy-4-(methylsulfonyl)cyclohexyl)methyl)-1H-pyrazole-3-carboxamide

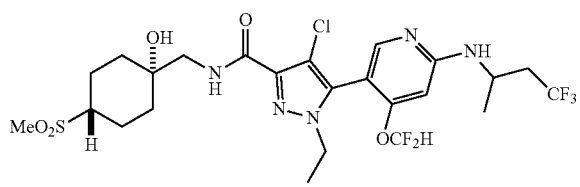

The title compound was prepared as described for the synthesis of Example 1, using ethyl 4-chloro-5-(4-(difluoromethoxy)-6-((4,4,4-trifluorobutan-2-yl)amino)pyridin-3-yl)-1-ethyl-1H-pyrazole-3-carboxylate (Intermediate 82) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate. $^1$H NMR (400 MHz, CDCl$_3$) δ 7.99 (s, 1H), 7.23 (t, J=6.2 Hz, 1H), 6.52 (ddd, J=74.0, 70.1, 1.8 Hz, 1H), 6.20 (s, 1H), 4.76 (t, J=8.5 Hz, 1H), 4.46-4.33 (m, 1H), 4.10-3.91 (m, 2H), 3.52-3.41 (m, 2H), 3.10-3.06 (m, 1H), 2.86-2.75 (m, 4H), 2.65-2.48 (m, 1H), 2.45-2.27 (m, 1H), 2.19-2.08 (m, 2H), 2.07-1.90 (m, 4H), 1.51-1.35 (m, 8H). MS (ESI) m/z: [M+H]$^+$. Found 632.2.

Example 85

4-Chloro-5-(4-(difluoromethoxy)-6-(((S*)-4,4,4-trifluorobutan-2-yl)amino)pyridin-3-yl)-1-ethyl-N-(((1s,4R)-1-hydroxy-4-(methylsulfonyl)cyclohexyl)methyl)-1H-pyrazole-3-carboxamide

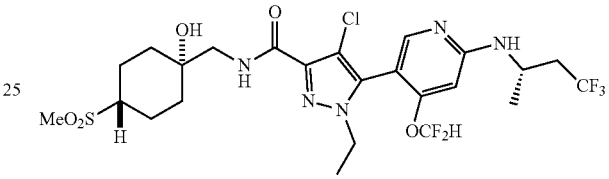

Example 86

4-Chloro-5-(4-(difluoromethoxy)-6-(((R*)-4,4,4-trifluorobutan-2-yl)amino)pyridin-3-yl)-1-ethyl-N-(((1s,4S)-1-hydroxy-4-(methylsulfonyl)cyclohexyl)methyl)-1H-pyrazole-3-carboxamide

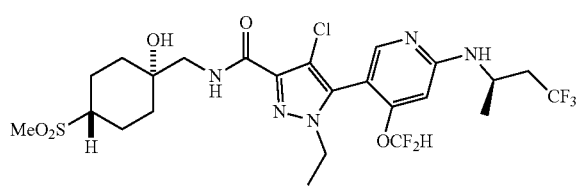

Example 84 was purified by SFC using a chiral stationary phase (Chiralpak AD-H, 85% CO$_2$, 15% MeOH and i-PrOH (1:1 v/v), 0.3% i-PrNH$_2$) to give a pair of enantiomers. The first-eluting isomer was Example 85, and the second-eluting isomer was Example 86. Example 85: $^1$H NMR (500 MHz, CDCl$_3$) δ 7.99 (s, 1H), 7.23 (t, J=6.4 Hz, 1H), 6.67-6.36 (m, 1H), 6.20 (s, 1H), 4.79-4.72 (m, 1H), 4.46-4.32 (m, 1H), 4.08-3.92 (m, 2H), 3.51-3.42 (m, 2H), 3.07 (s, 1H), 2.84-2.76 (m, 4H), 2.63-2.48 (m, 1H), 2.42-2.29 (m, 1H), 2.16-2.10 (m, 2H), 2.03-1.93 (m, 4H), 1.48-1.35 (m, 8H). MS (ESI) m/z: [M+H]$^+$. Found 632.2. Example 86: $^1$H NMR (500 MHz, CDCl$_3$) δ 8.00 (s, 1H), 7.23 (t, J=6.5 Hz, 1H), 6.67-6.36 (m, 1H), 6.20 (s, 1H), 4.79-4.72 (m, 1H), 4.45-4.34 (m, 1H), 4.07-3.92 (m, 2H), 3.51-3.42 (m, 2H), 3.06 (s, 1H), 2.85-2.76 (m, 4H), 2.60-2.49 (m, 1H), 2.41-2.31 (m, 1H), 2.17-2.1 (m, 2H), 2.01-1.93 (m, 4H), 1.48-1.37 (m, 8H). MS (ESI) m/z: [M+H]$^+$. Found 632.2.

Example 87

4-Chloro-5-(4-(difluoromethoxy)-6-((1,1,1-trifluoropentan-3-yl)amino)pyridin-3-yl)-1-ethyl-N-(((1s,4s)-1-hydroxy-4-(methylsulfonyl)cyclohexyl)methyl)-1H-pyrazole-3-carboxamide

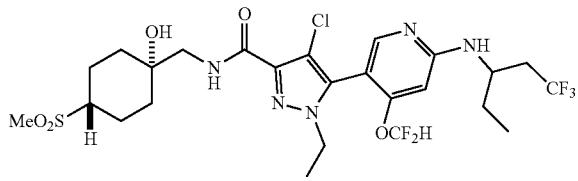

The title compound was prepared as described for the synthesis of Example 1, using ethyl 4-chloro-5-(4-(difluoromethoxy)-6-((1,1,1-trifluoropentan-3-yl)amino)pyridin-3-yl)-1-ethyl-1H-pyrazole-3-carboxylate (Intermediate 83) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate. $^1$H NMR (400 MHz, CDCl$_3$) δ 7.98 (s, 1H), 7.25-7.19 (m, 1H), 6.52 (ddd, J=74.1, 70.1, 1.6 Hz, 1H), 6.20 (s, 1H), 4.73 (t, J=10.3 Hz, 1H), 4.34-4.14 (m, 1H), 4.12-3.90 (m, 2H), 3.51-3.41 (m, 2H), 3.09 (s, 1H), 2.85-2.74 (m, 4H), 2.53-2.37 (m, 2H), 2.20-2.08 (m, 2H), 1.98 (q, J=12.3, 11.8 Hz, 4H), 1.89-1.76 (m, 1H), 1.76-1.63 (m, 1H), 1.50-1.32 (m, 5H), 1.03 (t, J=7.9, 6.8 Hz, 3H). MS (ESI) m/z: [M+H]$^+$. Found 646.2.

Example 88

4-Chloro-5-(4-(difluoromethoxy)-6-(((S*)-1,1,1-trifluoropentan-3-yl)amino)pyridin-3-yl)-1-ethyl-N-(((1s,4R)-1-hydroxy-4-(methylsulfonyl)cyclohexyl)methyl)-1H-pyrazole-3-carboxamide

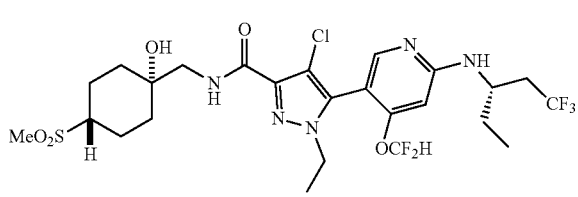

Example 89

4-Chloro-5-(4-(difluoromethoxy)-6-(((R*)-1,1,1-trifluoropentan-3-yl)amino)pyridin-3-yl)-1-ethyl-N-(((1s,4S)-1-hydroxy-4-(methylsulfonyl)cyclohexyl)methyl)-1H-pyrazole-3-carboxamide

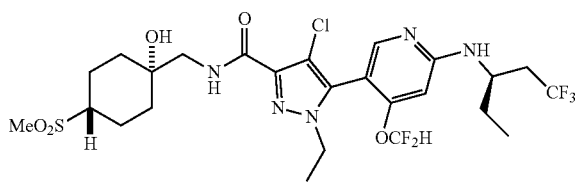

Example 87 was purified by SFC using a chiral stationary phase (Lux Cellulose-4, 70% CO$_2$, 27% MeCN, 3% MeOH) to give a pair of enantiomers. The first-eluting isomer was Example 88, and the second-eluting isomer was Example 89. Example 88: $^1$H NMR (400 MHz, CDCl$_3$) δ 7.91 (s, 1H), 7.16 (t, J=6.2 Hz, 1H), 6.45 (ddd, J=74.1, 70.1, 1.6 Hz, 1H), 6.13 (s, 1H), 4.73-4.62 (m, 1H), 4.23-4.07 (m, 1H), 4.01-3.83 (m, 2H), 3.45-3.33 (m, 2H), 3.01 (s, 1H), 2.80-2.66 (m, 4H), 2.44-2.29 (m, 2H), 2.11-2.01 (m, 2H), 1.97-1.82 (m, 4H), 1.82-1.69 (m, 1H), 1.69-1.56 (m, 1H), 1.42-1.28 (m, 5H), 0.96 (t, J=7.8, 6.8 Hz, 3H). MS (ESI) m/z: [M+H]$^+$. Found 646.5. Example 89: $^1$H NMR (400 MHz, CDCl$_3$) δ 7.91 (s, 1H), 7.18-7.12 (m, 1H), 6.45 (ddd, J=74.0, 70.0, 1.6 Hz, 1H), 6.13 (s, 1H), 4.71-4.61 (m, 1H), 4.23-4.07 (m, 1H), 4.01-3.84 (m, 2H), 3.43-3.37 (m, 2H), 3.02 (s, 1H), 2.79-2.67 (m, 4H), 2.43-2.29 (m, 2H), 2.12-2.01 (m, 2H), 1.99-1.84 (m, 4H), 1.82-1.69 (m, 1H), 1.69-1.56 (m, 1H), 1.42-1.28 (m, 5H), 0.96 (t, J=7.8, 6.8 Hz, 3H). MS (ESI) m/z: [M+H]$^+$. Found 646.5.

Example 90

4-Chloro-5-(6-(((1-cyclopropyl-3,3,3-trifluoropropyl)amino)-4-(difluoromethoxy)pyridin-3-yl)-1-ethyl-N-(((1s,4s)-1-hydroxy-4-(methylsulfonyl)cyclohexyl)methyl)-1H-pyrazole-3-carboxamide

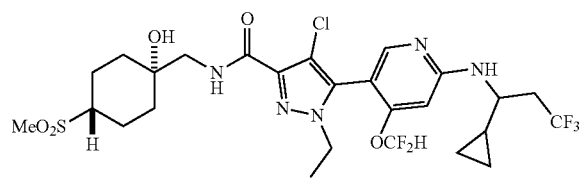

The title compound was prepared as described for the synthesis of Example 1, using ethyl 4-chloro-5-(6-(((1-cyclopropyl-3,3,3-trifluoropropyl)amino)-4-(difluoromethoxy)pyridin-3-yl)-1-ethyl-1H-pyrazole-3-carboxylate (Intermediate 84) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate. $^1$H NMR (500 MHz, CDCl$_3$) δ 7.95 (s, 1H), 7.24 (t, J=6.3 Hz, 1H), 6.52 (dd, J=74.0, 70.1, 1H), 6.21 (s, 1H), 4.96-4.89 (m, 1H), 4.05-3.92 (m, 2H), 3.70-3.55 (m, 1H), 3.51-3.42 (m, 2H), 3.10 (s, 1H), 2.85-2.76 (m, 4H), 2.73-2.49 (m, 2H), 2.16-2.09 (m, 2H), 2.03-1.93 (m, 4H), 1.44-1.36 (m, 5H), 1.15-1.07 (m, 1H), 0.74-0.67 (m, 1H), 0.64-0.57 (m, 1H), 0.47-0.36 (m, 2H). MS (ESI) m/z: [M+H]$^+$. Found 658.2.

Example 91

4-Chloro-5-(6-(((S*)-1-cyclopropyl-3,3,3-trifluoropropyl)amino)-4-(difluoromethoxy)pyridin-3-yl)-1-ethyl-N-(((1s,4R)-1-hydroxy-4-(methylsulfonyl)cyclohexyl)methyl)-1H-pyrazole-3-carboxamide

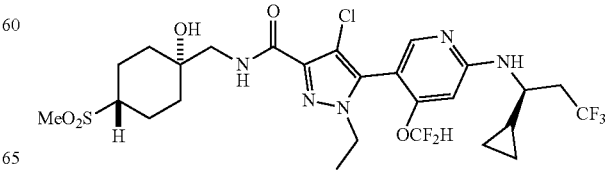

Example 92

4-Chloro-5-(6-(((R*)-1-cyclopropyl-3,3,3-trifluoropropyl)amino)-4-(difluoromethoxy)pyridin-3-yl)-1-ethyl-N-(((1s,4S)-1-hydroxy-4-(methylsulfonyl)cyclohexyl)methyl)-1H-pyrazole-3-carboxamide

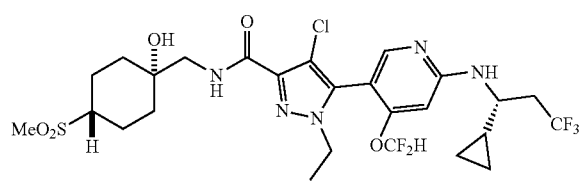

Example 90 was purified by SFC using a chiral stationary phase (Lux Cellulose-4, 70% CO₂, 27% MeCN, 3% MeOH) to give a pair of enantiomers. The first-eluting isomer was Example 91, and the second-eluting isomer was Example 92. Example 91: ¹H NMR (400 MHz, CDCl₃) δ 7.87 (s, 1H), 7.19-7.13 (m, 1H), 6.47 (ddd, J=73.8, 70.0, 2.1 Hz, 1H), 6.17 (s, 1H), 5.37-5.18 (m, 1H), 4.02-3.83 (m, 2H), 3.60-3.46 (m, 1H), 3.45-3.34 (m, 2H), 3.01 (s, 1H), 2.80-2.65 (m, 4H), 2.64-2.44 (m, 2H), 2.11-2.01 (m, 2H), 1.98-1.85 (m, 4H), 1.42-1.29 (m, 5H), 1.10-1.01 (m, 1H), 0.69-0.51 (m, 2H), 0.40-0.29 (m, 2H). MS (ESI) m/z: [M+H]⁺. Found 657.8. Example 92: ¹H NMR (400 MHz, CDCl₃) δ 7.87 (s, 1H), 7.19-7.13 (m, 1H), 6.47 (ddd, J=73.8, 70.0, 2.1 Hz, 1H), 6.17 (s, 1H), 5.37-5.18 (m, 1H), 4.02-3.83 (m, 2H), 3.60-3.46 (m, 1H), 3.45-3.34 (m, 2H), 3.01 (s, 1H), 2.80-2.65 (m, 4H), 2.64-2.44 (m, 2H), 2.11-2.01 (m, 2H), 1.98-1.85 (m, 4H), 1.42-1.29 (m, 5H), 1.10-1.01 (m, 1H), 0.69-0.51 (m, 2H), 0.40-0.29 (m, 2H). MS (ESI) m/z: [M+H]⁺. Found 657.8.

Example 93

4-Chloro-5-(6-((1-cyclopropylpropan-2-yl)amino)-4-(difluoromethoxy)pyridin-3-yl)-1-ethyl-N-(((1s,4s)-1-hydroxy-4-(methylsulfonyl)cyclohexyl)methyl)-1H-pyrazole-3-carboxamide

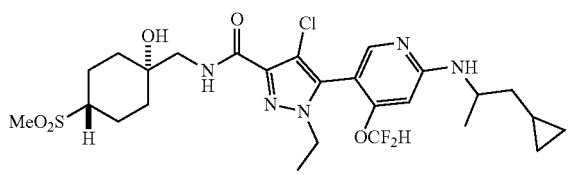

The title compound was prepared as described for the synthesis of Example 1, using ethyl 4-chloro-5-(6-((1-cyclopropylpropan-2-yl)amino)-4-(difluoromethoxy)pyridin-3-yl)-1-ethyl-1H-pyrazole-3-carboxylate (Intermediate 85) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate. ¹H NMR (500 MHz, CDCl₃) δ 7.95 (s, 1H), 7.23 (t, J=6.2 Hz, 1H), 6.53 (dd, J=74.2, 70.1, 1H), 6.17 (s, 1H), 4.93 (s, 1H), 4.08-3.87 (m, 3H), 3.52-3.41 (m, 2H), 3.11 (s, 1H), 2.85-2.76 (m, 4H), 2.16-2.09 (m, 2H), 2.04-1.93 (m, 4H), 1.58-1.47 (m, 2H), 1.43-1.36 (m, 5H), 1.32 (d, J=6.5 Hz, 3H), 0.82-0.72 (m, 1H), 0.55-0.47 (m, 2H), 0.16-0.07 (m, 2H). MS (ESI) m/z: [M+H]⁺. Found 604.3.

Example 94

4-Chloro-5-(6-(((S*)-1-cyclopropylpropan-2-yl)amino)-4-(difluoromethoxy)pyridin-3-yl)-1-ethyl-N-(((1s,4R)-1-hydroxy-4-(methylsulfonyl)cyclohexyl)methyl)-1H-pyrazole-3-carboxamide

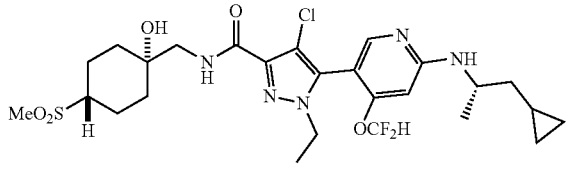

Example 95

4-Chloro-5-(6-(((R*)-1-cyclopropylpropan-2-yl)amino)-4-(difluoromethoxy)pyridin-3-yl)-1-ethyl-N-(((1s,4S)-1-hydroxy-4-(methylsulfonyl)cyclohexyl)methyl)-1H-pyrazole-3-carboxamide

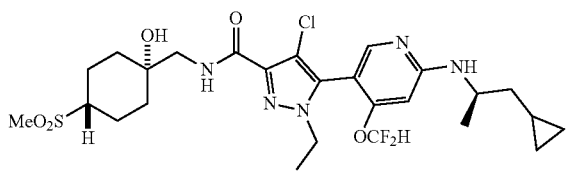

Example 93 was purified by SFC using a chiral stationary phase (Chiralpak AD-H, 80% CO₂, 20% i-PrOH, 0.3% i-PrNH₂) to give a pair of enantiomers. The first-eluting isomer was Example 94, and the second-eluting isomer was Example 95. Example 94: ¹H NMR (400 MHz, CDCl₃) δ 7.95 (s, 1H), 7.26-7.21 (m, 1H), 6.72-6.34 (m, 1H), 6.16 (s, 1H), 5.00-4.93 (m, 1H), 4.08-3.86 (m, 3H), 3.51-3.41 (m, 2H), 2.86-2.76 (m, 4H), 2.16-2.08 (m, 2H), 2.04-1.91 (m, 4H), 1.62-1.52 (m, 1H), 1.49-1.29 (m, 10H), 0.81-0.72 (m, 1H), 0.54-0.48 (m, 2H), 0.15-0.08 (m, 2H). MS (ESI) m/z: [M+H]⁺. Found 604.5. Example 95: ¹H NMR (400 MHz, CDCl₃) δ 7.94 (s, 1H), 7.30-7.24 (m, 1H), 6.73-6.35 (m, 1H), 6.19-6.15 (m, 1H), 5.02-4.93 (m, 1H), 4.09-3.86 (m, 3H), 3.51-3.41 (m, 2H), 2.88-2.76 (m, 4H), 2.16-2.07 (m, 2H), 2.03-1.89 (m, 4H), 1.62-1.51 (m, 1H), 1.50-1.28 (m, 10H), 0.81-0.71 (m, 1H), 0.54-0.47 (m, 2H), 0.15-0.08 (m, 2H). MS (ESI) m/z: [M+H]⁺. Found 604.5.

Example 96

4-Chloro-5-(6-((1-cyclopropyl-2-methylpropan-2-yl)amino)-4-(difluoromethoxy)pyridin-3-yl)-1-ethyl-N-(((1s,4s)-1-hydroxy-4-(methylsulfonyl)cyclohexyl)methyl)-1H-pyrazole-3-carboxamide

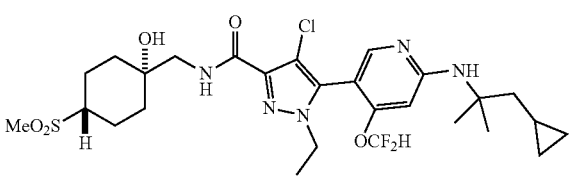

The title compound was prepared as described for the synthesis of Example 1, using ethyl 4-chloro-5-(6-((1-cyclopropyl-2-methylpropan-2-yl)amino)-4-(difluoromethoxy)pyridin-3-yl)-1-ethyl-1H-pyrazole-3-carboxylate (Intermediate 86) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate. $^1$H NMR (400 MHz, CDCl$_3$) δ 7.94 (s, 1H), 7.23 (t, J=6.2 Hz, 1H), 6.49 (dd, J=74.5, 70.2 Hz, 1H), 6.21-6.18 (m, 1H), 4.99 (s, 1H), 4.05-3.92 (m, 2H), 3.49-3.44 (m, 2H), 3.10 (s, 1H), 2.85-2.76 (m, 4H), 2.17-2.09 (m, 2H), 2.04-1.92 (m, 4H), 1.75-1.71 (m, 2H), 1.52 (s, 6H), 1.48-1.37 (m, 5H), 0.78-0.68 (m, 1H), 0.53-0.48 (m, 2H), 0.11-0.06 (m, 2H). MS (ESI) m/z: [M+H]$^+$. Found 618.3.

Example 97

4-Chloro-5-(4-(difluoromethyl)-6-((4,4,4-trifluoro-2-methylbutan-2-yl)amino)pyridin-3-yl)-1-ethyl-N-(((1s,4s)-1-hydroxy-4-(methylsulfonyl)cyclohexyl)methyl)-1H-pyrazole-3-carboxamide

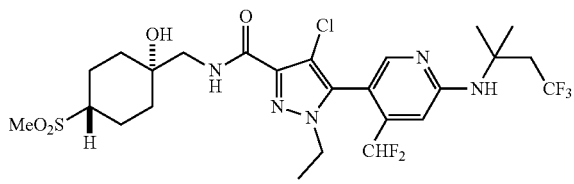 [SMILES: CCn1nc(C(=O)NC[C@]2(O)CC[C@@H](S(C)(=O)=O)CC2)c(Cl)c1-c1cnc(NC(C)(C)CC(F)(F)F)cc1C(F)F]

The title compound was prepared as described for the synthesis of Intermediate 59, using ethyl 4-chloro-5-(4-(difluoromethyl)-6-((4,4,4-trifluoro-2-methylbutan-2-yl)amino)pyridin-3-yl)-1-ethyl-1H-pyrazole-3-carboxylate (Intermediate 97) and (1s,4s)-1-(aminomethyl)-4-(methylsulfonyl)cyclohexan-1-ol hydrochloride (Intermediate 9) in place of ethyl 4-chloro-5-(4-(difluoromethoxy)pyridin-3-yl)-1-ethyl-1H-pyrazole-3-carboxylate and ((1r,4r)-4-(methylsulfonyl)cyclohexyl)methanamine hydrochloride. $^1$H NMR (400 MHz, CDCl$_3$) δ 7.95 (s, 1H), 7.25-7.20 (m, 1H), 6.70-6.65 (m, 1H), 6.51-6.20 (m, 1H), 4.77 (s, 1H), 4.06-3.89 (m, 2H), 3.47 (d, J=6.3 Hz, 2H), 3.10-2.77 (m, 7H), 2.18-2.09 (m, 2H), 2.05-1.92 (m, 4H), 1.64-1.58 (m, 6H), 1.50-1.34 (m, 5H); MS (ESI) m/z: [M+H]$^+$. Found 630.2.

Example 98

4-Chloro-1-ethyl-5-(4-methoxy-6-(((R)-1,1,1-trifluoropropan-2-yl)amino)pyridin-3-yl)-N-(((1r,4R)-4-(methylsulfonyl)cyclohexyl)methyl)-1H-pyrazole-3-carboxamide

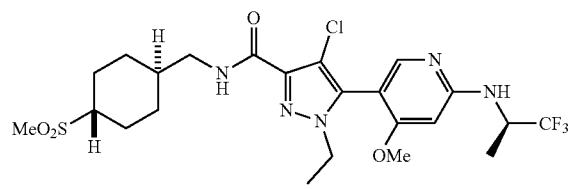 [SMILES: CCn1nc(C(=O)NC[C@H]2CC[C@H](S(C)(=O)=O)CC2)c(Cl)c1-c1cnc(N[C@H](C)C(F)(F)F)cc1OC]

The title compound was prepared as described for the synthesis of Example 1, using ethyl (R)-4-chloro-1-ethyl-5-(4-methoxy-6-((1,1,1-trifluoropropan-2-yl)amino)pyridin-3-yl)-1H-pyrazole-3-carboxylate (Intermediate 98) and ((1r,4r)-4-(methylsulfonyl)cyclohexyl)methanamine hydrochloride (Intermediate 13) in place of ethyl 5-(4-(difluoromethoxy)-6-((4,4,4-trifluoro-2-methylbutan-2-yl)amino)pyridin-3-yl)-1-ethyl-4-methyl-1H-pyrazole-3-carboxylate and (1s,4s)-1-(aminomethyl)-4-(methylsulfonyl)cyclohexanol hydrochloride. $^1$H NMR (500 MHz, CDCl$_3$) δ 7.86 (s, 1H), 6.06-6.00 (m, 1H), 5.03-4.68 (m, 2H), 4.03-3.88 (m, 2H), 3.82-3.78 (m, 3H), 3.39-3.28 (m, 2H), 2.87-2.81 (m, 4H), 2.32-2.23 (m, 2H), 2.11-2.05 (m, 2H), 1.72-1.64 (m, 1H), 1.63-1.53 (m, 3H), 1.46-1.42 (m, 3H), 1.36 (t, J=7.2 Hz, 3H), 1.19-1.08 (m, 2H). MS (ESI) m/z: [M+H]$^+$. Found 566.0.

In Vitro Biological Data

ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM 001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor® assay is shown as SEQ ID NO:4.

ThermoFluor® experiments were carried out using instruments owned by Janssen Research and Development, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 μL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 μM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 μL, followed by 1 μL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. *Biochemistry* 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data
RORγt (Full-Length Human) Reporter Assay:

Two similar reporter assay protocols, shown below, have been used to test the functional activity of RORγt modulatory compounds on transcriptional activation driven by full-length human RORγt. Both provide similar data and can be used interchangeably.

Conditions A

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega # E2261). The full-length coding sequence was used for human RORγt, i.e., nucleotides 142-1635 of human RORγt, transcript variant 2, NCBI Accession: NM_001001523.1 (SEQ ID NO:1). HEK293T cells were plated at 35,000 per well in 96-well plate in medium of DMEM with 10% FBS. After 18-22 hours incubation, the transfection was carried out by using a PEI solution with 170.5 ng total DNA/well (50 ng pCMV-BD-ROR plus 20 ng of pFR-Luc reporter and 0.5 ng of pRL-CMV reporter plus 100 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 50 μL Glo Lysis Buffer (Promega) for 10-15 minutes followed by 10 minute incubation with 50 μL Dual Glo reagent (Promega) at room temperature. Firefly luciferase luminescence was measured using a BMG Pherastar plate reader. To each well, 50 μL Stop and Glo reagent was added and incubated for 10 minutes at room temperature. Renilla luminescence was measured using a BMG Pherastar plate reader. To calculate the effect of compounds on RORγt activity, firefly values were normalized against values of DMSO only and values of reference compound at saturating concentration, then further normalized against Renilla signals. $IC_{50}$s were generated by plotting final Renilla normalized data against compound concentration and percent inhibition was calculated against DMSO control.

Conditions B

Cells used in this assay were transiently co-transfected with three different plasmids, one expressing the GAL4-DNA binding domain (DBD)-RORγt fusion protein under control of a CMV promoter (NH2-Gal4-DBD:RORC—COOH in pCMV-BD, Stratagene #211342), and two reporter plasmids—the firefly luciferase reporter under control of a GAL4 promoter (pFR-Luc 2×GAL4) and Renilla luciferase reporter under control of CMV promoter (pRL-CMV, Promega # E2261). The full-length coding sequence was used for human RORγt, i.e., nucleotides 142-1635 of human RORγt, transcript variant 2, NCBI Accession: NM_001001523.1 (SEQ ID NO:1). HEK293T cells were plated at 8750 cells per well in 384-well plate in medium of DMEM with 10% FBS. After 18-22 hours incubation, the transfection was carried out by using a PEI solution with 42.6 ng total DNA/well (12.5 ng pCMV-BD-ROR plus 5 ng of pFR-Luc reporter and 0.125 ng of pRL-CMV reporter plus 25 ng Carrier DNA (Clontech #630440) for each well). 4-6 hours after transfection, cells were treated with compounds for overnight in the medium with final concentration of FBS 1.3% and DMSO 0.1%. After overnight (16 to 20 hours) incubation, media were removed and cells were lysed with 20 μL Glo Lysis Buffer (Promega) for 10-15 minutes followed by 10 minute incubation with 20 μL Dual Glo reagent (Promega) at room temperature. Firefly luciferase luminescence was measured using a BMG Pherastar plate reader. To each well, 20 μL Stop and Glo reagent was added and incubated for 10 minutes at room temperature. Renilla luminescence was measured using a BMG Pherastar plate reader. To calculate the effect of compounds on RORγt activity, firefly values were normalized against values of DMSO only and values of reference compound at saturating concentration, then further normalized against Renilla signals. IC50s were generated by plotting final Renilla normalized data against compound concentration and percent inhibition was calculated against DMSO control.

Human Th17 Assay

The human Th17 assay tests the effect of RORγt modulatory compounds on IL-17 production by CD4 T cells under conditions which favor Th17 differentiation. Total $CD4^+$ T cells were isolated from the peripheral blood mononuclear cells (PBMC) of healthy donors using a $CD4^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at $1.5 \times 10^5$ per 100 μL per well. 50 μL of compound at titrated concentrations in DMSO were added into each well at final DMSO concentration at 0.2%. Cells were incubated for 1 hour, then 50 μL of Th17 cell differentiation medium was added to each well. The final concentrations of antibodies and cytokines (R&D Systems) in differentiation medium were: $3 \times 10^6$/mL anti-CD3/CD28 beads (prepared using human T cell activation/expansion kit, Miltenyi Biotec), 10 μg/mL anti-IL4, 10 μg/mL anti-IFNγ, 10 ng/mL IL1β, 10 ng/mL IL23, 50 ng/mL IL6, 3 ng/mL TGFβ and 20 U/mL IL2. Cells were cultured at 37° C. and 5% $CO_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

| Example # | ThermoFluor ® Assay, Kd (μM) | RORγt (FL) Reporter Assay A or B, $IC_{50}$ (μM) | RORγt (FL) Reporter Assay A or B, % inhibition @ 6 μM | Human Th17 Assay, $IC_{50}$ (μM) |
|---|---|---|---|---|
| 1 | 0.0033 | 0.043 | 108* | 0.0066 |
| 2 | 0.017 | 0.19 | 104* | ND |
| 3 | 0.081 | 0.62 | 94* | ND |
| 4 | 0.020 | 0.16 | 103* | ND |
| 5 | 0.00035 | 0.0071 | 123* | ND |
| 6 | 0.0043 | 0.043 | 121*** | ND |
| 7 | 0.0025 | 0.063 | 120* | ND |
| 8 | 0.0025 | 0.017 | 106* | ND |
| 9 | 0.0025 | 0.016 | 109* | ND |
| 10 | 0.0010 | 0.11 | 109* | ND |
| 11 | 0.0050 | 0.18 | 109* | ND |
| 12 | 0.0011 | 0.046 | 100* | ND |
| 13 | 0.0051 | 0.026 | 114* | ND |
| 14 | 0.0013 | 0.013 | 116* | ND |
| 15 | 0.00092 | 0.0092 | 112* | 0.0062 |
| 16 | 0.0038 | 0.016 | 121* | 0.017 |
| 17 | 0.0019 | 0.0080 | 107* | ND |
| 18 | 0.0012 | 0.012 | 113* | 0.0041 |
| 19 | 0.0066 | 0.042 | 90* | ND |
| 20 | 0.0021 | 0.029 | 99* | ND |
| 21 | 0.0026 | 0.16 | 96*** | ND |
| 22 | 0.013 | 0.085 | 112* | ND |
| 23 | 0.0047 | 0.0016 | 108* | ND |
| 24 | 0.019 | 0.15 | 93* | ND |
| 25 | 0.0054 | 0.038 | 100* | ND |
| 26 | 0.029 | 0.12 | 90* | ND |
| 27 | 0.011 | 0.026 | 111* | ND |
| 28 | 0.0042 | 0.35 | 95*** | ND |
| 29 | 0.0031 | 0.022 | 109*** | ND |
| 30 | 0.0059 | 0.030 | 97* | ND |
| 31 | 0.011 | 0.032 | 108* | ND |
| 32 | 0.00065 | 0.0067 | 105* | ND |
| 33 | 0.00078 | 0.011 | 108* | ND |
| 34 | 0.071 | 0.050 | 93 | ND |
| 35 | 0.25 | 0.14 | 88 | ND |
| 36 | 0.69 | 0.20 | 103 | ND |
| 37 | 0.030 | 0.030 | 97 | ND |
| 38 | 0.019 | 0.0098 | 107* | ND |
| 39 | 0.046 | 0.020 | 106* | ND |
| 40 | 0.063 | 0.13 | 90** | ND |
| 41 | 0.023 | 0.030 | 113* | ND |
| 42 | 0.016 | 0.022 | 112* | ND |
| 43 | 0.72 | 0.36 | 84 | ND |
| 44 | 2.0 | 0.71 | 83 | ND |
| 45 | 0.071 | 0.078 | 99** | ND |
| 46 | 0.047 | 0.027 | 105* | ND |
| 47 | 0.11 | 0.056 | 107*** | ND |
| 48 | 0.17 | 0.63 | 95 | ND |
| 49 | 0.00041 | 0.0043 | 99* | ND |
| 50 | 0.62 | 0.76 | 94 | ND |
| 51 | 3.3 | 1.3 | 56** | ND |
| 52 | 0.16 | 0.34 | 108 | ND |
| 53 | 0.45 | 0.86 | 60** | ND |
| 54 | 8.6 | 1.8 | 46** | ND |
| 55 | 0.11 | 0.060 | 113* | ND |
| 56 | 0.18 | 0.26 | 120* | ND |
| 57 | 0.032 | 0.025 | 114* | ND |
| 58 | 0.086 | 0.084 | 114* | ND |
| 59 | 0.011 | 0.016 | 108* | ND |
| 60 | 0.010 | 0.0030 | 107* | ND |
| 61 | 0.022 | 0.013 | 122* | ND |
| 62 | 0.62 | 0.18 | 97* | ND |
| 63 | 2.5 | 0.13 | 52*** | ND |
| 64 | ND | ND | ND | ND |
| 65 | 0.95 | 0.18 | 88* | ND |
| 66 | 0.011 | 0.015 | 108* | ND |
| 67 | 0.061 | 0.043 | 85* | ND |
| 68 | 0.0022 | 0.0035 | 106* | ND |
| 69 | 0.0056 | 0.012 | 111* | ND |
| 70 | ND | 0.035 | 106* | ND |
| 71 | 0.024 | 0.14 | 95* | ND |
| 72 | 0.073 | 0.32 | 86* | ND |
| 73 | ND | 1.0 | 79* | ND |
| 74 | 19 | 3.5 | 29* | ND |
| 75 | 0.39 | 0.055 | 90* | ND |
| 76 | ND | 0.30 | 64* | ND |
| 77 | 0.42 | 0.97 | 54* | ND |
| 78 | 1.2 | >3.0 | −60 | ND |
| 79 | 0.0026 | 0.010 | 100* | 0.013 |
| 80 | 0.0037 | 0.034 | 101* | ND |
| 81 | 0.19 | 0.071 | 68*** | ND |
| 82 | 0.00015 | 0.0035 | 108**** | ND |
| 83 | 0.00040 | 0.0090 | 117* | ND |
| 84 | 0.054 | 0.098 | 81* | ND |
| 85 | 0.039 | 0.24 | 94* | ND |
| 86 | 0.15 | 0.33 | 90* | ND |
| 87 | 0.044 | 0.23 | 26*** | ND |
| 88 | 0.061 | 1.3 | 74* | ND |
| 89 | 0.023 | 0.19 | 87* | ND |
| 90 | 0.024 | 0.038 | 46* | ND |
| 91 | 0.039 | 0.031 | 84* | ND |
| 92 | 0.020 | 0.013 | 76* | ND |
| 93 | 0.037 | >3.0 | −10* | ND |
| 94 | 0.12 | 2.0 | 34* | ND |
| 95 | 0.023 | 0.055 | 78* | ND |
| 96 | 0.0015 | ND | ND | ND |
| 97 | 0.00092 | 0.032 | 120* | 0.0033 |
| 98 | 0.022 | 0.12 | 98** | 0.14 |

ND: value not determined.
*% inhibition is shown at 3 μM compound concentration,
**% inhibition is shown at 2 μM compound concentration,
***% inhibition is shown at 1 μM compound concentration,
****% inhibition is shown at 0.33 μM compound concentration While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

We claim:

1. A compound of Formula I

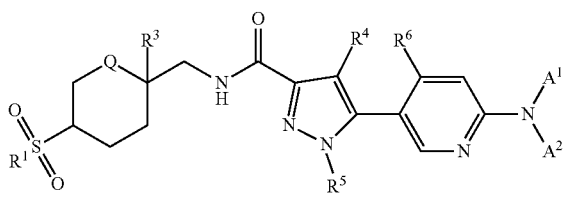

Formula I wherein $R^1$ is $C_{(1-4)}$alkyl, —$NH_2$, —NHC(O)$NH_2$, NHC(O)$C_{(1-4)}$alkyl, —NHC$_{(1-4)}$alkyl, —NHC(O)H, —NHC(O)NHC$_{(1-4)}$alkyl, or —N($C_{(1-4)}$alkyl)$_2$;

Q is $CHR^2$, NC(O)$CH_3$, $NCH_2C(O)NH_2$, NH, or O;

$R^2$ is H, —OH, or —$NH_2$;

$R^3$ is —H, —OH, —CN, —$NH_2$, —$CONH_2$, —$CO_2$H, —$CO_2C_{(1-4)}$alkyl, —$CH_2$OH, —$CH_2NH_2$, —$CH_2$CN, NHC$_{(1-4)}$alkyl, or —CONHC$_{(1-4)}$alkyl;

$R^4$ is —Cl, —$C_{(1-4)}$alkyl, —F, —CN, —C(O)$NH_2$,

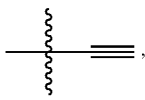

or —H; wherein said —C$_{(1-4)}$alkyl is optionally substituted with up to six fluorine atoms;

R$^5$ is —C$_{(1-4)}$alkyl, wherein said —C$_{(1-4)}$alkyl is optionally substituted with —CN, —OH, —OCH$_3$, —OCF$_3$, or up to six fluorine atoms;

R$^6$ is —H, —F, —Cl, —OCD$_3$, —CN, —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms;

A$^1$ is

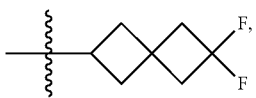 [SMILES: *C1CC2(C1)CC(F)(F)C2]

—C$_{(2-5)}$alkyl, —(CH$_2$)$_m$C$_{(3-6)}$cycloalkyl, wherein said —(CH$_2$)$_m$C$_{(3-6)}$cycloalkyl is optionally substituted with two fluorine atoms, —CF$_3$, —CH$_2$CF$_3$, or —OH, and wherein said —C$_{(2-5)}$alkyl is optionally substituted with —SCF$_3$, —OCH$_2$CF$_3$, cyclopropyl, and up to six fluorine atoms;

m is 0 or 1;

A$^2$ is H; or A$^1$ and A$^2$ are taken together with their attached nitrogen to form

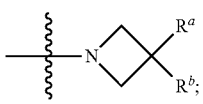

R$^a$ is —OCHF$_2$, —CH$_2$CF$_3$, —CF$_3$, or F;

R$^b$ is H or F.

and pharmaceutically acceptable salts thereof.

2. The compound of claim 1 wherein

R$^1$ is —C$_{(1-2)}$alkyl, —NH$_2$, —NHC(O)NH$_2$, NHC(O)C$_{(1-2)}$alkyl, —NHCH$_3$, —NHC(O)H, —NHC(O)NHCH$_3$, or —N(CH$_3$)$_2$;

R$^3$ is —H, —OH, —CN, —NH$_2$, —CONH$_2$, —CO$_2$H, —CO$_2$CH$_2$CH$_3$, or —CH$_2$OH;

R$^4$ is —Cl, —C$_{(1-4)}$alkyl, —F, —CN, —CF$_3$, —C(O)NH$_2$,

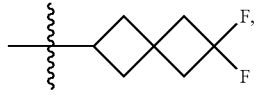 [SMILES: *C1CC2(C1)CC(F)(F)C2]

or —H;

R$^5$ is —C$_{(1-4)}$alkyl, wherein said —C$_{(1-4)}$alkyl is optionally substituted with —CN, —OH, or —OCH$_3$.

and pharmaceutically acceptable salts thereof.

3. The compound of claim 2 wherein

R$^1$ is —C$_{(1-2)}$alkyl, —NH$_2$, —NHC(O)NH$_2$, NHC(O)C$_{(1-2)}$alkyl, —NHCH$_3$, —NHC(O)H, or —NHC(O)NHCH$_3$;

Q is CHR$^2$;

R$^2$ is —H or —OH;

R$^3$ is —H, —OH, —CN, or —NH$_2$;

R$^4$ is —Cl, —C$_{(1-4)}$alkyl, —F, or —CN;

R$^5$ is —C$_{(1-4)}$alkyl;

R$^6$ is —H, —F, —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms.

and pharmaceutically acceptable salts thereof.

4. The compound of claim 3 wherein

R$^1$ is —C$_{(1-2)}$alkyl;

R$^3$ is —H or —OH;

R$^4$ is —Cl or —C$_{(1-4)}$alkyl;

R$^6$ is —C$_{(1-3)}$alkyl, or —OC$_{(1-3)}$alkyl, wherein said —C$_{(1-3)}$alkyl and said OC$_{(1-3)}$alkyl are optionally substituted with up to three fluorine atoms.

and pharmaceutically acceptable salts thereof.

5. The compound of claim 4 wherein

R$^1$ is —CH$_3$;

R$^4$ is —Cl or —CH$_3$;

R$^5$ is —CH$_2$CH$_3$;

R$^6$ is —C$_{(1-3)}$alkyl, —OCHF$_2$, or —OCH$_3$, wherein said —C$_{(1-3)}$alkyl is optionally substituted with up to three fluorine atoms;

A$^1$ is

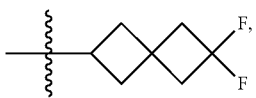 [SMILES: *C1CC2(C1)CC(F)(F)C2]

—C$_{(2-5)}$alkyl, —(CH$_2$)$_m$C$_{(3-6)}$cycloalkyl, wherein said —(CH$_2$)$_m$C$_{(3-6)}$cycloalkyl is optionally substituted with two fluorine atoms, —CF$_3$, or —CH$_2$CF$_3$, and wherein said —C$_{(2-5)}$alkyl is optionally substituted with —SCF$_3$, —OCH$_2$CF$_3$, cyclopropyl, and up to six fluorine atoms.

and pharmaceutically acceptable salts thereof.

6. The compound of claim 1, selected from the group consisting of:

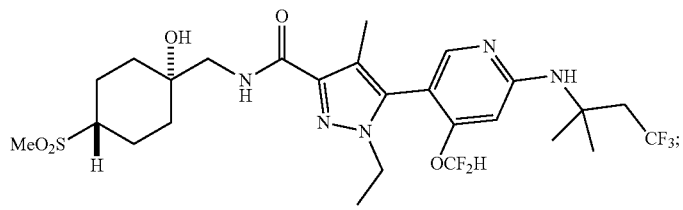

-continued
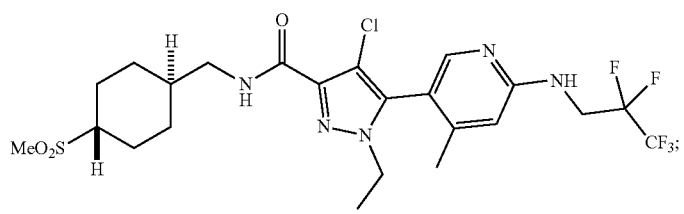
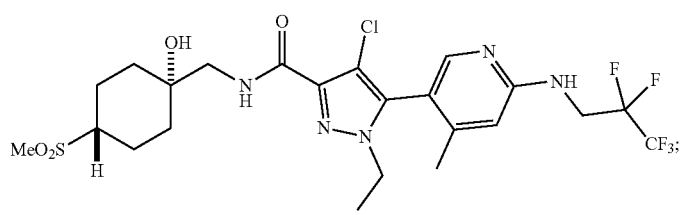
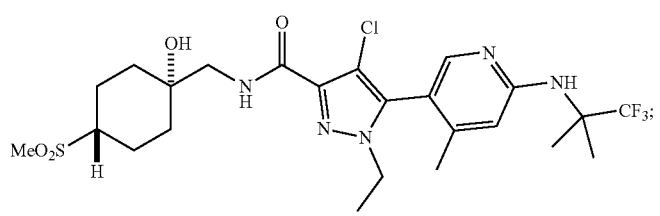
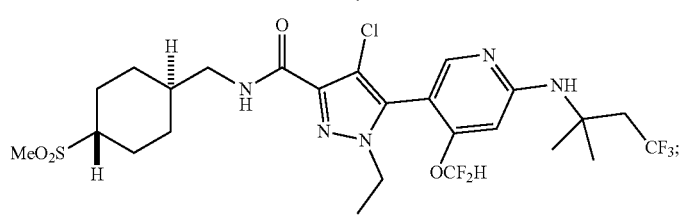
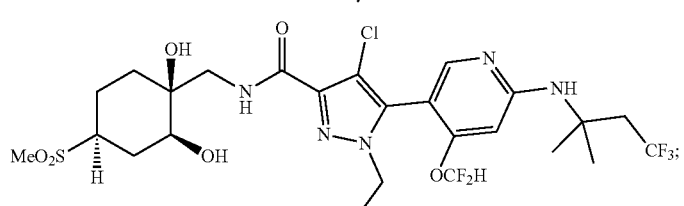
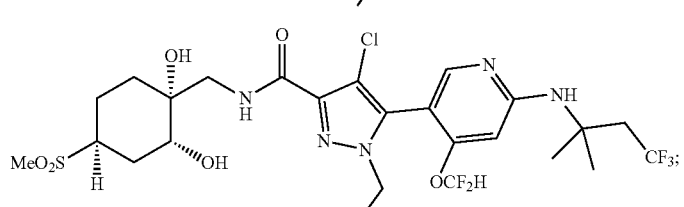
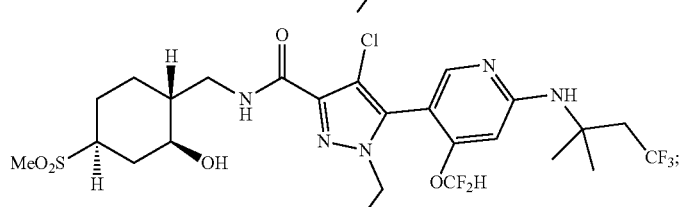
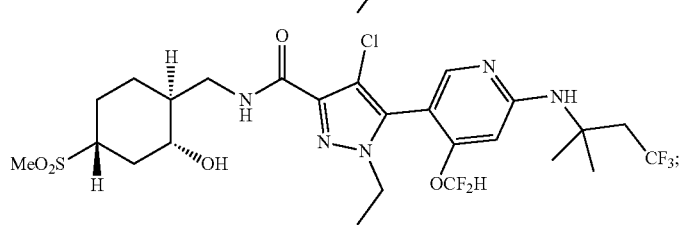

-continued
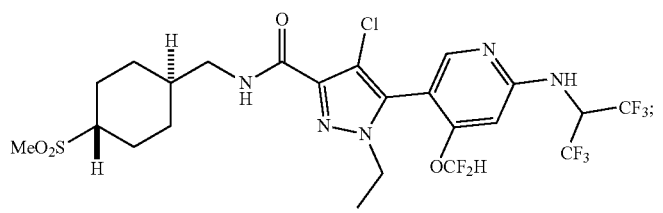
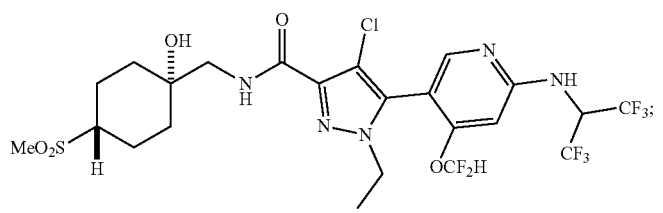
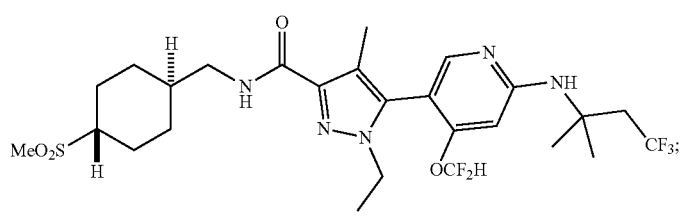
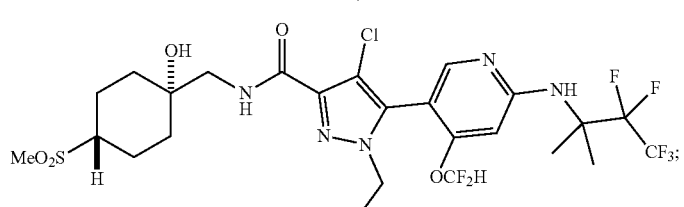
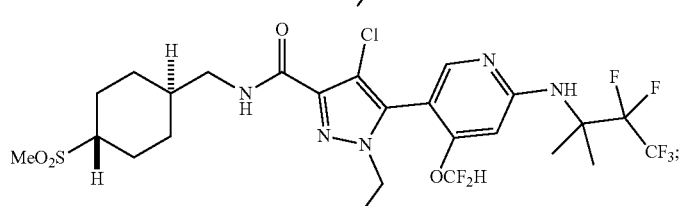
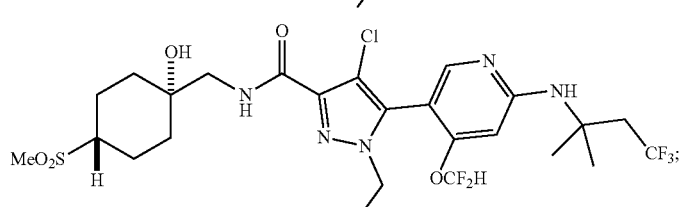
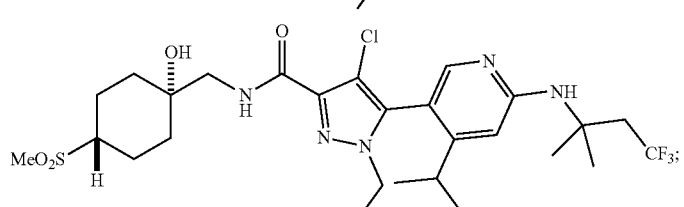
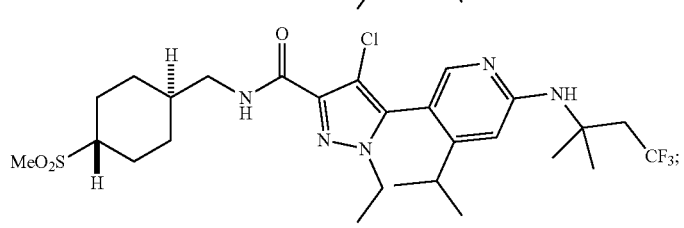

-continued
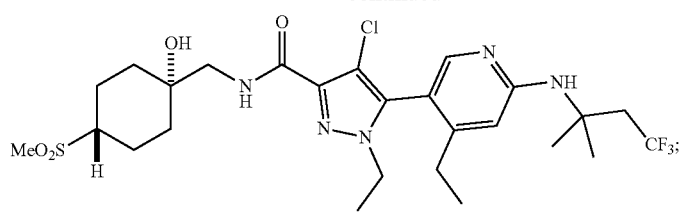
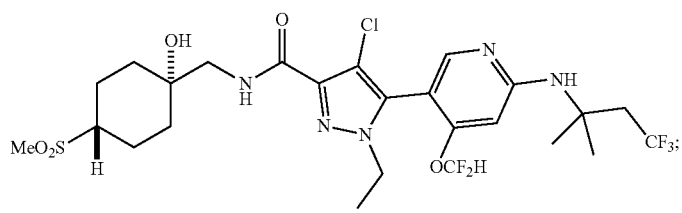
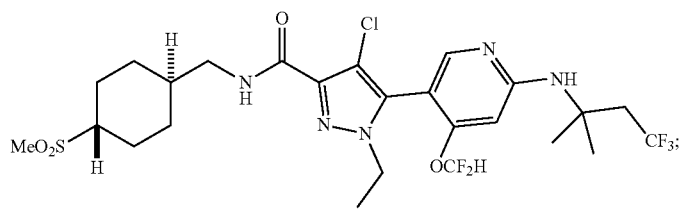
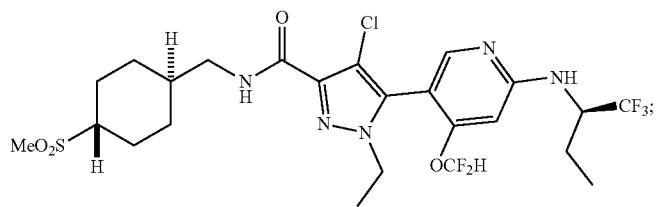
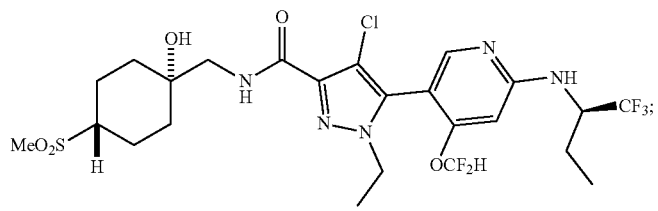
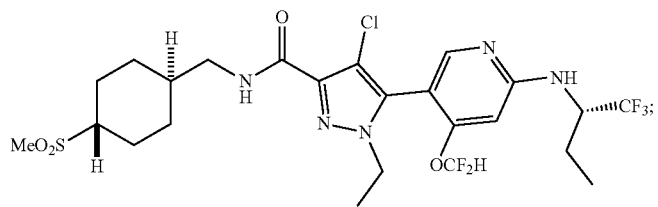
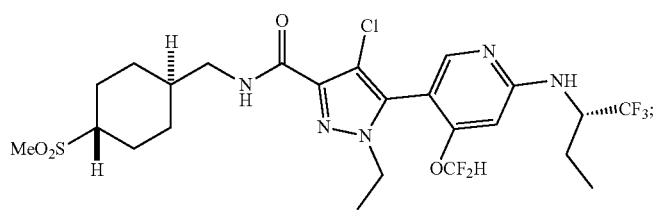
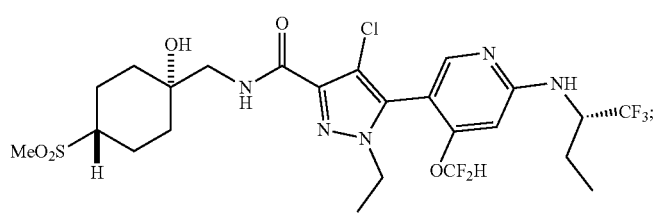

-continued
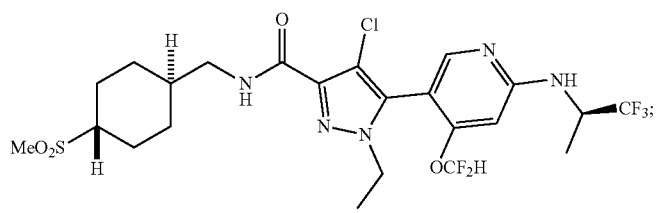
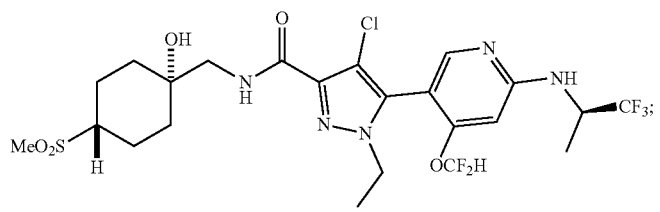
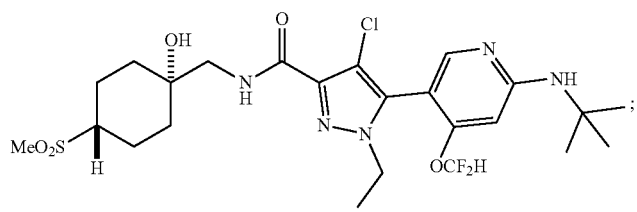
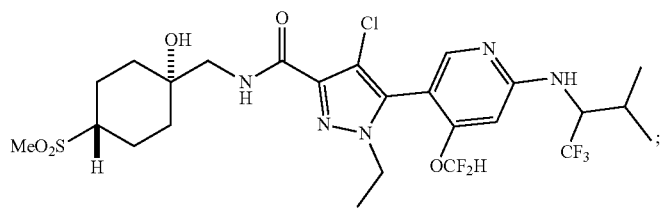
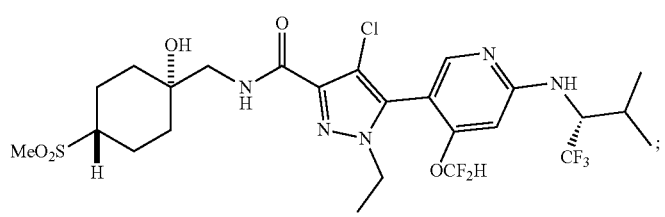
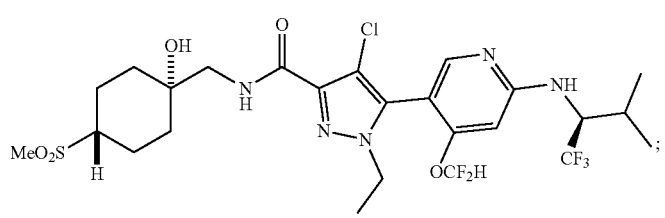
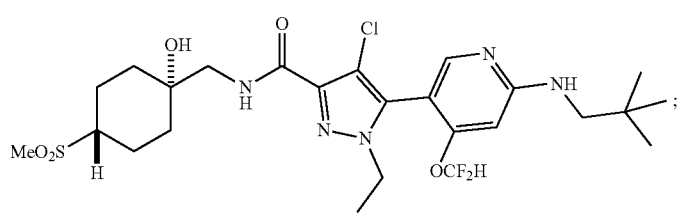
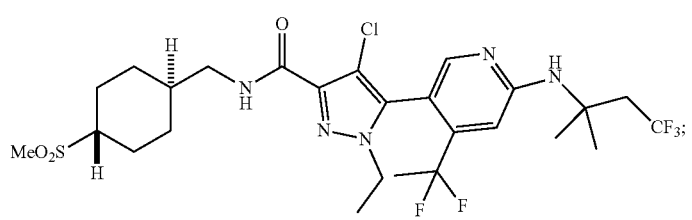

-continued
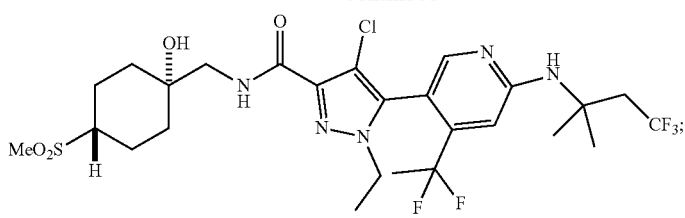
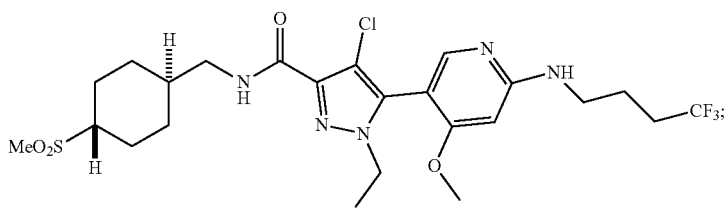
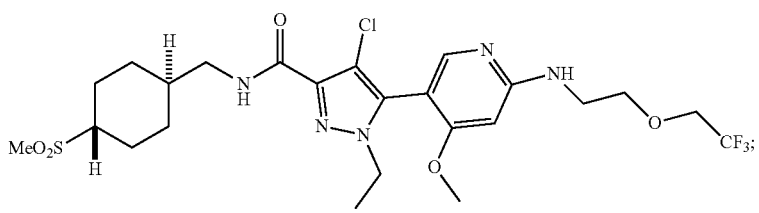
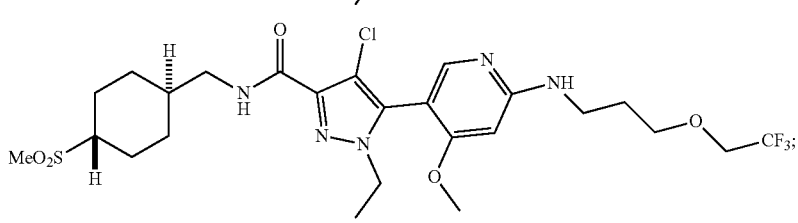
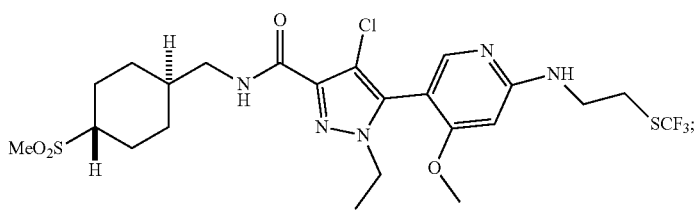
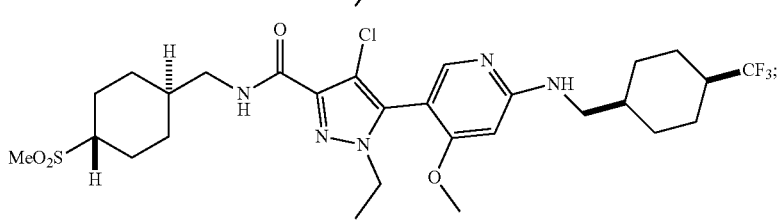
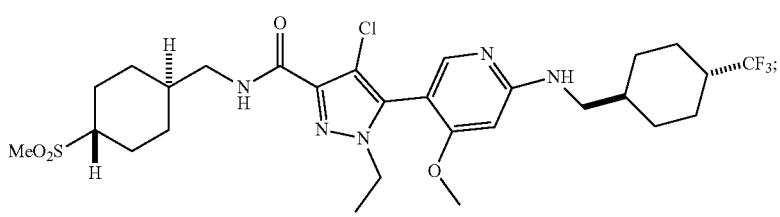
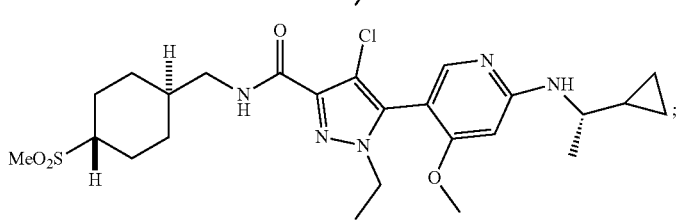

-continued
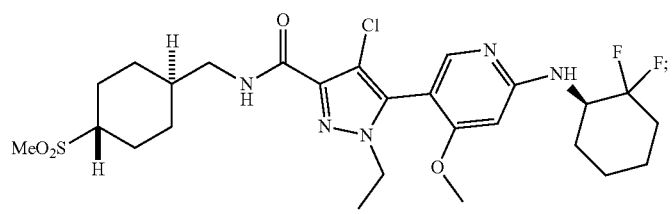
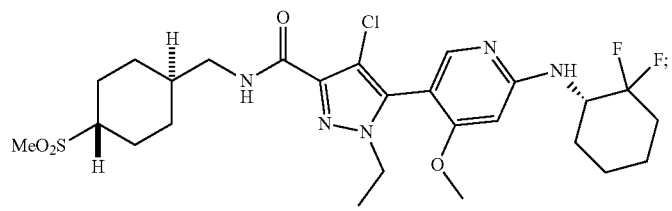
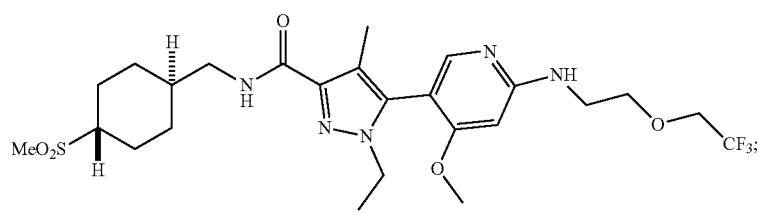
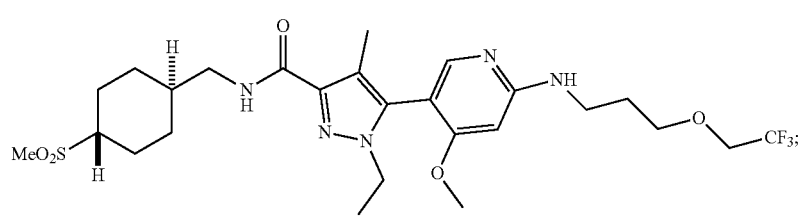
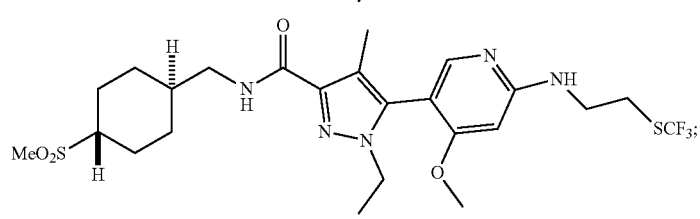
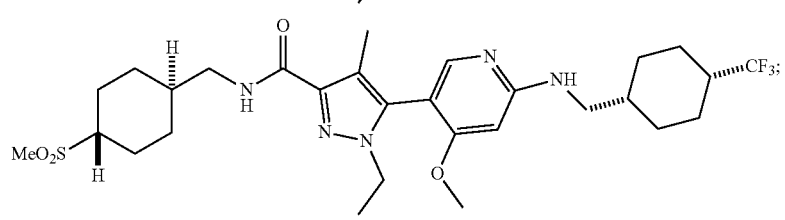
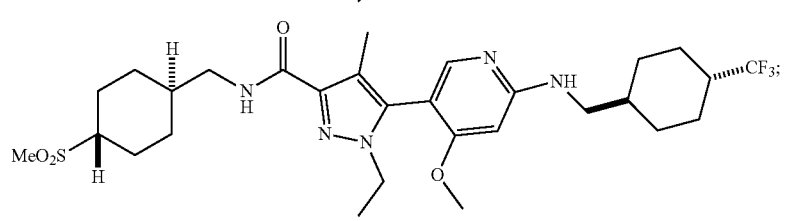
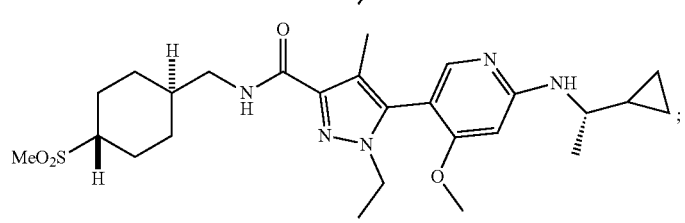

-continued
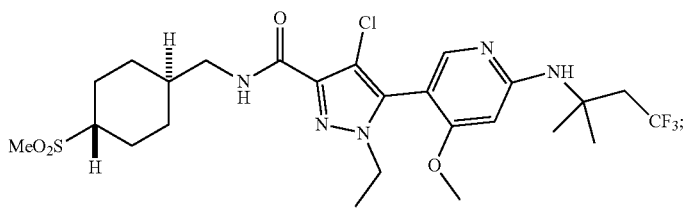
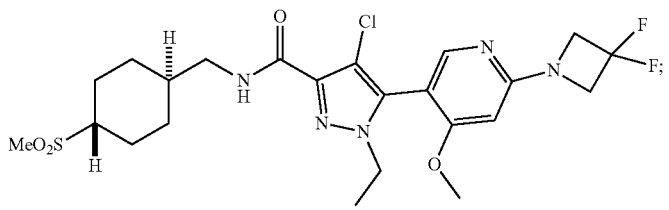
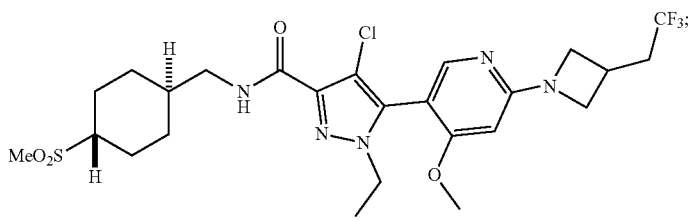
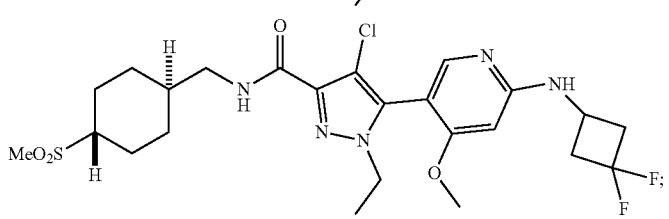
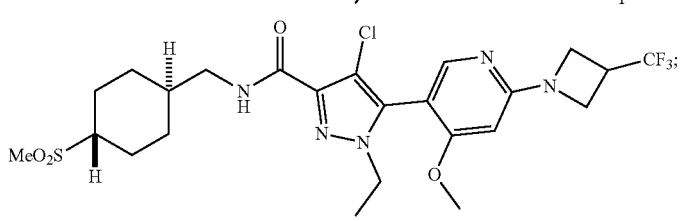
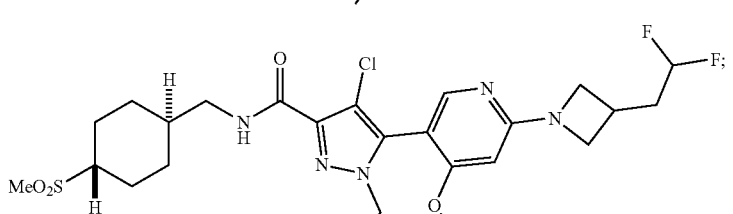
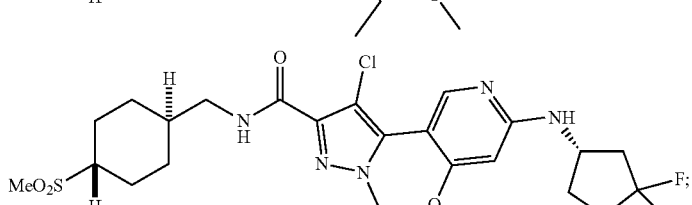
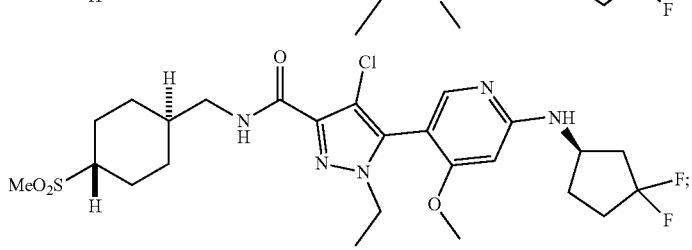

-continued
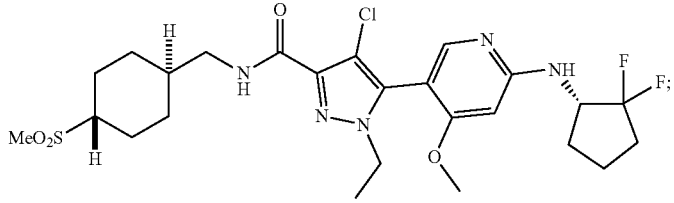
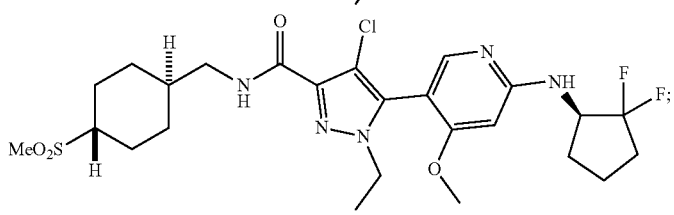
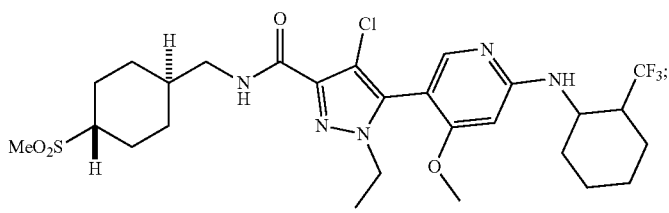
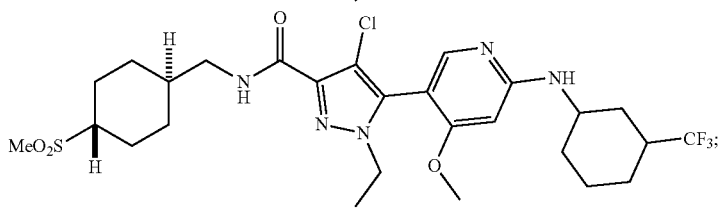
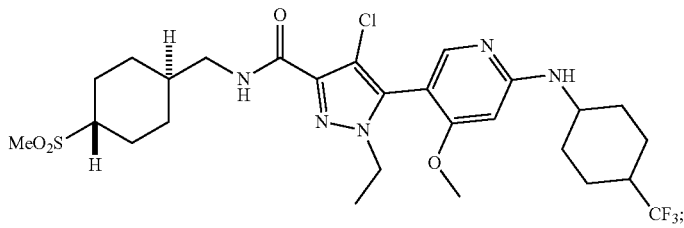
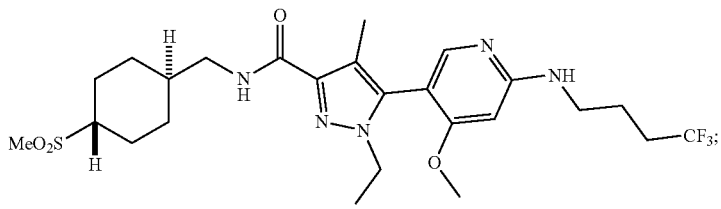
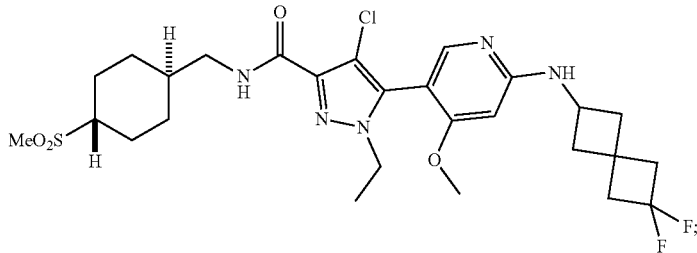
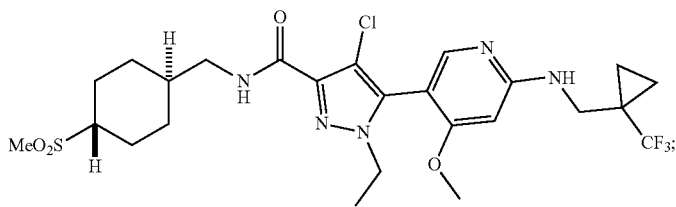

-continued
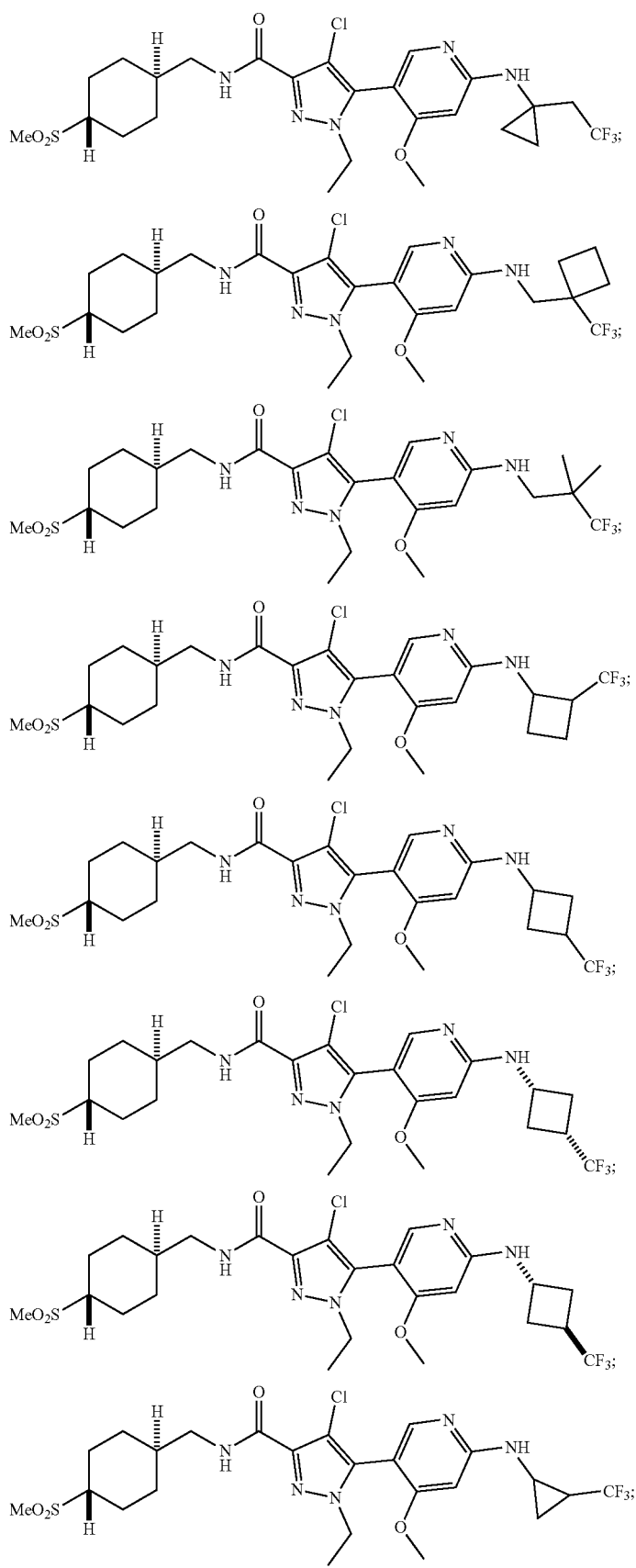

-continued
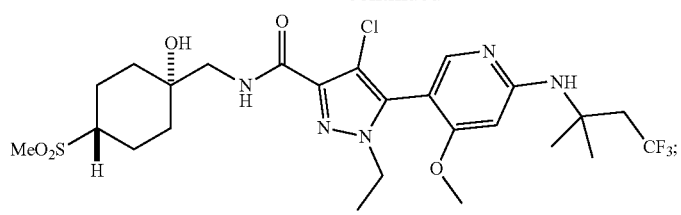
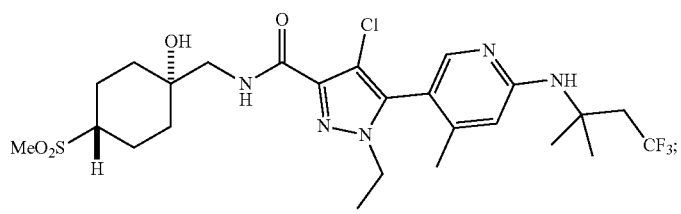
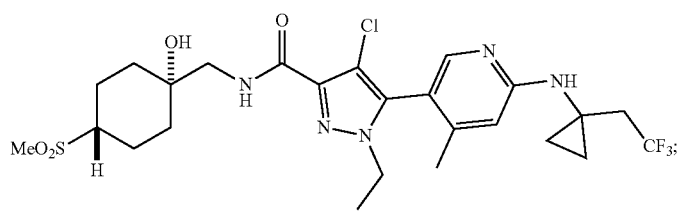
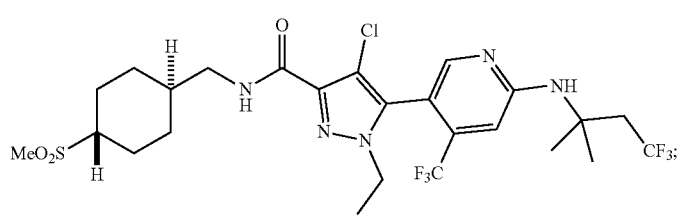
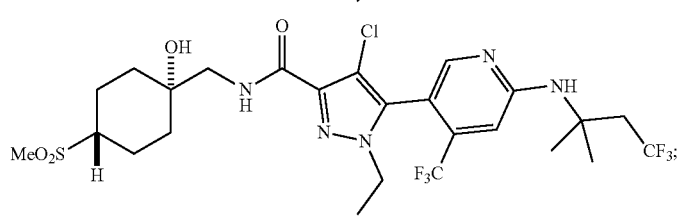
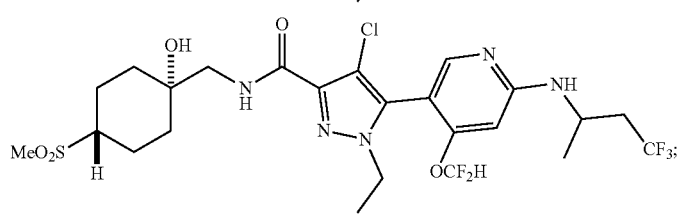
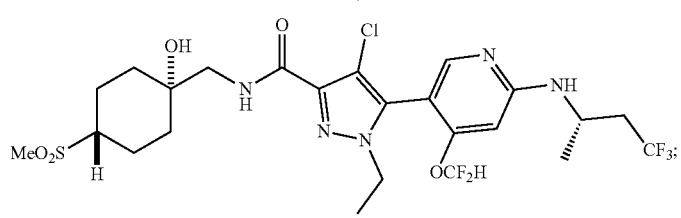
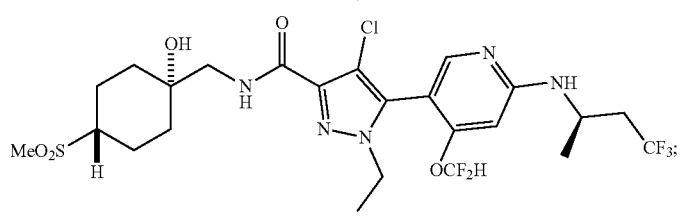

-continued
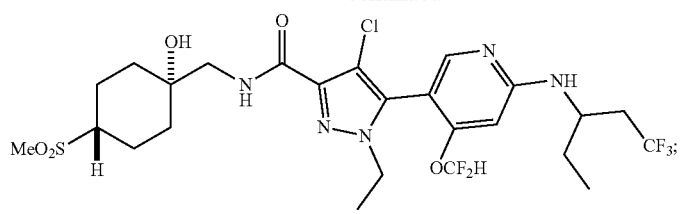
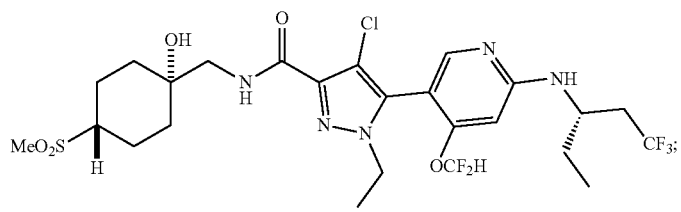
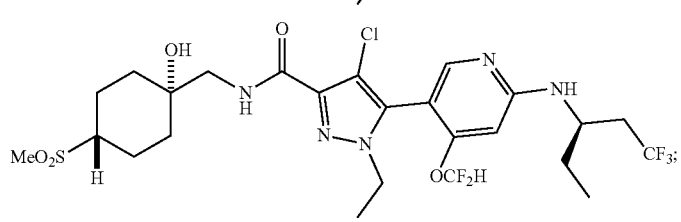
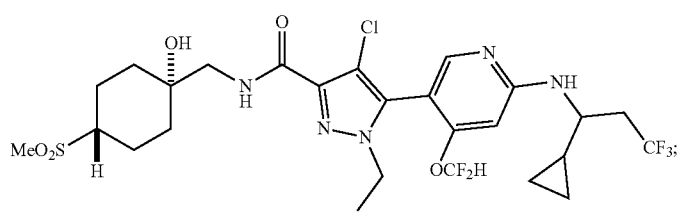
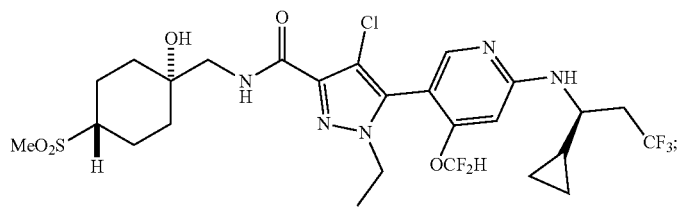
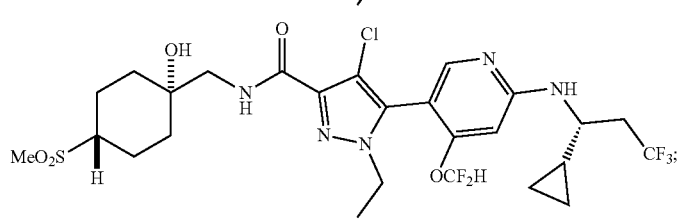
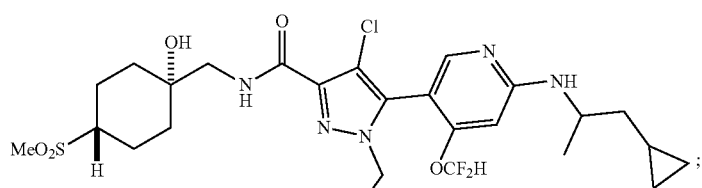
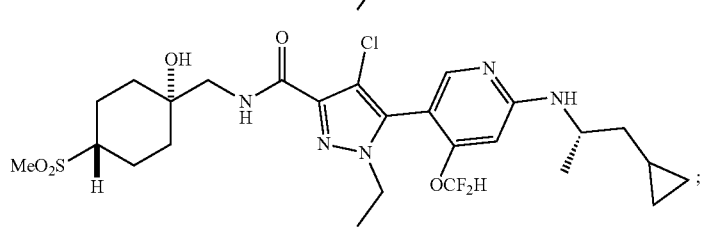

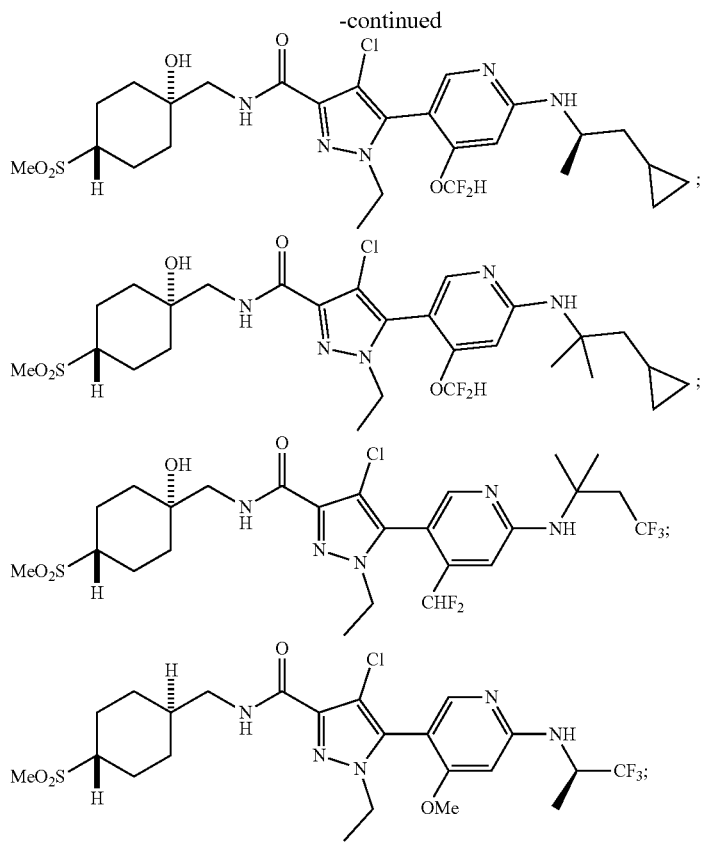

and pharmaceutically acceptable salts thereof.

7. A pharmaceutical composition, comprising a compound of claim 1 and a pharmaceutically acceptable carrier.

8. A pharmaceutical composition made by mixing a compound of claim 1 and a pharmaceutically acceptable carrier.

9. A process for making a pharmaceutical composition comprising mixing a compound of claim 1 and a pharmaceutically acceptable carrier.

10. A method for treating or ameliorating a RORγt mediated inflammatory syndrome, disorder or disease comprising administering to a subject in need thereof an effective amount of a compound of claim 1.

11. The method of claim 10, wherein the disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus.

12. The method of claim 10, wherein the disease is selected from the group consisting of: depression and metabolic syndrome.

13. The method of claim 11, wherein the disease is psoriasis.

14. The method of claim 11, wherein the disease is rheumatoid arthritis.

15. The method of claim 11, wherein the inflammatory bowel disease is ulcerative colitis.

16. The method of claim 11, wherein the inflammatory bowel disease is Crohn's disease.

17. The method of claim 11, wherein the disease is multiple sclerosis.

18. The method of claim 11, wherein the disease is neutrophilic asthma.

19. The method of claim 11, wherein the disease is steroid resistant asthma.

20. The method of claim 11, wherein the disease is psoriatic arthritis.

21. The method of claim 11, wherein the disease is ankylosing spondylitis.

22. The method of claim 11, wherein the disease is systemic lupus erythematosus.

23. The method of claim 11, wherein the disease is chronic obstructive pulmonary disorder.

24. The method of claim 12, wherein the disease is depression.

25. The method of claim 12, wherein the disease is metabolic syndrome.

26. A method of treating or ameliorating a syndrome, disorder or disease, in a subject in need thereof comprising administering to the subject an effective amount of a compound of claim 1 or composition or medicament thereof in a combination therapy with one or more anti-inflammatory agents, or immunosuppressive agents, wherein said syndrome, disorder or disease is selected from the group consisting of: rheumatoid arthritis and psoriasis.

27. A method of treating or ameliorating a syndrome, disorder or disease, in a subject in need thereof comprising administering to the subject an effective amount of a compound of claim 1 or composition or medicament thereof in a combination therapy with one or more anti-inflammatory agents, or immunosuppressive agents, wherein said syndrome, disorder or disease is selected from the group consisting of: psoriatic arthritis and psoriasis.

28. A method of inhibiting production of interleukin-17, comprising administering to a subject in need thereof an effective amount of a compound of claim 1.

* * * * *